(12) United States Patent  
Rewcastle et al.

(10) Patent No.: US 8,486,939 B2  
(45) Date of Patent: Jul. 16, 2013

(54) PYRIMIDINYL AND 1,3,5-TRIAZINYL BENZIMIDAZOLES AND THEIR USE IN CANCER THERAPY

(75) Inventors: Gordon William Rewcastle, Auckland (NZ); Kit Yee Tsang, Auckland (NZ); Swarnalatha Akuratiya Gamage, Auckland (NZ); Anna Claire Giddens, Auckland (NZ)

(73) Assignee: Pathway Therapeutics Inc., San Francisco, CA (US)

( * ) Notice: Subject to any disclaimer, the term of this patent is extended or adjusted under 35 U.S.C. 154(b) by 207 days.

(21) Appl. No.: 12/831,128

(22) Filed: Jul. 6, 2010

(65) Prior Publication Data

US 2011/0009405 A1    Jan. 13, 2011

Related U.S. Application Data

(60) Provisional application No. 61/223,684, filed on Jul. 7, 2009, provisional application No. 61/247,448, filed on Sep. 30, 2009, provisional application No. 61/318,195, filed on Mar. 26, 2010.

(51) Int. Cl.  
*A61K 31/535* (2006.01)  
*C07D 413/14* (2006.01)

(52) U.S. Cl.  
USPC ....................... 514/234.5; 544/113

(58) Field of Classification Search  
USPC ................... 514/234.5; 544/113; 3/234.5  
See application file for complete search history.

(56) References Cited

U.S. PATENT DOCUMENTS

| | | |
|---|---|---|
| 5,750,292 A | 5/1998 | Sato et al. |
| 6,251,900 B1 | 6/2001 | Kawashima et al. |
| 7,071,189 B2 | 7/2006 | Kawashima et al. |
| 7,153,853 B2 | 12/2006 | Kawashima et al. |
| 7,307,077 B2 | 12/2007 | Kawashima et al. |
| 2007/0244110 A1 | 10/2007 | Yaguchi et al. |
| 2008/0113987 A1 | 5/2008 | Haruta et al. |
| 2008/0287431 A1 | 11/2008 | Kawashima et al. |
| 2009/0181963 A1 | 7/2009 | Dehnhardt et al. |
| 2009/0192176 A1 | 7/2009 | Zask et al. |

(Continued)

FOREIGN PATENT DOCUMENTS

| | | |
|---|---|---|
| EP | 0711804 | 5/1996 |
| EP | 1864665 | 12/2007 |

(Continued)

OTHER PUBLICATIONS

Byrn et al., Solid-state Chemistry of Drugs, Second Edition, 1999, pp. 233-247.*

(Continued)

*Primary Examiner* — Rebecca Anderson  
(74) *Attorney, Agent, or Firm* — Jones Day

(57) ABSTRACT

Provided herein are pyrimidinyl and 1,3,5-triazinyl benzimidazoles of Formula I, and their pharmaceutical compositions, preparation, and use as agents or drugs for cancer therapy, either alone or in combination with radiation and/or other anticancer drugs.

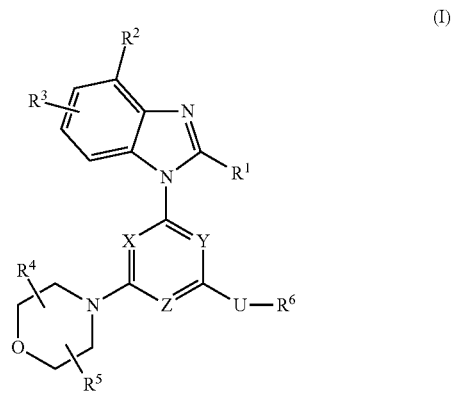

(I)

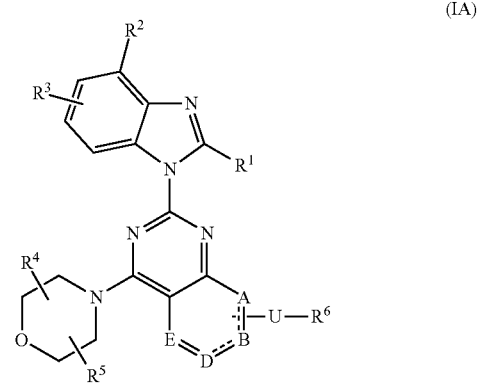

(IA)

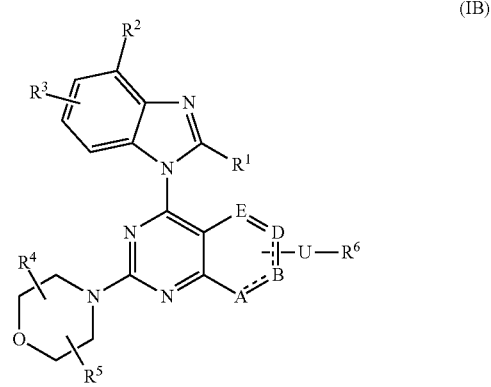

(IB)

87 Claims, No Drawings

U.S. PATENT DOCUMENTS

| | | |
|---|---|---|
| 2009/0233926 A1 | 9/2009 | Butterworth et al. |
| 2009/0270390 A1 | 10/2009 | Butterworth et al. |
| 2009/0325954 A1 | 12/2009 | Butterworth et al. |
| 2010/0022534 A1 | 1/2010 | Butterworth et al. |

FOREIGN PATENT DOCUMENTS

| | | |
|---|---|---|
| EP | 2050749 | 4/2009 |
| JP | 11174638 | 2/1999 |
| WO | WO 99/05138 | 2/1999 |
| WO | WO 01/81346 | 11/2001 |
| WO | WO 02/088112 | 11/2002 |
| WO | WO 2004/037812 | 5/2004 |
| WO | WO 2004/048365 | 6/2004 |
| WO | WO 2005/028467 | 3/2005 |
| WO | WO 2005/095389 | 10/2005 |
| WO | WO 2006/021881 | 3/2006 |
| WO | WO 2006/095906 | 9/2006 |
| WO | WO 2006/122806 | 11/2006 |
| WO | WO 2007/066099 | 6/2007 |
| WO | WO 2007/066103 | 6/2007 |
| WO | WO 2007/084786 | 7/2007 |
| WO | WO 2007/127183 | 8/2007 |
| WO | WO 2007/127175 | 11/2007 |
| WO | WO 2008/018426 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032041 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032086 | 3/2008 |
| WO | WO 2008/032089 | 3/2008 |
| WO | WO 2008/032091 | 3/2008 |
| WO | WO 2008/098058 | 8/2008 |
| WO | WO 2008/115974 | 9/2008 |
| WO | WO 2008/116129 | 9/2008 |
| WO | WO 2009/045174 | 4/2009 |
| WO | WO 2009/045175 | 4/2009 |
| WO | WO 2009/066775 | 5/2009 |
| WO | WO 2009/093981 | 7/2009 |
| WO | WO 2009/097490 | 8/2009 |
| WO | WO 2009/099163 | 8/2009 |
| WO | WO 2009/120094 | 10/2009 |
| WO | WO 2009/143313 | 11/2009 |
| WO | WO 2009/143317 | 11/2009 |
| WO | WO 2009/157880 | 12/2009 |
| WO | WO 2010/005558 | 1/2010 |
| WO | WO 2010/052569 | 5/2010 |
| WO | WO 2010/092962 | 8/2010 |
| WO | WO 2010/110685 * | 9/2010 |

OTHER PUBLICATIONS

Barber et al., "PI3Kgamma inhibition blocks glomerulonephritis and extends lifespan in a mouse model of systemic lupus," *Nat. Med.* 2005, 11, 933-935.

Berrie, "Phosphoinositide 3-kinase inhibition in cancer treatment," *Exp.Opin. Invest. Drugs* 2001, 10, 1085-1098.

Billottet et al., "A selective inhibitor of the PI10delta isoform of PI 3-kinase inhibits AML cell proliferation and survival and increases the cytotoxic effects of VP16," *Oncogene* 2006, 25, 6648-6659.

Camps et al., "Blockade of PI3Kgamma suppresses joint inflammation and damage in mouse models of rheumatoid arthritis," *Nat. Med.* 2005, 11, 936-943.

Foukas & Sheperd, "Phosphoinositide 3-kinase: the protein kinase that time forgot" *Biochem. Soc. Trans.* 2004, 32, 330-331.

Fry, "Phosphoinositide 3-kinase signalling in breast cancer: how big a role might it play?" *Breast Cancer Res.* 2001, 3, 304-312.

Fry, "Structure, regulation and function of phosphoinositide 3-kinases," *Biochem. Biophys. Acta* 1994, 1226, 237-268.

Gross et al., "Design and synthesis of tricyclic corticotropin-releasing factor-1 antagonists," *J. Med. Chem.* 2005, 48, 5780-5793.

Gymnopoulos et al., "Rare cancer-specific mutations in PIK3CA show gain of function," *Proc. Natl. Acad. Sci.*, 2007, 104, 5569-5574.

Hayakawa et al., "Synthesis and biological evaluation of pyrido[3',2':4,5]furo[3,2-d]pyrimidine derivatives as novel PI3 kinase p110alpha inhibitors," *Bioorg. Med. Chem. Lett.* 2007, 17, 2438-2442.

Hayakawa et al., "Synthesis and biological evaluation of imidazo[1,2-a]pyridine derivatives as novel PI3 kinase p110alpha inhibitors," *Bioorg. Med. Chem.* 2007, 15, 403-412.

Hayakawa et al., "Synthesis and biological evaluation of sulfonylhydrazone-substituted imidazo[1,2-a]pyridines as novel PI3 kinase p110alpha inhibitors," *Bioorg. Med. Chem.* 2007, 15, 5837-5844.

Horner et al., "Derivate des Chinoxalins als Isostere der Pteridine," *Justus Liebigs Annalen der Chemie* 1953, 579, 212-234.

Hu et al., "Inhibition of phosphatidylinositol 3'-kinase increases efficacy of paclitaxel in in vitro and in vivo ovarian cancer models," *Cancer Res.* 2002, 62, 1087-1092.

Huang et al., "The structure of a human p110alpha/p85alpha complex elucidates the effects of oncogenic PI3Kalpha mutations," *Science* 2007, 318, 1744-1748.

Ikenoue et al., "Functional analysis of PIK3CA gene mutations in human colorectal cancer," *Cancer Res.* 2005, 65, 4562-4567.

Jackson et al., "PI 3-kinase p110beta: a new target for antithrombotic therapy," *Nat. Med.* 2005, 11, 507-514.

Kang et al., "Phosphatidylinositol 3-kinase mutations identified in human cancer are oncogenic," *Proc. Natl. Acad. Sci. USA* 2005, 102, 802-807.

Knight et al., "A pharmacological map of the PI3-K family defines a role for p110alpha in insulin signaling," *Cell* 2006, 125, 733-747.

Kong et al., "ZSTK474 is an ATP-competitive inhibitor of class I phosphatidylinositol 3 kinase isoforms," *Cancer Sci.* 2007, 98, 1638-1642.

Lanni et al., "Design and synthesis of phenethyl benzo[1,4]oxazine-3-ones as potent inhibitors of PI3Kinasegamma," *Bioorg. Med. Chem. Lett.* 2007, 17, 756-760.

Maira et al., "Identification and characterization of NVP-BEZ235, a new orally available dual phosphatidylinositol 3-kinase/mammalian target of rapamycin inhibitor with potent in vivo antitumor activity," *Mol. Cancer Ther.* 2008, 7, 1851-1863.

Marshall et al., "Estimation of radiation-induced interphase cell death in cultures of human tumor material and in cell lines," *Oncol. Res.* 2004, 14, 297-304.

Miled et al., "Mechanism of two classes of cancer mutations in the phosphoinositide 3-kinase catalytic subunit," *Science* 2007, 317, 239-242.

Provencal et al., "Development of an efficient and scalable process of a respiratory syncytial virus inhibitor," *Org. Proc. Res. Dev.* 2004, 8, 903-908.

Pryde et al., "Novel selective inhibitors of neutral endopeptidase for the treatment of female sexual arousal disorder. Synthesis and activity of functionalized glutaramides," *J. Med. Chem.* 2006, 49, 4409-4424.

Raynaud et al., "Pharmacologic characterization of a potent inhibitor of class I phosphatidylinositide 3-kinases," *Cancer Res.* 2007, 67, 5840-5850.

Sabat et al., "The development of 2-benzimidazole substituted pyrimidine based inhibitors of lymphocyte specific kinase (Lck)," *Bioorg. Med. Che. Lett.* 2006, 16, 5973-5977.

Samuels et al., "High frequency of mutations of the PIK3CA gene in human cancers," *Science* 2004, 304, 554.

Semba et al., "The in vitro and in vivo effects of 2-(4-morpholinyl)-8-phenyl-chromone (LY294002), a specific inhibitor of phosphatidylinositol 3'-kinase, in human colon cancer cells," *Clin. Cancer Res.* 2002, 8, 1957-1963.

Shepherd, "Mechanisms regulating phosphoinositide 3-kinase signalling in insulin-sensitive tissues," *Acta Physiol. Scand.* 2005, 183, 3-12.

Stauffer et al., "Blocking the PI3K/PKB pathway in tumor cells," *Curr. Med. Chem. Anticancer Agents* 2005, 5, 449-462.

Stephens et al., "Phosphoinositide 3-kinases as drug targets in cancer," *Curr. Opin. Pharmacol.* 2005, 5, 357-365.

Stirdivant et al., "Cloning and mutagenesis of the p110 alpha subunit of human phosphoinositide 3'-hydroxykinase,"*Bioorg. Med. Chem.* 1997, 5, 65-74.

Toshiyuki et al., "Synthesis and antitumor activity of benzimidazolyl-1,3,5-triazine and benzimidazolylpyrimidine derivatives," *Chem. Pharm. Bull.* 2000, 48, 1778-1781.

Vanhaesebroeck and Waterfield, "Signaling by distinct classes of phosphoinositide 3-kinases," *Exp. Cell. Res.* 1999, 253, 239-254.

Volina et al., "Molecular cloning, cDNA sequence, and chromosomal localization of the human phosphatidylinositol 3-kinase p110 alpha (PIK3CA) gene," *Genomics* 1994, 24, 472-477.

Walker et al., "Structural determinants of phosphoinositide 3-kinase inhibition by wortmannin, LY294002, quercetin, myricetin, and staurosporine," *Mol .Cell.* 2000, 6, 909-919.

Wipf et al., "Synthesis and biological evaluation of synthetic viridins derived from C(20)-heteroalkylation of the steroidal PI-3-kinase inhibitor wortmannin," *Org. Biomol. Chem.*, 2004, 2, 1911-1920.

Yaguchi et al., "Antitumor activity of ZSTK474, a new phosphatidylinositol 3-kinase inhibitor," *J. Natl. Cancer Inst.* 2006, 98, 545-556.

Zask et al., "Synthesis and structure-activity relationships of ring-opened 17-hydroxywortmannins: potent phosphoinositide 3-kinase inhibitors with improved properties and anticancer efficacy," *J. Med. Chem.*, 2008, 51, 1319-1323.

Zhu et al., "Pegylated wortmannin and 17-hydroxywortmannin conjugates as phosphoinositide 3-kinase inhibitors active in human tumor xenograft models," *J. Med. Chem.*, 2006, 49, 1373-1378.

* cited by examiner

PYRIMIDINYL AND 1,3,5-TRIAZINYL BENZIMIDAZOLES AND THEIR USE IN CANCER THERAPY

CROSS REFERENCE TO RELATED APPLICATIONS

This application claims priority under 35 U.S.C. §119(e) to U.S. Provisional Application Nos. 61/223,684, filed Jul. 7, 2009; 61/247,448, filed Sep. 30, 2009; and 61/318,195, filed Mar. 26, 2010; the disclosure of each of which is incorporated herein by reference in its entirety.

FIELD

Provided herein are pyrimidinyl and 1,3,5-triazinyl benzimidazoles, and their pharmaceutical compositions, preparation, and use as agents or drugs for cancer therapy, either alone or in combination with radiation and/or other anticancer drugs.

BACKGROUND

Phosphoinositide-3-kinases (PI3Ks) are a group of lipid kinases, which phosphorylate the 3-hydroxyl of phosphoinositides. They are classified into at least three classes (Classes I, II, and III) and play an important role in cellular signaling (Stephens et al., Curr. Opin. Pharmacol. 2005, 5, 357). Class I enzymes are further classified into Classes Ia and Ib based on their mechanism of activation; Class Ia PI3Ks are heterodimeric structures consisting of a catalytic subunit (p110α, p110β, or p110δ) in complex with a regulatory p85 subunit, while the class-Ib PI3K (p110γ) is structurally similar but lacks the p85 regulatory subunit, and instead is activated by βγ subunits of heterotrimeric G-proteins (Walker et al., Mol. Cell. 2000, 6, 909). The human protein sequence of the p110α isoform is described in Volina et al., Genomics 1994, 24, 472; and Stirdivant et al., Bioorg. Med. Chem. 1997, 5, 65.

PI3Ks play a variety of roles in normal tissue physiology (Foukas & Shepherd, Biochem. Soc. Trans. 2004, 32, 330; Shepherd, Acta Physiol. Scand. 2005, 183, 3), with p110α having a specific role in cancer growth, p110β in thrombus formation mediated by integrin $α_{IIb}β_3$ (Jackson et al., Nat. Med. 2005, 11, 507), and p110γ in inflammation, rheumatoid arthritis (Camps et al., Nat. Med. 2005, 11, 936) and other chronic inflammation states (Barber et al., Nat. Med. 2005, 11, 933). The PI3K enzymes produce phosphoinositide 3,4, 5-triphosphate (PIP3) from the corresponding diphosphate (PIP2), thus recruiting AKT (protein kinase B) through its Pleckstrin homology (PH) domain to the plasma membrane. Once bound, AKT is phosphorylated and activated by other membrane bound kinases and is central to a cascade of events that lead to inhibition of apoptosis (Berrie, Exp. Opin. Invest. Drugs 2001, 10, 1085).

The p110α isoform is selectively amplified and activated in a number of cancer types (Stephens et al., Curr. Opin. Pharmacol. 2005, 5, 357; Stauffer et al., Curr. Med. Chem.—Anti-Cancer Agents 2005, 5, 449). In addition, there is a high frequency of non-random mutations in specific sites, primarily in the C2 domain and or the activation loop, of the kinase in several human cancer cell lines, including colon, brain, breast, and stomach (Samuels et al., Science 2004, 304, 554). This results in a constitutively active enzyme (Ikenoue et al., Cancer Res. 2005, 65, 4562; Kang et al., Proc. Natl. Acad. Sci. USA 2005, 102, 802), making p110α one of the most highly mutated oncogenes found in human tumors. Structural studies have shown that many of the mutations occur at residues lying at the interfaces between p110α and p85α or between the kinase domain of p110α and other domains within the catalytic subunit (Miled et al., Science 2007, 317, 239; Huang et al., Science 2007, 318, 1744).

While PI3K isoenzymes play important roles in many cellular processes, published experimental studies in mice with human tumor xenografts show that the pan-PI3K inhibitor LY294002 is well-tolerated, reduces signaling through the PI3K pathway, causes reduction of tumor volume, and is more active in cell lines over-expressing mutant forms of p110α than parental control cells (Semba et al., Clin. Cancer Res. 2002, 8, 1957; Hu et al., Cancer Res. 2002, 62, 1087).

Thus, PI3K, especially the p110α isoform, is an interesting target for drug intervention. Several classes of compounds have been identified as reversible inhibitors; for example, LY 294002 (non-selective) (Walker et al., Mol. Cell. 2000, 6, 909), PI103 (slightly α-selective) (Knight et al., Cell 2006, 125, 733; Hayakawa et al., Bioorg. Med. Chem. Lett. 2007, 17, 2438; Raynaud et al., Cancer Res. 2007, 67, 5840), ZSTK474 (non-selective) (Yaguchi et al., J. Natl. Cancer Inst. 2006, 98, 545; Kong et al., Cancer Sci. 2007, 98, 1639), TGX221 (β-selective) (Jackson et al., Nat. Med. 2005, 11, 507), oxazines (γ-selective) (Lanni et al., Bioorg. Med. Chem. Lett. 2007, 17, 756), IC87114 (δ-selective) (Sadhu et al. WO 2001/81346; Billottet et al., Oncogene 2006, 25, 6648), AS605240 (γ-selective) (Camps et al., Nat. Med. 2005, 11, 936), the imidazo[1,2-a]pyridines (α-selective) (Hayakawa et al., Bioorg. Med. Chem. 2007, 15, 403; Hayakawa et al., Bioorg. Med. Chem. 2007, 15, 5837), and the imidazo[4,5-c] quinoline NVP-BEZ235 (Garcia-Echeverria, et al., WO 2006/122806).

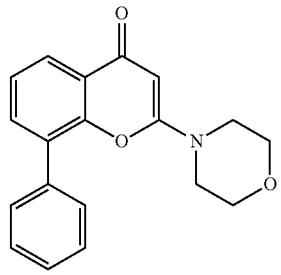

LY294002

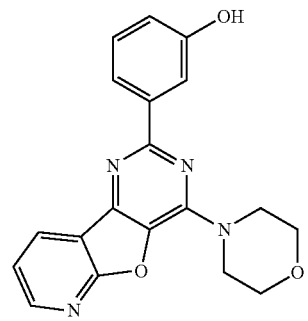

PI103

-continued
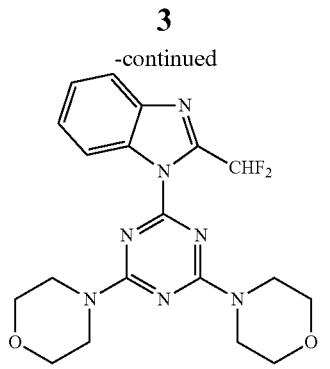
ZSTK474
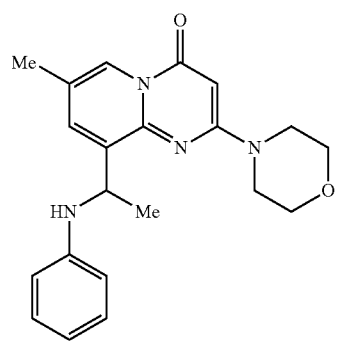
TGX221
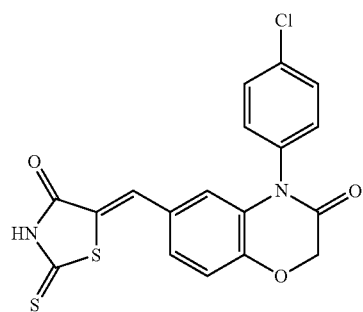
Oxazines
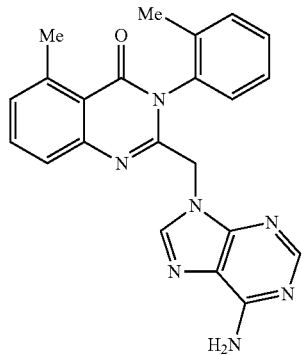
IC87114
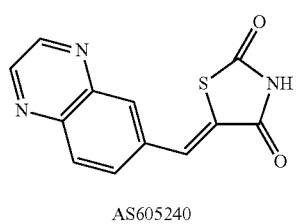
AS605240
-continued
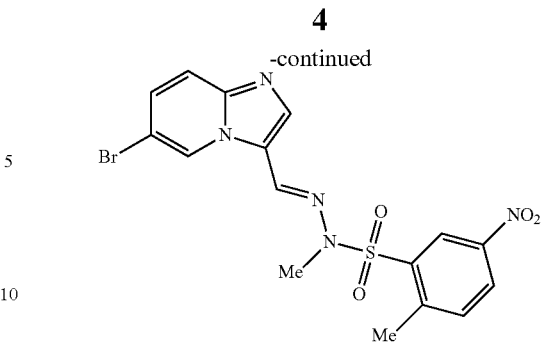
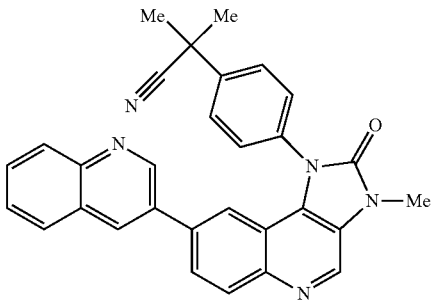
Imidazo[1,2-a]pyridine
NVP-BEZ235
Despite the advances in developing PI3K inhibitors, there is a need for PI3K inhibitors for treatment of cancer.
SUMMARY OF THE DISCLOSURE
Provided herein is a compound of Formula I, IA, or IB:
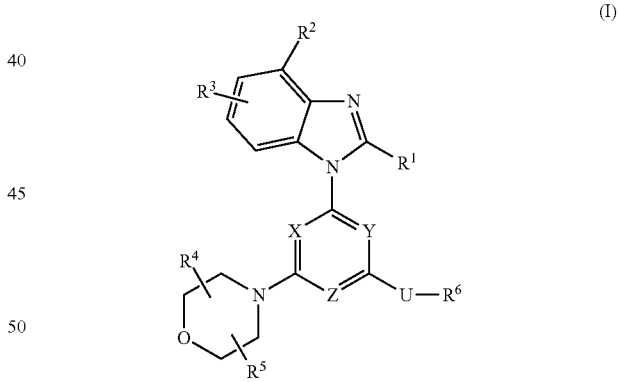
(I)
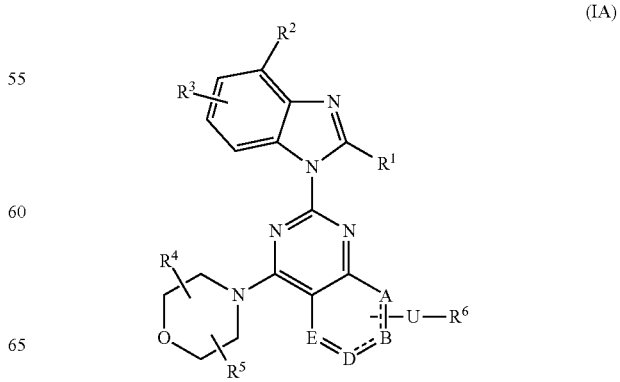
(IA)

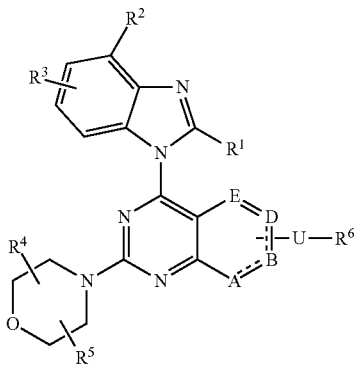

(IB)

or an enantiomer, a mixture of enantiomers, or a mixture of two or more diastereomers thereof; or a pharmaceutically acceptable salt, solvate, hydrate, or prodrug thereof; wherein:

each $R^1$ is independently hydrogen, $C_{1-6}$ alkyl, —S—$C_{1-6}$ alkyl, —S(O)—$C_{1-6}$ alkyl, or —SO$_2$—$C_{1-6}$ alkyl;

each $R^2$ and $R^3$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)N$R^{1b}R^{1c}$, —C(N$R^a$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2$$R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$$R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2$$R^{1a}$, —S(O)N$R^{1b}R^{1c}$, or —S(O)$_2$N$R^{1b}R^{1c}$;

each $R^4$ and $R^5$ is independently hydrogen or $C_{1-6}$ alkyl; or $R^4$ and $R^5$ are linked together to form a bond, $C_{1-6}$ alkylene, $C_{1-6}$ heteroalkylene, $C_{2-6}$ alkenylene, or $C_{2-6}$ heteroalkenylene;

each $R^6$ is independently $C_{6-14}$ aryl, $C_{7-15}$ aralkyl, heteroaryl, or heteroaryl-$C_{1-6}$ alkyl;

each U is independently a bond, —C(O)—, —C(O)O—, —C(O)N$R^{1a}$—, —O—, —OC(O)O—, —OC(O)N$R^{1a}$—, —N$R^{1a}$—, —N$R^{1a}$C(O)N$R^{1d}$—, —N$R^{1a}$S(O)—, —N$R^{1a}$S(O)$_2$—, —N$R^{1a}$S(O)N$R^{1d}$—, —N$R^{1a}$S(O)$_2$N$R^{1d}$—, —S—, —S(O)—, or —S(O)$_2$—;

each X, Y, and Z is independently N or $CR^7$, with the proviso that at least two of X, Y, and Z are nitrogen atoms; where $R^7$ is hydrogen or $C_{1-6}$ alkyl; and each A, B, D, and E is independently a bond, C, O, N, S, $NR^9$, $CR^9$, or $CR^9R^{10}$, where each $R^9$ and $R^{10}$ is independently hydrogen, halo, $C_{1-6}$ alkyl, $C_{2-6}$ alkenyl, or $C_{2-6}$ alkynyl; wherein the bonds between A, B, D, and E may be saturated or unsaturated; with the proviso that no more than one of A, B, D, and E are a bond;

each $R^{1a}$, $R^{1b}$, $R^{1c}$, and $R^{1d}$ is independently (i) hydrogen; or (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

wherein each alkyl, alkylene, heteroalkylene, alkenyl, alkenylene, heteroalkenylene, alkynyl, cycloalkyl, aryl, aralkyl, heteroaryl, and heterocyclyl in $R^1$, $R^2$, $R^3$, $R^4$, $R^5$, $R^6$, $R^7$, $R^9$, $R^{10}$, $R^{1a}$, $R^{1b}$, $R^{1c}$, or $R^{1d}$ is optionally substituted with one or more, in one embodiment, one, two, three, or four groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Q; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2$$R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)N$R^bR^c$, —S$R^a$, —S(O)$R^a$, and —S(O)N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) $R^b$ and $R^c$ together with the N atom to which they are attached form heterocyclyl, optionally substituted with one or more, in one embodiment, one, two, three, or four, substituents Q;

wherein each Q is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2$$R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)N$R^fR^g$, —S$R^e$, —S(O)$R^e$, and —S(O)N$R^fR^g$, wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Also provided herein is a compound of Formula I:

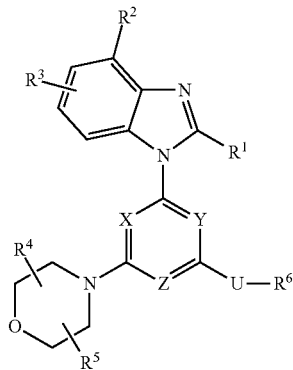

(I)

or an enantiomer, a mixture of enantiomers, or a mixture of two or more diastereomers thereof; or a pharmaceutically acceptable salt, solvate, hydrate, or prodrug thereof; wherein:

$R^1$ is hydrogen, $C_{1-6}$ alkyl, —S—$C_{1-6}$ alkyl, —S(O)—$C_{1-6}$ alkyl, or —SO$_2$—$C_{1-6}$ alkyl;

$R^2$ and $R^3$ are each independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)N$R^{1b}R^{1c}$, —C(N$R^a$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2$$R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$$R^{1d}$, —N$R^{1a}$S(O)N$R^{1b}R^{1c}$, —N$R^{1a}$ $S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$;

$R^4$ and $R^5$ are each independently hydrogen or $C_{1-6}$ alkyl;

$R^6$ is $C_{6-14}$ aryl, $C_{7-15}$ aralkyl, heteroaryl, or heteroaryl-$C_{1-6}$ alkyl;

U is a bond, —C(O)—, —C(O)O—, —C(O)NR$^{1a}$—, —O—, —OC(O)O—, —OC(O)NR$^{1a}$—, —NR$^{1a}$—, —NR$^{1a}$C(O)NR$^{1d}$—, —NR$^{1a}$S(O)—, —NR$^{1a}$S(O)$_2$—, —NR$^{1a}$S(O)NR$^{1d}$—, —NR$^{1a}$S(O)$_2$NR$^{1d}$—, —S—, —S(O)—, or —S(O)$_2$—;

X, Y, and Z are each independently N or $CR^7$, with the proviso that at least two of X, Y, and Z are nitrogen atoms; where $R^7$ is hydrogen or $C_{1-6}$ alkyl; and each $R^{1a}$, $R^{1b}$, $R^{1c}$, and $R^{1d}$ is independently (i) hydrogen; or (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

wherein each alkyl, alkenyl, alkynyl, cycloalkyl, aryl, aralkyl, heteroaryl, and heterocyclyl is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)NR$^b$R$^c$, —S(O)R$^a$, —S(O)$_2$R$^a$, and —S(O)NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) R$^b$ and R$^c$ together with the N atom to which they are attached form heterocyclyl, optionally substituted with one or more, in one embodiment, one, two, three, or four, substituents Q;

wherein each Q is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)NR$^f$R$^g$, —SR$^e$, —S(O)R$^e$, and —S(O)NR$^f$R$^g$, wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

Further provided herein are pharmaceutical compositions comprising a compound disclosed herein, e.g., a compound of Formula I, IA, or IB, including an enantiomer, a mixture of enantiomers, or a mixture of two or more diastereomers; or a pharmaceutically acceptable salt, solvate, hydrate, or prodrug thereof; in combination with one or more pharmaceutically acceptable carriers.

Additionally provided herein is a method for treating, preventing, or ameliorating one or more symptoms of a PI3K-mediated disorder, disease, or condition in a subject, comprising administering to the subject a therapeutically effective amount of a compound disclosed herein, e.g., a compound of Formula I, IA, or IB, an enantiomer, a mixture of enantiomers, a mixture of two or more diastereomers; or a pharmaceutically acceptable salt, solvate, hydrate, or prodrug thereof.

Provided herein is a method for modulating PI3K activity, comprising contacting a PI3K with a therapeutically effective amount of a compound disclosed herein, e.g., a compound of Formula I, IA, or IB, including an enantiomer, a mixture of enantiomers, or a mixture of two or more diastereomers; or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation*, 2nd Edition, Gibson Ed., CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "PI3K" refers to a phosphoinositide 3-kinase or mutant thereof, which is capable of phosphorylating the inositol ring of PI in the D-3 position. The term "PI3K mutant" is intended to include proteins substantially homologous to a native PI3K, i.e., proteins having one or more naturally or non-naturally occurring amino acid deletions, insertions, or substitutions (e.g., PI3K derivatives, homologs, and fragments), as compared to the amino acid sequence of a native PI3K. The amino acid sequence of a PI3K mutant is at least about 80% identical, at least about 90% identical, or at least about 95% identical to a native PI3K. Examples of PI3K include, but are not limited to, p110α, p110β, p110δ, p110γ, PI3K-C2α, PI3K-C2β, PI3K-C2γ, Vps34, mTOR, ATM, ATR, and DNA-PK. See, Fry, *Biochem. Biophys. Acta* 1994, 1226, 237-268; Vanhaesebroeck and Waterfield, *Exp. Cell. Res.* 1999, 253, 239-254; and Fry, *Breast Cancer Res.* 2001, 3, 304-312. PI3Ks are classified into at least three classes. Class I includes p110α, p110β, p110δ, and p110γ. Class II includes PI3K-C2α, PI3K-C2β, and PI3K-C2γ. Class III includes Vps34. Class IV includes mTOR, ATM, ATR, and DNA-PK. In certain embodiments, the PI3K is a Class I kinase. In certain embodiments, the PI3K is p110α, p110β, p110δ, or p110γ. In certain embodiments, the PI3K is a mutant of a Class I kinase. In certain embodiments, the PI3K is a p110α mutant. Examples of p110α mutants include, but are not limited to, R38H, G106V, K111N, K227E, N345K, C420R, P539R, E542K, E545A, E545G, E545K, Q546K, Q546P, E453Q, H710P, 1800L, T1025S, M1043I, M1043V, H1047L, H1047R, and H1047Y (Ikenoue et al., *Cancer Res.* 2005, 65, 4562-4567; Gymnopoulos et al., *Proc. Natl. Acad. Sci.*, 2007, 104, 5569-5574). In certain embodiments, the PI3K is a Class II kinase. In certain embodiments, the PI3K is PI3K-C2α, PI3K-C2β, or PI3K-C2γ. In certain embodiments, the PI3K is a Class III kinase. In certain embodiments, the PI3K is Vps34. In certain embodiments, the PI3K is a Class IV kinase. In certain embodiments, the PI3K is mTOR, ATM, ATR, or DNA-PK.

The terms "PI3K-mediated disorder or disease" and "a condition, disorder or disease mediated by PI3K" refer to a condition, disorder, or disease characterized by inappropriate, e.g., less than or greater than normal, PI3K activity. Inappropriate PI3K functional activity might arise as the result of PI3K expression in cells which normally do not express PI3K, increased PI3K expression or degree of intracellular activation; or decreased PI3K expression. A PI3K-mediated condition, disorder or disease may be completely or partially mediated by inappropriate PI3K activity. In particular, a PI3K-mediated condition, disorder or disease is one in which modulation of a PI3K enzyme activity results in some effect on the underlying condition or disorder, e.g., a PI3K inhibitor results in some improvement in at least some of patients being treated.

The term "alkyl" refers to a linear or branched saturated monovalent hydrocarbon radical, wherein the alkyl may optionally be substituted as described herein. As used herein, the term "alkyl" encompasses both linear and branched alkyl, unless otherwise specified. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and 2-propyl), butyl (including all isomeric forms, e.g., n-butyl, 2-methylpropyl (isobutyl), 1-methylpropyl (sec-butyl), and 1,1-dimethylethyl (t-butyl)), pentyl (including all isomeric forms, e.g., n-propyl, 2-methylbutyl (isopropyl), and 2,2-dimethylpropyl (neopentyl)), hexyl (including all isomeric forms, n-hexyl, 2-methylpentyl (isohexyl), 3-methylpentyl, 2,3-dimethylbutyl, and 2,2-dimethylbutyl (neohexyl)), heptyl (including all isomeric forms, e.g., n-heptyl, 2-methylhexyl, 3-methylhexyl, 2,2-dimethylpentyl, 2,3-dimethylpentyl, 2,4-dimethylpentyl, 3-ethylpentyl, and 2,2,3-trimethylbutyl), octyl (including all isomeric forms, e.g., n-octyl, 2-methylheptyl, 3-methylheptyl, 2,5-dimethylhexyl, and 2,2,4-trimethylpentyl (isooctyl)), nonyl (including all isomeric forms, e.g., n-nonyl), decyl (including all isomeric forms, e.g., n-decyl), undecyl (including all isomeric forms, e.g., n-undecyl), dodecyl (including all isomeric forms, e.g., n-dodecyl), tridecyl (including all isomeric forms, e.g., n-tridecyl), tetradecyl (including all isomeric forms, e.g., n-tetradecyl), pentadecyl (including all isomeric forms, e.g., n-pentadecyl), hexadecyl (including all isomeric forms, e.g., n-hexadecyl (palmityl)), heptadecyl (including all isomeric forms, e.g., n-heptadecyl), octadecyl (including all isomeric forms, e.g., n-octadecyl (stearyl)), nonadecyl (including all isomeric forms, e.g., n-nonadecyl), and icosyl (including all isomeric forms, e.g., n-icosyl).

The term "alkylene" refers to a linear or branched saturated divalent hydrocarbon radical, wherein the alkylene may optionally be substituted as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms).

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —$CH_2O$—, —$CH_2OCH_2$—, —$CH_2CH_2O$—, —$CH_2NH$—, —$CH_2NHCH_2$—, —$CH_2CH_2NH$—, —$CH_2S$—, —$CH_2SCH_2$—, and —$CH_2CH_2S$—. In certain embodiments, heteroalkylene may also be optionally substituted as described herein.

The term "alkenyl" refers to a linear or branched monovalent hydrocarbon radical, which contains one or more, in one embodiment, one to five, carbon-carbon double bonds. The alkenyl may be optionally substituted as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one to five, in another embodiment, one, carbon-carbon double bond(s). The alkenylene may be optionally substituted as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "heteroalkenylene" refers to a linear or branched divalent hydrocarbon radical, which contains one or more, in one embodiment, one to five, in another embodiment, one, carbon-carbon double bond(s), and which contains one or more heteroatoms each independently selected from O, S, and N in the hydrocarbon chain. The heteroalkenylene may be optionally substituted as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH=CHO—, —CH=CHOCH$_2$—, —CH=CHCH$_2$O—, —CH=CHS—, —CH=CHSCH$_2$—, —CH=CHCH$_2$S—, or —CH=CHCH$_2$NH—.

The term "alkynyl" refers to a linear or branched monovalent hydrocarbon radical, which contains one or more, in one embodiment, one to five, carbon-carbon triple bonds. The alkynyl may be optionally substituted as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C☐CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated bridged and/or non-bridged monovalent hydrocarbon radical, which may be optionally substituted as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "aralkyl" or "aryl-alkyl" refers to a monovalent alkyl group substituted with aryl. In certain embodiments, the alkyl and aryl moieties are optionally substituted as described herein.

The term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "halogen", "halide" or "halo" refers to fluorine, chlorine, bromine, and/or iodine.

The term "optionally substituted" is intended to mean that a group, such as an alkyl, alkenyl, alkynyl, cycloalkyl, aryl, aralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)OR$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)NR$^b$R$^c$, —NR$^a$S(O)$_2$NR$^b$R$^c$, —S(O)R$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) R$^b$ and R$^c$ together with the N atom to which they are attached form heteroaryl or heterocyclyl, optionally substituted with one or more, in one embodiment, one, two, three, or four, substituents Q. As used herein, all groups that can be substituted are "optionally substituted," unless otherwise specified.

In one embodiment, each Q is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

The phrase "an enantiomer, a mixture of enantiomers, or a mixture of two or more diastereomers thereof; or a pharmaceutically acceptable salt, solvate, hydrate, or prodrug thereof" has the same meaning as the phrase "a single enantiomer, a mixture of enantiomers, or a mixture of diastereomers of the compound referenced therein; or a pharmaceutically acceptable salt, solvate, hydrate, or prodrug of the compound referenced therein, or an enantiomer, a mixture of enantiomers, or a mixture of diastereomers of the compound referenced therein."

Compounds

In one embodiment, provided herein is a compound of Formula I, IA, or IB:

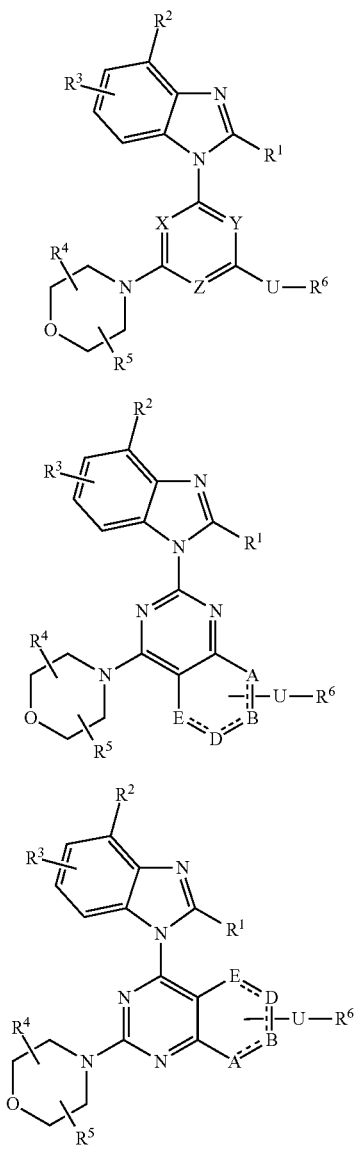

or an enantiomer, a mixture of enantiomers, or a mixture of two or more diastereomers thereof; or a pharmaceutically acceptable salt, solvate, hydrate, or prodrug thereof; wherein:

each $R^1$ is independently hydrogen, $C_{1-6}$ alkyl, —S—$C_{1-6}$ alkyl, —S(O)—$C_{1-6}$ alkyl, or —SO$_2$—$C_{1-6}$ alkyl;

each $R^2$ and $R^3$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)N$R^{1b}R^{1c}$, —C(N$R^a$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

each $R^4$ and $R^5$ is independently hydrogen or $C_{1-6}$ alkyl; or $R^4$ and $R^5$ are linked together to form a bond, $C_{1-6}$ alkylene, $C_{1-6}$ heteroalkylene, $C_{2-6}$ alkenylene, or $C_{2-6}$ heteroalkenylene;

each $R^6$ is independently $C_{6-14}$ aryl, $C_{7-15}$ aralkyl, heteroaryl, or heteroaryl-$C_{1-6}$ alkyl;

each U is independently a bond, —C(O)—, —C(O)O—, —C(O)N$R^{1a}$—, —O—, —OC(O)O—, —OC(O)N$R^{1a}$—, —N$R^{1a}$—, —N$R^{1a}$C(O)N$R^{1d}$—, —N$R^{1a}$S(O)—, —N$R^{1a}$S(O)$_2$—, —N$R^{1a}$S(O)N$R^{1d}$—, —N$R^{1a}$S(O)$_2$N$R^{1d}$—, —S—, —S(O)—, or —S(O)$_2$—;

each X, Y, and Z is independently N or C$R^7$, with the proviso that at least two of X, Y, and Z are nitrogen atoms; where $R^7$ is hydrogen or $C_{1-6}$ alkyl; and each A, B, D, and E is independently a bond, C, O, N, S, N$R^9$, C$R^9$, or C$R^9R^{10}$, where each $R^9$ and $R^{10}$ is independently hydrogen, halo, $C_{1-6}$ alkyl, $C_{2-6}$ alkenyl, or $C_{2-6}$ alkynyl; wherein the bonds between A, B, D, and E may be saturated or unsaturated; with the proviso that no more than one of A, B, D, and E are a bond;

each $R^{1a}$, $R^{1b}$, $R^{1c}$, and $R^{1d}$ is independently (i) hydrogen; or (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

wherein each alkyl, alkylene, heteroalkylene, alkenyl, alkenylene, heteroalkenylene, alkynyl, cycloalkyl, aryl, aralkyl, heteroaryl, and heterocyclyl in $R^1$, $R^2$, $R^3$, $R^4$, $R^5$, $R^6$, $R^7$, $R^9$, $R^{10}$, $R^{1a}$, $R^{1b}$, $R^{1c}$, or $R^{1d}$ is optionally substituted with one or more, in one embodiment, one, two, three, or four groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Q; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)N$R^bR^c$, —S$R^a$, —S(O)$R^a$, and —S(O)N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) $R^b$ and $R^c$ together with the N atom to which they are attached form heterocyclyl, optionally substituted with one or more, in one embodiment, one, two, three, or four, substituents Q;

wherein each Q is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S (O)R$^h$, —NR$^e$S(O)NR$^f$R$^g$, —SR$^e$, —S(O)R$^e$, and —S(O)NR$^f$R$^g$, wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In another embodiment, provided herein is a compound of Formula I:

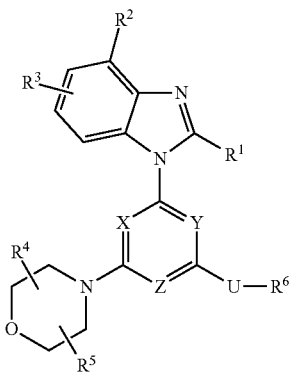

(I)

or an enantiomer, a mixture of enantiomers, or a mixture of two or more diastereomers thereof; or a pharmaceutically acceptable salt, solvate, hydrate, or prodrug thereof; wherein:

R$^1$ is hydrogen, C$_{1-6}$ alkyl, —S—C$_{1-6}$ alkyl, —S(O)—C$_{1-6}$ alkyl, or —SO$_2$—C$_{1-6}$ alkyl;

R$^2$ and R$^3$ are each independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (c) —C(O)R$^{1a}$, —C(O)OR$^{1b}$, —C(O)NR$^{1b}$R$^{1c}$, —C(NR$^a$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^4$ and R$^5$ are each independently hydrogen or C$_{1-6}$ alkyl;

R$^6$ is C$_{6-14}$ aryl, C$_{7-15}$ aralkyl, heteroaryl, or heteroaryl-C$_{1-6}$ alkyl;

U is a bond, —C(O)—, —C(O)O—, —C(O)NR$^{1a}$—, —O—, —OC(O)O—, —OC(O)NR$^{1a}$—, —NR$^{1a}$—, —NR$^{1a}$C(O)NR$^{1d}$—, —NR$^{1a}$S(O)—, —NR$^{1a}$S(O)$_2$—, —NR$^{1a}$S(O)NR$^{1d}$—, —NR$^{1a}$S(O)$_2$NR$^{1d}$—, —S—, —S(O)—, or —S(O)$_2$—;

X, Y, and Z are each independently N or CR$^7$, with the proviso that at least two of X, Y, and Z are nitrogen atoms; where R$^7$ is hydrogen or C$_{1-6}$ alkyl; and each R$^{1a}$, R$^{1b}$, R$^{1c}$, and R$^{1d}$ is independently (i) hydrogen; or (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl;

wherein each alkyl, alkenyl, alkynyl, cycloalkyl, aryl, aralkyl, heteroaryl, and heterocyclyl is optionally substituted with one or more groups, each independently selected from (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each optionally substituted with one or more, in one embodiment, one, two, three, or four, substituents Q; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)NR$^b$R$^c$, —SR$^a$, —S(O)R$^a$, and —S(O)NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or (iii) R$^b$ and R$^c$ together with the N atom to which they are attached form heterocyclyl, optionally substituted with one or more, in one embodiment, one, two, three, or four, substituents Q;

wherein each Q is independently selected from the group consisting of (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)NR$^f$R$^g$, —SR$^e$, —S(O)R$^e$, and —S(O)NR$^f$R$^g$, wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In one embodiment, provided herein is a compound of Formula I, wherein R$^1$, R$^2$, R$^3$, R$^4$, R$^5$, R$^6$, U, X, Y, and Z are each as defined herein, with the proviso that when one of X, Y, and Z is CH, and U is a bond, R$^6$ is not phenyl.

In another embodiment, provided herein is a compound of Formula I, wherein R$^1$, R$^2$, R$^3$, R$^4$, R$^5$, R$^6$, U, X, Y, and Z are each as defined herein, with the proviso that when X, Y, and Z is N, and R$^6$ is C$_{6-14}$ aryl or heteroaryl, then U is not a bond.

In yet another embodiment, provided herein is a compound of Formula I, wherein R$^1$, R$^2$, R$^3$, R$^4$, R$^5$, R$^6$, U, X, Y, and Z are each as defined herein, with the proviso that when R$^2$, R$^3$, R$^4$, and R$^5$ are hydrogen, X, Y, and Z are N, and U is a bond, R$^6$ is not substituted phenyl.

In yet another embodiment, provided herein is a compound of Formula I, wherein R$^1$, R$^2$, R$^3$, R$^4$, R$^5$, R$^6$, U, X, Y, and Z are each as defined herein, with the proviso that when R$^2$, R$^3$, R$^4$, and R$^5$ are hydrogen, X, Y, and Z are N, and U is a bond, R$^6$ is not substituted 3-pyridinyl or 4-pyridinyl.

In yet another embodiment, provided herein is a compound of Formula I, wherein R$^1$, R$^2$, R$^3$, R$^4$, R$^5$, R$^6$, U, X, Y, and Z are each as defined herein, with the proviso that when R$^2$, R$^3$, R$^4$, and R$^5$ are hydrogen, X, Y, and Z are N, and U is a bond, R$^6$ is not substituted 5-pyrimidinyl.

In yet another embodiment, provided herein is a compound of Formula I, wherein R$^1$, R$^2$, R$^3$, R$^4$, R$^5$, R$^6$, U, X, Y, and Z are each as defined herein, with the proviso that when R$^2$, R$^4$, and R$^5$ are hydrogen, X, Y, and Z are N, and U is a bond, R$^6$ is not unsubstituted 4-indolyl.

In yet another embodiment, provided herein is a compound of Formula I, wherein R$^1$, R$^2$, R$^3$, R$^4$, R$^5$, R$^6$, U, X, Y, and Z are each as defined herein, with the proviso that when R$^2$, R$^4$, and R$^5$ are hydrogen, X, Y, and Z are N, and U is a bond, R$^6$ is not phenyl, 3-pyridinyl, 4-pyridinyl, 5-pyrimidinyl, or 4-indolyl.

In yet another embodiment, provided herein is a compound of Formula I, wherein R$^1$, R$^2$, R$^3$, R$^4$, R$^5$, R$^6$, U, X, Y, and Z are each as defined herein, with the proviso that when R$^2$, R$^4$, and $R^5$ are hydrogen, X, Y, and Z are N, and U is a bond, $R^6$ is not phenyl, pyridinyl, pyrimidinyl, or indolyl.

In another embodiment, provided herein is a compound of Formula II:

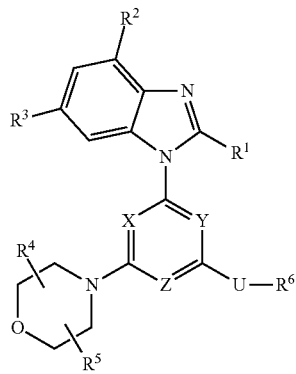

(II)

or an enantiomer, a mixture of enantiomers, or a mixture of two or more diastereomers thereof; or a pharmaceutically acceptable salt, solvate, hydrate, or prodrug thereof; wherein $R^1$, $R^2$, $R^3$, $R^4$, $R^5$, $R^6$, U, X, Y, and Z are each as defined herein.

In one embodiment, provided herein is a compound of Formula II, wherein $R^1$, $R^2$, $R^3$, $R^4$, $R^5$, $R^6$, U, X, Y, and Z are each as defined herein, with the proviso that when one of X, Y, and Z is CH, and U is a bond, $R^6$ is not phenyl.

In another embodiment, provided herein is a compound of Formula II, wherein $R^1$, $R^2$, $R^3$, $R^4$, $R^5$, $R^6$, U, X, Y, and Z are each as defined herein, with the proviso that when X, Y, and Z is N, and $R^6$ is $C_{6-14}$ aryl or heteroaryl, then U is not a bond.

In yet another embodiment, provided herein is a compound of Formula II, wherein $R^1$, $R^2$, $R^3$, $R^4$, $R^5$, $R^6$, U, X, Y, and Z are each as defined herein, with the proviso that when $R^2$, $R^3$, $R^4$, and $R^5$ are hydrogen, X, Y, and Z are N, and U is a bond, $R^6$ is not substituted phenyl.

In yet another embodiment, provided herein is a compound of Formula II, wherein $R^1$, $R^2$, $R^3$, $R^4$, $R^5$, $R^6$, U, X, Y, and Z are each as defined herein, with the proviso that when $R^2$, $R^3$, $R^4$, and $R^5$ are hydrogen, X, Y, and Z are N, and U is a bond, $R^6$ is not substituted 3-pyridinyl or 4-pyridinyl.

In yet another embodiment, provided herein is a compound of Formula II, wherein $R^1$, $R^2$, $R^3$, $R^4$, $R^5$, $R^6$, U, X, Y, and Z are each as defined herein, with the proviso that when $R^2$, $R^3$, $R^4$, and $R^5$ are hydrogen, X, Y, and Z are N, and U is a bond, $R^6$ is not substituted 5-pyrimidinyl.

In yet another embodiment, provided herein is a compound of Formula II, wherein $R^1$, $R^2$, $R^3$, $R^4$, $R^5$, $R^6$, U, X, Y, and Z are each as defined herein, with the proviso that when $R^2$, $R^4$, and $R^5$ are hydrogen, X, Y, and Z are N, and U is a bond, $R^6$ is not unsubstituted 4-indolyl.

In yet another embodiment, provided herein is a compound of Formula II, wherein $R^1$, $R^2$, $R^3$, $R^4$, $R^5$, $R^6$, U, X, Y, and Z are each as defined herein, with the proviso that when $R^2$, $R^4$, and $R^5$ are hydrogen, X, Y, and Z are N, and U is a bond, $R^6$ is not phenyl, 3-pyridinyl, 4-pyridinyl, 5-pyrimidinyl, or 4-indolyl.

In yet another embodiment, provided herein is a compound of Formula II, wherein $R^1$, $R^2$, $R^3$, $R^4$, $R^5$, $R^6$, U, X, Y, and Z are each as defined herein, with the proviso that when $R^2$, $R^4$, and $R^5$ are hydrogen, X, Y, and Z are N, and U is a bond, $R^6$ is not phenyl, pyridinyl, pyrimidinyl, or indolyl.

In yet another embodiment, provided herein is a compound of Formula III:

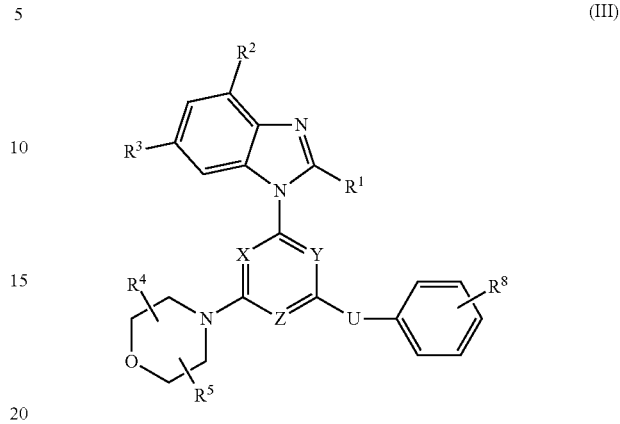

(III)

or an enantiomer, a mixture of enantiomers, or a mixture of two or more diastereomers thereof; or a pharmaceutically acceptable salt, solvate, hydrate, or prodrug thereof; wherein:

$R^1$, $R^2$, $R^3$, $R^4$, $R^5$, X, Y, and Z are each as defined herein;

U is —C(O)—, —C(O)O—, —C(O)$NR^{1a}$—, —O—, —OC(O)O—, —OC(O)$NR^{1a}$—, —$NR^{1a}$—, —$NR^{1a}$C(O)$NR^{1d}$—, —$NR^{1a}$S(O)—, —$NR^{1a}$S(O)$_2$—, —$NR^{1a}$S(O)$NR^{1d}$—, —$NR^{1a}$S(O)$_2NR^{1d}$—, —S—, —S(O)—, or —S(O)$_2$—; and $R^8$ is (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; each optionally substituted with one or more substituents as described herein; or (c) —C(O)$R^{1a}$, —C(O)$OR^{1b}$, —C(O)$NR^{1b}R^{1c}$, —C($NR^a$)$NR^{1b}R^{1c}$, —$OR^{1a}$, —OC(O)$R^{1a}$, —OC(O)$OR^{1a}$, —OC(O)$NR^{1b}R^{1c}$, —OC(=$NR^{1a}$)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$NR^{1b}R^{1c}$, —$NR^{1a}$C(=$NR^{1d}$)$NR^{1b}R^{1c}$, —$NR^{1a}$S(O)$R^{1d}$, —$NR^{1a}$S(O)$_2R^{1d}$, —$NR^{1a}$S(O)—$NR^{1b}R^{1c}$, —$NR^{1a}$S(O)$_2NR^{1b}R^{1c}$, —$SR^{1a}$, —S(O)$R^{1a}$, —S(O)$_2R^{1a}$, —S(O)$NR^{1b}R^{1c}$, or —S(O)$_2NR^{1b}R^{1c}$; where $R^{1a}$, $R^{1b}$, $R^{1c}$, and $R^{1d}$ are each as defined herein.

In yet another embodiment, provided herein is a compound of Formula IV:

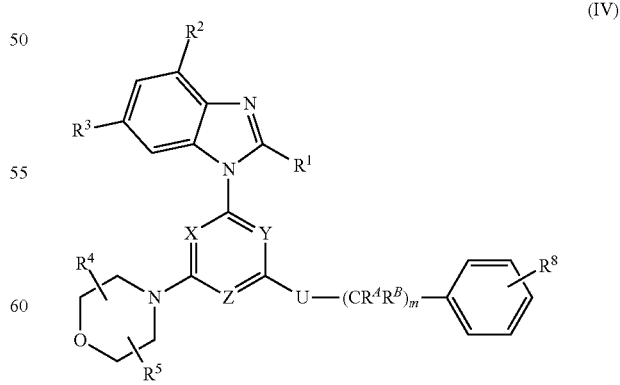

(IV)

or an enantiomer, a mixture of enantiomers, or a mixture of two or more diastereomers thereof; or a pharmaceutically acceptable salt, solvate, hydrate, or prodrug thereof;

wherein:

R$^1$, R$^2$, R$^3$, R$^4$, R$^5$, R$^8$, X, Y, and Z are each as defined herein;

U is a bond, —C(O)—, —C(O)O—, —C(O)NR$^{1a}$—, —O—, —OC(O)O—, —OC(O)NR$^{1a}$—, —NR$^{1a}$—, —NR$^{1a}$C(O)NR$^{1d}$—, —NR$^{1a}$S(O)—, —NR$^{1a}$S(O)$_2$—, —NR$^{1a}$S(O)NR$^{1d}$—, —NR$^{1a}$S(O)$_2$NR$^{1d}$—, —S—, —S(O)—, or —S(O)$_2$—;

R$^A$ and R$^B$ are each independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; each optionally substituted with one or more substituents as described herein; and m is an integer of 1, 2, or 3.

In yet another embodiment, provided herein is a compound of Formula V:

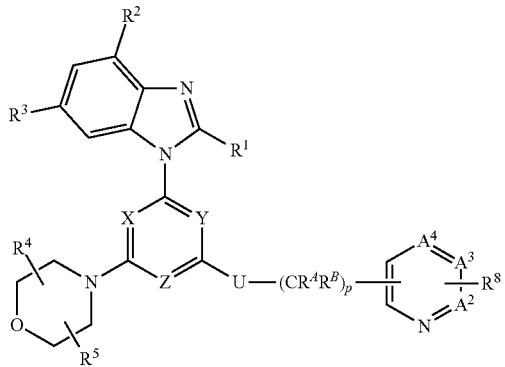

(V)

or an enantiomer, a mixture of enantiomers, or a mixture of two or more diastereomers thereof; or a pharmaceutically acceptable salt, solvate, hydrate, or prodrug thereof; wherein:

R$^1$, R$^2$, R$^3$, R$^4$, R$^5$, U, X, Y, and Z are each as defined herein;

A$^2$, A$^3$, and A$^4$ are each independently N or CR$^8$; with the proviso that no more than one of A$^2$, A$^3$, and A$^4$ is N;

R$^A$ and R$^B$ are each independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; each optionally substituted with one or more substituents as described herein;

p is an integer of 0, 1, 2, or 3; and each R$^8$ is independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; each optionally substituted with one or more substituents as described herein; or (c) —C(O)R$^{1a}$, —COOR$^{1b}$, —C(O)NR$^{1b}$R$^{1c}$, —C(NR$^a$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is as defined herein.

In yet another embodiment, provided herein is a compound of Formula V or an enantiomer, a mixture of enantiomers, or a mixture of two or more diastereomers thereof; or a pharmaceutically acceptable salt, solvate, hydrate, or prodrug thereof;

wherein:

R$^1$, R$^2$, R$^3$, R$^4$, R$^5$, R$^8$, R$^A$, R$^B$, U, X, Y, and Z, and p are each as defined herein; and A$^2$, A$^3$, and A$^4$ are each independently C, N, or CR$^8$; with the proviso that no more than one of A$^2$, A$^3$, and A$^4$ is N.

In one embodiment, provided herein is a compound of Formula V, wherein R$^1$, R$^2$, R$^3$, R$^4$, R$^5$, R$^8$, R$^A$, R$^B$, A$^2$, A$^3$, A$^4$, U, X, Y, Z, and p are each as defined herein, with the proviso that when X, Y, and Z is N, A$^2$ and A$^4$ are CR$^8$, and p is 0, then U is not a bond.

In certain embodiments, A$^2$ is C. In certain embodiments, A$^2$ is N. In certain embodiments, A$^2$ is CR$^8$, where R$^8$ is as defined herein. In certain embodiments, A$^2$ is CH. In certain embodiments, A$^3$ is C. In certain embodiments, A$^3$ is N. In certain embodiments, A$^3$ is CR$^8$, where R$^8$ is as defined herein. In certain embodiments, A$^3$ is CH. In certain embodiments, A$^4$ is C. In certain embodiments, A$^4$ is N. In certain embodiments, A$^4$ is CR$^8$, where R$^8$ is as defined herein. In certain embodiments, A$^4$ is CH.

In certain embodiments, A$^2$, A$^3$ and A$^4$ are independently CR$^8$, wherein R$^8$ is as defined herein. In certain embodiments, A$^2$, A$^3$, and A$^4$ are CH. In certain embodiments, A$^2$ is N, and A$^3$ and A$^4$ are independently CR$^8$, wherein R$^8$ is as defined herein. In certain embodiments, A$^2$ and A$^4$ are independently CR$^8$, and A$^3$ is N, wherein R$^8$ is as defined herein. In certain embodiments, A$^2$ and A$^3$ are independently CR$^8$, and A$^4$ is N, wherein R$^8$ is as defined herein.

In yet another embodiment, provided herein is a compound of Formula VI:

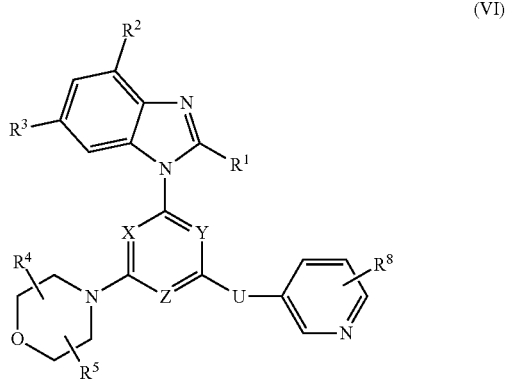

(VI)

or an enantiomer, a mixture of enantiomers, or a mixture of two or more diastereomers thereof; or a pharmaceutically acceptable salt, solvate, hydrate, or prodrug thereof; wherein:

R$^1$, R$^2$, R$^3$, R$^4$, R$^5$, U, X, Y, and Z are each as defined herein; and R$^8$ is (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; each optionally substituted with one or more substituents as described herein; or (c) —C(O)R$^{1a}$, —C(O)OR$^{1b}$, —C(O)NR$^{1b}$R$^{1c}$, —C(NR$^a$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is as defined herein.

In one embodiment, R$^8$ in Formula VI is hydrogen.

In another embodiment, provided herein is a compound of Formula VI, wherein $R^1$, $R^2$, $R^3$, $R^4$, $R^5$, $R^8$, U, X, Y, and Z are each as defined herein, with the proviso that when $R^2$, $R^3$, $R^4$, and $R^5$ are hydrogen, X, Y, and Z are N, and U is a bond; $R^8$ is hydrogen.

In yet another embodiment, provided herein is a compound of Formula VI, wherein $R^1$, $R^2$, $R^3$, $R^4$, $R^5$, $R^8$, U, X, Y, and Z are each as defined herein, with the proviso that when X, Y, and Z is N, then U is not a bond.

In yet another embodiment, provided herein is a compound of Formula VII:

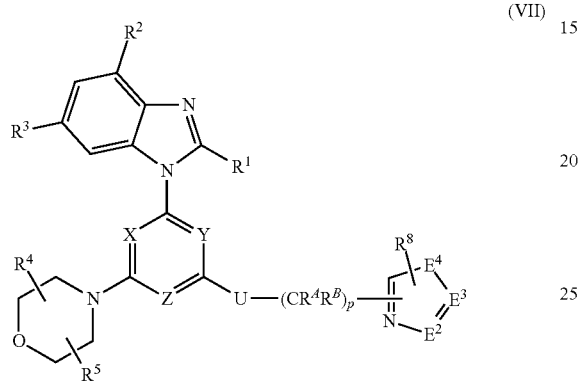

(VII)

or an enantiomer, a mixture of enantiomers, or a mixture of two or more diastereomers thereof; or a pharmaceutically acceptable salt, solvate, hydrate, or prodrug thereof; wherein:

$R^1$, $R^2$, $R^3$, $R^4$, $R^5$, U, X, Y, and Z are each as defined herein;

$E^2$, $E^3$, and $E^4$ are each independently $CR^8$, N or $NR^8$, O, or S;

$R^A$ and $R^B$ are each independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; each optionally substituted with one or more substituents as described herein;

p is an integer of 0, 1, 2, or 3; and each $R^8$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; each optionally substituted with one or more substituents as described herein; or (c) —C(O)$R^{1a}$, —C(O)O$R^{1b}$, —C(O)N$R^{1b}R^{1c}$, —C(N$R^a$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is as defined herein.

In yet another embodiment, provided herein is a compound of Formula VII or an enantiomer, a mixture of enantiomers, or a mixture of two or more diastereomers thereof; or a pharmaceutically acceptable salt, solvate, hydrate, or prodrug thereof; wherein $R^1$, $R^2$, $R^3$, $R^4$, $R^5$, $R^8$, $R^A$, $R^B$, U, X, Y, Z, and p are each as defined herein; and $E^2$, $E^3$, and $E^4$ are each independently C, N, O, S, $CR^8$, or $NR^8$.

In certain embodiments, $E^2$, $E^3$, and $E^4$ are $CR^8$, wherein $R^8$ is as defined herein. In certain embodiments, $E^2$ and $E^4$ are $CR^8$, and $E^3$ is $NR^8$, O, or S, wherein $R^8$ is as defined herein.

In certain embodiments, $E^2$ and $E^3$ are N, and $E^4$ is $CR^8$. In certain embodiments, $E^2$, $E^3$, and $E^4$ are N.

In yet another embodiment, provided herein is a compound of Formula Ia or Ib:

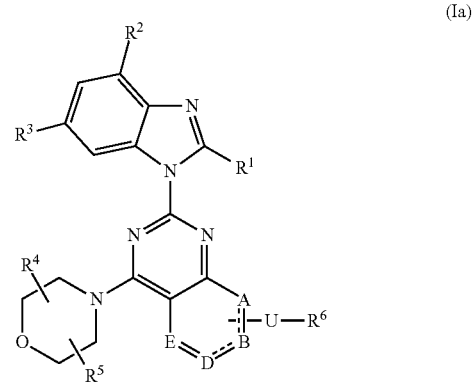

(Ia)

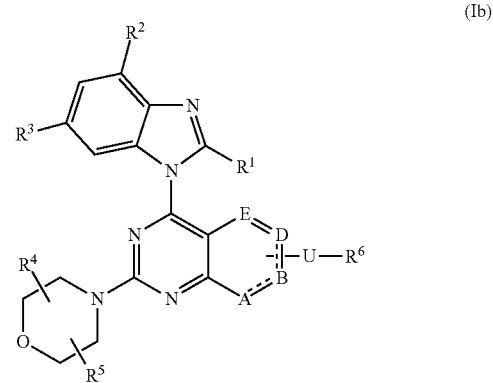

(Ib)

or an enantiomer, a mixture of enantiomers, or a mixture of two or more diastereomers thereof; or a pharmaceutically acceptable salt, solvate, hydrate, or prodrug thereof; wherein $R^1$, $R^2$, $R^3$, $R^4$, $R^5$, $R^6$, A, B, D, E, and U are each as defined herein.

In yet another embodiment, the compound of Formula Ib has the structure of Formula VIII:

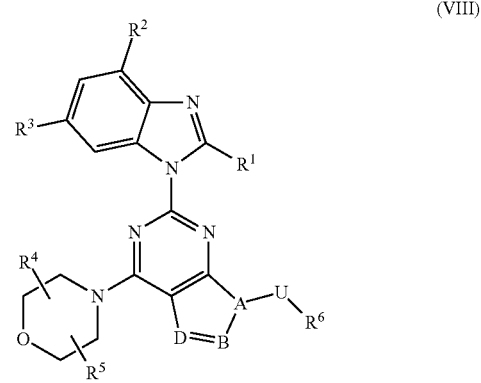

(VIII)

or an enantiomer, a mixture of enantiomers, or a mixture of two or more diastereomers thereof; or a pharmaceutically acceptable salt, solvate, hydrate, or prodrug thereof; wherein $R^1$, $R^2$, $R^3$, $R^4$, $R^5$, $R^6$, A, B, D, and U are each as defined herein, and the bond between D and B is a single or double bond. In one embodiment, A is N. In another embodiment, A and D are N. In yet another embodiment, A and D are N, B is $CR^9$, and the bond between B and D is a double bond, where $R^9$ is as defined herein. In yet another embodiment, A and D are N, B is CH, and the bond between B and D is a double bond. In yet another embodiment, A, B and D are N, and the bond between B and D is a double bond. In yet another embodiment, A is N, B and D are each independently $CR^9$, and the bond between B and D is a double bond, where $R^9$ is as defined herein. In yet another embodiment, A is N, B and D are each CH, and the bond between B and D is a double bond. In yet another embodiment, A is N, B and D are each independently $CHR^9$, and the bond between B and D is a single bond, where $R^9$ is as defined herein. In still another embodiment, A is N, B and D are each $CH_2$, and the bond between B and D is a single bond.

In still another embodiment, the compound of Formula Ib has the structure of Formula IX:

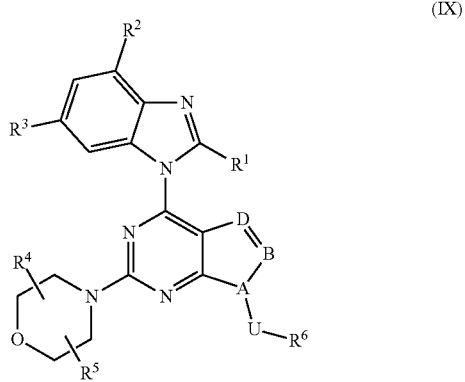

(IX)

or an enantiomer, a mixture of enantiomers, or a mixture of two or more diastereomers thereof; or a pharmaceutically acceptable salt, solvate, hydrate, or prodrug thereof; wherein $R^1$, $R^2$, $R^3$, $R^4$, $R^5$, $R^6$, A, B, D, and U are each as defined herein, and the bond between D and B is a single or double bond. In one embodiment, A is N. In another embodiment, A and D are N. In yet another embodiment, A and D are N, B is $CR^9$, and the bond between B and D is a double bond, where $R^9$ is as defined herein. In yet another embodiment, A and D are N, B is CH, and the bond between B and D is a double bond. In yet another embodiment, A, B and D are N, and the bond between B and D is a double bond. In yet another embodiment, A is N, B and D are each independently $CR^9$, and the bond between B and D is a double bond, where $R^9$ is as defined herein. In yet another embodiment, A is N, B and D are each CH, and the bond between B and D is a double bond. In yet another embodiment, A is N, B and D are each independently $CHR^9$, and the bond between B and D is a single bond, where $R^9$ is as defined herein. In still another embodiment, A is N, B and D are each $CH_2$, and the bond between B and D is a single bond.

The groups, $R^1$, $R^2$, $R^3$, $R^4$, $R^5$, $R^6$, $R^8$, $R^A$, $R^B$, A, B, D, E, U, X, Y, Z, m, and p in Formulae provided herein, e.g., Formulae I, IA, IB, Ia, Ib, II, III, IV, V, VI, VII, VIII, and IX, are further defined in the embodiments described herein. All combinations of the embodiments provided herein for such groups are within the scope of this disclosure.

In certain embodiments, $R^1$ is hydrogen, $C_{1-6}$ alkyl, —S—$C_{1-6}$ alkyl, —S(O)—$C_{1-6}$ alkyl, or —$SO_2$—$C_{1-6}$ alkyl; where each alkyl is optionally substituted with one or more substituents as described herein. In certain embodiments, $R^1$ is hydrogen, $C_{1-6}$ alkyl, or —$SO_2$—$C_{1-6}$ alkyl. In certain embodiments, $R^1$ is hydrogen. In certain embodiments, $R^1$ is $C_{1-6}$ alkyl, optionally substituted with one or more substituents as described herein. In certain embodiments, $R^1$ is $C_{1-6}$ alkyl, substituted with one or more, in one embodiment, one to three, halo. In certain embodiments, $R^1$ is $C_{1-6}$ alkyl, substituted with one to three, in one embodiment, one, two, or three, fluoro groups. In certain embodiments, $R^1$ is methyl, fluoromethyl, difluoromethyl, or trifluoromethyl. In certain embodiments, $R^1$ is difluoromethyl. In certain embodiments, $R^1$ is —S—$C_{1-6}$ alkyl, optionally substituted with one or more substituents as described herein. In certain embodiments, $R^1$ is methanesulfanyl (—$SCH_3$). In certain embodiments, $R^1$ is —S(O)—$C_{1-6}$ alkyl, optionally substituted with one or more substituents as described herein. In certain embodiments, $R^1$ is methanesulfinyl (—$SOCH_3$). In certain embodiments, $R^1$ is —$SO_2$—$C_{1-6}$ alkyl, optionally substituted with one or more substituents as described herein. In certain embodiments, $R^1$ is methanesulfonyl (—$SO_2CH_3$).

In certain embodiments, $R^2$ is (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents as described herein; or (c) —$C(O)R^{1a}$, —$C(O)OR^{1b}$, —$C(O)NR^{1b}R^{1c}$, —$C(NR^a)NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$, where each $R^{1a}$, $R^{1b}$, $R^{1c}$, and $R^{1d}$ is as described herein. In certain embodiments, $R^2$ is hydrogen. In certain embodiments, $R^2$ is cyano, halo, or nitro. In certain embodiments, $R^2$ is $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents as described herein. In certain embodiments, $R^2$ is —$C(O)R^{1a}$, —$C(O)OR^{1b}$, —$C(O)NR^{1b}R^{1c}$, or —$C(NR^a)NR^{1b}R^{1c}$, wherein $R^{1a}$, $R^{1b}$, and $R^{1c}$ are each as defined herein. In certain embodiments, $R^2$ is —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, or —$OS(O)_2NR^{1b}R^{1c}$, wherein $R^{1a}$, $R^{1b}$, and $R^{1c}$ are each as defined herein. In certain embodiments, $R^2$ is —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, or —$NR^{1a}S(O)_2NR^{1b}R^{1c}$, wherein $R^{1a}$, $R^{1b}$, $R^{1c}$, and $R^{1d}$ are each as defined herein. In certain embodiments, $R^2$ is —$SR^{1a}$, —$S(O)R^{1a}$, —$S(O)_2R^{1a}$, —$S(O)NR^{1b}R^{1c}$, or —$S(O)_2NR^{1b}R^{1c}$; wherein $R^{1a}$, $R^{1b}$, and $R^{1c}$ are each as defined herein. In certain embodiments, $R^2$ is —$OR^{1a}$, wherein $R^{1a}$ is methyl, ethyl, or propyl (e.g., n-propyl, isopropyl, or 2-isopropyl), each optionally substituted with one or more substituents as described herein. In certain embodiments, $R^2$ is methoxy, ethoxy, propoxy, or isopropoxy. In certain embodiments, $R^2$ is methoxy.

In certain embodiments, $R^3$ is (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents as described herein; or (c) —$C(O)R^{1a}$, —$C(O)OR^{1b}$, —$C(O)NR^{1b}R^{1c}$, —$C(NR^a)NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C (O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$, where each R$^{1a}$, R$^{1b}$, R$^{1c}$, and R$^{1d}$ is as described herein. In certain embodiments, R$^3$ is hydrogen. In certain embodiments, R$^3$ is cyano, halo, or nitro. In certain embodiments, R$^3$ is C$_{1-6}$ alkyl, C$_{2-6}$ alkenyl, C$_{2-6}$ alkynyl, C$_{3-7}$ cycloalkyl, C$_{6-44}$ aryl, C$_{7-15}$ aralkyl, heteroaryl, or heterocyclyl, each optionally substituted with one or more substituents as described herein. In certain embodiments, R$^3$ is —C(O)R$^{1a}$, —C(O)OR$^{1b}$, —C(O)NR$^{1b}$R$^{1c}$, or —C(NR$^a$)NR$^{1b}$R$^{1c}$, wherein R$^{1a}$, R$^{1b}$, and R$^{1c}$ are each as defined herein. In certain embodiments, R$^3$ is —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, or —OS(O)$_2$NR$^{1b}$R$^{1c}$, wherein R$^{1a}$, R$^{1b}$, and R$^{1c}$ are each as defined herein. In certain embodiments, R$^3$ is —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, or —NR$^{1a}$S(O)$_2$NR$^{1b}$R$^{1c}$, wherein R$^{1a}$, R$^{1b}$, R$^{1c}$, and R$^{1d}$ are each as defined herein. In certain embodiments, R$^3$ is amino. In certain embodiments, R$^3$ is —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein R$^{1a}$, R$^{1b}$, and R$^{1c}$ are each as defined herein. In certain embodiments, R$^3$ is —OR$^{1a}$, wherein R$^{1a}$ is methyl, ethyl, or propyl (e.g., n-propyl, isopropyl, or 2-isopropyl), each optionally substituted with one or more substituents as described herein. In certain embodiments, R$^3$ is methoxy, ethoxy, propoxy, or isopropoxy.

In certain embodiments, R$^4$ is hydrogen or C$_{1-6}$ alkyl, optionally substituted with one or more substituents as described herein. In certain embodiments, R$^4$ is hydrogen. In certain embodiments, R$^4$ is C$_{1-6}$ alkyl, optionally substituted with one or more substituents as described herein. In certain embodiments, R$^4$ is hydrogen, methyl, ethyl, or propyl (e.g., n-propyl, isopropyl, or 2-isopropyl), each optionally substituted with one or more substituents as described herein. In certain embodiments, R$^4$ is methyl, ethyl, n-propyl, or isopropyl.

In certain embodiments, R$^5$ is hydrogen or C$_{1-6}$ alkyl, optionally substituted with one or more substituents as described herein. In certain embodiments, R$^5$ is hydrogen. In certain embodiments, R$^5$ is C$_{1-6}$ alkyl, optionally substituted with one or more substituents as described herein. In certain embodiments, R$^5$ is hydrogen, methyl, ethyl, or propyl (e.g., n-propyl, isopropyl, or 2-isopropyl), each optionally substituted with one or more substituents as described herein. In certain embodiments, R$^5$ is methyl, ethyl, n-propyl, or isopropyl.

In certain embodiments, R$^4$ and R$^5$ are both hydrogen.

In certain embodiments, R$^4$ and R$^5$ are linked together to form a bond. In certain embodiments, R$^4$ and R$^5$ are linked together to form C$_{1-6}$ alkylene, optionally substituted with one or more substituents. In certain embodiments, R$^4$ and R$^5$ are linked together to form methylene, ethylene, or propylene, each optionally substituted with one or more substituents.

In certain embodiments, R$^6$ is C$_{6-14}$ aryl, C$_{7-15}$ aralkyl, heteroaryl, or heteroaryl-C$_{1-6}$ alkyl, each substituted with one or more substituents as described herein. In certain embodiments, R$^6$ is C$_{6-14}$ aryl, optionally substituted with one or more substituents as described herein. In certain embodiments, R$^6$ is phenyl, optionally substituted with one or more substituents as described herein. In certain embodiments, R$^6$ is phenyl, optionally substituted with one or more substituents Q, each independently selected from the group consisting of halo, cyano, nitro, amino, and methoxy. In certain embodiments, R$^6$ is phenyl, aminophenyl, nitrophenyl, or methoxyphenyl. In certain embodiments, R$^6$ is phenyl, 3-aminophenyl, 3-nitrophenyl, or 3-methoxyphenyl.

In certain embodiments, R$^6$ is C$_{7-15}$ aralkyl, optionally substituted with one or more substituents as described herein. In certain embodiments, R$^6$ is —(CR$^A$R$^B$)$_m$—C$_{6-14}$ aryl, wherein R$^A$ and R$^B$ are independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; and m is an integer of 1, 2, or 3; and where each alkyl, alkenyl, alkynyl, cycloalkyl, aryl, aralkyl, heteroaryl, and heterocyclyl is optionally substituted with one or more substituents as described herein. In certain embodiments, R$^6$ is —(CH$_2$)$_m$—C$_{6-14}$ aryl, where m is an integer of 1, 2, or 3, and the aryl is optionally substituted with one or more substituents as described herein. In certain embodiments, R$^6$ is benzyl, optionally substituted with one or more substituents as described herein. In certain embodiments, R$^6$ is benzyl. In certain embodiments, R$^6$ is phenyl-ethyl, optionally substituted with one or more substituents as described herein. In certain embodiments, R$^6$ is benzyl or 2-phenylethyl.

In certain embodiments, R$^6$ is heteroaryl, optionally substituted with one or more substituents as described herein. In certain embodiments, R$^6$ is pyrazolyl, imidazolyl, thiazolyl, 1,2,3-triazolyl, tetrazolyl, pyridinyl, pyridazinyl, pyrimidinyl, pyrazinyl, or quinolinyl, each optionally substituted with one or more substituents as described herein. In certain embodiments, each substituent is independently -L-(CR$^C$R$^D$)$_n$—R$^E$, wherein R$^C$ and R$^D$ are each as defined herein; R$^E$ is hydrogen, —NR$^F$R$^G$, or heterocyclyl; L is a bond, —O—, or —N(R$^H$)—; R$^F$, R$^G$, and R$^H$ are each independently hydrogen or C$_{1-6}$ alkyl; and n is an integer of 0, 1, 2, or 3; and wherein each alkyl and heterocyclyl is independently and optionally substituted with one or more substituents as described herein. In certain embodiments, R$^C$ is hydrogen. In certain embodiments, R$^D$ is hydrogen. In certain embodiments, R$^C$ and R$^D$ are hydrogen. In certain embodiments, R$^C$ is hydrogen, methylamino, dimethylamino, pyrrolidinyl, piperidinyl, or morpholinyl, wherein the pyrrolidinyl, piperidinyl, and morpholinyl are independently, optionally substituted with methyl. In certain embodiments, L is a bond, —O—, —NH—, or —N(CH$_3$)—.

In certain embodiments, each substituent on R$^6$ is independently selected from the group consisting of amino, fluoro, chloro, methyl, (dimethylamino)methyl, (dimethylamino)ethyl, (dimethylamino)propyl, morpholinylmethyl, (morpholinyl)ethyl, (morpholinyl)propyl, methoxy, (dimethylamino)ethoxy, (dimethylamino)propoxy, (morpholinyl)ethoxy, (morpholinyl)propoxy, (methyl-piperidinyl)oxy, (methyl-pyrrolidinyl)oxy, methylamino, dimethylamino, (dimethylamino)ethylamino, (dimethylaminoethyl)(methyl)amino, (dimethylamino)propylamino, ((dimethylamino)propyl)(methyl)amino, (morpholinyl)ethylamino, ((morpholinyl)ethyl)(methyl)amino, (morpholinyl)propylamino, ((morpholinyl)propyl)(methyl)amino, methyl-piperidinylamino, (methyl-piperidinyl)(methyl)amino, methyl-piperazinyl, or (dimethylamino)-piperidinyl. In certain embodiments, each substituent on R$^6$ is independently selected from the group consisting of amino, fluoro, chloro, methyl, (dimethylamino)methyl, 2-(dimethylamino)ethyl, 3-(dimethylamino)propyl, 4-morpholinylmethyl, 2-(4-morpholinyl)ethyl, 3-(4-morpholinyl)propyl, methoxy, 2-(dimethylamino)ethoxy, 3-(dimethylamino)propoxy, 2-(4-morpholinyl)ethoxy, 3-(4-morpholinyl)propoxy, (1-methyl-4-piperidinyl)oxy, (1-methyl-3-pyrrolidinyl)oxy, methylamino, dimethylamino, 2-(dimethylamino)ethylamino, (2-dimethylaminoethyl)-

(methyl)amino, 3-(dimethylamino)propylamino, (3-(dimethylamino)propyl)(methyl)amino, 2-(4-morpholinyl)ethylamino, (2-(4-morpholinyl)ethyl)(methyl)amino, 3-(4-morpholinyl)-propylamino, (3-(4-morpholinyl)propyl)(methyl)amino, 1-methyl-4-piperidinylamino, (1-methyl-4-piperidinyl)(methyl)amino, 4-methyl-1-piperazinyl, and 4-(dimethylamino)-1-piperidinyl.

In certain embodiments, $R^6$ is pyrazolyl, methyl-pyrazolyl, [2-(dimethylamino)ethyl]-pyrazolyl, [3-(dimethylamino)propyl]-pyrazolyl, [2-(4-morpholinyl)ethyl]-pyrazolyl, or [3-(4-morpholinyl)propyl]-pyrazolyl. In certain embodiments, $R^6$ is pyrazol-1-yl, 1H-pyrazol-4-yl, 1-methyl-1H-pyrazol-3-yl, 1-methyl-1H-pyrazol-4-yl, 1-methyl-1H-pyrazol-5-yl, 1-[2-(dimethylamino)ethyl]-1H-pyrazol-4-yl, 1-[3-(dimethylamino)propyl]-1H-pyrazol-4-yl, 1-[2-(4-morpholinyl)ethyl]-1H-pyrazol-4-yl, or 1-[3-(4-morpholinyl)propyl]-1H-pyrazol-4-yl.

In certain embodiments, $R^6$ is imidazolyl or methyl-imidazolyl. In certain embodiments, $R^6$ is imidazol-1-yl or 1-methyl-1H-imidazol-5-yl.

In certain embodiments, $R^6$ is thiazolyl, [(dimethylamino)methyl]-thiazolyl, or (4-morpholinylmethyl)-thiazolyl. In certain embodiments, $R^6$ is 1,3-thiazol-5-yl, 2-[(dimethylamino)methyl]-1,3-thiazol-5-yl, or 2-(4-morpholinylmethyl)-1,3-thiazol-5-yl.

In certain embodiments, $R^6$ is triazolyl or methyl-1,2,3-triazolyl. In certain embodiments, $R^6$ is 1-methyl-1H-1,2,3-triazol-4-yl, 1-methyl-1H-1,2,3-triazol-5-yl, or 2-methyl-2H-1,2,3-triazol-4-yl.

In certain embodiments, $R^6$ is tetrazolyl or methyl-tetrazolyl. In certain embodiments, $R^6$ is 1-methyl-1H-tetrazol-5-yl or 2-methyl-2H-tetrazol-5-yl.

In certain embodiments, $R^6$ is pyrazinyl, aminopyrazinyl, or methoxypyrazinyl. In certain embodiments, $R^6$ is 2-pyrazinyl, 5-amino-2-pyrazinyl, 6-amino-2-pyrazinyl, or 6-methoxy-2-pyrazinyl.

In certain embodiments, $R^6$ is pyridazinyl or methoxypyridazinyl. In certain embodiments, $R^6$ is pyridazin-3-yl,r pyridazin-4-yl, or 6-methoxypyridazin-3-yl.

In certain embodiments, $R^6$ is pyridinyl, fluoropyridinyl, chloropyridinyl, amino-pyridinyl, methylamino-pyridinyl, dimethylamino-pyridinyl, [2-(dimethylamino)ethylamino]-pyridinyl, [(2-dimethylaminoethyl)(methyl)amino]-pyridinyl, [3-(dimethylamino)propylamino]-pyridinyl, [(3-(dimethylamino)propyl)(methyl)amino]-pyridinyl, [2-(4-morpholinyl)ethylamino]-pyridinyl, [(2-(4-morpholinyl)ethyl)-(methyl)amino]-pyridinyl, [3-(4-morpholinyl)propylamino]-pyridinyl, [(3-(4-morpholinyl)propyl)(methyl)amino]-pyridinyl, (4-methyl-1-piperazinyl)-pyridinyl, [4-(dimethylamino)-1-piperidinyl]-pyridinyl, [1-methyl-4-piperidinylamino]-pyridinyl, [(1-methyl-4-piperidinyl)(methyl)amino]-pyridinyl, methoxy-pyridinyl, [2-(dimethylamino)ethoxy]-pyridinyl, [3-(dimethylamino)propoxy]-pyridinyl, [2-(4-morpholinyl)ethoxy]-pyridinyl, [3-(4-morpholinyl)propoxy]-pyridinyl, [(1-methyl-4-piperidinyl)oxy]-pyridinyl, [(1-methyl-3-pyrrolidinyl)oxy]-pyridinyl, [2-(dimethylamino)ethyl]-pyridinyl, and [2-(4-morpholinyl)ethyl]-pyridinyl. In certain embodiments, $R^6$ is pyridinyl.

In certain embodiments, $R^6$ is pyridin-2-yl, pyridin-3-yl, pyridin-4-yl, 2-fluoropyridin-5-yl, 2-chloropyridin-5-yl, 2-amino-5-pyridinyl, 2-methylamino-3-pyridinyl, 2-dimethylamino-5-pyridinyl, 2-[2-(dimethylamino)ethylamino]-5-pyridinyl, 2-[(2-dimethylaminoethyl)(methyl)amino]-3-pyridinyl, 2-[3-(dimethylamino)propylamino]-5-pyridinyl, 2-[(3-(dimethylamino)propyl)(methyl)amino]-5-pyridinyl, 2-[2-(4-morpholinyl)ethylamino]-3-pyridinyl, 2-[(2-(4-morpholinyl)ethyl)(methyl)amino]-3-pyridinyl, 2-[3-(4-morpholinyl)propylamino]-3-pyridinyl, 2-[(3-(4-morpholinyl)propyl)(methyl)amino]-3-pyridinyl, 6-(4-methyl-1-piperazinyl)-3-pyridinyl, 6-[4-(dimethylamino)-1-piperidinyl]-3-pyridinyl, 2-[1-methyl-4-piperidinylamino]-5-pyridinyl, 2-[(1-methyl-4-piperidinyl)(methyl)amino]-5-pyridinyl, 2-methoxy-4-pyridinyl, 4-methoxy-3-pyridinyl, 5-methoxy-3-pyridinyl, 6-methoxy-3-pyridinyl, 2-[2-(dimethylamino)ethoxy]-4-pyridinyl, 5-(2-(dimethylamino)ethoxy)-2-pyridinyl, 6-[2-(dimethylamino)ethoxy]-3-pyridinyl, 2-[3-(dimethylamino)propoxy]-4-pyridinyl, 2-[3-(dimethylamino)propoxy]-5-pyridinyl, 5-[3-(dimethylamino)propoxy]-3-pyridinyl, 6-[3-(dimethylamino)propoxy]-3-pyridinyl, 2-[2-(4-morpholinyl)ethoxy]-4-pyridinyl, 5-[2-(4-morpholinyl)ethoxy]-3-pyridinyl, 6-[2-(4-morpholinyl)ethoxy]-3-pyridinyl, 2-[3-(4-morpholinyl)propoxy]-4-pyridinyl, 5-[3-(4-morpholinyl)propoxy]-3-pyridinyl, 6-[3-(4-morpholinyl)propoxy]-3-pyridinyl, 6-[(1-methyl-4-piperidinyl)oxy]-3-pyridinyl, 6-[(1-methyl-3-pyrrolidinyl)oxy]-3-pyridinyl, 2-[2-(dimethylamino)ethyl]-3-pyridinyl, and 2-[2-(4-morpholinyl)ethyl]-3-pyridinyl. In certain embodiments, $R^6$ is 3-pyridinyl.

In certain embodiments, $R^6$ is pyrimidinyl, chloro-pyrimidinyl, methoxy-pyrimidinyl, [2-(dimethylamino)ethyl]-pyrimidinyl, [2-(4-morpholinyl)ethyl]-pyrimidinyl, [2-(dimethylamino)ethoxy]-pyrimidinyl, [3-(dimethylamino)propoxy]-pyrimidinyl, [2-(4-morpholinyl)ethoxy]-pyrimidinyl, [3-(4-morpholinyl)propoxy]-pyrimidinyl, amino-pyrimidinyl, [2-(dimethylamino)ethylamino]-pyrimidinyl, [(2-(dimethylamino)ethyl)(methyl)amino]-pyrimidinyl, [3-(dimethylamino)propylamino]-pyrimidinyl, [(3-(dimethylamino)propyl)(methyl)amino]-pyrimidinyl, [2-(4-morpholinyl)ethylamino]-pyrimidinyl, [(2-(4-morpholinyl)ethyl)(methyl)amino]-pyrimidinyl, [3-(4-morpholinyl)propylamino]-pyrimidinyl, [(3-(4-morpholinyl)propyl)(methyl)amino]-pyrimidinyl, (4-methyl-1-piperazinyl)-pyrimidinyl, [4-(dimethylamino)-1-piperidinyl]-pyrimidinyl, (1-methyl-4-piperazinylamino)-pyrimidinyl, [(1-methyl-4-piperazinyl)(methyl)amino]-pyrimidinyl, [(1-methyl-4-piperidinyl)oxy]-pyrimidinyl, or [(1-methyl-3-pyrrolidinyl)oxy]-pyrimidinyl.

In certain embodiments, $R^6$ is pyrimidin-2-yl, pyrimidin-4-yl, pyrimidin-5-yl, 2-chloro-5-pyrimidinyl, 2-methoxy-5-pyrimidinyl, 6-methoxy-4-pyrimidinyl, 2-[2-(dimethylamino)ethyl]-5-pyrimidinyl, 2-[2-(4-morpholinyl)ethyl]-5-pyrimidinyl, 2-[2-(dimethylamino)ethoxy]-5-pyrimidinyl, 2-[3-(dimethylamino)propoxy]-5-pyrimidinyl, 2-[2-(4-morpholinyl)ethoxy]-5-pyrimidinyl, 2-[3-(4-morpholinyl)propoxy]-5-pyrimidinyl, 2-amino-5-pyrimidinyl, 2-[2-(dimethylamino)ethylamino]-5-pyrimidinyl, 2-[(2-(dimethylamino)ethyl)(methyl)amino]-5-pyrimidinyl, 2-[3-(dimethylamino)propylamino]-5-pyrimidinyl, 2-[(3-(dimethylamino)propyl)(methyl)amino]-5-pyrimidinyl, 2-[2-(4-morpholinyl)ethylamino]-5-pyrimidinyl, 2-[(2-(4-morpholinyl)ethyl)(methyl)amino]-5-pyrimidinyl, 2-[3-(4-morpholinyl)propylamino]-5-pyrimidinyl, 2-[(3-(4-morpholinyl)propyl)(methyl)amino]-5-pyrimidinyl, 2-(4-methyl-1-piperazinyl)-5-pyrimidinyl, 2-[4-(dimethylamino)-1-piperidinyl]-5-pyrimidinyl, 2-(1-methyl-4-piperazinylamino)-5-pyrimidinyl, 2-[(1-methyl-4-piperazinyl)(methyl)amino]-5-pyrimidinyl, 2-[(1-methyl-4-piperidinyl)oxy]-5-pyrimidinyl, or 2-[(1-methyl-3-pyrrolidinyl)oxy]-5-pyrimidinyl.

In certain embodiments, $R^6$ is heteroalkylquinolinyl. In certain embodiments, $R^6$ is quinolin-2-yl, quinolin-3-yl, quinolin-4-yl, quinolin-5-yl, quinolin-6-yl, quinolin-7-yl, or quinolin-8-yl.

In certain embodiments, $R^6$ is heteroaryl-$C_{1-6}$ alkyl, optionally substituted with one or more substituents as described herein. In certain embodiments, $R^6$ is heteroaryl-$(CR^{6a}R^{6b})_p$—, wherein $R^{6a}$ and $R^{6b}$ are each as defined herein; p is an integer of 1, 2, or 3; and the heteroaryl is optionally substituted with one or more substituents as described herein. In certain embodiments, $R^6$ is heteroaryl-$(CH_2)_p$—, wherein p is an integer of 1, 2, or 3; and the heteroaryl is optionally substituted with one or more substituents as described herein. In certain embodiments, $R^6$ is imidazolylethyl, pyridinylmethyl, or pyridinylethyl. In certain embodiments, $R^6$ is 2-pyridinylmethyl, 3-pyridinylmethyl, 4-pyridinylmethyl, 2-(1H-imidazol-4-yl)ethyl, 2-(2-pyridinyl)ethyl, 2-(3-pyridinyl)ethyl, or 2-(4-pyridinyl)ethyl.

In certain embodiments, each $R^8$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)N$R^{1b}R^{1c}$, —C(N$R^a$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is as defined herein. In certain embodiments, $R^8$ is hydrogen. In certain embodiments, each $R^8$ is independently -L-$(CR^CR^D)_n$—$R^E$, wherein $R^C$ and $R^D$ are each as defined herein; $R^E$ is hydrogen, —N$R^FR^G$, or heterocyclyl; L is a bond, —O—, or —N($R^H$)—; $R^F$, $R^G$, and $R^H$ are each independently hydrogen or $C_{1-6}$ alkyl; and n is an integer of 0, 1, 2, or 3; and wherein each alkyl and heterocyclyl is independently and optionally substituted with one or more substituents as described herein. In certain embodiments, $R^C$ is hydrogen. In certain embodiments, $R^D$ is hydrogen. In certain embodiments, $R^C$ and $R^D$ are hydrogen. In certain embodiments, $R^E$ is hydrogen, methylamino, dimethylamino, pyrrolidinyl, piperidinyl, or morpholinyl, wherein the pyrrolidinyl, piperidinyl, and morpholinyl are independently, optionally substituted with methyl. In certain embodiments, L is a bond, —O—, —NH—, or —N(CH$_3$)—.

In certain embodiments, each $R^8$ is independently selected from the group consisting of amino, fluoro, chloro, methyl, (dimethylamino)methyl, (dimethylamino)ethyl, (dimethylamino)propyl, morpholinylmethyl, (morpholinyl)ethyl, (morpholinyl)propyl, methoxy, (dimethylamino)ethoxy, (dimethylamino)propoxy, (morpholinyl)ethoxy, (morpholinyl)propoxy, (methyl-piperidinyl)oxy, (methyl-pyrrolidinyl)oxy, methylamino, dimethylamino, (dimethylamino)ethylamino, (dimethylaminoethyl)(methyl)amino, (dimethylamino)propylamino, ((dimethylamino)propyl)(methyl)amino, (morpholinyl)ethylamino, ((morpholinyl)ethyl)(methyl)amino, (morpholinyl)propylamino, ((morpholinyl)propyl)(methyl)amino, methyl-piperidinylamino, (methyl-piperidinyl)(methyl)amino, methyl-piperazinyl, or (dimethylamino)-piperidinyl.

In certain embodiments, each $R^8$ is independently selected from the group consisting of amino, fluoro, chloro, methyl, (dimethylamino)methyl, 2-(dimethylamino)ethyl, 3-(dimethylamino)propyl, 4-morpholinylmethyl, 2-(4-morpholinyl)ethyl, 3-(4-morpholinyl)propyl, methoxy, 2-(dimethylamino)ethoxy, 3-(dimethylamino)propoxy, 2-(4-morpholinyl)ethoxy, 3-(4-morpholinyl)propoxy, (1-methyl-4-piperidinyl)oxy, (1-methyl-3-pyrrolidinyl)oxy, methylamino, dimethylamino, 2-(dimethylamino)ethylamino, (2-dimethylaminoethyl)(methyl)amino, 3-(dimethylamino)propylamino, (3-(dimethylamino)propyl)(methyl)amino, 2-(4-morpholinyl)ethylamino, (2-(4-morpholinyl)ethyl)(methyl)amino, 3-(4-morpholinyl)propylamino, (3-(4-morpholinyl)propyl)(methyl)amino, 1-methyl-4-piperidinylamino, (1-methyl-4-piperidinyl)(methyl)amino, 4-methyl-1-piperazinyl, or 4-(dimethylamino)-1-piperidinyl.

In certain embodiments, $R^A$ is hydrogen. In certain embodiments, $R^B$ is hydrogen. In certain embodiments, $R^A$ and $R^B$ are hydrogen.

In certain embodiments, A is independently a bond. In certain embodiments, A is independently a nitrogen, oxygen, or sulfur atom. In certain embodiments, A is N. In certain embodiments, A is independently $CR^9$ or $CHR^9$, where $R^9$ is as defined herein. In certain embodiments, A is independently $CR^9$, where $R^9$ is hydrogen, halo, or $C_{1-6}$ alkyl.

In certain embodiments, B is independently a bond. In certain embodiments, B is independently a nitrogen, oxygen, or sulfur atom. In certain embodiments, B is N. In certain embodiments, B is independently $CR^9$ or $CHR^9$, where $R^9$ is as defined herein. In certain embodiments, B is independently $CR^9$, where $R^9$ is hydrogen, halo, or $C_{1-6}$ alkyl. In certain embodiments, B is CH. In certain embodiments, B is $CH_2$.

In certain embodiments, D is independently a bond. In certain embodiments, D is independently a nitrogen, oxygen, or sulfur atom. In certain embodiments, D is N. In certain embodiments, D is independently $CR^9$ or $CHR^9$, where $R^9$ is as defined herein. In certain embodiments, D is independently $CR^9$, where $R^9$ is hydrogen, halo, or $C_{1-6}$ alkyl. In certain embodiments, D is CH. In certain embodiments, D is $CH_2$.

In certain embodiments, E is independently a bond. In certain embodiments, E is independently a nitrogen, oxygen, or sulfur atom. In certain embodiments, E is N. In certain embodiments, E is independently $CR^9$ or $CHR^9$, where $R^9$ is as defined herein. In certain embodiments, E is independently $CR^9$, where $R^9$ is hydrogen, halo, or $C_{1-6}$ alkyl. In certain embodiments, E is CH. In certain embodiments, E is $CH_2$.

In certain embodiments, U is a bond, —C(O)—, —C(O)O—, —C(O)N$R^{1a}$—, —O—, —OC(O)O—, —OC(O)N$R^{1a}$—, —N$R^{1a}$—, —N$R^{1a}$C(O)N$R^{1d}$, —N$R^{1a}$S(O)—, —N$R^{1a}$S(O)$_2$—, —N$R^{1a}$S(O)N$R^{1d}$, —N$R^{1a}$S(O)$_2$N$R^{1d}$—, —S—, —S(O)—, or —S(O)$_2$—, where $R^{1a}$ and $R^{1d}$ are each as defined here. In certain embodiments, U is a bond. In certain embodiments, U is not a bond. In certain embodiments, U is —C(O)—, —C(O)O—, or —C(O)N$R^{1a}$—; wherein $R^{1a}$ is as defined herein. In certain embodiments, U is —O—, —OC(O)O—, or —OC(O)N$R^{1a}$—, wherein $R^{1a}$ is as defined herein. In certain embodiments, U is —N$R^{1a}$—, —N$R^{1a}$C(O)N$R^{1d}$—, —N$R^{1a}$S(O)—, —N$R^{1a}$S(O)$_2$—, —N$R^{1a}$S(O)N$R^{1d}$—, or —N$R^{1a}$S(O)$_2$N$R^{1d}$—; wherein $R^{1a}$ and $R^{1d}$ are each as defined herein. In certain embodiments, U is —N$R^{1a}$—, wherein $R^{1a}$ is hydrogen or $C_{1-6}$ alkyl, optionally substituted with one or more substituents as described herein. In certain embodiments, U is —NH— or —N(CH$_3$)—. In certain embodiments, U is —NH—. In certain embodiments, U is —S—, —S(O)—, or —S(O)$_2$—.

In certain embodiments, X is nitrogen or $CR^7$, wherein $R^7$ is as defined herein. In certain embodiments, X is nitrogen or CH. In certain embodiments, Y is nitrogen or $CR^7$, wherein $R^7$ is as defined herein. In certain embodiments, Y is nitrogen or CH. In certain embodiments, Z is nitrogen or $CR^7$, wherein $R^7$ is as defined herein. In certain embodiments, Z is nitrogen or CH.

In certain embodiments, X, Y, and Z are nitrogen. In certain embodiments, X and Y are nitrogen, and Z is CH. In certain embodiments, X and Z are nitrogen, and Y is CH. In certain embodiments, Y and Z are nitrogen, and X is CH.

In certain embodiments, m is an integer of 1, 2, or 3. In certain embodiments, m is 0. In certain embodiments, m is 1. In certain embodiments, m is 2. In certain embodiments, m is 3.

In certain embodiments, p is an integer of 0, 1, 2, or 3. In certain embodiments, p is 0. In certain embodiments, p is 1. In certain embodiments, p is 2. In certain embodiments, p is 3.

In one embodiment, provided herein is a compound selected from:

4-[2-(difluoromethyl)-1H-benzimidazol-1-yl]-6-(4-morpholinyl)-N-(3-pyridinyl)-1,3,5-triazin-2-amine;
4-[2-(difluoromethyl)-4-methoxy-1H-benzimidazol-1-yl]-6-(4-morpholinyl)-N-(3-pyridinyl)-1,3,5-triazin-2-amine;
4-[2-(difluoromethyl)-4-methoxy-1H-benzimidazol-1-yl]-N-methyl-6-(4-morpholinyl)-N-(3-pyridinyl)-1,3,5-triazin-2-amine;
4-[2-(methylsulfanyl)-1H-benzimidazol-1-yl]-6-(4-morpholinyl)-N-(3-pyridinyl)-1,3,5-triazin-2-amine;
4-[2-(methylsulfonyl)-1H-benzimidazol-1-yl]-6-(4-morpholinyl)-N-(3-pyridinyl)-1,3,5-triazin-2-amine;
4-[2-(difluoromethyl)-1H-benzimidazol-1-yl]-6-(4-morpholinyl)-N-phenyl-1,3,5-triazin-2-amine;
4-[2-(difluoromethyl)-1H-benzimidazol-1-yl]-N-methyl-6-(4-morpholinyl)-N-phenyl-1,3,5-triazin-2-amine;
N-benzyl-4-[2-(difluoromethyl)-1H-benzimidazol-1-yl]-6-(4-morpholinyl)-1,3,5-triazin-2-amine;
N-benzyl-4-[2-(difluoromethyl)-1H-benzimidazol-1-yl]-N-methyl-6-(4-morpholinyl)-1,3,5-triazin-2-amine;
2-(difluoromethyl)-1-[4-(4-morpholinyl)-6-phenoxy-1,3,5-triazin-2-yl]-1H-benzimidazole;
2-(difluoromethyl)-1-[4-(4-morpholinyl)-6-(phenylsulfanyl)-1,3,5-triazin-2-yl]-1H-benzimidazole;
2-(difluoromethyl)-1-[4-(4-morpholinyl)-6-(phenylsulfonyl)-1,3,5-triazin-2-yl]-1H-benzimidazole;
N-(2-chloro-5-pyrimidinyl)-4-[2-(difluoromethyl)-4-methoxy-1H-benzimidazol-1-yl]-6-(4-morpholinyl)-1,3,5-triazin-2-amine;
4-[2-(difluoromethyl)-1H-benzimidazol-1-yl]-N-methyl-6-(4-morpholinyl)-N-(5-pyrimidinyl)-1,3,5-triazin-2-amine;
4-[2-(difluoromethyl)-4-methoxy-1H-benzimidazol-1-yl]-N-methyl-6-(4-morpholinyl)-N-(5-pyrimidinyl)-1,3,5-triazin-2-amine;
2-(difluoromethyl)-1-[4-(4-morpholinyl)-6-(3-pyridinyl)-1,3,5-triazin-2-yl]-1H-benzimidazole;
2-(difluoromethyl)-4-methoxy-1-[4-(4-morpholinyl)-6-(3-pyridinyl)-1,3,5-triazin-2-yl]-1H-benzimidazole;
2-(difluoromethyl)-4-methoxy-1-[4-(4-morpholinyl)-6-(1H-pyrazol-4-yl)-1,3,5-triazin-2-yl]-1H-benzimidazole;
N-[3-({5-[2-[2-(difluoromethyl)-1H-benzimidazol-1-yl]-6-(4-morpholinyl)-4-pyrimidinyl]-2-pyridinyl}oxy)propyl]-N,N-dimethylamine;
2-[2-(difluoromethyl)-1H-benzimidazol-1-yl]-6-(4-morpholinyl)-4,5'-bipyrimidine;
2-[2-(difluoromethyl)-4-methoxy-1H-benzimidazol-1-yl]-6-(4-morpholinyl)-4,5'-bipyrimidine;
2-[2-(difluoromethyl)-4-methoxy-1H-benzimidazol-1-yl]-6-(4-morpholinyl)-2'-methoxy-4,5'-bipyrimidine;
2-[2-(difluoromethyl)-1H-benzimidazol-1-yl]-6-(4-morpholinyl)-4,5'-bipyrimidine-2'-amine;
2-(difluoromethyl)-4-methoxy-1-[4-(4-morpholinyl)-6-(1H-pyrazol-1-yl)-1,3,5-triazin-2-yl]-1H-benzimidazole;
2-(difluoromethyl)-4-methoxy-1-[4-(4-morpholinyl)-6-(1H-pyrazol-1-yl)-1,3,5-triazin-2-yl]-1H-benzimidazol-6-ylamine;
2-(difluoromethyl)-4-methoxy-1-[4-(1-methyl-1H-pyrazol-3-yl)-6-(4-morpholinyl)-1,3,5-triazin-2-yl]-1H-benzimidazol-6-ylamine;
2-(difluoromethyl)-4-methoxy-1-[4-(4-morpholinyl)-6-(1H-pyrazol-4-yl)-1,3,5-triazin-2-yl]-1H-benzimidazol-6-ylamine;
2-(difluoromethyl)-1-[4-(1H-imidazol-1-yl)-6-(4-morpholinyl)-1,3,5-triazin-2-yl]-4-methoxy-1H-benzimidazole; and
2-(difluoromethyl)-4-methoxy-1-[4-(4-morpholinyl)-6-(3-pyridinyl)-2-pyrimidinyl]-1H-benzimidazol-6-ylamine;
and enantiomers, mixtures of enantiomers, or mixtures of two or more diastereomers thereof; and pharmaceutically acceptable salts, solvates, hydrates, and prodrugs thereof.

In another embodiment, provided herein is a compound selected from:

N-[4-[6-amino-2-(difluoromethyl)-4-methoxy-1H-benzimidazol-1-yl]-6-(4-morpholinyl)-1,3,5-triazin-2-yl]-N-(3-pyridinyl)amine;
$N^5$-[4-[2-(difluoromethyl)-4-methoxy-1H-benzimidazol-1-yl]-6-(4-morpholinyl)-1,3,5-triazin-2-yl]-2,5-pyridinediamine;
$N^5$-[4-[2-(difluoromethyl)-4-methoxy-1H-benzimidazol-1-yl]-6-(4-morpholinyl)-1,3,5-triazin-2-yl]-$N^2$-[3-(dimethylamino)propyl]-2,5-pyridinediamine;
$N^5$-[4-[2-(difluoromethyl)-4-methoxy-1H-benzimidazol-1-yl]-6-(4-morpholinyl)-1,3,5-triazin-2-yl]-$N^2$-[3-(dimethylamino)propyl]-$N^2$-methyl-2,5-pyridinediamine;
4-[2-(difluoromethyl)-4-methoxy-1H-benzimidazol-1-yl]-N-(6-methoxy-3-pyridinyl)-6-(4-morpholinyl)-1,3,5-triazin-2-amine;
4-[2-(difluoromethyl)-4-methoxy-1H-benzimidazol-1-yl]-N-{6-[3-(dimethylamino)propoxy]-3-pyridinyl}-6-(4-morpholinyl)-1,3,5-triazin-2-amine;
4-[2-(difluoromethyl)-1H-benzimidazol-1-yl]-6-(4-morpholinyl)-N-(5-pyrimidinyl)-1,3,5-triazin-2-amine;
4-[2-(difluoromethyl)-1H-benzimidazol-1-yl]-6-(4-morpholinyl)-N-(3-pyridazinyl)-1,3,5-triazin-2-amine;
4-[2-(difluoromethyl)-1H-benzimidazol-1-yl]-N-(1-methyl-1H-imidazol-5-yl)-6-(4-morpholinyl)-1,3,5-triazin-2-amine;
4-[2-(difluoromethyl)-1H-benzimidazol-1-yl]-N-(1-methyl-1H-pyrazol-5-yl)-6-(4-morpholinyl)-1,3,5-triazin-2-amine;
2-(difluoromethyl)-1-[4-(1H-imidazol-1-yl)-6-(4-morpholinyl)-1,3,5-triazin-2-yl]-4-methoxy-1H-benzimidazol-6-ylamine;
2-(difluoromethyl)-4-methoxy-1-[4-(1-methyl-1H-pyrazol-4-yl)-6-(4-morpholinyl)-1,3,5-triazin-2-yl]-1H-benzimidazole;
N-(2-{4-[4-[2-(difluoromethyl)-4-methoxy-1H-benzimidazol-1-yl]-6-(4-morpholinyl)-1,3,5-triazin-2-yl]-1H-pyrazol-1-yl}ethyl)-N,N-dimethylamine;
N-(3-{4-[4-[2-(difluoromethyl)-4-methoxy-1H-benzimidazol-1-yl]-6-(4-morpholinyl)-1,3,5-triazin-2-yl]-1H-pyrazol-1-yl}propyl)-N,N-dimethylamine; and
2-(difluoromethyl)-4-methoxy-1-[4-(4-morpholinyl)-6-(3-pyridinyl)-1,3,5-triazin-2-yl]-1H-benzimidazol-6-ylamine;
and enantiomers, mixtures of enantiomers, or mixtures of two or more diastereomers thereof; and pharmaceutically acceptable salts, solvates, hydrates, and prodrugs thereof.

In yet another embodiment, provided herein is a compound selected from:

2-[2-(difluoromethyl)-1H-benzimidazol-1-yl]-6-(4-morpholinyl)-N-(3-pyridinyl)-4-pyrimidinamine;
2-[2-(difluoromethyl)-4-methoxy-1H-benzimidazol-1-yl]-6-(4-morpholinyl)-N-(3-pyridinyl)-4-pyrimidinamine;
4-[2-(difluoromethyl)-1H-benzimidazol-1-yl]-6-(4-morpholinyl)-N-(3-pyridinyl)-2-pyrimidinamine;
4-[2-(difluoromethyl)-4-methoxy-1H-benzimidazol-1-yl]-6-(4-morpholinyl)-N-(3-pyridinyl)-2-pyrimidinamine;
6-[2-(difluoromethyl)-1H-benzimidazol-1-yl]-2-(4-morpholinyl)-N-(3-pyridinyl)-4-pyrimidinamine;
6-[2-(difluoromethyl)-4-methoxy-1H-benzimidazol-1-yl]-2-(4-morpholinyl)-N-(3-pyridinyl)-4-pyrimidinamine;
2-(difluoromethyl)-1-[4-(4-morpholinyl)-6-(3-pyridinyl)-2-pyrimidinyl]-1H-benzimidazole;
2-(difluoromethyl)-4-methoxy-1-[4-(4-morpholinyl)-6-(3-pyridinyl)-2-pyrimidinyl]-1H-benzimidazole;
2-(difluoromethyl)-1-[6-(4-morpholinyl)-2-(3-pyridinyl)-4-pyrimidinyl]-1H-benzimidazole;
2-(difluoromethyl)-4-methoxy-1-[6-(4-morpholinyl)-2-(3-pyridinyl)-4-pyrimidinyl]-1H-benzimidazole;
2-(difluoromethyl)-1-[2-(4-morpholinyl)-6-(3-pyridinyl)-4-pyrimidinyl]-1H-benzimidazole;
2-(difluoromethyl)-4-methoxy-1-[2-(4-morpholinyl)-6-(3-pyridinyl)-4-pyrimidinyl]-1H-benzimidazole;
4-[4-methoxy-2-(methylsulfonyl)-1H-benzimidazol-1-yl]-6-(4-morpholinyl)-N-(3-pyridinyl)-1,3,5-triazin-2-amine;
4-[2-(difluoromethyl)-1H-benzimidazol-1-yl]-6-(4-morpholinyl)-N-(2-pyridinyl)-1,3,5-triazin-2-amine;
4-[2-(difluoromethyl)-4-methoxy-1H-benzimidazol-1-yl]-6-(4-morpholinyl)-N-(2-pyridinyl)-1,3,5-triazin-2-amine;
4-[2-(difluoromethyl)-1H-benzimidazol-1-yl]-6-(4-morpholinyl)-N-(4-pyridinyl)-1,3,5-triazin-2-amine;
4-[2-(difluoromethyl)-4-methoxy-1H-benzimidazol-1-yl]-6-(4-morpholinyl)-N-(4-pyridinyl)-1,3,5-triazin-2-amine;
4-[2-(difluoromethyl)-1H-benzimidazol-1-yl]-6-(4-morpholinyl)-N-(4-pyrimidinyl)-1,3,5-triazin-2-amine;
4-[2-(difluoromethyl)-4-methoxy-1H-benzimidazol-1-yl]-6-(4-morpholinyl)-N-(4-pyrimidinyl)-1,3,5-triazin-2-amine;
4-[2-(difluoromethyl)-4-methoxy-1H-benzimidazol-1-yl]-6-(4-morpholinyl)-N-(5-pyrimidinyl)-1,3,5-triazin-2-amine;
2-(difluoromethyl)-1-[4-(4-morpholinyl)-6-(3-pyridinyloxy)-1,3,5-triazin-2-yl]-1H-benzimidazole;
2-(difluoromethyl)-4-methoxy-1-[4-(4-morpholinyl)-6-(3-pyridinyloxy)-1,3,5-triazin-2-yl]-1H-benzimidazole;
2-(difluoromethyl)-1-[4-(4-morpholinyl)-6-(5-pyrimidinyloxy)-1,3,5-triazin-2-yl]-1H-benzimidazole;
2-(difluoromethyl)-4-methoxy-1-[4-(4-morpholinyl)-6-(5-pyrimidinyloxy)-1,3,5-triazin-2-yl]-1H-benzimidazole;
4-[2-(difluoromethyl)-4-methoxy-1H-benzimidazol-1-yl]-N-(1-methyl-1H-pyrazol-4-yl)-6-(4-morpholinyl)-1,3,5-triazin-2-amine;
4-[2-(difluoromethyl)-1H-benzimidazol-1-yl]-N-(1-methyl-1H-pyrazol-4-yl)-6-(4-morpholinyl)-1,3,5-triazin-2-amine;
4-[2-(difluoromethyl)-1H-benzimidazol-1-yl]-6-(4-morpholinyl)-N-(2-pyridinylmethyl)-1,3,5-triazin-2-amine;
4-[2-(difluoromethyl)-4-methoxy-1H-benzimidazol-1-yl]-6-(4-morpholinyl)-N-(2-pyridinylmethyl)-1,3,5-triazin-2-amine;
4-[2-(difluoromethyl)-1H-benzimidazol-1-yl]-6-(4-morpholinyl)-N-(3-pyridinylmethyl)-1,3,5-triazin-2-amine;
4-[2-(difluoromethyl)-4-methoxy-1H-benzimidazol-1-yl]-6-(4-morpholinyl)-N-(3-pyridinylmethyl)-1,3,5-triazin-2-amine;
4-[2-(difluoromethyl)-1H-benzimidazol-1-yl]-6-(4-morpholinyl)-N-(4-pyridinylmethyl)-1,3,5-triazin-2-amine;
4-[2-(difluoromethyl)-4-methoxy-1H-benzimidazol-1-yl]-6-(4-morpholinyl)-N-(4-pyridinylmethyl)-1,3,5-triazin-2-amine;
4-[2-(difluoromethyl)-1H-benzimidazol-1-yl]-N-methyl-6-(4-morpholinyl)-N-(2-pyridinylmethyl)-1,3,5-triazin-2-amine;
4-[2-(difluoromethyl)-4-methoxy-1H-benzimidazol-1-yl]-N-methyl-6-(4-morpholinyl)-N-(2-pyridinylmethyl)-1,3,5-triazin-2-amine;
4-[2-(difluoromethyl)-1H-benzimidazol-1-yl]-N-methyl-6-(4-morpholinyl)-N-(3-pyridinylmethyl)-1,3,5-triazin-2-amine;
4-[2-(difluoromethyl)-4-methoxy-1H-benzimidazol-1-yl]-N-methyl-6-(4-morpholinyl)-N-(3-pyridinylmethyl)-1,3,5-triazin-2-amine;
4-[2-(difluoromethyl)-1H-benzimidazol-1-yl]-N-methyl-6-(4-morpholinyl)-N-(4-pyridinylmethyl)-1,3,5-triazin-2-amine;
4-[2-(difluoromethyl)-4-methoxy-1H-benzimidazol-1-yl]-N-methyl-6-(4-morpholinyl)-N-(4-pyridinylmethyl)-1,3,5-triazin-2-amine;
2-(difluoromethyl)-1-[4-(4-morpholinyl)-6-(2-pyridinylmethoxy)-1,3,5-triazin-2-yl]-1H-benzimidazole;
2-(difluoromethyl)-4-methoxy-1-[4-(4-morpholinyl)-6-(2-pyridinylmethoxy)-1,3,5-triazin-2-yl]-1H-benzimidazole;
2-(difluoromethyl)-1-[4-(4-morpholinyl)-6-(3-pyridinylmethoxy)-1,3,5-triazin-2-yl]-1H-benzimidazole;
2-(difluoromethyl)-4-methoxy-1-[4-(4-morpholinyl)-6-(3-pyridinylmethoxy)-1,3,5-triazin-2-yl]-1H-benzimidazole;
2-(difluoromethyl)-1-[4-(4-morpholinyl)-6-(4-pyridinylmethoxy)-1,3,5-triazin-2-yl]-1H-benzimidazole;
2-(difluoromethyl)-4-methoxy-1-[4-(4-morpholinyl)-6-(4-pyridinylmethoxy)-1,3,5-triazin-2-yl]-1H-benzimidazole;
4-[2-(difluoromethyl)-1H-benzimidazol-1-yl]-6-(4-morpholinyl)-N-[2-(2-pyridinyl)ethyl]-1,3,5-triazin-2-amine;
4-[2-(difluoromethyl)-4-methoxy-1H-benzimidazol-1-yl]-6-(4-morpholinyl)-N-[2-(2-pyridinyl)ethyl]-1,3,5-triazin-2-amine;
4-[2-(difluoromethyl)-1H-benzimidazol-1-yl]-6-(4-morpholinyl)-N-[2-(3-pyridinyl)ethyl]-1,3,5-triazin-2-amine;
4-[2-(difluoromethyl)-4-methoxy-1H-benzimidazol-1-yl]-6-(4-morpholinyl)-N-[2-(3-pyridinyl)ethyl]-1,3,5-triazin-2-amine;
4-[2-(difluoromethyl)-1H-benzimidazol-1-yl]-6-(4-morpholinyl)-N-[2-(4-pyridinyl)ethyl]-1,3,5-triazin-2-amine;
4-[2-(difluoromethyl)-4-methoxy-1H-benzimidazol-1-yl]-6-(4-morpholinyl)-N-[2-(4-pyridinyl)ethyl]-1,3,5-triazin-2-amine;
4-[2-(difluoromethyl)-1H-benzimidazol-1-yl]-N-[2-(1H-imidazol-4-yl)ethyl]-6-(4-morpholinyl)-1,3,5-triazin-2-amine;
4-[2-(difluoromethyl)-4-methoxy-1H-benzimidazol-1-yl]-N-[2-(1H-imidazol-4-yl)ethyl]-6-(4-morpholinyl)-1,3,5-triazin-2-amine;
N-[4-[6-amino-2-(difluoromethyl)-1H-benzimidazol-1-yl]-6-(4-morpholinyl)-1,3,5-triazin-2-yl]-N-(3-pyridinyl)amine;
N-[4-[2-(difluoromethyl)-6-(methylamino)-1H-benzimidazol-1-yl]-6-(4-morpholinyl)-1,3,5-triazin-2-yl]-N-(3-pyridinyl)amine;

N-[4-[2-(difluoromethyl)-4-methoxy-6-(methylamino)-1H-benzimidazol-1-yl]-6-(4-morpholinyl)-1,3,5-triazin-2-yl]-N-(3-pyridinyl)amine;

N-[4-[2-(difluoromethyl)-6-(dimethylamino)-1H-benzimidazol-1-yl]-6-(4-morpholinyl)-1,3,5-triazin-2-yl]-N-(3-pyridinyl)amine;

N-[4-[2-(difluoromethyl)-6-(dimethylamino)-4-methoxy-1H-benzimidazol-1-yl]-6-(4-morpholinyl)-1,3,5-triazin-2-yl]-N-(3-pyridinyl)amine;

4-[2-(difluoromethyl)-1H-benzimidazol-1-yl]-N-(6-methoxy-3-pyridinyl)-6-(4-morpholinyl)-1,3,5-triazin-2-amine;

4-[2-(difluoromethyl)-1H-benzimidazol-1-yl]-N-(2-methoxy-4-pyridinyl)-6-(4-morpholinyl)-1,3,5-triazin-2-amine;

4-[2-(difluoromethyl)-4-methoxy-1H-benzimidazol-1-yl]-N-(2-methoxy-4-pyridinyl)-6-(4-morpholinyl)-1,3,5-triazin-2-amine;

4-[2-(difluoromethyl)-1H-benzimidazol-1-yl]-N-(2-methoxy-5-pyrimidinyl)-6-(4-morpholinyl)-1,3,5-triazin-2-amine;

4-[2-(difluoromethyl)-4-methoxy-1H-benzimidazol-1-yl]-N-(2-methoxy-5-pyrimidinyl)-6-(4-morpholinyl)-1,3,5-triazin-2-amine;

4-[2-(difluoromethyl)-1H-benzimidazol-1-yl]-N-{6-[2-(dimethylamino)ethoxy]-3-pyridinyl}-6-(4-morpholinyl)-1,3,5-triazin-2-amine;

4-[2-(difluoromethyl)-4-methoxy-1H-benzimidazol-1-yl]-N-{6-[2-(dimethylamino)ethoxy]-3-pyridinyl}-6-(4-morpholinyl)-1,3,5-triazin-2-amine;

4-[2-(difluoromethyl)-1H-benzimidazol-1-yl]-6-(4-morpholinyl)-N-{6-[2-(4-morpholinyl)ethoxy]-3-pyridinyl}-1,3,5-triazin-2-amine;

4-[2-(difluoromethyl)-4-methoxy-1H-benzimidazol-1-yl]-6-(4-morpholinyl)-N-{6-[2-(4-morpholinyl)ethoxy]-3-pyridinyl}-1,3,5-triazin-2-amine;

4-[2-(difluoromethyl)-1H-benzimidazol-1-yl]-N-{6-[3-(dimethylamino)propoxy]-3-pyridinyl}-6-(4-morpholinyl)-1,3,5-triazin-2-amine;

4-[2-(difluoromethyl)-1H-benzimidazol-1-yl]-6-(4-morpholinyl)-N-{6-[3-(4-morpholinyl)propoxy]-3-pyridinyl}-1,3,5-triazin-2-amine;

4-[2-(difluoromethyl)-4-methoxy-1H-benzimidazol-1-yl]-6-(4-morpholinyl)-N-{6-[3-(4-morpholinyl)propoxy]-3-pyridinyl}-1,3,5-triazin-2-amine;

$N^5$-[4-[2-(difluoromethyl)-1H-benzimidazol-1-yl]-6-(4-morpholinyl)-1,3,5-triazin-2-yl]-2,5-pyridinediamine;

$N^5$-[4-[2-(difluoromethyl)-1H-benzimidazol-1-yl]-6-(4-morpholinyl)-1,3,5-triazin-2-yl]-$N^2$-methyl-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2$-methyl-2,5-pyridinediamine;

$N^5$-[4-[2-(difluoromethyl)-1H-benzimidazol-1-yl]-6-(4-morpholinyl)-1,3,5-triazin-2-yl]-$N^2,N^2$-dimethyl-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2,N^2$-dimethyl-2,5-pyridinediamine;

$N^5$-[4-[2-(difluoromethyl)-1H-benzimidazol-1-yl]-6-(4-morpholinyl)-1,3,5-triazin-2-yl]-$N^2$-[2-(dimethylamino)ethyl]-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2$-[2-(dimethylamino)ethyl]-2,5-pyridinediamine;

$N^5$-[4-[2-(difluoromethyl)-1H-benzimidazol-1-yl]-6-(4-morpholinyl)-1,3,5-triazin-2-yl]-$N^2$-[2-(4-morpholinyl)ethyl]-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2$-[2-(4-morpholinyl)ethyl]-2,5-pyridinediamine;

$N^5$-[4-[2-(difluoromethyl)-1H-benzimidazol-1-yl]-6-(4-morpholinyl)-1,3,5-triazin-2-yl]-$N^2$-[2-(dimethylamino)ethyl]-$N^2$-methyl-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2$-[2-(dimethylamino)ethyl]-$N^2$-methyl-2,5-pyridinediamine;

$N^5$-[4-[2-(difluoromethyl)-1H-benzimidazol-1-yl]-6-(4-morpholinyl)-1,3,5-triazin-2-yl]-$N^2$-methyl-$N^2$-[2-(4-morpholinyl)ethyl]-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-[2-(4-morpholinyl)ethyl]-2,5-pyridinediamine;

$N^5$-[4-[2-(difluoromethyl)-1H-benzimidazol-1-yl]-6-(4-morpholinyl)-1,3,5-triazin-2-yl]-$N^2$-[3-(dimethylamino)propyl]-2,5-pyridinediamine;

$N^5$-[4-[2-(difluoromethyl)-1H-benzimidazol-1-yl]-6-(4-morpholinyl)-1,3,5-triazin-2-yl]-$N^2$-[3-(dimethylamino)propyl]-$N^2$-methyl-2,5-pyridinediamine;

$N^5$-[4-[2-(difluoromethyl)-1H-benzimidazol-1-yl]-6-(4-morpholinyl)-1,3,5-triazin-2-yl]-$N^2$-[3-(4-morpholinyl)propyl]-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2$-[3-(4-morpholinyl)propyl]-2,5-pyridinediamine;

$N^5$-[4-[2-(difluoromethyl)-1H-benzimidazol-1-yl]-6-(4-morpholinyl)-1,3,5-triazin-2-yl]-$N^2$-methyl-$N^2$-[3-(4-morpholinyl)propyl]-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-[3-(4-morpholinyl)propyl]-2,5-pyridinediamine;

4-[2-(difluoromethyl)-1H-benzimidazol-1-yl]-N-{6-[2-(dimethylamino)ethyl]-3-pyridinyl}-6-(4-morpholinyl)-1,3,5-triazin-2-amine;

4-[2-(difluoromethyl)-4-methoxy-1H-benzimidazol-1-yl]-N-{6-[2-(dimethylamino)ethyl]-3-pyridinyl}-6-(4-morpholinyl)-1,3,5-triazin-2-amine;

4-[2-(difluoromethyl)-1H-benzimidazol-1-yl]-6-(4-morpholinyl)-N-{6-[2-(4-morpholinyl)ethyl]-3-pyridinyl}-1,3,5-triazin-2-amine;

4-[2-(difluoromethyl)-4-methoxy-1H-benzimidazol-1-yl]-6-(4-morpholinyl)-N-{6-[2-(4-morpholinyl)ethyl]-3-pyridinyl}-1,3,5-triazin-2-amine;

4-[2-(difluoromethyl)-1H-benzimidazol-1-yl]-N-{2-[2-(dimethylamino)ethyl]-5-pyrimidinyl}-6-(4-morpholinyl)-1,3,5-triazin-2-amine;

4-[2-(difluoromethyl)-4-methoxy-1H-benzimidazol-1-yl]-N-{2-[2-(dimethylamino)ethyl]-5-pyrimidinyl}-6-(4-morpholinyl)-1,3,5-triazin-2-amine;

4-[2-(difluoromethyl)-1H-benzimidazol-1-yl]-6-(4-morpholinyl)-N-{2-[2-(4-morpholinyl)ethyl]-5-pyrimidinyl}-1,3,5-triazin-2-amine;

4-[2-(difluoromethyl)-4-methoxy-1H-benzimidazol-1-yl]-6-(4-morpholinyl)-N-{2-[2-(4-morpholinyl)ethyl]-5-pyrimidinyl}-1,3,5-triazin-2-amine;

4-[2-(difluoromethyl)-1H-benzimidazol-1-yl]-N-{5-[2-(dimethylamino)ethoxy]-3-pyridinyl}-6-(4-morpholinyl)-1,3,5-triazin-2-amine;

4-[2-(difluoromethyl)-4-methoxy-1H-benzimidazol-1-yl]-N-{5-[2-(dimethylamino)ethoxy]-3-pyridinyl}-6-(4-morpholinyl)-1,3,5-triazin-2-amine;

4-[2-(difluoromethyl)-4-methoxy-1H-benzimidazol-1-yl]-6-(4-morpholinyl)-N-{5-[2-(4-morpholinyl)ethoxy]-3-pyridinyl}-1,3,5-triazin-2-amine;

4-[2-(difluoromethyl)-1H-benzimidazol-1-yl]-6-(4-morpholinyl)-N-{5-[2-(4-morpholinyl)ethoxy]-3-pyridinyl}-1,3,5-triazin-2-amine;

4-[2-(difluoromethyl)-1H-benzimidazol-1-yl]-N-{5-[3-(dimethylamino)propoxy]-3-pyridinyl}-6-(4-morpholinyl)-1,3,5-triazin-2-amine;

4-[2-(difluoromethyl)-4-methoxy-1H-benzimidazol-1-yl]-N-{5-[3-(dimethylamino)propoxy]-3-pyridinyl}-6-(4-morpholinyl)-1,3,5-triazin-2-amine;

4-[2-(difluoromethyl)-1H-benzimidazol-1-yl]-6-(4-morpholinyl)-N-{5-[3-(4-morpholinyl)propoxy]-3-pyridinyl}-1,3,5-triazin-2-amine;

4-[2-(difluoromethyl)-4-methoxy-1H-benzimidazol-1-yl]-6-(4-morpholinyl)-N-{5-[3-(4-morpholinyl)propoxy]-3-pyridinyl}-1,3,5-triazin-2-amine;

4-[2-(difluoromethyl)-1H-benzimidazol-1-yl]-N-{2-[2-(dimethylamino)ethoxy]-4-pyridinyl}-6-(4-morpholinyl)-1,3,5-triazin-2-amine;

4-[2-(difluoromethyl)-4-methoxy-1H-benzimidazol-1-yl]-N-{2-[2-(dimethylamino)ethoxy]-4-pyridinyl}-6-(4-morpholinyl)-1,3,5-triazin-2-amine;

4-[2-(difluoromethyl)-1H-benzimidazol-1-yl]-6-(4-morpholinyl)-N-{2-[2-(4-morpholinyl)ethoxy]-4-pyridinyl}-1,3,5-triazin-2-amine;

4-[2-(difluoromethyl)-4-methoxy-1H-benzimidazol-1-yl]-6-(4-morpholinyl)-N-{2-[2-(4-morpholinyl)ethoxy]-4-pyridinyl}-1,3,5-triazin-2-amine;

4-[2-(difluoromethyl)-1H-benzimidazol-1-yl]-N-{2-[3-(dimethylamino)propoxy]-4-pyridinyl}-6-(4-morpholinyl)-1,3,5-triazin-2-amine;

4-[2-(difluoromethyl)-4-methoxy-1H-benzimidazol-1-yl]-N-{2-[3-(dimethylamino)propoxy]-4-pyridinyl}-6-(4-morpholinyl)-1,3,5-triazin-2-amine;

4-[2-(difluoromethyl)-1H-benzimidazol-1-yl]-6-(4-morpholinyl)-N-{2-[3-(4-morpholinyl)propoxy]-4-pyridinyl}-1,3,5-triazin-2-amine;

4-[2-(difluoromethyl)-4-methoxy-1H-benzimidazol-1-yl]-6-(4-morpholinyl)-N-{2-[3-(4-morpholinyl)propoxy]-4-pyridinyl}-1,3,5-triazin-2-amine;

4-[2-(difluoromethyl)-1H-benzimidazol-1-yl]-N-{2-[2-(dimethylamino)ethoxy]-5-pyrimidinyl}-6-(4-morpholinyl)-1,3,5-triazin-2-amine;

4-[2-(difluoromethyl)-4-methoxy-1H-benzimidazol-1-yl]-N-{2-[2-(dimethylamino)ethoxy]-5-pyrimidinyl}-6-(4-morpholinyl)-1,3,5-triazin-2-amine;

4-[2-(difluoromethyl)-1H-benzimidazol-1-yl]-N-{2-[3-(dimethylamino)propoxy]-5-pyrimidinyl}-6-(4-morpholinyl)-1,3,5-triazin-2-amine;

4-[2-(difluoromethyl)-4-methoxy-1H-benzimidazol-1-yl]-N-{2-[3-(dimethylamino)propoxy]-5-pyrimidinyl}-6-(4-morpholinyl)-1,3,5-triazin-2-amine;

4-[2-(difluoromethyl)-1H-benzimidazol-1-yl]-6-(4-morpholinyl)-N-{2-[2-(4-morpholinyl)ethoxy]-5-pyrimidinyl}-1,3,5-triazin-2-amine;

4-[2-(difluoromethyl)-4-methoxy-1H-benzimidazol-1-yl]-6-(4-morpholinyl)-N-{2-[2-(4-morpholinyl)ethoxy]-5-pyrimidinyl}-1,3,5-triazin-2-amine;

4-[2-(difluoromethyl)-1H-benzimidazol-1-yl]-6-(4-morpholinyl)-N-{2-[3-(4-morpholinyl)propoxy]-5-pyrimidinyl}-1,3,5-triazin-2-amine;

4-[2-(difluoromethyl)-4-methoxy-1H-benzimidazol-1-yl]-6-(4-morpholinyl)-N-{2-[3-(4-morpholinyl)propoxy]-5-pyrimidinyl}-1,3,5-triazin-2-amine;

$N^5$-[4-[2-(difluoromethyl)-4-methoxy-1H-benzimidazol-1-yl]-6-(4-morpholinyl)-1,3,5-triazin-2-yl]-$N^2$-[2-(dimethylamino)ethyl]-2,5-pyrimidinediamine;

$N^5$-[4-[2-(difluoromethyl)-1H-benzimidazol-1-yl]-6-(4-morpholinyl)-1,3,5-triazin-2-yl]-$N^2$-[2-(dimethylamino)ethyl]-2,5-pyrimidinediamine;

$N^5$-[4-[2-(difluoromethyl)-1H-benzimidazol-1-yl]-6-(4-morpholinyl)-1,3,5-triazin-2-yl]-$N^2$-[2-(dimethylamino)ethyl]-$N^2$-methyl-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-$N^2$-[2-(dimethylamino)ethyl]-$N^2$-methyl-2,5-pyrimidinediamine;

$N^5$-[4-[2-(difluoromethyl)-1H-benzimidazol-1-yl]-6-(4-morpholinyl)-1,3,5-triazin-2-yl]-$N^2$-[3-(dimethylamino)propyl]-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-$N^2$-[3-(dimethylamino)propyl]-2,5-pyrimidinediamine;

$N^5$-[4-[2-(difluoromethyl)-1H-benzimidazol-1-yl]-6-(4-morpholinyl)-1,3,5-triazin-2-yl]-$N^2$-[3-(dimethylamino)propyl]-$N^2$-methyl-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-$N^2$-[3-(dimethylamino)propyl]-$N^2$-methyl-2,5-pyrimidinediamine;

$N^5$-[4-[2-(difluoromethyl)-1H-benzimidazol-1-yl]-6-(4-morpholinyl)-1,3,5-triazin-2-yl]-$N^2$-[2-(4-morpholinyl)ethyl]-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-$N^2$-[2-(4-morpholinyl)ethyl]-2,5-pyrimidinediamine;

$N^5$-[4-[2-(difluoromethyl)-1H-benzimidazol-1-yl]-6-(4-morpholinyl)-1,3,5-triazin-2-yl]-$N^2$-methyl-$N^2$-[2-(4-morpholinyl)ethyl]-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-[2-(4-morpholinyl)ethyl]-2,5-pyrimidinediamine;

$N^5$-[4-[2-(difluoromethyl)-1H-benzimidazol-1-yl]-6-(4-morpholinyl)-1,3,5-triazin-2-yl]-$N^2$-[3-(4-morpholinyl)propyl]-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-$N^2$-[3-(4-morpholinyl)propyl]-2,5-pyrimidinediamine;

$N^5$-[4-[2-(difluoromethyl)-1H-benzimidazol-1-yl]-6-(4-morpholinyl)-1,3,5-triazin-2-yl]-$N^2$-methyl-$N^2$-[3-(4-morpholinyl)propyl]-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-[3-(4-morpholinyl)propyl]-2,5-pyrimidinediamine;

4-[2-(difluoromethyl)-1H-benzimidazol-1-yl]-N-[6-(4-methyl-1-piperazinyl)-3-pyridinyl]-6-(4-morpholinyl)-1,3,5-triazin-2-amine;

4-[2-(difluoromethyl)-4-methoxy-1H-benzimidazol-1-yl]-N-[6-(4-methyl-1-piperazinyl)-3-pyridinyl]-6-(4-morpholinyl)-1,3,5-triazin-2-amine;

4-[2-(difluoromethyl)-1H-benzimidazol-1-yl]-N-[2-(4-methyl-1-piperazinyl)-5-pyrimidinyl]-6-(4-morpholinyl)-1,3,5-triazin-2-amine;

4-[2-(difluoromethyl)-4-methoxy-1H-benzimidazol-1-yl]-N-[2-(4-methyl-1-piperazinyl)-5-pyrimidinyl]-6-(4-morpholinyl)-1,3,5-triazin-2-amine;

4-[2-(difluoromethyl)-1H-benzimidazol-1-yl]-N-{6-[4-(dimethylamino)-1-piperidinyl]-3-pyridinyl}-6-(4-morpholinyl)-1,3,5-triazin-2-amine;

4-[2-(difluoromethyl)-4-methoxy-1H-benzimidazol-1-yl]-N-{6-[4-(dimethylamino)-1-piperidinyl]-3-pyridinyl}-6-(4-morpholinyl)-1,3,5-triazin-2-amine;

4-[2-(difluoromethyl)-1H-benzimidazol-1-yl]-N-{2-[4-(dimethylamino)-1-piperidinyl]-5-pyrimidinyl}-6-(4-morpholinyl)-1,3,5-triazin-2-amine;

4-[2-(difluoromethyl)-4-methoxy-1H-benzimidazol-1-yl]-N-{2-[4-(dimethylamino)-1-piperidinyl]-5-pyrimidinyl}-6-(4-morpholinyl)-1,3,5-triazin-2-amine;

$N^5$-[4-[2-(difluoromethyl)-1H-benzimidazol-1-yl]-6-(4-morpholinyl)-1,3,5-triazin-2-yl]-$N^2$-(1-methyl-4-piperidinyl)-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2$-(1-methyl-4-piperidinyl)-2,5-pyridinediamine;

$N^5$-[4-[2-(difluoromethyl)-1H-benzimidazol-1-yl]-6-(4-morpholinyl)-1,3,5-triazin-2-yl]-$N^2$-methyl-$N^2$-(1-methyl-4-piperidinyl)-2,5-pyridinediamine;

$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-(1-methyl-4-piperidinyl)-2,5-pyridinediamine;

$N^5$-[4-[2-(difluoromethyl)-1H-benzimidazol-1-yl]-6-(4-morpholinyl)-1,3,5-triazin-2-yl]-$N^2$-(1-methyl-4-piperidinyl)-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-$N^2$-(1-methyl-4-piperidinyl)-2,5-pyrimidinediamine;

$N^5$-[4-[2-(difluoromethyl)-1H-benzimidazol-1-yl]-6-(4-morpholinyl)-1,3,5-triazin-2-yl]-$N^2$-methyl-$N^2$-(1-methyl-4-piperidinyl)-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-(1-methyl-4-piperidinyl)-2,5-pyrimidinediamine;

4-[2-(difluoromethyl)-1H-benzimidazol-1-yl]-N-{6-[(1-methyl-4-piperidinyl)oxy]-3-pyridinyl}-6-(4-morpholinyl)-1,3,5-triazin-2-amine;

4-[2-(difluoromethyl)-4-methoxy-1H-benzimidazol-1-yl]-N-{6-[(1-methyl-4-piperidinyl)oxy]-3-pyridinyl}-6-(4-morpholinyl)-1,3,5-triazin-2-amine;

4-[2-(difluoromethyl)-1H-benzimidazol-1-yl]-N-{2-[(1-methyl-4-piperidinyl)oxy]-5-pyrimidinyl}-6-(4-morpholinyl)-1,3,5-triazin-2-amine;

4-[2-(difluoromethyl)-4-methoxy-1H-benzimidazol-1-yl]-N-{2-[(1-methyl-4-piperidinyl)oxy]-5-pyrimidinyl}-6-(4-morpholinyl)-1,3,5-triazin-2-amine;

4-[2-(difluoromethyl)-1H-benzimidazol-1-yl]-N-{6-[(1-methyl-3-pyrrolidinyl)oxy]-3-pyridinyl}-6-(4-morpholinyl)-1,3,5-triazin-2-amine;

4-[2-(difluoromethyl)-4-methoxy-1H-benzimidazol-1-yl]-N-{6-[(1-methyl-3-pyrrolidinyl)oxy]-3-pyridinyl}-6-(4-morpholinyl)-1,3,5-triazin-2-amine;

4-[2-(difluoromethyl)-1H-benzimidazol-1-yl]-N-{2-[(1-methyl-3-pyrrolidinyl)oxy]-5-pyrimidinyl}-6-(4-morpholinyl)-1,3,5-triazin-2-amine;

4-[2-(difluoromethyl)-4-methoxy-1H-benzimidazol-1-yl]-N-{2-[(1-methyl-3-pyrrolidinyl)oxy]-5-pyrimidinyl}-6-(4-morpholinyl)-1,3,5-triazin-2-amine;

4-[2-(difluoromethyl)-1H-benzimidazol-1-yl]-N-{1-[2-(dimethylamino)ethyl]-1H-pyrazol-4-yl}-6-(4-morpholinyl)-1,3,5-triazin-2-amine;

4-[2-(difluoromethyl)-4-methoxy-1H-benzimidazol-1-yl]-N-{1-[2-(dimethylamino)ethyl]-1H-pyrazol-4-yl}-6-(4-morpholinyl)-1,3,5-triazin-2-amine;

4-[2-(difluoromethyl)-1H-benzimidazol-1-yl]-6-(4-morpholinyl)-N-{1-[2-(4-morpholinyl)ethyl]-1H-pyrazol-4-yl}-1,3,5-triazin-2-amine;

4-[2-(difluoromethyl)-4-methoxy-1H-benzimidazol-1-yl]-6-(4-morpholinyl)-N-{1-[2-(4-morpholinyl)ethyl]-1H-pyrazol-4-yl}-1,3,5-triazin-2-amine;

4-[2-(difluoromethyl)-1H-benzimidazol-1-yl]-N-{1-[3-(dimethylamino)propyl]-1H-pyrazol-4-yl}-6-(4-morpholinyl)-1,3,5-triazin-2-amine;

4-[2-(difluoromethyl)-4-methoxy-1H-benzimidazol-1-yl]-N-{1-[3-(dimethylamino)propyl]-1H-pyrazol-4-yl}-6-(4-morpholinyl)-1,3,5-triazin-2-amine;

4-[2-(difluoromethyl)-1H-benzimidazol-1-yl]-6-(4-morpholinyl)-N-{1-[3-(4-morpholinyl)propyl]-1H-pyrazol-4-yl}-1,3,5-triazin-2-amine;

4-[2-(difluoromethyl)-4-methoxy-1H-benzimidazol-1-yl]-6-(4-morpholinyl)-N-{1-[3-(4-morpholinyl)propyl]-1H-pyrazol-4-yl}-1,3,5-triazin-2-amine;

4-[2-(difluoromethyl)-1H-benzimidazol-1-yl]-6-(4-morpholinyl)-N-(1,3-thiazol-5-yl)-1,3,5-triazin-2-amine;

4-[2-(difluoromethyl)-4-methoxy-1H-benzimidazol-1-yl]-6-(4-morpholinyl)-N-(1,3-thiazol-5-yl)-1,3,5-triazin-2-amine;

4-[2-(difluoromethyl)-1H-benzimidazol-1-yl]-N-{2-[(dimethylamino)methyl]-1,3-thiazol-5-yl}-6-(4-morpholinyl)-1,3,5-triazin-2-amine;

4-[2-(difluoromethyl)-4-methoxy-1H-benzimidazol-1-yl]-N-{2-[(dimethylamino)methyl]-1,3-thiazol-5-yl}-6-(4-morpholinyl)-1,3,5-triazin-2-amine;

4-[2-(difluoromethyl)-1H-benzimidazol-1-yl]-6-(4-morpholinyl)-N-[2-(4-morpholinylmethyl)-1,3-thiazol-5-yl]-1,3,5-triazin-2-amine;

4-[2-(difluoromethyl)-4-methoxy-1H-benzimidazol-1-yl]-6-(4-morpholinyl)-N-[2-(4-morpholinylmethyl)-1,3-thiazol-5-yl]-1,3,5-triazin-2-amine;

4-[2-(difluoromethyl)-1H-benzimidazol-1-yl]-N-(1-methyl-1H-imidazol-5-yl)-6-(4-morpholinyl)-1,3,5-triazin-2-amine;

4-[2-(difluoromethyl)-1H-benzimidazol-1-yl]-N-(1-methyl-1H-1,2,3-triazol-5-yl)-6-(4-morpholinyl)-1,3,5-triazin-2-amine;

4-[2-(difluoromethyl)-4-methoxy-1H-benzimidazol-1-yl]-N-(1-methyl-1H-1,2,3-triazol-5-yl)-6-(4-morpholinyl)-1,3,5-triazin-2-amine;

4-[2-(difluoromethyl)-1H-benzimidazol-1-yl]-N-(2-methyl-2H-1,2,3-triazol-4-yl)-6-(4-morpholinyl)-1,3,5-triazin-2-amine;

4-[2-(difluoromethyl)-4-methoxy-1H-benzimidazol-1-yl]-N-(2-methyl-2H-1,2,3-triazol-4-yl)-6-(4-morpholinyl)-1,3,5-triazin-2-amine;

4-[2-(difluoromethyl)-1H-benzimidazol-1-yl]-N-(1-methyl-1H-1,2,3-triazol-4-yl)-6-(4-morpholinyl)-1,3,5-triazin-2-amine;

4-[2-(difluoromethyl)-4-methoxy-1H-benzimidazol-1-yl]-N-(1-methyl-1H-1,2,3-triazol-4-yl)-6-(4-morpholinyl)-1,3,5-triazin-2-amine;

4-[2-(difluoromethyl)-1H-benzimidazol-1-yl]-N-(2-methyl-2H-tetrazol-5-yl)-6-(4-morpholinyl)-1,3,5-triazin-2-amine;

4-[2-(difluoromethyl)-4-methoxy-1H-benzimidazol-1-yl]-N-(2-methyl-2H-tetrazol-5-yl)-6-(4-morpholinyl)-1,3,5-triazin-2-amine;

4-[2-(difluoromethyl)-1H-benzimidazol-1-yl]-N-(1-methyl-1H-tetrazol-5-yl)-6-(4-morpholinyl)-1,3,5-triazin-2-amine;

4-[2-(difluoromethyl)-4-methoxy-1H-benzimidazol-1-yl]-N-(1-methyl-1H-tetrazol-5-yl)-6-(4-morpholinyl)-1,3,5-triazin-2-amine;

2-(difluoromethyl)-1-[4-(4-morpholinyl)-6-(4-pyridinyl)-1,3,5-triazin-2-yl]-1H-benzimidazole;

2-(difluoromethyl)-4-methoxy-1-[4-(4-morpholinyl)-6-(4-pyridinyl)-1,3,5-triazin-2-yl]-1H-benzimidazole;

2-(difluoromethyl)-1-[4-(4-morpholinyl)-6-(5-pyrimidinyl)-1,3,5-triazin-2-yl]-1H-benzimidazole;
2-(difluoromethyl)-4-methoxy-1-[4-(4-morpholinyl)-6-(5-pyrimidinyl)-1,3,5-triazin-2-yl]-1H-benzimidazole;
2-(difluoromethyl)-1-[4-(2-methoxy-5-pyrimidinyl)-6-(4-morpholinyl)-1,3,5-triazin-2-yl]-1H-benzimidazole;
2-(difluoromethyl)-4-methoxy-1-[4-(2-methoxy-5-pyrimidinyl)-6-(4-morpholinyl)-1,3,5-triazin-2-yl]-1H-benzimidazole;
2-(difluoromethyl)-1-[4-(6-methoxy-3-pyridinyl)-6-(4-morpholinyl)-1,3,5-triazin-2-yl]-1H-benzimidazole;
2-(difluoromethyl)-4-methoxy-1-[4-(6-methoxy-3-pyridinyl)-6-(4-morpholinyl)-1,3,5-triazin-2-yl]-1H-benzimidazole;
2-(difluoromethyl)-1-[4-(5-methoxy-3-pyridinyl)-6-(4-morpholinyl)-1,3,5-triazin-2-yl]-1H-benzimidazole;
2-(difluoromethyl)-4-methoxy-1-[4-(5-methoxy-3-pyridinyl)-6-(4-morpholinyl)-1,3,5-triazin-2-yl]-1H-benzimidazole;
2-(difluoromethyl)-1-[4-(2-methoxy-4-pyridinyl)-6-(4-morpholinyl)-1,3,5-triazin-2-yl]-1H-benzimidazole;
2-(difluoromethyl)-4-methoxy-1-[4-(2-methoxy-4-pyridinyl)-6-(4-morpholinyl)-1,3,5-triazin-2-yl]-1H-benzimidazole;
2-(difluoromethyl)-1-[4-(1-methyl-1H-pyrazol-4-yl)-6-(4-morpholinyl)-1,3,5-triazin-2-yl]-1H-benzimidazole;
2-(difluoromethyl)-4-methoxy-1-[4-(1-methyl-1H-pyrazol-4-yl)-6-(4-morpholinyl)-1,3,5-triazin-2-yl]-1H-benzimidazole;
2-(difluoromethyl)-1-[4-(4-morpholinyl)-6-(1,3-thiazol-5-yl)-1,3,5-triazin-2-yl]-1H-benzimidazole;
2-(difluoromethyl)-4-methoxy-1-[4-(4-morpholinyl)-6-(1,3-thiazol-5-yl)-1,3,5-triazin-2-yl]-1H-benzimidazole;
$N^5$-[4-[2-(difluoromethyl)-1H-benzimidazol-1-yl]-6-(4-morpholinyl)-1,3,5-triazin-2-yl]-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-2,5-pyrimidinediamine;
5-[4-[2-(difluoromethyl)-1H-benzimidazol-1-yl]-6-(4-morpholinyl)-1,3,5-triazin-2-yl]-2-pyridinamine;
5-[4-[2-(difluoromethyl)-4-methoxy-1H-benzimidazol-1-yl]-6-(4-morpholinyl)-1,3,5-triazin-2-yl]-2-pyridinamine;
5-[4-[2-(difluoromethyl)-1H-benzimidazol-1-yl]-6-(4-morpholinyl)-1,3,5-triazin-2-yl]-2-pyrimidinamine;
5-[4-[2-(difluoromethyl)-4-methoxy-1H-benzimidazol-1-yl]-6-(4-morpholinyl)-1,3,5-triazin-2-yl]-2-pyrimidinamine;
4-[2-(difluoromethyl)-1H-benzimidazol-1-yl]-6-(4-morpholinyl)-N-(2-pyrazinyl)-1,3,5-triazin-2-amine;
4-[2-(difluoromethyl)-4-methoxy-1H-benzimidazol-1-yl]-6-(4-morpholinyl)-N-(2-pyrazinyl)-1,3,5-triazin-2-amine;
$N^2$-[4-[2-(difluoromethyl)-1H-benzimidazol-1-yl]-6-(4-morpholinyl)-1,3,5-triazin-2-yl]-2,5-pyrazinediamine;
$N^2$-[4-[2-(difluoromethyl)-4-methoxy-1H-benzimidazol-1-yl]-6-(4-morpholinyl)-1,3,5-triazin-2-yl]-2,5-pyrazinediamine;
$N^2$-[4-[2-(difluoromethyl)-1H-benzimidazol-1-yl]-6-(4-morpholinyl)-1,3,5-triazin-2-yl]-2,6-pyrazinediamine;
$N^2$-[4-[2-(difluoromethyl)-4-methoxy-1H-benzimidazol-1-yl]-6-(4-morpholinyl)-1,3,5-triazin-2-yl]-2,6-pyrazinediamine;
4-[2-(difluoromethyl)-1H-benzimidazol-1-yl]-N-(6-methoxy-2-pyrazinyl)-6-(4-morpholinyl)-1,3,5-triazin-2-amine;
4-[2-(difluoromethyl)-4-methoxy-1H-benzimidazol-1-yl]-N-(6-methoxy-2-pyrazinyl)-6-(4-morpholinyl)-1,3,5-triazin-2-amine;
6-[4-[2-(difluoromethyl)-1H-benzimidazol-1-yl]-6-(4-morpholinyl)-1,3,5-triazin-2-yl]-2-pyrazinamine;
6-[4-[2-(difluoromethyl)-4-methoxy-1H-benzimidazol-1-yl]-6-(4-morpholinyl)-1,3,5-triazin-2-yl]-2-pyrazinamine;
2-(difluoromethyl)-1-[4-(6-methoxy-2-pyrazinyl)-6-(4-morpholinyl)-1,3,5-triazin-2-yl]-1H-benzimidazole;
2-(difluoromethyl)-4-methoxy-1-[4-(6-methoxy-2-pyrazinyl)-6-(4-morpholinyl)-1,3,5-triazin-2-yl]-1H-benzimidazole; and
N-[4-[6-amino-2-(difluoromethyl)-4-methoxy-1H-benzimidazol-1-yl]-6-(4-morpholinyl)-1,3,5-triazin-2-yl]-N-(3-pyridinyl)amine;
and enantiomers, mixtures of enantiomers, or mixtures of two or more diastereomers thereof; and pharmaceutically acceptable salts, solvates, hydrates, and prodrugs thereof.

In yet another embodiment, provided herein is a compound selected from:
N-[4-[2-(difluoromethyl)-1H-benzimidazol-1-yl]-6-(4-morpholinyl)-1,3,5-triazin-2-yl]-3-quinolinamine;
4-[2-(difluoromethyl)-1H-benzimidazol-1-yl]-6-(4-morpholinyl)-N-(2-pyrimidinyl)-1,3,5-triazin-2-amine;
4-[2-(difluoromethyl)-1H-benzimidazol-1-yl]-6-(4-morpholinyl)-N-(4-pyrimidinyl)-1,3,5-triazin-2-amine;
4-[2-(difluoromethyl)-1H-benzimidazol-1-yl]-6-(4-morpholinyl)-N-(5-pyrimidinyl)-1,3,5-triazin-2-amine;
4-[2-(difluoromethyl)-1H-benzimidazol-1-yl]-N-(4-methoxy-3-pyridinyl)-6-(4-morpholinyl)-1,3,5-triazin-2-amine;
4-[2-(difluoromethyl)-4-methoxy-1H-benzimidazol-1-yl]-N-(6-fluoro-3-pyridinyl)-6-(4-morpholinyl)-1,3,5-triazin-2-amine;
N-(6-chloro-3-pyridinyl)-4-[2-(difluoromethyl)-4-methoxy-1H-benzimidazol-1-yl]-6-(4-morpholinyl)-1,3,5-triazin-2-amine;
4-(2-(difluoromethyl)-4-methoxy-1H-benzimidazol-1-yl)-N-(6-methoxypyrimidin-4-yl)-6-morpholino-1,3,5-triazin-2-amine;
4-[2-(difluoromethyl)-4-methoxy-1H-benzimidazol-1-yl]-6-(4-morpholinyl)-N-(3-pyridazinyl)-1,3,5-triazin-2-amine; and
4-[2-(difluoromethyl)-4-methoxy-1H-benzimidazol-1-yl]-N-(6-methoxy-3-pyridazinyl)-6-(4-morpholinyl)-1,3,5-triazin-2-amine;
and enantiomers, mixtures of enantiomers, or mixtures of two or more diastereomers thereof; and pharmaceutically acceptable salts, solvates, hydrates, and prodrugs thereof.

In still another embodiment, provided herein is a compound selected from:
4-(4-(2-(difluoromethyl)-4-methoxy-1H-benzo[d]imidazol-1-yl)-7-(pyridin-3-yl)-6,7-dihydro-5H-pyrrolo[2,3-d]pyrimidin-2-yl)morpholine;
4-(4-(2-(difluoromethyl)-4-methoxy-1H-benzo[d]imidazol-1-yl)-7-(pyridin-3-yl)-7H-pyrrolo[2,3-d]pyrimidin-2-yl)morpholine;
4-(6-(2-(difluoromethyl)-4-methoxy-1H-benzo[d]imidazol-1-yl)-9-(pyridin-3-yl)-9H-purin-2-yl)morpholine;
4-(7-(2-(difluoromethyl)-4-methoxy-1H-benzo[d]imidazol-1-yl)-3-(pyridin-3-yl)-3H-[1,2,3]triazolo[4,5-d]pyrimidin-5-yl)morpholine;
4-(2-(2-(difluoromethyl)-4-methoxy-1H-benzo[d]imidazol-1-yl)-9-(pyridin-3-yl)-9H-purin-6-yl)morpholine;

4-(5-(2-(difluoromethyl)-4-methoxy-1H-benzo[d]imidazol-1-yl)-3-(pyridin-3-yl)-3H-[1,2,3]triazolo[4,5-d]pyrimidin-7-yl)morpholine;

2-[2-(difluoromethyl)-4-methoxy-1H-benzo[d]imidazol-1-yl]-6-(4-morpholinyl)-9-(3-pyridinyl)-9H-purine;

2-[2-(difluoromethyl)-4-methoxy-1H-benzo[d]imidazol-1-yl]-6-(4-morpholinyl)-9-(5-pyrimidinyl)-9H-purine;

6-[2-(difluoromethyl)-4-methoxy-1H-benzo[d]imidazol-1-yl]-2-(4-morpholinyl)-9-(3-pyridinyl)-9H-purine; and 6-[2-(difluoromethyl)-4-methoxy-1H-benzimidazol-1-yl]-2-(4-morpholinyl)-9-(5-pyrimidinyl)-9H-purine;

and enantiomers, mixtures of enantiomers, or mixtures of two or more diastereomers thereof; and pharmaceutically acceptable salts, solvates, hydrates, and prodrugs thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexane-sulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In certain embodiments, the compounds provided herein are pharmacologically acceptable salts of the compounds with one or more of hydrochloric, sulfuric, phosphoric, acetic, citric, oxalic, malonic, salicylic, malic, fumaric, succinic, ascorbic, maleic, methanesulfonic, and isoethonic acids; or with one or more of potassium carbonate, sodium or potassium hydroxide, ammonia, triethylamine, and triethanolamine.

The compound provided herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs*

1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

The compound provided herein can be prepared, isolated, or obtained by any method known to one of skill in the art, and the following examples are only representative and do not exclude other related procedures.

For example, the compounds of Formula I can be prepared via aromatic substitution of a halo-1,3,5-triazine or halo-pyrimidine, e.g., chloro-1,3,5-triazine 1, with HUR$^6$ (Method A), as illustrated in Scheme 1, where U is N, O, or S.

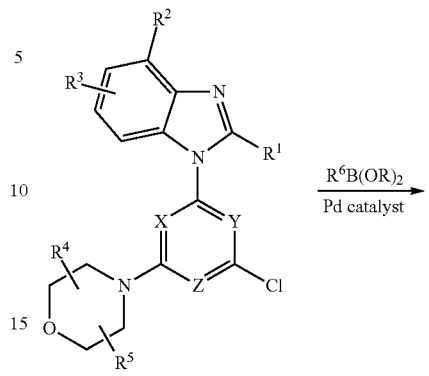

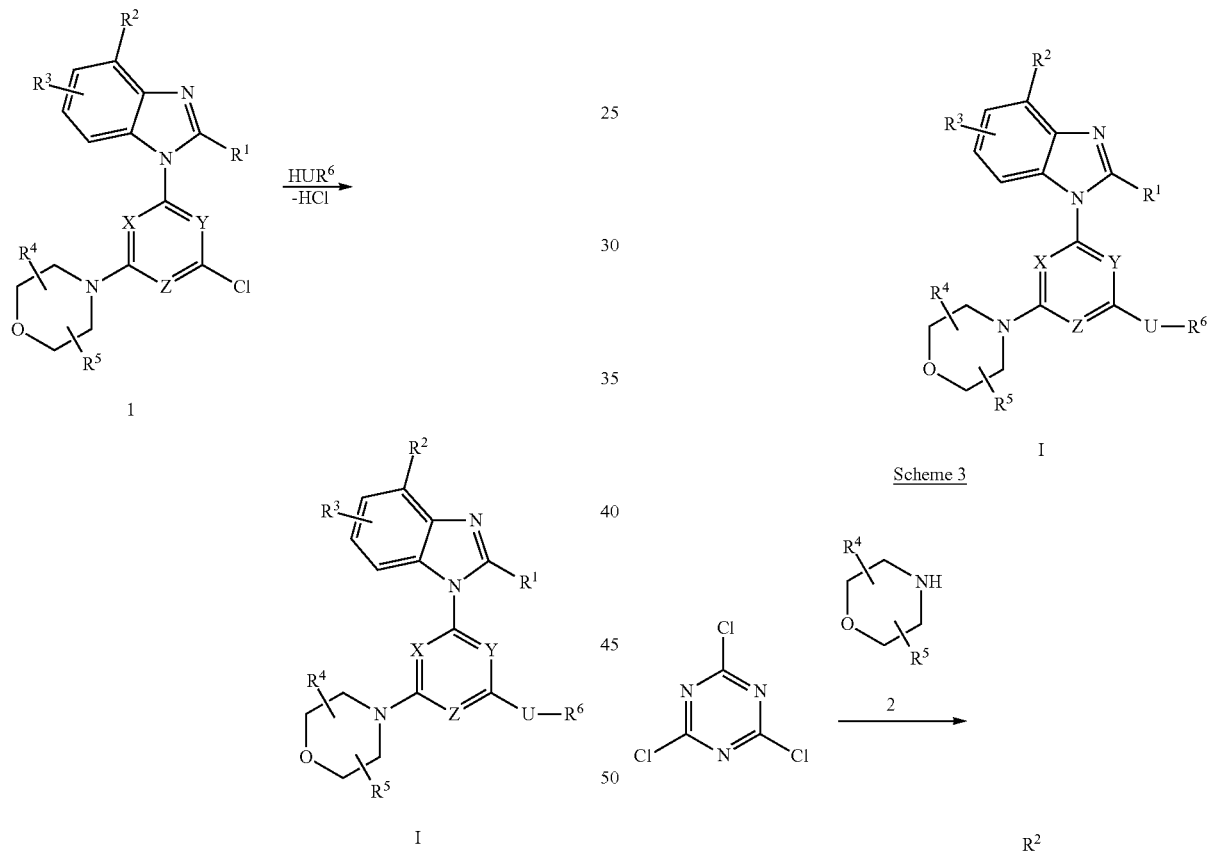

The compounds of Formula I where U is a direct bond can be prepared via the replacement of a halo group of a halo-1,3,5-triazine or halopyrimidine with an R$^6$ group, e.g., via Suzuki coupling by using a boronic acid or boronate ester of R$^6$ under palladium catalyzed reaction conditions (Method B), as illustrated in Scheme 2, where R is hydrogen or alkyl.

The halo-1,3,5-triazine or halo-pyrimidine used in Methods A and B can also be prepared, isolated, or obtained by any method known to one of skill in the art. For example, the halo-1,3,5-triazine can be prepare via aromatic substitution reactions of chlorotriazine with two different amines, compounds 2 and 4, as shown in Scheme 3.

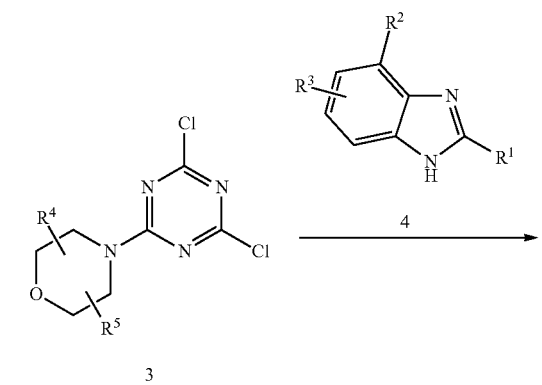

-continued

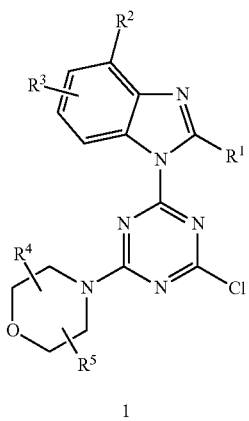

1

The compounds of Formula I can also be prepared by the combination of a benzimidazole unit with a pyrimidinyl or 1,3,5-triazinyl unit containing a preformed U—R$^6$ bond (Method C), as illustrated in Scheme 4.

The benzimidazole 4 used in Schemes 3 and 4 can also be prepared, isolated, or obtained by any method known to one of skill in the art. For example, the benzimidazle 4 can be as shown in Scheme 5.

Scheme 4

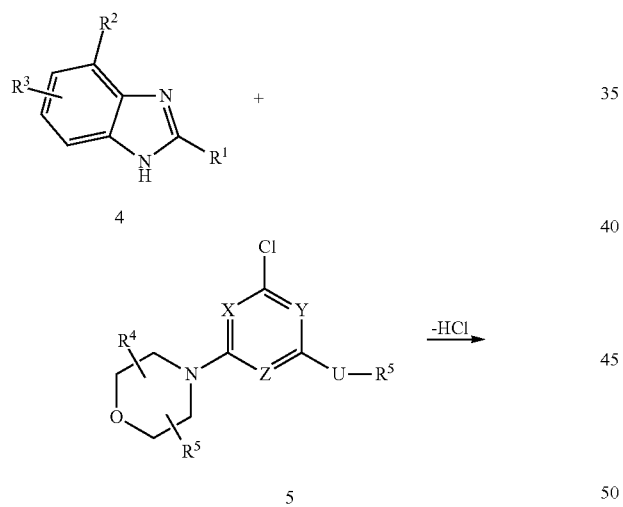

-continued
Scheme 5

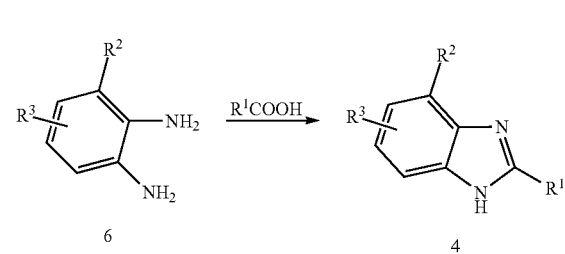

The compounds of Formula I can be prepared by the modification of existing compounds of Formula I (Method D), such as illustrated in Scheme 6, wherein $R^{1A}$, $R^{2A}$, $R^{3A}$, $R^{4A}$, $R^{5A}$, $R^{6A}$, and $U^A$ are defined the same as $R^1$, $R^2$, $R^3$, $R^4$, $R^5$ $R^6$, and U, respectively, but at least one of $R^{1A}$, $R^{2A}$, $R^{3A}$, $R^{4A}$, $R^{5A}$, $R^{6A}$, or $U^A$ is different from $R^1$, $R^2$, $R^3$, $R^4$, $R^5$, $R^6$, or U.

Scheme 6

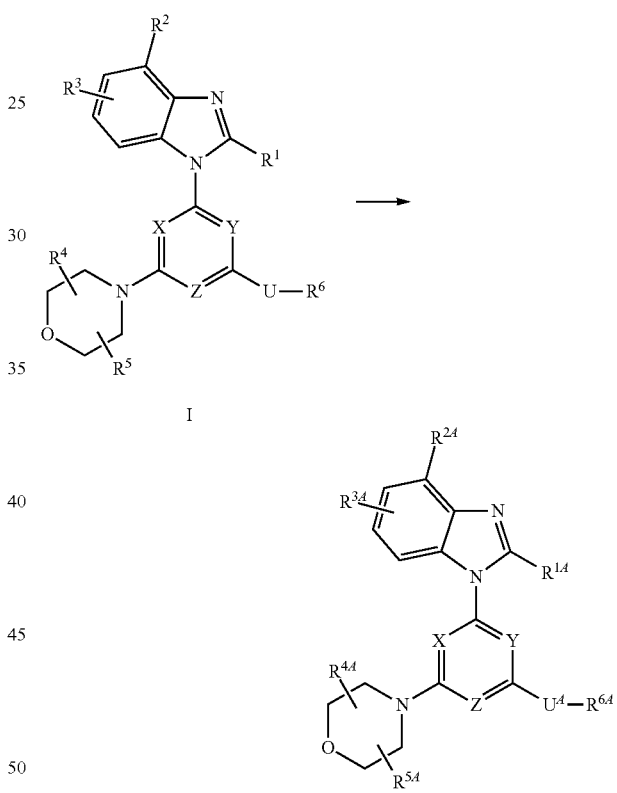

The compounds of Formula I, Ia, or Ib can also be prepared as shown in Scheme 7.

Scheme 7

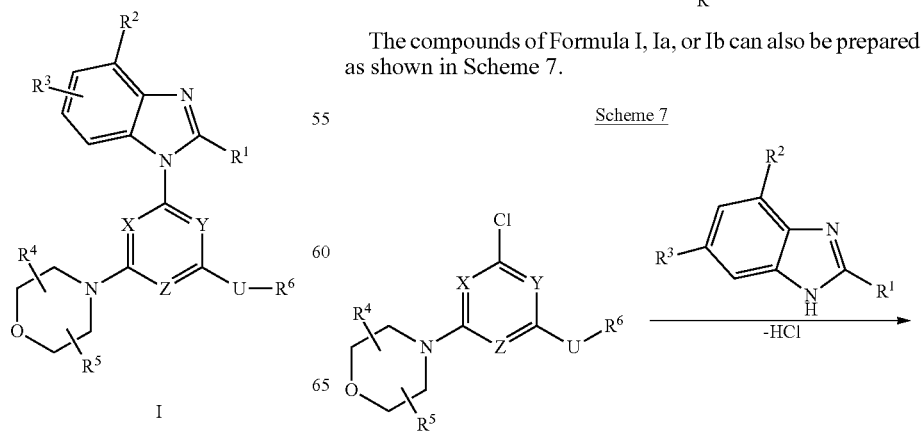

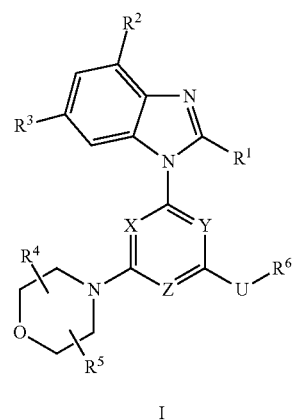

I

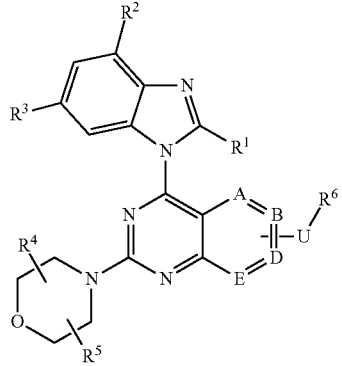

Ib

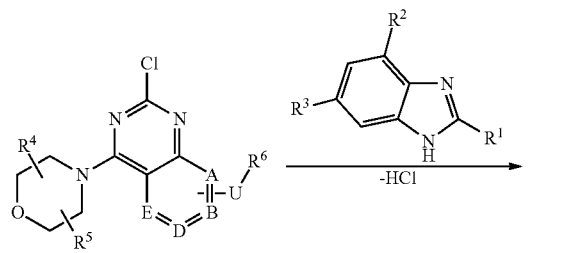

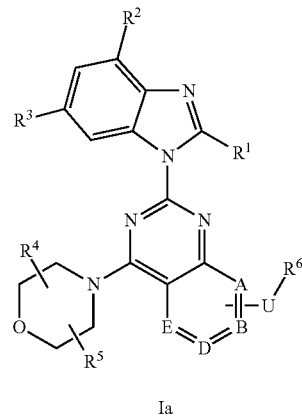

Ia

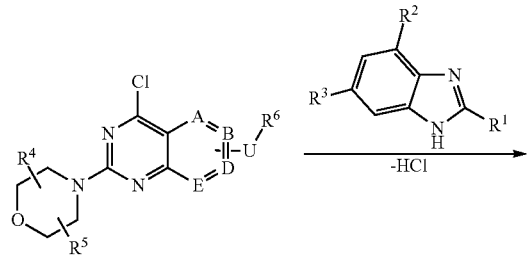

Pharmaceutical Compositions

In one embodiment, provided herein is a pharmaceutical composition comprising a compound of Formula I, IA, or IB as defined herein, and a pharmaceutically acceptable excipient, adjuvant, carrier, buffer, or stabiliser.

In one embodiment, the pharmaceutically acceptable excipient, adjuvant, carrier, buffer, or stabiliser is non-toxic and does not interfere with the efficacy of the active ingredient. The precise nature of the carrier or other material will depend on the route of administration, which may be oral or by injection, such as cutaneous, subcutaneous, or intravenous injection.

In another embodiment, the pharmaceutical compositions are provided in a dosage form for parenteral administration, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. Preservatives, stabilisers, buffers, antioxidants, and/or other additives may be included as required.

In one embodiment, the pharmaceutical compositions are provided in a dosage form for oral administration, which comprise the compound provided herein, and one or more pharmaceutically acceptable excipients or carriers. The pharmaceutical compositions provided herein that are formulated for oral administration may be in tablet, capsule, powder, or liquid form. A tablet may comprise a solid carrier or an adjuvant. Liquid pharmaceutical compositions generally comprise a liquid carrier such as water, petroleum, animal or vegetable oils, or mineral oil or synthetic oil. Physiological saline solution, dextrose or other saccharide solution, or glycols such as ethylene glycol, propylene glycol, or polyethylene glycol may be included. A capsule may comprise a solid carrier such as gelatin.

In yet another embodiment, the pharmaceutical compositions are provided in a dosage form for topical administration, which comprise the compound provided herein, and one or more pharmaceutically acceptable excipients or carriers.

The pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd Edition, Rathbone et al., Eds., Marcel Dekker, Inc.: New York, N.Y., 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In another embodiment, the pharmaceutical compositions provided herein further comprise one or more chemotherapeutic agents as defined herein.

In yet another embodiment, provided herein is the use of a compound of Formula I, IA, or IB in the manufacture of a medicament for the treatment of cancer. In certain embodiments, the medicament is in tablet, capsule, powder, or liquid form. In certain embodiments, the medicament is formulated as described herein.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided is a method of treating, preventing, or ameliorating one or more symptoms of a disorder, disease, or condition associated with PI3K activity in a subject, which comprises administering to the subject a therapeutically effective amount of the compound provided herein, e.g., a compound of Formula I, IA, or IB, including an enantiomer, a mixture of enantiomers, or a mixture of two or more diastereomers thereof; or a pharmaceutically acceptable salt, solvate, hydrate, or prodrug thereof.

In another embodiments, provided is a method of treating, preventing, or ameliorating one or more symptoms of a disorder, disease, or condition responsive to the modulation of PI3K activity in a subject, which comprises administering to the subject a therapeutically effective amount of the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof.

In yet another embodiment, provided is a method of treating, preventing, or ameliorating one or more symptoms of a disorder, disease, or condition mediated by a PI3K enzyme in a subject, which comprises administering to the subject a therapeutically effective amount of the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof.

In yet another embodiment, provided is a method of treating, preventing, or ameliorating one or more symptoms of cancer in a subject, which comprises administering to the subject a therapeutically effective amount of the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof.

In yet another embodiment, provided herein are uses of the compound provided herein, e.g., a compound of Formula I, IA, or IB, including an enantiomer, a mixture of enantiomers, or a mixture of two or more diastereomers thereof; or a pharmaceutically acceptable salt, solvate, hydrate, or prodrug thereof, in the manufacture of a medicament for the treatment of cancer.

In certain embodiments, the compound selectively targets the p110α subunit of PI3K. In certain embodiments, the compound selectively inhibits the PI3K via its interaction with its p110α subunit. In certain embodiments, the compound selectively alkylates the p110α subunit of PI3K.

In certain embodiments, the PI3K is a wild type PI3K. In certain embodiments, the PI3K is a PI3K mutant.

In certain embodiments, the PI3K is a Class I kinase. In certain embodiments, the PI3K is p110α, p110β, p110δ, or p110γ. In certain embodiments, the PI3K is a wild type of a Class I kinase. In certain embodiments, the PI3K is a mutant of a Class I kinase.

In certain embodiments, the PI3K is p110α. In certain embodiments, the PI3K is a wild type of p110α. In certain embodiments, the PI3K is a p110α mutant. In certain embodiments, the p110α mutant is R38H, G106V, K111N, K227E, N345K, C420R, P539R, E542K, E545A, E545G, E545K, Q546K, Q546P, E453Q, H710P, I800L, T1025S, M1043I, M1043V, H1047L, H1047R, or H1047Y. In certain embodiments, the p110α mutant is R38H, K111N, N345K, C420R, P539R, E542K, E545A, E545G, E545K, Q546K, Q546P, I800L, T1025S, M1043I, H1047L, H1047R, or H1047Y. In certain embodiments, the p110α mutant is C420R, E542K, E545A, E545K, Q546K, I800L, M1043I, H1047L, or H1047Y.

In certain embodiments, the PI3K is a Class IV kinase. In certain embodiments, the PI3K is a wild type of a Class IV kinase. In certain embodiments, the PI3K is a mutant of a Class IV kinase. In certain embodiments, the PI3K is mTOR, ATM, ATR, or DNA-PK. In certain embodiments, the PI3K is mTOR.

In one embodiment, the subject is a mammal. In another embodiment, the subject is a human. In yet another embodiment, the subject is a primate other than a human, a farm animal such as cattle, a sport animal, or a pet such as a horse, dog, or cat.

In certain embodiments, the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof; has improved pharmacokinetic properties (e.g., solubility, bioavailability, volume of distribution, AUC, $C_{max}$, steady state concentration, percentage of protein binding, $t_{1/2}$, rate of elimination, clearance, renal clearance, metabolic clearance, elimination rate constant, and/or toxicity) as compared to known PI3K inhibitors.

In certain embodiments, the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof; has a half-life in a subject ranging from about 10 min to about 100 hrs, from about 20 min to about 50 hrs, from about 1 to about 25 hrs, or from about 2 to 10 hrs.

In certain embodiments, the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof; is administered daily in a single dose or divided doses for a total daily dose sufficient to achieve a plasma concentration of the compound at steady state ranging from about 0.001 to about 100, from about 0.01 to about 10, from about 0.1 to about 5, or from about 0.1 to about 1 µM. As used herein, the term "plasma concentration at steady state" is the concentration reached after a period of administration of a compound. Once steady state is reached, there are minor peaks and troughs on the time dependent curve of the plasma concentration of the compound administered.

In certain embodiments, the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof; is administered in a single dose or divided doses for a total daily dose sufficient to achieve a $C_{max}$ ranging from about 0.1 to about 100, from about 0.2 to about 50, from about 0.5 to about 25, or from about 1 to about 10 µM.

In certain embodiments, the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof; is administered in a single dose or divided doses for a total daily dose sufficient to achieve a $C_{max}$ ranging from about 0.1 to about 100, from about 0.2 to about 50, from about 1 to about 20, or from about 1 to about 10 µg/mL.

In certain embodiments, the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof; is administered in a single dose or divided doses for a total daily dose sufficient to achieve an AUC ranging from about 1 to about 1,000, from about 10 to about 500, from about 20 to about 250, or from about 50 to about 100 µg*hr/mL.

In certain embodiments, the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof; is administered in a single dose or divided doses for a total daily dose sufficient to achieve an AUC ranging from about 1 to about 1,000, from about 10 to about 500, from about 20 to about 250, or from about 50 to about 100 µM*hr.

The disorders, diseases, or conditions treatable with the compound provided herein, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, non-secretory myeloma, osteosclerotic myeloma, plasma cell leukemia, solitary plasmacytoma, and extramedullary plasmacytoma; (6) Waldenström's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of the disorders, diseases, or conditions described herein, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided herein are methods of modulating PI3K activity, comprising contacting a PIK3 enzyme with the compound provided herein, e.g., the compound of Formula I, IA, or IB, including an enantiomer, a mixture of enantiomers, or a mixture of two or more diastereomers thereof; or a pharmaceutically acceptable salt, solvate, hydrate, or prodrug thereof. In one embodiment, the PIK3 enzyme is inside a cell.

In certain embodiments, the PI3K is a wild PI3K. In certain embodiments, the PI3K is a PI3K mutant.

In certain embodiments, the PI3K is a Class I kinase. In certain embodiments, the PI3K is p110α, p110β, p110δ, or p110γ. In certain embodiments, the PI3K is a wild type of a Class I kinase. In certain embodiments, the PI3K is a mutant of a Class I kinase.

In certain embodiments, the PI3K is p110α. In certain embodiments, the PI3K is a wild type of p110α. In certain embodiments, the PI3K is a p110α mutant. In certain embodiments, the p110α mutant is R38H, G106V, K111N, K227E, N345K, C420R, P539R, E542K, E545A, E545G, E545K, Q546K, Q546P, E453Q, H710P, I800L, T1025S, M1043I, M1043V, H1047L, H1047R, or H1047Y. In certain embodiments, the p110α mutant is R38H, K111N, N345K, C420R, P539R, E542K, E545A, E545G, E545K, Q546K, Q546P, I800L, T1025S, M1043I, H1047L, H1047R, or H1047Y. In certain embodiments, the p110α mutant is C420R, E542K, E545A, E545K, Q546K, I800L, M1043I, H1047L, or H1047Y.

In certain embodiments, the PI3K is a Class IV kinase. In certain embodiments, the PI3K is a wild type of a Class IV kinase. In certain embodiments, the PI3K is a mutant of a Class IV kinase. In certain embodiments, the PI3K is mTOR, ATM, ATR, or DNA-PK. In certain embodiments, the PI3K is mTOR.

In certain embodiments, the compounds provided herein, e.g., a compound of Formula I, IA, or IB, including an enantiomer, a mixture of enantiomers, or a mixture of two or more diastereomers thereof; or a pharmaceutically acceptable salt, solvate, hydrate, or prodrug thereof, show inhibitory activity against a PI3K and a mutant thereof.

In certain embodiments, the compounds provided herein, e.g., a compound of Formula I, IA, or IB, including an enantiomer, a mixture of enantiomers, or a mixture of two or more diastereomers thereof; or a pharmaceutically acceptable salt, solvate, hydrate, or prodrug thereof, show inhibitory activity against a wild type of a PI3K. In certain embodiments, the PI3K is p110α. In certain embodiments, the PI3K is mTOR.

In certain embodiments, the compounds provided herein, e.g., a compound of Formula I, IA, or IB, including an enantiomer, a mixture of enantiomers, or a mixture of two or more diastereomers thereof; or a pharmaceutically acceptable salt, solvate, hydrate, or prodrug thereof, show inhibitory activity against a PI3K mutant. In certain embodiments, the PI3K mutant is a PI3K mutant. In certain embodiments, the PI3K mutant is a p110α mutant. In certain embodiments, the p110α mutant is C420R, E542K, E545A, E545K, Q546K, 1800L, M1043I, H1047L, or H1047Y.

The compounds provided herein, e.g., a compound of Formula I, IA, or IB, including an enantiomer, a mixture of enantiomers, or a mixture of two or more diastereomers thereof; or a pharmaceutically acceptable salt, solvate, hydrate, or prodrug thereof, can also be combined or used in combination with other agents or therapies useful in the treatment, prevention, or amelioration of one or more symptoms of the disorders, diseases, or conditions for which the compounds provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, infectious diseases, and those pathologies noted herein.

Suitable other therapeutic agents can also include, but are not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

In certain embodiments, the other therapies that may be used in combination with the compounds provided herein include, but are not limited to, surgery, endocrine therapy, biologic response modifiers (e.g., interferons, interleukins, and tumor necrosis factor (TNF)), hyperthermia and cryotherapy, and agents to attenuate any adverse effects (e.g., antiemetics).

In certain embodiments, the other therapeutic agents that may be used in combination with the compounds provided herein include, but are not limited to, alkylating drugs (mechlorethamine, chlorambucil, cyclophosphamide, melphalan, and ifosfamide), antimetabolites (cytarabine (also known as cytosine arabinoside or Ara-C), HDAC (high dose cytarabine), and methotrexate), purine antagonists and pyrimidine antagonists (6-mercaptopurine, 5-fluorouracil, cytarbine, and gemcitabine), spindle poisons (vinblastine, vincristine, and vinorelbine), podophyllotoxins (etoposide, irinotecan, and topotecan), antibiotics (daunorubicin, doxorubicin, bleomycin, and mitomycin), nitrosoureas (carmustine and lomustine), enzymes (asparaginase), and hormones (tamoxifen, leuprolide, flutamide, and megestrol), imatinib, adriamycin, dexamethasone, and cyclophosphamide. For a more comprehensive discussion of updated cancer therapies; See, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In another embodiment, the method provided herein comprises administration of a compound of Formula I, IA, or IB, together with administering one or more chemotherapeutic agents and/or therapies selected from: alkylation agents (e.g., cisplatin, carboplatin); antimetabolites (e.g., methotrexate and 5-FU); antitumour antibiotics (e.g., adriamymycin and bleomycin); antitumour vegetable alkaloids (e.g., taxol and etoposide); antitumor hormones (e.g., dexamethasone and tamoxifen); antitumour immunological agents (e.g., interferon $\alpha$, $\beta$, and $\gamma$); radiation therapy; and surgery. In certain embodiments, the one or more chemotherapeutic agents and/or therapies are administered to the subject before, during, or after the administration of the compound of Formula I, IA, or IB as defined herein.

Such other agents, or drugs, can be administered, by a route and in an amount commonly used therefor, simultaneously or sequentially with the compounds provided herein, e.g., a compound of Formula I, IA, or IB, including a single enantiomer, a mixture of enantiomers, or a mixture of diastereomers thereof; or a pharmaceutically acceptable salt, solvate, or prodrug thereof. When the compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to the compound provided herein.

The weight ratio of the compound provided herein to the second active ingredient can be varied, and will depend upon the effective dose of each ingredient. Generally, an effective dose of each will be used. Thus, for example, when the compound provided herein is combined with a NSAID, the weight ratio of the compound to the NSAID can range from about 1,000:1 to about 1:1,000, or about 200:1 to about 1:200. Combinations of the compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of the compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); M (molar); mM (millimolar); µM (micromolar); eq. (equivalent); Hz (Hertz); MHz (megahertz); mmol (millimoles); hr or hrs (hours); min (minutes); mp (melting point); HRMS (high resolution mass spectrometry); FAB, (fast atom bambardment); aq. (aqueous); DMF (dimethylormamide); DMSO (dimethylsulfoxide); DMSO-$d_6$ (deuterated dimethylsulfoxide); EtOH (ethanol); EtOAc (ethyl acetate); i-Pr$_2$O (diisopropyl ether); MeOH (methanol); THF (tetrahydrofuran); DIPEA (N,N-diisopropylethylamine); DMAP (dimethylaminopyridine); HOAc (acetic acid); LDA (lithium diisopropylamine); TFA (trifluoroacetic acid); EDCI (1-ethyl-3-(3'-dimethylamino-propyl)carbodiimide); CDI, (N,N'-carbonyldiimidazole); TBDMSCl (tert-butylchlorodimethylsilane); TBAF (tetra-n-butylammonium fluoride); Me (methyl); Et (ethyl); $PdCl_2(dppf)$, ((1,1'-bis(diphenylphosphino)ferrocene) dichloropalladium(II)); NaHMDS [sodium hexamethyldisilazane or sodium bis(trimethylsilyl)amide)]; and EDTA (ethylenediaminetetraacetic acid).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated herein are intended to exemplify the applicable chemistry through the use of specific examples and are not indicative of the scope of the disclosure.

General Experimental Information.

Elemental analyses (combustion analysis) were carried out in the Microchemical Laboratory, University of Otago, Dunedin, New Zealand. Melting points were determined on an Electrothermal 9100 Melting Point Apparatus. NMR spectra were obtained on a Bruker Avance-400 spectrometer at 400 MHz for $^1H$ and 100 MHz for $^{13}C$ spectra, referenced to TMS ($Si(CH_3)_4$). Mass spectra were determined on a VG-70SE mass spectrometer using an ionizing potential of 70 eV at a nominal resolution of 1,000. High-resolution spectra were obtained at nominal resolutions of 3,000, 5,000, or 10,000 as appropriate. All MS spectra were obtained as electron impact (EI) using perfluorokerosene (PFK) as a reference unless otherwise stated. Column chromatography was carried out on silica gel (Merck 230-400 mesh), unless otherwise stated.

Example 1

Synthesis of 4-[2-(difluoromethyl)-1H-benzimidazol-1-yl]-6-(4-morpholinyl)-N-(3-pyridinyl)-1,3,5-triazin-2-amine

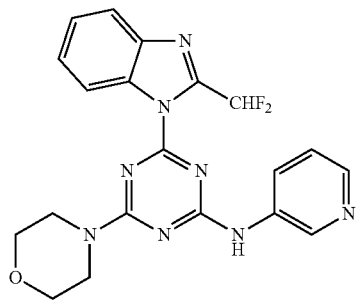 [SMILES: FC(F)c1nc2ccccc2n1-c1nc(Nc2cccnc2)nc(N2CCOCC2)n1]

The compound was synthesized according to Method A.

1-[4-Chloro-6-(4-morpholinyl)-1,3,5-triazin-2-yl]-2-(difluoromethyl)-1H-benzimidazole (U.S. Pat. Appl. Publ. No. US 2007/244110) (0.183 g, 0.5 mmol) was added to a mixture of 3-aminopyridine (0.20 g, 2 mmol) and LDA (1.0 mL, 2 M in THF, 2 mmol) in 10 mL THF at room temperature. After 5 min, the mixture was neutralized with HOAc, diluted with water, extracted with EtOAc, and dried ($Na_2SO_4$). Chromatography on alumina eluting with $CH_2Cl_2$/EtOAc (4:1) gave a solid, which was recrystallized from i-$Pr_2O$ to give 92 mg (43% yield) of (4-[2-(difluoromethyl)-1H-benzimidazol-1-yl]-6-(4-morpholinyl)-N-(3-pyridinyl)-1,3,5-triazin-2-amine: mp (i-$Pr_2O$) 228-230° C.; $^1H$ NMR ($CDCl_3$) δ 8.86 (br, 1H), 8.42 (d, J=2.0 Hz, 1H), 8.38 (d, J=6.2 Hz, 1H), 7.98 (d, J=8.2 Hz, 1H), 7.89 (dd, J=6.2, 2.9 Hz, 1H), 7.58 (br t, $J_{HF}$=53.8 Hz, 1H), 7.42 (m, 2H), 7.34 (dd, J=8.3, 4.7 Hz, 1H), 7.28 (m, exchangeable with $D_2O$, 1H), 3.93 (m, 4H), 3.82 (m, 4H); Anal. Calcd. for $C_{20}H_{18}F_2N_8O$: C, 56.6; H, 4.3; N, 26.4. Found: C, 56.5; H, 4.4; N, 26.1%.

Example 2

Synthesis of 4-[2-(difluoromethyl)-4-methoxy-1H-benzimidazol-1-yl]-6-(4-morpholinyl)-N-(3-pyridinyl)-1,3,5-triazin-2-amine

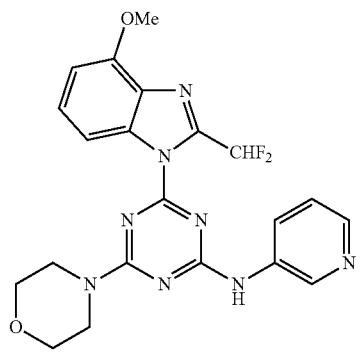 [SMILES: COc1cccc2c1nc(C(F)F)n2-c1nc(Nc2cccnc2)nc(N2CCOCC2)n1]

The compound was synthesized according to Method A.

2-Amino-3-methoxynitrobenzene (15.10 g, 0.09 mol) was hydrogenated over palladium on carbon in methanol, and the solution was filtered through celite into a methanolic HCl solution. The solvent was removed under vacuum and the resulting hydrochloride salt was combined with difluoroacetic acid (19.2 g, 0.18 mol) and 4 M HCl (100 mL). The mixture was heated under reflux for 3 hr, diluted with water, decolourized with charcoal, and filtered through celite. Neutralization with aqueous ammonia gave 2-difluoromethyl-4-methoxy-1H-benzimidazole (15.2 g, 84%) as a solid: $^1H$ NMR ($CDCl_3$) (tautomeric mixture) δ 9.95-9.70 (m, exchangeable with $D_2O$, 1H), 7.44 (br d, J=7.9 Hz, 0.4H), 7.31-7.24 (m, 1H), 7.12 (br d, J=8.0 Hz, 0.5H), 6.89 (t, $J_{HF}$=53.8 Hz, 1H), 6.82-6.74 (m, 1H), 4.03 and 3.98 (2s, 3H).

A mixture of 3.96 g (20 mmol) of the above benzimidazole, 4.70 g (20 mmol) of 2,4-dichloro-6-(4-morpholinyl)-1,3,5-triazine, and 22 g (80 mmol) of powdered $K_2CO_3$ in 150 mL of DMF at room temperature was stirred rapidly for 3 hr and then diluted with water. The resulting precipitate was collected, washed with water, and then with cold ethanol, and dried to give 6.82 g (86%) of 1-[4-chloro-6-(4-morpholinyl)-1,3,5-triazin-2-yl]-2-(difluoromethyl)-4-methoxy-1H-benzimidazole: mp ($CHCl_3$/EtOH) 263-266° C.; $^1H$ NMR ($CDCl_3$) δ 7.99 (d, J=8.4 Hz, 1H), 7.48 (t, $J_{HF}$=53.4 Hz, 1H), 7.40 (t, J=8.3 Hz, 1H), 6.86 (d, J=8.1 Hz, 1H), 4.05 (s, 3H), 3.96 (m, 4H), 3.82 (m, 4H); Anal. Calcd. for $C_{16}H_{15}ClF_2N_6O_2$: C, 48.4; H, 3.8; N, 21.2. Found: C, 48.3; H, 3.8; N, 21.1%.

To a solution of 3-aminopyridine (1.88 g, 20 mmol) in 100 mL THF was added LDA (10 mL, 2 M in THF; 20 mmol) and to the resulting suspension was added 1.99 g (5 mmol) of 1-[4-chloro-6-(4-morpholinyl)-1,3,5-triazin-2-yl]-2-(difluoromethyl)-4-methoxy-1H-benzimidazole at room temperature. After 5 min. the reaction was neutralized with acetic acid and diluted with water. After the pH was made slightly alkaline with aq. $NH_3$, the precipitate was collected, washed with hot water, and dried. Recrystallization from EtOH (using CH₂Cl₂ to aid initial solubility) gave 1.65 g (73% yield) of 4-[2-(difluoromethyl)-4-methoxy-1H-benzimidazol-1-yl]-6-(4-morpholinyl)-N-(3-pyridinyl)-1,3,5-triazin-2-amine: mp 221-223° C.; ¹H NMR (CDCl₃) δ 8.86 (br, 1H), 8.42 (d, J=2.0 Hz, 1H), 7.99 (d, J=7.8 Hz, 1H), 7.92 (d, J=8.1 Hz, 1H), 7.48 (br t, $J_{HF}$=53.6 Hz, 1H), 7.35-7.31 (m, 2H), 7.22 (m, exchangeable with D₂O, 1H), 6.82 (d, J=8.0 Hz, 1H), 4.04 (s, 3H), 3.92 (m, 4H), 3.81 (m, 4H); Anal. Calcd. for C₂₁H₂₀F₂N₈O₂: C, 55.5; H, 4.4; N, 24.7. Found: C, 55.5; H, 4.4; N, 24.4%.

A suspension of 4-[2-(difluoromethyl)-4-methoxy-1H-benzimidazol-1-yl]-6-(4-morpholinyl)-N-(3-pyridinyl)-1,3,5-triazin-2-amine in MeOH was treated with a slight excess of methanesulfonic acid, to give a clear solution. Addition of EtOAc gave a precipitate, which was collected by filtration and washed with EtOAc. Recrystallization from MeOH/EtOAc gave 4-[2-(difluoromethyl)-4-methoxy-1H-benzimidazol-1-yl]-6-(4-morpholinyl)-N-(3-pyridinyl)-1,3,5-triazin-2-amine methanesulfonate: mp 279-282° C.; ¹H NMR (d₆-DMSO) δ 10.63 (s, exchangeable with D₂O, 1H), 9.19 (s, 1H), 8.55 (d, J=5.5 Hz, 1H), 8.53 (m, 1H), 8.08 (m, 1H), 7.90 (dd, J=8.5, 5.4 Hz, 1H), 7.82 (br t, $J_{HF}$=53.0 Hz, 1H), 7.43 (t, J=8.2 Hz, 1H), 6.98 (d, J=7.8 Hz, 1H), 4.56 (br m, exchangeable with D₂O, 1H), 3.99 (s, 3H), 3.86 (m, 4H), 3.75 (m, 4H); Anal. Calcd. for C₂₂H₂₄F₂N₈O₅S: C, 48.0; H, 4.4; N, 20.4. Found: C, 47.8; H, 4.4; N, 20.2%.

Example 3

Synthesis of 4-[2-(difluoromethyl)-4-methoxy-1H-benzimidazol-1-yl]-N-methyl-6-(4-morpholinyl)-N-(3-pyridinyl)-1,3,5-triazin-2-amine

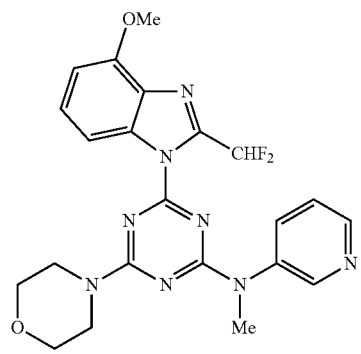 [SMILES: COc1cccc2c1nc(C(F)F)n2-c1nc(N2CCOCC2)nc(N(C)c2cccnc2)n1]

The compound was synthesized according to Method D.

A solution of 4-[2-(difluoromethyl)-4-methoxy-1H-benzimidazol-1-yl]-6-(4-morpholinyl)-N-(3-pyridinyl)-1,3,5-triazin-2-amine (0.544 g, 1 mmol) in 15 mL DMF was treated with of NaH and then a slight excess iodomethane was added. After 10 min, the reaction was neutralized with acetic acid and diluted with water. After the pH was made slightly alkaline with aq. NH₃, the precipitate was collected and dried. Chromatography on alumina eluting with CH₂Cl₂/EtOAc (9:1) gave 0.26 g (53% yield) of 4-[2-(difluoromethyl)-4-methoxy-1H-benzimidazol-1-yl]-N-methyl-6-(4-morpholinyl)-N-(3-pyridinyl)-1,3,5-triazin-2-amine: mp (MeOH) 200-201° C.; ¹H NMR (DMSO-d₆) δ 8.67 (d, J=2.2 Hz, 1H), 8.55 (d, J=4.1 Hz, 1H), 7.89 (ddd, J=8.1, 2.6, 1.5 Hz, 1H), 7.70-7.29 (m, 3H), 6.90 (d, J=8.0 Hz, 1H), 3.94 (s, 3H), 3.84-3.61 (m, 8H), 3.55 (s, 3H); Anal. Calcd. for C₂₂H₂₂F₂N₈O₂: C, 56.4; H, 4.7; N, 23.9. Found: C, 56.5; H, 4.75; N, 24.5%.

Example 4

Synthesis of 4-[2-(methylsulfanyl)-1H-benzimidazol-1-yl]-6-(4-morpholinyl)-N-(3-pyridinyl)-1,3,5-triazin-2-amine

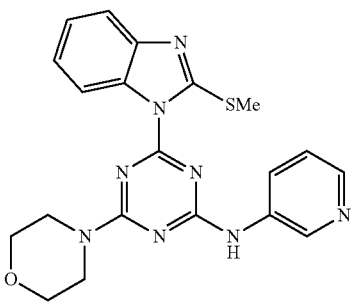 [SMILES: CSc1nc2ccccc2n1-c1nc(Nc2cccnc2)nc(N2CCOCC2)n1]

The compound was synthesized according to Method A.

A mixture of 2-(methylsulfanyl)-1H-benzimidazole (1.64 g, 10 mmol), 2,4-dichloro-6-(4-morpholinyl)-1,3,5-triazine (2.35 g, 10 mmol), and powdered K₂CO₃ (11 g, 80 mmol) in DMF (50 mL) was stirred at room temperature for 1 hr. The mixture was diluted with water and the resulting precipitate was collected, washed with water and then ethanol, and dried to give 3.56 g (98% yield) of 1-[4-chloro-6-(4-morpholinyl)-1,3,5-triazin-2-yl]-2-(methylsulfanyl)-1H-benzimidazole: mp (CHCl₃/EtOH) 260-261° C.; ¹H NMR (CDCl₃) δ 8.42 (br dd, J=7.0, 1.9 Hz, 1H), 7.65 (br dd, J=6.8, 1.9 Hz, 1H), 7.30 (m, 2H), 4.06 (m, 2H), 3.95 (m, 2H), 3.84 (m, 2H), 3.80 (m, 2H), 2.74 (s, 3H); Anal. Calcd. for C₁₅H₁₅ClN₆OS: C, 49.65; H, 4.2; N, 23.2. Found: C, 49.8; H, 4.1; N, 23.1%.

A solution of 3-aminopyridine (2 g, 21 mmol) in 100 mL THF was treated with 10.6 mL (21 mmol) 2 M LDA in THF to give a suspension which was treated with 1.81 g (5 mmol) of 1-[4-chloro-6-(4-morpholinyl)-1,3,5-triazin-2-yl]-2-(methylsulfanyl)-1H-benzimidazole at room temperature. After 5 min, the mixture was neutralized with HOAc and diluted with water to give 1.65 g (78%) of 4-[2-(methylsulfanyl)-1H-benzimidazol-1-yl]-6-(4-morpholinyl)-N-(3-pyridinyl)-1,3,5-triazin-2-amine: mp (CHCl₃/EtOH) 240-241° C.; ¹H NMR (CDCl₃) δ 8.85 (br s, 1H), 8.39 (d, J=4.0 Hz, 1H), 8.34 (d, J=7.5 Hz, 1H), 8.02 (d, J=7.3 Hz, 1H), 7.66 (dd, J=7.9, 0.5 Hz, 1H), 7.32 (dd, J=8.5, 4.9 Hz, 1H), 7.28 (dt, J=7.3, 1.1 Hz, 1H), 7.22 (t, J=7.4 Hz, 1H), 7.15 (br s, exchangeable with D₂O, 1H), 4.05 (m, 2H), 3.90 (m, 2H), 3.81 (m, 4H), 2.73 (s, 3H); Anal. Calcd. for C₂₀H₂₀N₈OS: C, 57.1; H, 4.8; N, 26.65. Found: C, 57.0; H, 4.9; N, 27.0%.

Example 5

Synthesis of 4-[2-(methylsulfonyl)-1H-benzimidazol-1-yl]-6-(4-morpholinyl)-N-(3-pyridinyl)-1,3,5-triazin-2-amine

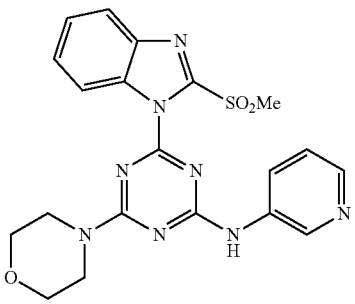 [SMILES: CS(=O)(=O)c1nc2ccccc2n1-c1nc(Nc2cccnc2)nc(N2CCOCC2)n1]

The compound was synthesized according to Method D.

A solution of 0.421 g (1 mmol) of 4-[2-(methylsulfanyl)-1H-benzimidazol-1-yl]-6-(4-morpholinyl)-N-(3-pyridinyl)-1,3,5-triazin-2-amine (from Example 4) in 130 mL acetone and 20 mL HOAc was treated with 1 g KMnO$_4$ in 10 mL water at room temperature. After 30 min, the reaction was decolorized with aq. Na$_2$SO$_3$ solution and the acetone was removed under vacuum. The residue was diluted with water and the pH adjusted to neutral to give a precipitate which was dissolved in CHCl$_3$ and dried. Chromatography on alumina, eluting with CHCl$_3$/EtOAc (9:1) gave 140 mg (31%) of 4-[2-(methylsulfonyl)-1H-benzimidazol-1-yl]-6-(4-morpholinyl)-N-(3-pyridinyl)-1,3,5-triazin-2-amine: mp (MeOH) 208-211° C.; $^1$H NMR (CDCl$_3$) 8.88 (br s, 1H), 8.38 (dd, J=4.7, 1.4 Hz, 1H), 8.26 (d, J=7.9 Hz, 1H), 8.00 (d, J=7.8 Hz, 1H), 7.77 (dd, J=7.3, 1.2 Hz, 1H), 7.46-7.38 (m, 3H; 2H after D$_2$O exchange), 7.31 (dd, J=8.3, 4.7 Hz, 1H), 4.08 (m, 2H), 3.83 (m, 2H), 3.76 (m, 4H), 3.62 (s, 3H); Anal. Calcd. for C$_{20}$H$_{20}$N$_8$O$_3$S 0.5H$_2$O: C, 52.0; H, 4.6; N, 24.3. Found: C, 51.8; H, 4.6; N, 24.3%.

Example 6

Synthesis of 4-[2-(difluoromethyl)-1H-benzimidazol-1-yl]-6-(4-morpholinyl)-N-phenyl-1,3,5-triazin-2-amine

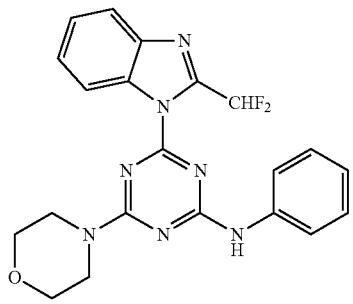

The compound was synthesized according to Method A.

A mixture of 1-[4-chloro-6-(4-morpholinyl)-1,3,5-triazin-2-yl]-2-(difluoromethyl)-1H-benzimidazole (92 mg, 0.25 mmol) and aniline (58 mg, 0.625 mmol) in dioxane (5 mL) was heated under reflux for 1 hr and cooled. Dilution with water gave a white precipitate, which was recrystallised from MeOH to give 52 mg (49% yield) of 4-[2-(difluoromethyl)-1H-benzimidazol-1-yl]-6-(4-morpholinyl)-N-phenyl-1,3,5-triazin-2-amine: mp 171-174° C.; $^1$H NMR (CDCl$_3$) δ 8.40 (m, 1H), 7.89 (m, 1H), 7.58 (t, J$_{HF}$=54.7 Hz, 1H), 7.55 (d, J=7.5 Hz, 1H), 7.43-7.38 (m, 4H), 7.20 (t, J=7.3 Hz, 1H), 7.09 (br, exchangeable with D$_2$O, 1H), 3.93 (m, 4H), 3.81 (m, 4H); Anal. Calc. for C$_{21}$H$_{19}$F$_2$N$_7$O: C, 59.6; H, 4.5; N, 23.2. Found: C, 59.6; H, 4.5; N, 23.3%.

Example 7

Synthesis of 4-[2-(difluoromethyl)-1H-benzimidazol-1-yl]-N-methyl-6-(4-morpholinyl)-N-phenyl-1,3,5-triazin-2-amine

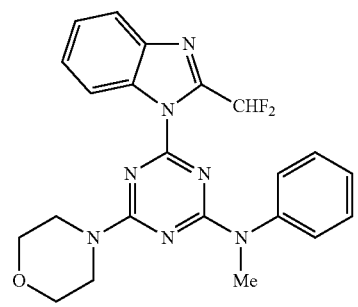 [SMILES: CN(c1ccccc1)c1nc(N2CCOCC2)nc(-n2c(C(F)F)nc3ccccc32)n1]

The compound was synthesized according to Method A.

A mixture of 1-[4-chloro-6-(4-morpholinyl)-1,3,5-triazin-2-yl]-2-(difluoromethyl)-1H-benzimidazole (92 mg, 0.25 mmol) and N-methylaniline (67 mg, 0.625 mmol) in dioxane (5 mL) was heated under reflux for 1 hr and cooled. Dilution with water gave a precipitate, which was collected and dried. Chromatography on SiO$_2$ eluting with CH$_2$Cl$_2$ gave 70 mg (64% yield) of 4-[2-(difluoromethyl)-1H-benzimidazol-1-yl]-N-methyl-6-(4-morpholinyl)-N-phenyl-1,3,5-triazin-2-amine: mp (hexanes) 160-162° C.; $^1$H NMR (CDCl$_3$) δ 8.04 (m, 1H), 7.82 (d, J=7.8 Hz, 1H), 7.49 (t, J=7.6 Hz, 2H), 7.45-7.06 (m, 7H), 3.91 (m, 4H), 3.81 (m, 4H), 3.56 (s, 3H); Anal. Calc. for C$_{22}$H$_{21}$F$_2$N$_7$O: C, 60.4; H, 4.8; N, 22.4. Found: C, 60.2; H, 5.0; N, 22.5%.

Example 8

Synthesis of N-benzyl-4-[2-(difluoromethyl)-1H-benzimidazol-1-yl]-6-(4-morpholinyl)-1,3,5-triazin-2-amine

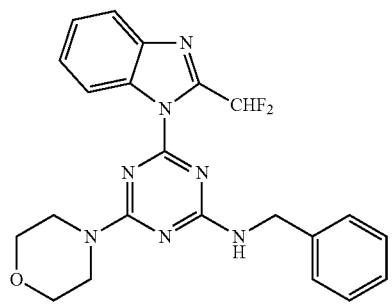 [SMILES: FC(F)c1nc2ccccc2n1-c1nc(NCc2ccccc2)nc(N2CCOCC2)n1]

The compound was synthesized according to Method A.

A mixture of 1-[4-chloro-6-(4-morpholinyl)-1,3,5-triazin-2-yl]-2-(difluoromethyl)-1H-benzimidazole (92 mg, 0.25 mmol) and benzylamine (67 mg, 0.625 mmol) in dioxane (5 mL) was heated to reflux for 5 min and cooled. The mixture was diluted with water to give a white precipitate, which was recrystallised from EtOH to give 73 mg (67% yield) of N-benzyl-4-[2-(difluoromethyl)-1H-benzimidazol-1-yl]-6-(4-morpholinyl)-1,3,5-triazin-2-amine: mp 185-188° C.; $^1$H NMR (CDCl$_3$) (rotamers) δ 8.41 and 8.28 (2d, J=7.4 and 7.7

Hz, 1H), 7.89 (m, 1H), 7.64 and 7.50 (2t, $J_{HF}$=53.8 and 53.7 Hz, 1H), 7.43-7.29 (m, 7H), 5.62 (m, exchangeable with D$_2$O, 1H), 4.72 and 4.68 (2d, J=6.0 and 5.9 Hz, 2H), 3.89 (m, 4H), 3.78 (m, 4H); Anal. Calc. for C$_{22}$H$_{21}$F$_2$N$_7$O: C, 60.4; H, 4.8; N, 22.4. Found: C, 60.6; H, 4.8; N, 22.7%.

Example 9

Synthesis of N-benzyl-4-[2-(difluoromethyl)-1H-benzimidazol-1-yl]-N-methyl-6-(4-morpholinyl)-1,3,5-triazin-2-amine

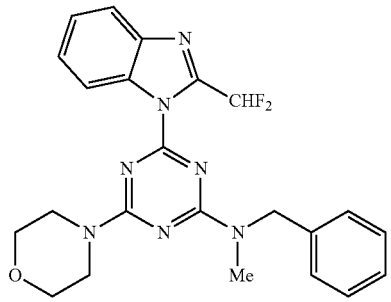 [SMILES: CN(Cc1ccccc1)c1nc(N2CCOCC2)nc(-n2c(C(F)F)nc3ccccc32)n1]

The compound was synthesized according to Method A.

A mixture of 1-[4-chloro-6-(4-morpholinyl)-1,3,5-triazin-2-yl]-2-(difluoromethyl)-1H-benzimidazole (92 mg, 0.25 mmol) and N-methylbenzylamine (76 mg, 0.625 mmol) in dioxane (5 mL) was heated to reflux for 5 min and cooled. The mixture was diluted with water to give a white precipitate, which was recrystallised from EtOH to give N-benzyl-4-[2-(difluoromethyl)-1H-benzimidazol-1-yl]-N-methyl-6-(4-morpholinyl)-1,3,5-triazin-2-amine: mp 147-150° C.; $^1$H NMR (CDCl$_3$) (rotamers) δ 8.45 and 8.22 (2d, J=7.6 and 7.9 Hz, 1H), 7.90 and 7.85 (2d, J=8.3 and 7.7 Hz, 1H), 7.68 and 7.44 (2t, $J_{HF}$=53.7 and 53.6 Hz, 1H), 7.43-7.25 (m, 7H), 4.92 and 4.90 (2s, 2H), 3.95-3.73 (m, 8H), 3.22 and 3.20 (2s, 3H); Anal. Calc. for C$_{23}$H$_{23}$F$_2$N$_7$O: C, 61.2; H, 5.1; N, 21.7. Found: C, 61.45; H, 5.2; N, 21.95%.

Example 10

Synthesis of 2-(difluoromethyl)-1-[4-(4-morpholinyl)-6-phenoxy-1,3,5-triazin-2-yl]-1H-benzimidazole

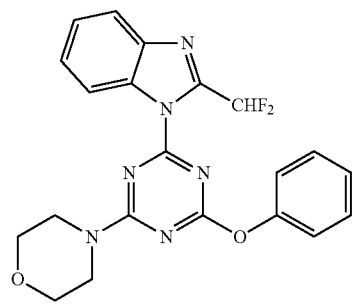 [SMILES: FC(F)c1nc2ccccc2n1-c1nc(Oc2ccccc2)nc(N2CCOCC2)n1]

The compound was synthesized according to Method A.

Phenol (200 mg, 21 mmol) and NaOH (85 mg, 21 mmol) were combined in water to give a clear solution, which was then evaporated to dryness. 1-[4-Chloro-6-(4-morpholinyl)-1,3,5-triazin-2-yl]-2-(difluoromethyl)-1H-benzimidazole (184 mg, 0.5 mmol) and tris[2-(2-methoxyethoxy)ethyl]amine (TDA-1; 16 mg, 0.05 mmol) were added and the mixture was heated under reflux in dioxane (10 mL) for 2 hr. After cooling, the mixture was diluted with water to give a white solid, which was collected and recrystallised from MeOH to give 93 mg (44% yield) of 2-(difluoromethyl)-1-[4-(4-morpholinyl)-6-phenoxy-1,3,5-triazin-2-yl]-1H-benzimidazole: mp 228-231° C.; $^1$H NMR (CDCl$_3$) δ 8.06 (d, J=8.2 Hz, 1H), 7.84 (d, J=7.8 Hz, 1H), 7.49 (br t, J=7.9 Hz, 2H), 7.36 (br t, J=7.5 Hz, 2H), 7.30 (dt, J=7.6, 1.1 Hz, 1H), 7.22 (m, 2H), 7.11 (t, $J_{HF}$=53.6 Hz, 1H), 3.99-3.93 (m, 4H), 3.86-3.79 (m, 4H); Anal. Calc. for C$_{21}$H$_{18}$F$_2$N$_6$O$_2$: C, 59.4; H, 4.3; N, 19.8. Found: C, 59.65; H, 4.2; N, 19.9%.

Example 11

Synthesis of 2-(difluoromethyl)-1-[4-(4-morpholinyl)-6-(phenylsulfanyl)-1,3,5-triazin-2-yl]-1H-benzimidazole

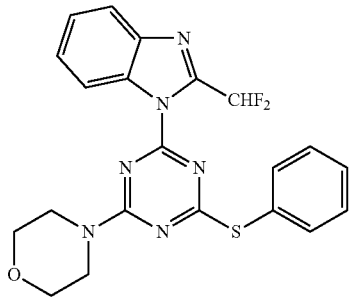 [SMILES: FC(F)c1nc2ccccc2n1-c1nc(Sc2ccccc2)nc(N2CCOCC2)n1]

The compound was synthesized according to Method A.

Thiophenol (230 mg, 2.1 mmol) and NaOH (85 mg, 2.1 mmol) were combined in water to give a clear solution, which was then evaporated to dryness. 1-[4-Chloro-6-(4-morpholinyl)-1,3,5-triazin-2-yl]-2-(difluoromethyl)-1H-benzimidazole (184 mg, 0.5 mmol) and tris[2-(2-methoxyethoxy)ethyl]amine (TDA-1; 16 mg, 0.05 mmol) were added and the mixture was heated under reflux in dioxane (10 mL) for 2 hr. After cooling, the mixture was diluted with water to give a solid, which was recrystallised from EtOH to give 167 mg (76% yield) of 2-(difluoromethyl)-1-[4-(4-morpholinyl)-6-(phenylsulfanyl)-1,3,5-triazin-2-yl]-1H-benzimidazole: mp 245-248° C.; $^1$H NMR (CDCl$_3$) δ 7.83 (t, J=8.6 Hz, 2H), 7.67 (dd, J=8.1, 1.3 Hz, 2H), 7.58 (br t, J=7.4 Hz, 1H), 7.52 (br t, J=7.3 Hz, 2H), 7.34 (dt, J=7.9, 1.2 Hz, 1H), 7.25 (dd, J=7.8, 1.2 Hz, 1H), 6.91 (t, $J_{HF}$=53.5 Hz, 1H), 3.89 (m, 4H), 3.82-3.77 (m, 4H); Anal. Calc. for C$_{21}$H$_{18}$F$_2$N$_6$OS: C, 57.3; H, 4.1; N, 19.1. Found: C, 57.2; H, 4.1; N, 19.2%.

Example 12

Synthesis of 2-(difluoromethyl)-1-[4-(4-morpholinyl)-6-(phenylsulfonyl)-1,3,5-triazin-2-yl]-1H-benzimidazole

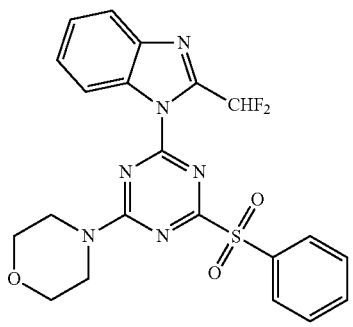 [SMILES: O=S(=O)(c1ccccc1)c1nc(N2CCOCC2)nc(-n2c(C(F)F)nc3ccccc32)n1]

The compound was synthesized according to Method D.

A solution of 0.1 g (0.23 mmol) of (2-(difluoromethyl)-1-[4-(4-morpholinyl)-6-(phenylsulfanyl)-1,3,5-triazin-2-yl]-1H-benzimidazole (from Example 11) in 10 mL acetone and 10 mL HOAc was treated with portions of 4% aq. $KMnO_4$ until the color remained. The mixture was then decolorized with aq. $Na_2SO_3$ solution, neutralized with aq. $NH_3$ and extracted with $CH_2Cl_2$. Chromatography on silica eluting with $CH_2Cl_2$/EtOAc (9:1) gave 26 mg (24% yield) of 2-(difluoromethyl)-1-[4-(4-morpholinyl)-6-(phenylsulfonyl)-1,3,5-triazin-2-yl]-1H-benzimidazole: mp (EtOH) 237-239° C.; $^1$H NMR ($CDCl_3$) δ 8.13 (dd, J=8.4, 1.2 Hz, 2H), 7.99 (d, J=7.7 Hz, 1H), 7.86 (d, J=7.5 Hz, 1H), 7.80 (dt, J=7.5, 1.8 Hz, 1H), 7.67 (t, J=7.8 Hz, 2H), 7.41 (dt, J=7.8, 1.3 Hz, 1H), 7.35 (dt, J=7.8, 1.3 Hz, 1H), 7.13 (t, $J_{HF}$=53.3 Hz, 1H), 4.04 (m, 2H), 3.98 (m, 2H), 3.84 (m, 4H); Anal. Calc. for $C_{21}H_{18}F_2N_6O_3S$: C, 53.4; H, 3.8; N, 17.8. Found: C, 53.4; H, 3.8; N, 18.0%.

Example 13

Synthesis of 4-[2-(difluoromethyl)-1H-benzimidazol-1-yl]-6-(4-morpholinyl)-N-(2-pyridinylmethyl)-1,3,5-triazin-2-amine

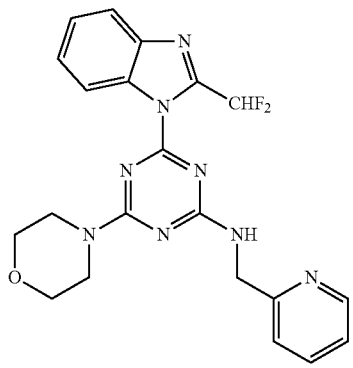 [SMILES: FC(F)c1nc2ccccc2n1-c1nc(NCc2ccccn2)nc(N2CCOCC2)n1]

The compound was synthesized according to Method A.

A stirred mixture of 1-[4-chloro-6-(4-morpholinyl)-1,3,5-triazin-2-yl]-2-(difluoromethyl)-1H-benzimidazole (0.183 g, 0.5 mmol) and 2-aminomethylpyridine (0.135 g, 1.25 mmol) in 10 mL dioxane was heated gently until a clear solution was obtained. After cooling, the mixture was diluted with water to give an oily solid, which was recrystallized from aqueous MeOH to give 0.11 g (50% yield) of 4-[2-(difluoromethyl)-1H-benzimidazol-1-yl]-6-(4-morpholinyl)-N-(2-pyridinylmethyl)-1,3,5-triazin-2-amine: mp 192-193° C.; $^1$H NMR ($CDCl_3$) (rotamers) δ 8.65 (d, J=1.8 Hz, 1H), 8.57 (dd, J=4.7, 1.0 Hz, 1H), 8.40 and 8.25 (2d, J=7.5 and 5.5 Hz, 1H), 7.88 (m, 1H), 7.70 (d, J=7.7 Hz, 1H), 7.62 (t, $J_{HF}$=54.5 Hz, 1H), 7.43-7.37 (m, 2H), 7.30 (ddd, J=7.9, 4.8, 0.7 Hz, 1H), 5.75 and 5.64 (2 m, exchangeable with $D_2O$, 1H), 4.76 and 4.69 (2 d, J=5.7 and 5.8 Hz, 2H), 3.87 (m, 4H), 3.78 (m, 4H); Anal. Calcd. for $C_{21}H_{20}F_2N_8O$: C, 57.5; H, 4.6; N, 25.6. Found: C, 57.5; H, 4.5; N, 25.6%.

Example 14

Synthesis of 4-[2-(difluoromethyl)-1H-benzimidazol-1-yl]-6-(4-morpholinyl)-N-(3-pyridinylmethyl)-1,3,5-triazin-2-amine

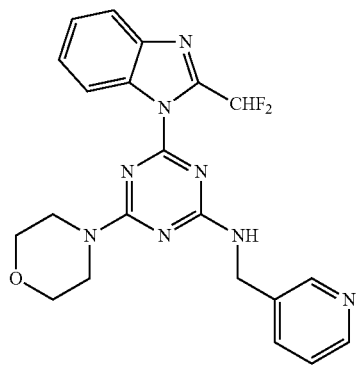 [SMILES: FC(F)c1nc2ccccc2n1-c1nc(NCc2cccnc2)nc(N2CCOCC2)n1]

The compound was synthesized according to Method A.

A stirred mixture of 1-[4-chloro-6-(4-morpholinyl)-1,3,5-triazin-2-yl]-2-(difluoromethyl)-1H-benzimidazole (0.183 g, 0.5 mmol) and 3-aminomethylpyridine (0.135 g, 1.25 mmol) in 10 mL dioxane was heated under gentle reflux for 5 min. After cooling, the mixture was diluted with water to give an oily solid, which was recrystallized from MeOH to give 0.13 g (59% yield) of 4-[2-(difluoromethyl)-1H-benzimidazol-1-yl]-6-(4-morpholinyl)-N-(3-pyridinylmethyl)-1,3,5-triazin-2-amine: mp 160-161° C.; $^1$H NMR ($CDCl_3$) (rotamers) δ 8.61 (d, J=4.4 Hz, 1H), 8.42 and 8.32 (2d, J=7.6 and 8.4 Hz, 1H), 7.89-7.87 (m, 1H), 7.70 (dt, J=7.7, 1.65 Hz, 1H), 7.65 and 7.59 (2t, $J_{HF}$=53.7 and 53.5 Hz, 1H), 7.43-7.37 (m, 2H), 7.34 (br t, J=8.7 Hz, 1H), 7.24 (br t, J=6.2 Hz, 1H), 6.55 and 6.41 (2 m, exchangeable with $D_2O$, 1H), 4.82 and 4.78 (2 d, J=5.3 and 5.1 Hz, 2H), 3.88 (m, 4H), 3.78 (m, 4H); Anal. Calcd. for $C_{21}H_{20}F_2N_8O$: C, 57.5; H, 4.6; N, 25.6. Found: C, 57.7; H, 4.5; N, 25.7%.

Example 15

Synthesis of 4-[2-(difluoromethyl)-1H-benzimidazol-1-yl]-6-(4-morpholinyl)-N-(4-pyridinylmethyl)-1,3,5-triazin-2-amine

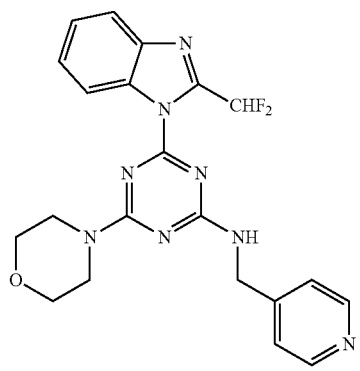 [SMILES: FC(F)c1nc2ccccc2n1-c1nc(NCc2ccncc2)nc(N2CCOCC2)n1]

The compound was synthesized according to Method A.

A stirred mixture of 1-[4-chloro-6-(4-morpholinyl)-1,3,5-triazin-2-yl]-2-(difluoromethyl)-1H-benzimidazole (0.183 g, 0.5 mmol) and 4-aminomethylpyridine (0.135 g, 1.25 mmol) in 10 mL dioxane was heated under gentle reflux for 5 min, before being cooled and diluted with water. The mixture was extracted with CH$_2$Cl$_2$ and the organic layer was dried with Na$_2$SO$_4$. Chromatography on alumina, eluting with CH$_2$Cl$_2$/EtOAc (9:1), followed by chromatography on silica, eluting with CH$_2$Cl$_2$/EtOAc (3:2) gave 56 mg (26% yield) of 4-[2-(difluoromethyl)-1H-benzimidazol-1-yl]-6-(4-morpholinyl)-N-(4-pyridinylmethyl)-1,3,5-triazin-2-amine: mp 188-190° C.; $^1$H NMR (CDCl$_3$) (rotamers) δ8.60 (br s, 2H), 8.42 and 8.13 (2d, J=7.4 and 8.0 Hz, 1H), 7.88 (m, 1H), 7.64 (t, $J_{HF}$=53.6 Hz, 1H), 7.44-7.25 (m, 4H), 5.78 and 5.71 (2 m, exchangeable with D$_2$O, 1H), 4.74 and 4.70 (2 d, J=6.0 and 6.0 Hz, 2H), 3.92-3.69 (m, 8H).

Example 16

Synthesis of 4-[2-(difluoromethyl)-1H-benzimidazol-1-yl]-6-(4-morpholinyl)-N-(2-pyridinyl)-1,3,5-triazin-2-amine

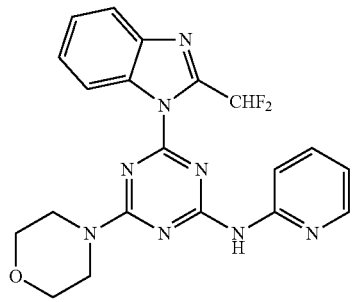 [SMILES: FC(F)c1nc2ccccc2n1-c1nc(Nc2ccccn2)nc(N2CCOCC2)n1]

The compound was synthesized according to Method A.

To 0.224 g (2.38 mmol) of 2-aminopyridine in THF (3 mL) was added 2.5 mL of lithium bis(trimethylsilyl)amide (1 M solution in THF) and the mixture was stirred for 10 min. A solution of 0.204 g (0.56 mmol) of 1-[4-chloro-6-(4-morpholinyl)-1,3,5-triazin-2-yl]-2-(difluoromethyl)-1H-benzimidazole in THF (4 mL) was added and the mixture was stirred for 1 hr. The resulting mixture was neutralized with acetic acid, diluted with water and extracted with EtOAc. The organic layer was washed with water and aqueous NH$_3$, and dried. After removal of the solvent, the residue was purified by chromatography on alumina, eluting with CH$_2$Cl$_2$/EtOAc (1:5) to give an orange powder. Recrystallization from EtOH/CH$_2$Cl$_2$ gave 31.5 mg (13% yield) of 4-[2-(difluoromethyl)-1H-benzimidazol-1-yl]-6-(4-morpholinyl)-N-(2-pyridinyl)-1,3,5-triazin-2-amine: mp 230-232° C.; $^1$H NMR (CDCl$_3$) δ 8.41-8.37 (m, 2H), 8.20 (d, J=8.4 Hz, 1H), 8.12 (br s, 1H), 7.91-7.89 (m, 1H), 7.75 (td, J=7.5, 1.8 Hz, 1H), 7.60 (t, $J_{HF}$=53.5 Hz, 1H), 7.45-7.39 (m, 2H), 7.05 (ddd, J=7.3, 4.9, 0.9 Hz, 1H), 3.96-3.94 (m, 4H), 3.85-3.82 (m, 4H); HRMS (FAB$^+$) MNa$^+$ Calcd. for C$_{20}$H$_{18}$F$_2$N$_8$NaO: m/z 447.1466. Found: m/z 447.1464.

Example 17

Synthesis of 4-[2-(difluoromethyl)-1H-benzimidazol-1-yl]-6-(4-morpholinyl)-N-(4-pyridinyl)-1,3,5-triazin-2-amine

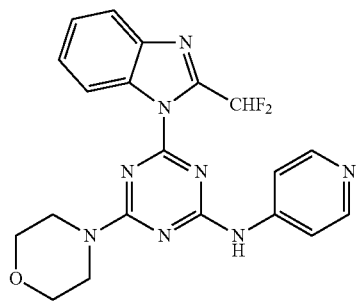 [SMILES: FC(F)c1nc2ccccc2n1-c1nc(Nc2ccncc2)nc(N2CCOCC2)n1]

The compound was synthesized according to Method A.

A mixture of 0.048 g (0.51 mmol) of 4-aminopyridine and 0.095 g (0.26 mmol) of 1-[4-chloro-6-(4-morpholinyl)-1,3,5-triazin-2-yl]-2-(difluoromethyl)-1H-benzimidazole in DMSO (1.5 mL) was heated at 120° C. for 1 hr. The reaction mixture was cooled to room temperature and water was added. The solid was collected by filtration and washed with water to give 0.022 g (20% yield) of 4-[2-(difluoromethyl)-1H-benzimidazol-1-yl]-6-(4-morpholinyl)-N-(4-pyridinyl)-1,3,5-triazin-2-amine: mp (MeOH) 222-224° C.; $^1$H NMR (DMSO-d$_6$) δ 10.30 (br s, 1H), 8.59-8.46 (m, 3H), 7.91-7.86 (m, 4H), 7.55-7.44 (m, 2H), 3.88 (br s, 4H), 3.77-3.76 (m, 4H); HRMS (FAB$^+$) MNa$^+$ Calcd. for C$_{20}$H$_{18}$F$_2$N$_8$NaO: m/z 447.1466. Found: m/z 447.1464; HRMS (FAB$^+$) MH$^+$ Calcd. for C$_{20}$H$_{19}$F$_2$N$_8$NO: m/z 425.1644. Found: m/z 425.1629.

Example 18

Synthesis of N-[4-[2-(difluoromethyl)-1H-benzimidazol-1-yl]-6-(4-morpholinyl)-1,3,5-triazin-2-yl]-3-quinolinamine

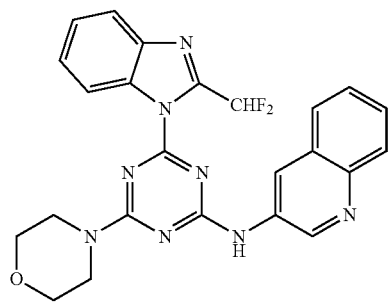 [SMILES: FC(F)c1nc2ccccc2n1-c1nc(Nc2cnc3ccccc3c2)nc(N2CCOCC2)n1]

The compound was synthesized according to Method A.

To a solution of 0.323 g (2.24 mmol) of 3-aminoquinoline in THF (5 mL) at 0° C. was added 1.6 mL of NaHMDS (2 M solution in THF), and the mixture was stirred for 15 min. A solution of 0.280 g (0.77 mmol) of 1-[4-chloro-6-(4-morpholinyl)-1,3,5-triazin-2-yl]-2-(difluoromethyl)-1H-benzimidazole in THF (4 mL) was added and the resulting mixture was stirred for 1 hr at RT. The resulting mixture was neutralized with acetic acid, diluted with water, and extracted with EtOAc. The organic layer was washed sequentially with water and aq. NH$_3$, dried, and concentrated. Chromatography on alumina, eluting first with hexanes/EtOAc (1:1), and then CH$_2$Cl$_2$-EtOAc (1:3) gave a pink powder. Recrystallization from ethanol gave 0.167 g (46% yield) of N-[4-[2-(difluoromethyl)-1H-benzimidazol-1-yl]-6-(4-morpholinyl)-1,3,5-triazin-2-yl]-3-quinolinamine: mp 270-273° C.; $^1$H NMR (CDCl$_3$) δ 9.08 (br s, 1H), 8.48-8.43 (m, 2H), 8.12 (d, J=8.4 Hz, 1H), 7.93-7.90 (m, 1H), 7.80 (dd, J=8.0, 1.1 Hz, 1H), 7.69 (dt, J=6.9, 1.4 Hz, 1H), 7.61-7.41 (m, 4H), 7.30 (d, J=5.3 Hz, 1H), 3.97-3.95 (m, 4H), 3.83 (s, 4H); Anal. Calcd. for C$_{24}$H$_{20}$F$_2$N$_8$O: C, 60.75; H, 4.3; N, 23.6. Found: C, 60.7; H, 4.2; N, 23.5%.

Example 19

Synthesis of 4-[2-(difluoromethyl)-1H-benzimidazol-1-yl]-6-(4-morpholinyl)-N-(2-pyrimidinyl)-1,3,5-triazin-2-amine

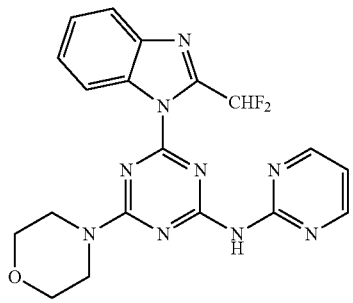 [SMILES: FC(F)c1nc2ccccc2n1-c1nc(Nc2ncccn2)nc(N2CCOCC2)n1]

The compound was synthesized according to Method A.

To a solution of 0.214 g (2.25 mmol) of 2-aminopyrimidine in THF (4 mL) at 0° C. was added 1.25 mL of NaHMDS (2 M solution in THF) and the mixture was stirred for 20 min. A solution of 0.275 g (0.75 mmol) of 1-[4-chloro-6-(4-morpholinyl)-1,3,5-triazin-2-yl]-2-(difluoromethyl)-1H-benzimidazole in THF (4 mL) was added, and the resulting mixture was stirred for 1 hr at RT. After neutralization with acetic acid, the mixture was diluted with water and extracted with EtOAc. The organic layer was washed sequentially with water and aq. NH$_3$, dried and concentrated. Chromatography on alumina, eluting first with hexanes/EtOAc (4:1), then with CH$_2$Cl$_2$/EtOAc (1:3) gave an orange powder. Recrystallization from ethanol gave 0.098 g (31% yield) of 4-[2-(difluoromethyl)-1H-benzimidazol-1-yl]-6-(4-morpholinyl)-N-(2-pyrimidinyl)-1,3,5-triazin-2-amine: mp 261-263° C.; $^1$H NMR (CDCl$_3$) δ8.69-8.67 (m, 3H), 8.34 (t, J$_{HF}$=53.3 Hz, 1H), 8.07 (br s, 1H), 7.91 (dd, J=7.9, 0.9 Hz, 1H), 7.49-7.40 (m, 2H), 7.05 (t, J=4.8 Hz, 1H), 3.96 (m, 4H), 3.83 (m, 4H); Anal. Calcd. for C$_{19}$H$_{17}$F$_2$N$_9$O: C, 53.65; H, 4.0; N, 29.6. Found: C, 53.6; H, 4.1; N, 29.4%.

Example 20

Synthesis of 4-[2-(difluoromethyl)-1H-benzimidazol-1-yl]-6-(4-morpholinyl)-N-(4-pyrimidinyl)-1,3,5-triazin-2-amine

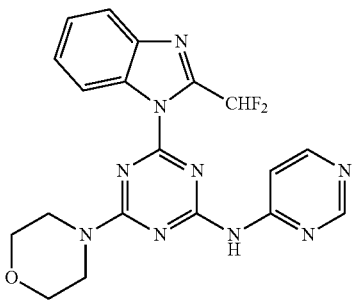 [SMILES: FC(F)c1nc2ccccc2n1-c1nc(Nc2ccncn2)nc(N2CCOCC2)n1]

The compound was synthesized according to Method A.

To a solution of 0.214 g (2.25 mmol) of 4-aminopyrimidine in THF (4.5 mL) at 0° C. was added 1.25 mL of NaHMDS (2 M solution in THF), and the mixture stirred for 20 min. A solution of 0.282 g (0.77 mmol) of 1-[4-chloro-6-(4-morpholinyl)-1,3,5-triazin-2-yl]-2-(difluoromethyl)-1H-benzimidazole in THF (6 mL) was added and the resulting mixture was stirred for 1 hr at RT. After neutralization with acetic acid, the mixture was diluted with water and extracted with EtOAc. The organic layer was washed sequentially with water and aq. NH$_3$, dried and concentrated. Chromatography on alumina, eluting with CH$_2$Cl$_2$/EtOAc (1:3) gave a white powder. Recrystallization from ethanol gave 0.020 g (6% yield) of 4-[2-(difluoromethyl)-1H-benzimidazol-1-yl]-6-(4-morpholinyl)-N-(4-pyrimidinyl)-1,3,5-triazin-2-amine: mp 233-235° C.; $^1$H NMR (CDCl$_3$) δ8.92 (d, J=1.4 Hz, 1H), 8.67 (d, J=5.8 Hz, 1H), 8.39 (dd, J=6.8, 1.7 Hz, 1H), 8.22 (dd, J=5.8, 1.3 Hz, 1H), 8.01 (s, 1H), 7.92 (dd, J=6.8, 1.7 Hz, 1H), 7.56 (t, J$_{HF}$=53.5 Hz, 1H), 7.49-7.43 (m, 2H), 3.98-3.96 (m, 4H), 3.86-3.85 (m, 4H); Anal. Calcd. for C$_{19}$H$_{17}$F$_2$N$_9$O: C, 53.65; H, 4.1; N, 29.6. Found: C, 53.35; H, 4.2; N, 29.4%.

Example 21

Synthesis of 4-[2-(difluoromethyl)-1H-benzimidazol-1-yl]-6-(4-morpholinyl)-N-(5-pyrimidinyl)-1,3,5-triazin-2-amine

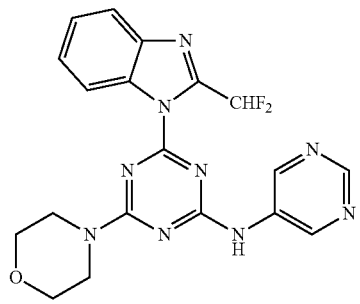 [SMILES: FC(F)c1nc2ccccc2n1-c1nc(Nc2cncnc2)nc(N2CCOCC2)n1]

The compound was synthesized according to Method A.

To a solution of 0.186 g (1.96 mmol) of 5-aminopyrimidine in THF (4 mL) at 0° C. was added 1.1 mL of NaHMDS (2 M solution in THF), and the mixture was stirred for 15 min. A solution of 0.238 g (0.65 mmol) of 1-[4-chloro-6-(4-morpholinyl)-1,3,5-triazin-2-yl]-2-(difluoromethyl)-1H-benzimidazole in THF (5 mL) was added and the resulting mixture was stirred for 1 hr at RT. After neutralization with acetic acid, the mixture was diluted with water and extracted with EtOAc. The organic layer was washed sequentially with water and aq. NH$_3$, dried and concentrated. Chromatography on alumina, eluting first with CH$_2$Cl$_2$/EtOAc (1:9) and then with CH$_2$Cl$_2$/EtOAc (1:3) to CH$_2$Cl$_2$/EtOAc (7:3) gave an off-white powder. Recrystallization from ethanol gave 0.123 g (47% yield) of 4-[2-(difluoromethyl)-1H-benzimidazol-1-yl]-6-(4-morpholinyl)-N-(5-pyrimidinyl)-1,3,5-triazin-2-amine: mp 290-292° C.; $^1$H NMR (CDCl$_3$) δ9.07 (s, 2H), 9.02 (s, 1H), 8.37 (d, J=7.2 Hz, 1H), 7.89 (dd, J=7.7, 1.5 Hz, 1H), 7.57 (t, J=53.7 Hz, 1H), 7.47-7.40 (m, 2H), 7.11 (s, 1H), 3.95-3.92 (m, 4H), 3.83 (br s, 4H); Anal. Calcd. for C$_{19}$H$_{17}$F$_2$N$_9$O: C, 53.65; H, 4.1; N, 29.6. Found: C, 53.4; H, 4.2; N, 29.4%.

Example 22

Synthesis of 4-[2-(difluoromethyl)-1H-benzimidazol-1-yl]-6-(4-morpholinyl)-N-(2-pyrazinyl)-1,3,5-triazin-2-amine

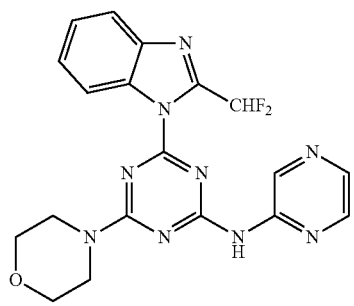 [SMILES: FC(F)c1nc2ccccc2n1-c1nc(Nc2cnccn2)nc(N2CCOCC2)n1]

The compound was synthesized according to Method A.

To a solution of 0.219 g (2.30 mmol) of aminopyrazine in THF (5 mL) at 0° C. was added 1.3 mL of NaHMDS (2 M solution in THF), and the mixture was stirred for 15 min. A solution of 0.238 g (0.65 mmol) of 1-[4-chloro-6-(4-morpholinyl)-1,3,5-triazin-2-yl]-2-(difluoromethyl)-1H-benzimidazole in THF (6 mL) was added, and the resulting mixture was stirred for 1 hr at RT. After neutralization with acetic acid, the mixture was diluted with water and extracted with EtOAc. The organic layer was washed sequentially with water and aq. $NH_3$, dried and concentrated. Chromatography on alumina, eluting first with hexanes/EtOAc (1:1) and then with $CH_2Cl_2$/EtOAc (1:4) to $CH_2Cl_2$/EtOAc (1:1) gave a white powder. Recrystallization from ethanol/$CH_2Cl_2$ gave 0.170 g (54% yield) of 4-[2-(difluoromethyl)-1H-benzimidazol-1-yl]-6-(4-morpholinyl)-N-(2-pyrazinyl)-1,3,5-triazin-2-amine: mp 271-274° C.; $^1$H NMR (CDCl$_3$) δ 9.59 (s, 1H), 8.42-8.33 (m, 3H), 7.92 (d, J=7.4 Hz, 1H), 7.81 (s, 1H), 7.60 (t, $J_{HF}$=53.5 Hz, 1H), 7.48-7.41 (m, 2H), 3.98 (d, J=4.2 Hz, 4H), 3.85 (d, J=4.2 Hz, 4H); Anal. Calcd. for $C_{19}H_{17}F_2N_9O$: C, 53.65; H, 4.1; N, 29.6. Found: C, 53.9; H, 3.8; N, 29.7%.

Example 23

Synthesis of 4-[2-(difluoromethyl)-1H-benzimidazol-1-yl]-6-(4-morpholinyl)-N-(3-pyridazinyl)-1,3,5-triazin-2-amine

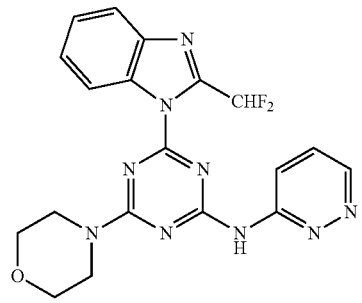 [SMILES: FC(F)c1nc2ccccc2n1-c1nc(Nc2cccnn2)nc(N2CCOCC2)n1]

The compound was synthesized according to Method A.

A mixture of 0.063 g (0.486 mmol) of 6-chloro-3-pyridazinamine (*J. Med. Chem.* 2006, 49, 4409-4424), 0.022 g (0.55 mmol) of NaOH, and 0.045 g of 10% Pd/C in ethanol (15 mL) was stirred under an atmosphere of hydrogen for 18 hrs. After filtration through celite, the solvent was concentrated to give 0.046 g (99.5% yield) of 3-aminopyridazine: $^1$H NMR (DMSO-d$_6$) δ8.39 (dd, J=4.4, 1.2 Hz, 1H), 7.21 (dd, J=8.8, 4.4 Hz, 1H), 6.74 (dd, J=9.2, 1.6 Hz, 1H), 6.26 (br s, 2H).

To a solution of 0.159 g (1.67 mmol) of 3-aminopyridazine in THF (3 mL) at 0° C. was added 0.93 mL of NaHMDS (2 M solution in THF), and the mixture was stirred for 15 min. A solution of 0.317 g (0.84 mmol) of 1-[4-chloro-6-(4-morpholinyl)-1,3,5-triazin-2-yl]-2-(difluoromethyl)-1H-benzimidazole in THF (6 mL) was added and the resulting mixture was stirred for 1 hr at RT. After neutralization with acetic acid, the mixture was diluted with water and extracted with EtOAc. The organic layer was washed sequentially with water and aq. $NH_3$, dried and concentrated. Chromatography on alumina, eluting first with hexane-EtOAc (8:2) then with $CH_2Cl_2$/EtOAc (2:1) to $CH_2Cl_2$/EtOAc (1:1) gave a white powder. Recrystallization from ethanol/$CH_2Cl_2$ gave 0.065 g (18% yield) of 4-[2-(difluoromethyl)-1H-benzimidazol-1-yl]-6-(4-morpholinyl)-N-(3-pyridazinyl)-1,3,5-triazin-2-amine: mp 271-273° C.; $^1$H NMR (DMSO-d$_6$) δ 11.16 (br s, 1H), 8.98 (dd, J=4.7, 1.4 Hz, 1H), 8.67 (d, J=8.0 Hz, 1H), 8.61 (d, $J_{HF}$=8.4 Hz, 1H), 8.08 (t, $J_{HF}$=52.8 Hz, 1H), 7.86 (dd, J=7.7, 0.7 Hz, 1H), 7.73 (dd, J=9.1, 4.7 Hz, 1H), 7.53-7.43 (m, 2H), 3.86 (s, 4H), 3.75 (s, 4H); Anal. Calcd. for $C_{19}H_{17}F_2N_9O$: C, 53.65; H, 4.1; N, 29.6. Found: C, 53.7; H, 4.2; N, 29.5%.

Example 24

Synthesis of 2-(difluoromethyl)-1-[4-(4-morpholinyl)-6-(3-pyridinyloxy)-1,3,5-triazin-2-yl]-1H-benzimidazole

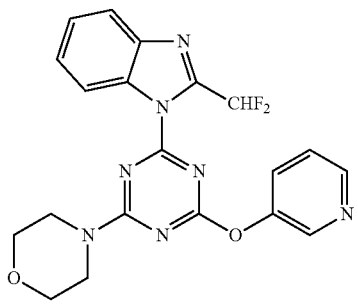 [SMILES: FC(F)c1nc2ccccc2n1-c1nc(Oc2cccnc2)nc(N2CCOCC2)n1]

The compound was synthesized according to Method A.

A mixture of 0.301 g (3.16 mmol) of 3-hydroxypyridine and 0.132 g (3.30 mmol) of NaOH was stirred in water until a clear solution was obtained. The water was removed and the residue was combined with a mixture of 0.301 g (3.16 mmol) of 1-[4-chloro-6-(4-morpholinyl)-1,3,5-triazin-2-yl]-2-(difluoromethyl)-1H-benzimidazole and 0.02 g (0.06 mmol) of tris[2-(2-methoxyethoxy)ethyl]amine (TDA-1) in dioxane (12 mL). The resulting mixture was heated under reflux for 2 hr before being cooled, and diluted with water. The resulting precipitate was collected by filtration, and recrystallized from methanol to give 0.160 g (50% yield) of 2-(difluoromethyl)-1-[4-(4-morpholinyl)-6-(3-pyridinyloxy)-1,3,5-triazin-2-yl]-1H-benzimidazole: mp 229-231° C.; $^1$H NMR (CDCl$_3$) δ8.63-8.60 (m, 2H), 8.12 (dd, J=7.1, 1.4 Hz, 1H), 7.87 (dd, J=7.1, 1.4 Hz, 1H), 7.59 (ddd, J=8.3, 2.7, 1.4 Hz, 1H), 7.45 (ddd, J=8.2, 4.6, 0.3 Hz, 1H), 7.41-7.34 (m, 2H), 7.25 (t, $J_{HF}$=53.6 Hz, 1H), 3.99-3.96 (m, 2H), 3.89-3.83 (m, 4H), 3.79-3.77 (m, 2H); Anal. Calcd. for $C_{20}H_{17}F_2N_7O_2$ 0.7$H_2O$: C, 54.8; H, 4.2; N, 22.4. Found: C, 54.5; H, 4.0; N, 22.0%.

Example 25

Synthesis of 4-[2-(difluoromethyl)-1H-benzimidazol-1-yl]-N-(1-methyl-1H-pyrazol-4-yl)-6-(4-morpholinyl)-1,3,5-triazin-2-amine

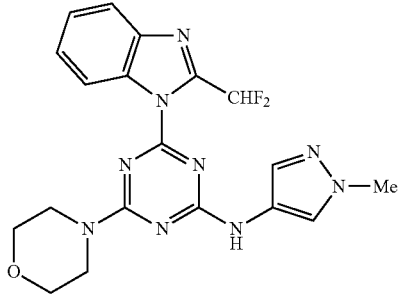 [SMILES: Cn1cc(Nc2nc(N3CCOCC3)nc(-n3c(C(F)F)nc4ccccc43)n2)cn1]

The compound was synthesized according to Method A.

A mixture of 0.996 g (8.82 mmol) of 4-nitropyrazole (J. Med. Chem. 2005, 48, 5780-5793) and 1.33 g (10.6 mmol) of dimethyl sulphate in 10 mL of 1 M NaOH was heated at 35° C. for 48 hrs. The reaction mixture was cooled to RT and the precipitate was filtered, washed with water, and dried to give 0.561 g (50% yield) of 1-methyl-4-nitro-1H-pyrazole: $^1$H NMR (DMSO-$d_6$) δ8.83 (s, 1H), 8.22 (s, 1H), 3.91 (s, 3H).

A mixture of 0.144 g (1.14 mmol) 1-methyl-4-nitro-1H-pyrazole, 0.017 g (0.07 mmol) platinum oxide, and ethyl acetate (5 mL) in ethanol (15 mL) was stirred under 2 atmospheres of hydrogen for 14 hrs. The catalyst was removed by filtration through a pad of celite and the solvent was removed to give 0.080 mg (73% yield) of 4-amino-1-methyl-1H-pyrazole as a purple residue, which was used in the next step without further purification: $^1$H NMR (DMSO-$d_6$) δ6.98 (s, 1H), 6.88 (s, 1H), 3.76 (br s, 2H), 3.65 (s, 3H).

A mixture of 0.405 g (4.27 mmol) of 4-amino-1-methylpyrazole and 0.695 g (1.90 mmol) of 1-[4-chloro-6-(4-morpholinyl)-1,3,5-triazin-2-yl]-2-(difluoromethyl)-1H-benzimidazole in DMSO (5 mL) was heated at 125° C. for 15 min. The reaction mixture was cooled to room temperature and water was added. The solid was collected by filtration, washed with water, and dried. Chromatography on alumina, eluting with hexanes/EtOAc (1:1) gave a brown powder. Recrystallization from ethanol/$CH_2Cl_2$ gave 0.145 g (18% yield) of 4-[2-(difluoromethyl)-1H-benzimidazol-1-yl]-N-(1-methyl-1H-pyrazol-4-yl)-6-(4-morpholinyl)-1,3,5-triazin-2-amine: mp 225-226° C.; $^1$H NMR (DMSO-$d_6$) (rotamers) δ 10.00 (s, 1H), 9.73 (s, 0.2H), 8.60 (d, J=8.0 Hz, 1H), 8.29 (d, J=7.6 Hz, 0.2H), 7.92 (t, $J_{HF}$=52.8 Hz, 1H), 7.86-7.80 (m, 2.6H), 7.68 (t, $J_{HF}$=52.6 Hz, 0.2H), 7.59 (s, 1H), 7.52-7.42 (m, 2.9H), 3.85-3.82 (m, 8.4H), 3.75-3.73 (m, 4.8H); Anal. Calcd. for $C_{19}H_{19}F_2N_9O$ 0.06EtOAc 0.24$H_2O$: C, 52.9; H, 4.6; N, 28.8. Found: C, 52.9; H, 4.5; N, 28.6%.

Example 26

Synthesis of 4-[2-(difluoromethyl)-1H-benzimidazol-1-yl]-N-(4-methoxy-3-pyridinyl)-6-(4-morpholinyl)-1,3,5-triazin-2-amine

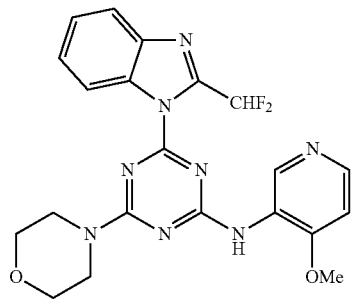 [SMILES: COc1ccncc1Nc1nc(N2CCOCC2)nc(-n2c(C(F)F)nc3ccccc32)n1]

The compound was synthesized according to Method A.

A mixture of 0.475 g (3.08 mmol) of 4-methoxy-3-nitropyridine (Org. Process Res. Dev. 2004, 8, 903-908) and 0.301 g (2.84 mmol) of 10% palladium on carbon in ethanol (30 mL) was stirred under an atmosphere of hydrogen for 48 hrs. The catalyst was removed by filtration through a pad of celite, and the solvent was removed to give 0.380 mg (99%) of 3-amino-4-methoxypyridine as a pink powder, which was used in the next step without further purification: $^1$H NMR (DMSO-$d_6$) δ8.09 (dd, J=6.4, 1.2 Hz, 1H), 7.93 (d, J=1.2 Hz, 1H), 7.36 (d, J=6.4 Hz, 1H), 6.01 (br s, 2H), 4.06 (s, 3H).

To a solution of 0.134 g (1.08 mmol) of 3-amino-4-methoxypyridine in THF (3 mL) was added 0.5 mL of butyllithium (2.5 M solution in hexanes), and the mixture was stirred for 15 min. A solution of 0.133 g (0.36 mmol) of 1-[4-chloro-6-(4-morpholinyl)-1,3,5-triazin-2-yl]-2-(difluoromethyl)-1H-benzimidazole in THF (6 mL) was added and the resulting mixture was stirred for 1 hr. After neutralization with acetic acid, the mixture was diluted with water and extracted with EtOAc. The organic layer was washed sequentially with water and aq. $NH_3$, dried, and concentrated. Chromatography on alumina, eluting first with hexanes/EtOAc (1:1) and then with $CH_2Cl_2$/EtOAc (2:3) gave a white powder. Recrystallization from ethanol/$CH_2Cl_2$ gave 0.078 g (48% yield) of 4-[2-(difluoromethyl)-1H-benzimidazol-1-yl]-N-(4-methoxy-3-pyridinyl)-6-(4-morpholinyl)-1,3,5-triazin-2-amine: mp 161-163° C.; $^1$H NMR (DMSO-$d_6$) δ9.43 (br s, 1H), 8.61-8.37 (m, 3H), 7.83-7.81 (m, 2H), 7.41 (br s, 2H), 7.20 (d, J=5.6 Hz, 1H), 3.89 (s, 3H), 3.81 (s, 4H), 3.71 (s, 4H); Anal. Calcd. for $C_{21}H_{20}F_2N_8O_2$: C, 55.5; H, 4.4; N, 24.7. Found: C, 55.5; H, 4.4; N, 24.5%.

Example 27

Synthesis of 4-[2-(difluoromethyl)-4-methoxy-1H-benzimidazol-1-yl]-N-(4-methoxy-3-pyridinyl)-6-(4-morpholinyl)-1,3,5-triazin-2-amine

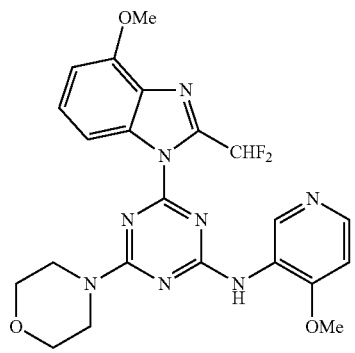 [SMILES: COc1ccncc1Nc1nc(N2CCOCC2)nc(-n2c(C(F)F)nc3c(OC)cccc32)n1]

The compound was synthesized according to Method A.

To a solution of 0.121 g (0.98 mmol) of 3-amino-4-methoxypyridine in THF (3 mL) was added 0.44 mL of butyllithium (2.5 M solution in hexanes), and the mixture stirred for 15 min. A solution of 0.128 g (0.32 mmol) of 1-[4-chloro-6-(4-morpholinyl)-1,3,5-triazin-2-yl]-2-(difluoromethyl)-4-methoxy-1H-benzimidazole in THF (6 mL) was added and the resulting mixture was stirred for 1 hr. After neutralization with acetic acid, the mixture was diluted with water and extracted with EtOAc. The organic layer was washed sequentially with water and aq. $NH_3$, dried, and concentrated. Chromatography on alumina, eluting first with hexanes/EtOAc (8:2) and then with $CH_2Cl_2$/EtOAc (2:1) to $CH_2Cl_2$/EtOAc (1:1) gave a yellow powder. Recrystallization from ethanol/$CH_2Cl_2$ gave 0.065 g (42% yield) of 4-[2-(difluoromethyl)-4-methoxy-1H-benzimidazol-1-yl]-N-(4-methoxy-3-pyridinyl)-6-(4-morpholinyl)-1,3,5-triazin-2-amine: mp 239-241° C.; $^1$H NMR ($CDCl_3$) δ 9.43 (br s, 1H), 8.31 (d, J=5.6 Hz, 1H), 7.96 (d, J=8.2 Hz, 1H), 7.54 (t, $J_{HF}$=53.4 Hz, 1H), 7.39-7.35 (m, 2H), 6.89 (d, J=5.6 Hz, 1H), 6.83 (d, J=8.2 Hz, 1H), 4.05 (s, 3H), 4.00 (s, 3H), 3.94 (s, 4H), 3.82-3.80 (m, 4H); Anal. Calcd. for $C_{22}H_{22}F_2N_8O_3$: C, 54.5; H, 4.6; N, 23.1. Found: C, 54.4; H, 4.5; N, 22.9%.

Example 28

Synthesis of 4-[2-(difluoromethyl)-4-methoxy-1H-benzimidazol-1-yl]-N-(6-methoxy-3-pyridinyl)-6-(4-morpholinyl)-1,3,5-triazin-2-amine

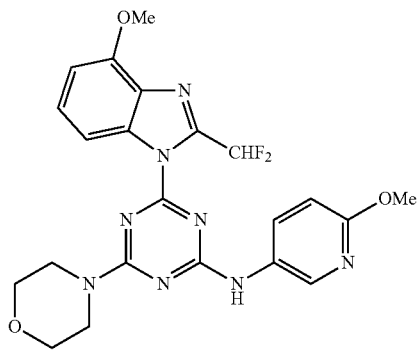

The compound was synthesized according to Method A.

To a solution of 0.310 g (2.50 mmol) of 5-amino-2-methoxypyridine in THF (3 mL) at 0° C. was added 1.35 mL of lithium diisopropylamide (2 M solution in benzene/heptanes/THF), and the mixture was stirred for 20 min. A solution of 0.240 g (0.61 mmol) of 1-[4-chloro-6-(4-morpholinyl)-1,3,5-triazin-2-yl]-2-(difluoromethyl)-4-methoxy-1H-benzimidazole in THF (5 mL) was added, and the resulting mixture was stirred for 1 hr at RT. After neutralization with acetic acid, the mixture was diluted with water and extracted with EtOAc. The organic layer was washed sequentially with water and aq. $NH_3$, dried, and concentrated. Chromatography on alumina, eluting first with hexanes/EtOAc (1:1) and then with $CH_2Cl_2$/EtOAc (1:3) gave a reddish powder. Recrystallization from ethanol/$CH_2Cl_2$ gave 0.010 g (4% yield) of 4-[2-(difluoromethyl)-4-methoxy-1H-benzimidazol-1-yl]-N-(6-methoxy-3-pyridinyl)-6-(4-morpholinyl)-1,3,5-triazin-2-amine: mp 201-202° C.; $^1$H NMR ($CDCl_3$) δ 8.33 (br s, 1H), 7.93 (br s, 1H), 7.79 (dd, J=8.8, 2.7 Hz, 1H), 7.32-7.31 (m, 2H), 6.88-6.79 (m, 3H), 4.04 (s, 3H), 3.97 (s, 3H), 3.90 (s, 4H), 3.79 (s, 4H); Anal. Calcd. for $C_{22}H_{22}F_2N_8O_3$: C, 54.5; H, 4.6; N, 23.1. Found: C, 54.6; H, 4.5; N, 22.9%.

Example 29

Synthesis of 4-[2-(difluoromethyl)-4-methoxy-1H-benzimidazol-1-yl]-N-(6-fluoro-3-pyridinyl)-6-(4-morpholinyl)-1,3,5-triazin-2-amine

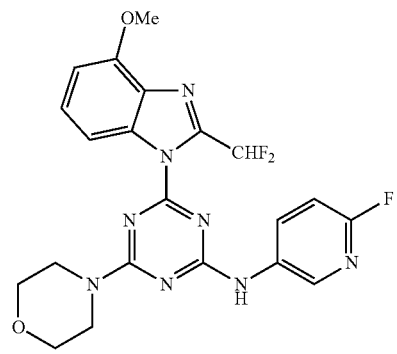 [SMILES: COc1cccc2c1nc(C(F)F)n2-c1nc(Nc2ccc(F)nc2)nc(N2CCOCC2)n1]

The compound was synthesized according to Method A.

To 0.240 g (2.14 mmol) of 5-amino-2-fluoropyridine in THF (5 mL) was added 0.94 mL of n-butyllithium (2.5 M solution in hexanes), and the mixture was stirred for 10 min. A solution of 0.283 g (0.71 mmol) of 1-[4-chloro-6-(4-morpholinyl)-1,3,5-triazin-2-yl]-2-(difluoromethyl)-4-methoxy-1H-benzimidazole (Example 2) in THF (5 mL) was added. The resulting mixture was stirred at room temperature for 1 hr. After neutralization with acetic acid, the mixture was diluted with water and extracted with EtOAc. The organic layer was washed successively with water and aqueous $NH_3$, and dried. Removal of the solvent followed by chromatography on alumina eluting first with hexanes/EtOAc (1:1) and then $CH_2Cl_2$/EtOAc (1:3) gave a brown powder. Recrystallization from ethanol/$CH_2Cl_2$ gave 0.135 g (40% yield) of 4-[2-(difluoromethyl)-4-methoxy-1H-benzimidazol-1-yl]-N-(6-fluoro-3-pyridinyl)-6-(4-morpholinyl)-1,3,5-triazin-2-amine: mp 261-263° C.; $^1$H NMR ($CDCl_3$) δ 8.44 (br s, 1H), 8.03-8.01 (m, 1H), 7.90 (br s, 1H), 7.61-7.31 (m, 2H), 7.07 (br s, 1H), 6.99 (dd, J=8.3, 3.4 Hz, 1H), 6.83 (d, J=8.0 Hz, 1H), 4.05 (s, 3H), 3.93-3.88 (m, 4H), 3.80 (s, 4H); Anal. Calcd. for $C_{21}H_{19}F_3N_8O_2$: C, 53.4; H, 4.05; N, 23.7. Found: C, 53.5; H, 4.0; N, 23.8%.

Example 30

Synthesis of N-(6-chloro-3-pyridinyl)-4-[2-(difluoromethyl)-4-methoxy-1H-benzimidazol-1-yl]-6-(4-morpholinyl)-1,3,5-triazin-2-amine

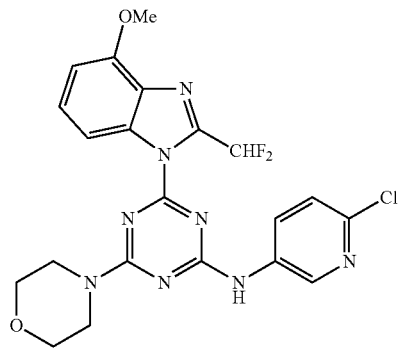 [SMILES: COc1cccc2c1nc(C(F)F)n2-c1nc(Nc2ccc(Cl)nc2)nc(N2CCOCC2)n1]

The compound was synthesized according to Method A.

To 0.246 g (1.92 mmol) of 5-amino-2-chloropyridine in THF (4 mL) was added 0.85 mL of n-butyllithium (2.5 M solution in hexanes), and the mixture was stirred for 10 min. A solution of 0.260 g (0.66 mmol) of 1-[4-chloro-6-(4-morpholinyl)-1,3,5-triazin-2-yl]-2-(difluoromethyl)-4-methoxy-1H-benzimidazole (Example 2) in THF (5 mL) was added. The resulting mixture was stirred at room temperature for 1 hr. After neutralization with acetic acid, the mixture was diluted with water and extracted with EtOAc. The organic layer was washed successively with water and aqueous $NH_3$, and dried. Removal of the solvent and chromatography of the residue on alumina eluting first with hexanes/EtOAc (1:1) and then with $CH_2Cl_2$-EtOAc (1:5) gave a brown powder. Recrystallization from ethanol/$CH_2Cl_2$ gave 0.016 g (5% yield) of N-(6-chloro-3-pyridinyl)-4-[2-(difluoromethyl)-4-methoxy-1H-benzimidazol-1-yl]-6-(4-morpholinyl)-1,3,5-triazin-2-amine: mp 260-262° C.; $^1$H NMR ($CDCl_3$) δ 8.69 (s, 1H), 7.95-7.90 (m, 2H), 7.48 (t, J=53.5 Hz, 1H), 7.37-7.33 (m, 2H), 7.11 (s, 1H), 6.83 (d, J=8.0 Hz, 1H), 4.05 (s, 3H), 3.94-3.87 (m, 4H), 3.81 (m, 4H); Anal. Calcd. for $C_{21}H_{19}ClF_2N_8O_2$: C, 51.6; H, 3.9; N, 22.9; Cl, 7.25. Found: C, 52.1; H, 3.9; N, 22.5; Cl, 7.1%.

Example 31

Synthesis of 4-[2-(difluoromethyl)-4-methoxy-1H-benzimidazol-1-yl]-6-(4-morpholinyl)-N-(5-pyrimidinyl)-1,3,5-triazin-2-amine

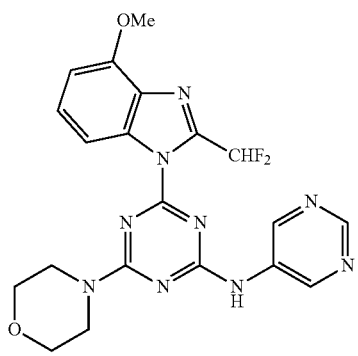 [SMILES: COc1cccc2c1nc(C(F)F)n2-c1nc(Nc2cncnc2)nc(N2CCOCC2)n1]

The compound was synthesized according to Method A.

To 0.207 g (2.18 mmol) of 5-aminopyrimidine in THF (4 mL) was added 0.96 mL of n-butyllithium (2.5 M solution in hexanes) and the mixture stirred for 10 min. A solution of 0.260 g (0.66 mmol) of 1-[4-chloro-6-(4-morpholinyl)-1,3,5-triazin-2-yl]-2-(difluoromethyl)-4-methoxy-1H-benzimidazole (Example 2) in THF (5 mL) was added. The resulting mixture was stirred at room temperature for 1 hr. After neutralization with acetic acid, the mixture was diluted with water, and extracted with EtOAc. The organic layer was washed successively with water and aqueous $NH_3$, and dried. Removal of the solvent, followed by chromatography on silica eluting with hexanes/EtOAc (1:1) gave a yellow powder. Recrystallization from ethanol/$CH_2Cl_2$ gave 0.068 g (20% yield) of 4-[2-(difluoromethyl)-4-methoxy-1H-benzimidazol-1-yl]-6-(4-morpholinyl)-N-(5-pyrimidinyl)-1,3,5-triazin-2-amine: mp 293-295° C.; $^1$H NMR ($CDCl_3$) δ 9.07 (s, 2H), 9.01 (s, 1H), 7.92 (d, J=8.4 Hz, 1H), 7.48 (t, $J_{HF}$=53.2 Hz, 1H), 7.37 (t, J=8.2 Hz, 1H), 7.14 (s, 1H), 6.84 (d, J=8.0 Hz, 1H), 4.05 (s, 3H), 3.95-3.90 (m, 4H), 3.82-3.81 (m, 4H); Anal. Calcd. for $C_{20}H_{19}F_2N_9O_2$: C, 52.75; H, 4.2; N, 27.7. Found: C, 52.9; H, 4.2; N, 27.7%.

Example 32

Synthesis of 4-(2-(difluoromethyl)-4-methoxy-1H-benzimidazol-1-yl)-N-(6-methoxypyrimidin-4-yl)-6-morpholino-1,3,5-triazin-2-amine

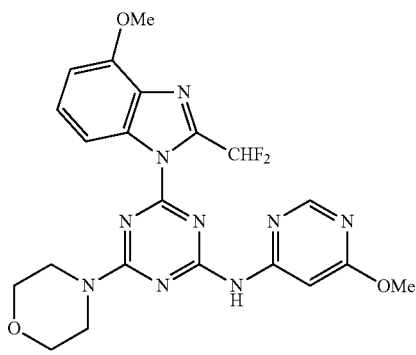 [SMILES: COc1cc(Nc2nc(N3CCOCC3)nc(-n3c(C(F)F)nc4c(OC)cccc43)n2)ncn1]

The compound was synthesized according to Method A.

To 0.282 g (2.25 mmol) of 4-amino-6-methoxypyrimidine in THF (4 mL) was added 1.30 mL of NaHMDS (2 M solution in THF) and the mixture was stirred for 10 min. A solution of 0.297 g (0.75 mmol) of 1-[4-chloro-6-(4-morpholinyl)-1,3,5-triazin-2-yl]-2-(difluoromethyl)-4-methoxy-1H-benzimidazole (Example 2) in THF (5 mL) was added. The resulting mixture was stirred at room temperature for 1 hr. After neutralization with acetic acid, the mixture was diluted with water, and extracted with EtOAc. The organic layer was washed successively with water and aqueous $NH_3$, and dried. Removal of the solvent, followed by chromatography on silica eluting with $CH_2Cl_2$/EtOAc (1:1) gave a white powder. Recrystallization from ethanol/$CH_2Cl_2$ gave 0.103 g (30% yield) of 4-(2-(difluoromethyl)-4-methoxy-1H-benzimidazol-1-yl)-N-(6-methoxypyrimidin-4-yl)-6-morpholino-1,3,5-triazin-2-amine: mp 256-259° C.; $^1$H NMR ($CDCl_3$) δ 8.52 (s, 1H), 7.96-7.94 (m, 2H), 7.59 (s, 1H), 7.49 (t, $J_{HF}$=53.5 Hz, 1H), 7.36 (d, J=8.4 Hz, 1H), 6.84 (d, J=8.1 Hz, 1H), 4.06 (s, 3H), 4.00 (s, 3H), 3.99-3.96 (m, 4H), 3.84 (s, 4H); HRMS (FAB $MH^+$) Calcd for $C_{21}H_{22}F_2N_9O_3$: m/z 486.1808. Found: m/z 486.1808.

Example 33

Synthesis of 4-[2-(difluoromethyl)-4-methoxy-1H-benzimidazol-1-yl]-6-(4-morpholinyl)-N-(3-pyridazinyl)-1,3,5-triazin-2-amine

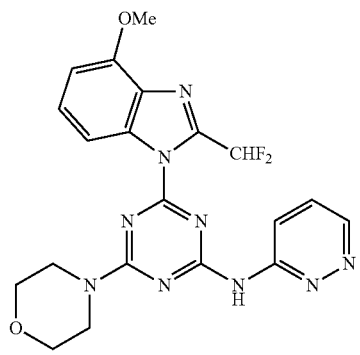 [SMILES: COc1cccc2c1nc(C(F)F)n2-c1nc(Nc2cccnn2)nc(N2CCOCC2)n1]

The compound was synthesized according to Method A.

To 0.215 g (2.26 mmol) of 3-aminopyridazine (Example 23) in THF (4 mL) was added 1.30 mL of NaHMDS (2 M solution in THF), and the mixture was stirred for 10 min. A solution of 0.297 g (0.75 mmol) of 1-[4-chloro-6-(4-morpholinyl)-1,3,5-triazin-2-yl]-2-(difluoromethyl)-4-methoxy-1H-benzimidazole (Example 2) in THF (5 mL) was added. The resulting mixture was stirred at room temperature for 1 hr. After neutralization with acetic acid, the mixture was diluted with water and extracted with EtOAc. The organic layer was washed successively with water and aqueous $NH_3$, and dried. Removal of the solvent, followed by chromatography on silica eluting with $CH_2Cl_2$/EtOAc (1:1) gave a white powder. Recrystallization from ethanol/$CH_2Cl_2$ gave 0.103 g (30% yield) of 4-[2-(difluoromethyl)-4-methoxy-1H-benzimidazol-1-yl]-6-(4-morpholinyl)-N-(3-pyridazinyl)-1,3,5-triazin-2-amine: mp 261-263° C.; $^1$H NMR (DMSO-$d_6$) δ11.13 (s, 1H), 8.97 (dd, J=4.7, 1.4 Hz, 1H), 8.38 (d, J=8.4 Hz, 1H), 8.20 (d, J=8.4 Hz, 1H), 8.05 (t, $J_{HF}$=52.9 Hz, 1H), 7.73 (dd, J=9.1, 4.7 Hz, 1H), 7.41 (t, J=8.3 Hz, 1H), 6.97 (d, J=7.8 Hz, 1H), 3.98 (s, 3H), 3.85 (s, 4H), 3.75 (s, 4H); Anal. Calcd. for $C_{20}H_{19}F_2N_9O_2$: C, 52.75; H, 4.2; N, 27.7. Found: C, 52.7; H, 4.25; N, 27.7%.

Example 34

Synthesis of 4-[2-(difluoromethyl)-4-methoxy-1H-benzimidazol-1-yl]-N-(6-methoxy-3-pyridazinyl)-6-(4-morpholinyl)-1,3,5-triazin-2-amine

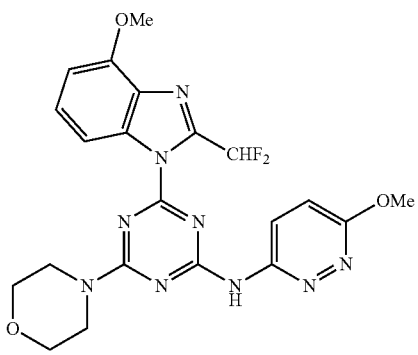 [SMILES: COc1ccc(Nc2nc(N3CCOCC3)nc(-n3c(C(F)F)nc4c(OC)cccc43)n2)nn1]

The compound was synthesized according to Method A.

To 0.216 g (1.73 mmol) of 6-methoxy-3-pyridazinamine (*J. Med. Chem.* 2006, 49, 4409-4424) in THF (3 mL) was added 0.97 mL of NaHMDS (2 M solution in THF), and the mixture was stirred for 10 min. A solution of 0.233 g (0.59 mmol) of 1-[4-chloro-6-(4-morpholinyl)-1,3,5-triazin-2-yl]-2-(difluoromethyl)-4-methoxy-1H-benzimidazole (Example 2) was added and the resulting mixture was stirred for 10 min. The resulting mixture was neutralized with acetic acid, diluted with water, and extracted with EtOAc. The organic layer was washed successively with water and aqueous $NH_3$, dried, and concentrated. Recrystallization from ethanol/$CH_2Cl_2$ gave 0.086 g (30% yield) of 4-[2-(difluoromethyl)-4-methoxy-1H-benzimidazol-1-yl]-N-(6-methoxy-3-pyridazinyl)-6-(4-morpholinyl)-1,3,5-triazin-2-amine: mp 256-259° C.; $^1$H NMR (DMSO-$d_6$) δ 10.85 (s, 1H), 8.24 (d, J=9.2 Hz, 1H), 8.15 (d, J=7.7 Hz, 1H), 7.99 (t, $J_{HF}$=52.6 Hz, 1H), 7.40 (t, J=8.2 Hz, 1H), 7.29 (d, J=9.5 Hz, 1H), 6.96 (d, J=8.0 Hz, 1H), 4.00 (s, 3H), 3.97 (s, 3H), 3.84-3.79 (m, 4H), 3.72 (s, 4H); Anal. Calcd. For $C_{21}H_{21}F_2N_9O_3$·0.5$H_2O$: C, 51.1; H, 4.5; N, 25.5. Found: C, 51.4; H, 4.6; N, 25.0%.

Example 35

Synthesis of 4-[2-(difluoromethyl)-1H-benzimidazol-1-yl]-6-(4-morpholinyl)-N-(5-pyrimidinyl)-1,3,5-triazin-2-amine

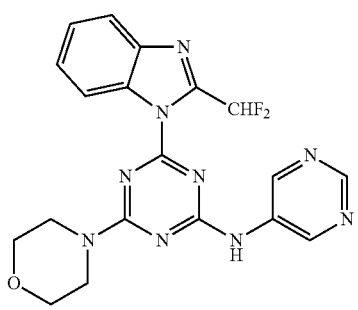 [SMILES: FC(F)c1nc2ccccc2n1-c1nc(Nc2cncnc2)nc(N2CCOCC2)n1]

The compound was synthesized according to Method A.

To 0.186 g (1.96 mmol) of 5-aminopyrimidine in THF (4 mL) was added 1.1 mL of NaHMDS (2 M solution in THF) at 0° C. and the mixture was stirred for 15 min. A solution of 0.238 g (0.65 mmol) of 1-[4-chloro-6-(4-morpholinyl)-1,3,5-triazin-2-yl]-2-(difluoromethyl)-1H-benzimidazole in THF (5 mL) was added and the resulting mixture WAS stirred for 1 hr at room temperature. The resulting mixture was neutralized with acetic acid, diluted with water, and extracted with EtOAc. The organic layer was washed with water, and aq. $NH_3$, and dried. Removal of the solvent, followed by chromatography on alumina, eluting with $CH_2Cl_2$/EtOAc (1:9), then $CH_2Cl_2$/EtOAc (1:3), gave an off-white powder. Recrystallization from ethanol gave 0.123 g (47% yield) of 4-[2-(difluoromethyl)-1H-benzimidazol-1-yl]-6-(4-morpholinyl)-N-(5-pyrimidinyl)-1,3,5-triazin-2-amine: mp 290-292° C.; $^1$H NMR (CDCl$_3$) δ9.07 (s, 2H), 9.02 (s, 1H), 8.37 (d, J=7.2 Hz, 1H), 7.89 (dd, J=7.7, 1.5 Hz, 1H), 7.57 (t, $J_{HF}$=53.7 Hz, 1H), 7.47-7.40 (m, 2H), 7.11 (s, 1H), 3.95-3.92 (m, 4H), 3.83 (br s, 4H); Anal. Calcd. for $C_{19}H_{17}F_2N_9O$: C, 53.65; H, 4.0; N, 29.6. Found: C, 53.4; H, 4.2; N, 29.4%.

To 99 mg (0.23 mmol) of the above compound in $CH_2Cl_2$ (3 mL) was added 16 μL (0.25 mmol) of methanesulfonic acid in MeOH (0.5 mL). The mixture was stirred for 5 min and concentrated in vacuo to give a white powder. Recrystallization from MeOH/EtOAc gave 85 mg (71%) of 4-[2-(difluoromethyl)-1H-benzimidazol-1-yl]-6-(4-morpholinyl)-N-(5-pyrimidinyl)-1,3,5-triazin-2-amine methanesulfonate: mp 163-166° C.; $^1$H NMR (DMSO-$d_6$) δ 10.32 (s, 1H), 9.13 (s, 2H), 8.92 (s, 1H), 8.56 (br s, 1H), 8.13-7.77 (m, 2H), 7.53-7.43 (m, 2H), 3.85 (s, 4H), 3.76-3.69 (m, 4H), 2.35 (s, 3H); Anal. Calcd. for $C_{20}H_{21}F_2N_9O_4S$·0.31$H_2O$: C, 45.6; H, 4.1; N, 23.9. Found: C, 45.2; H, 4.35; N, 23.8%.

Example 36

Synthesis of 4-[2-(difluoromethyl)-4-methoxy-1H-benzimidazol-1-yl]-6-(4-morpholinyl)-N-(4-pyrimidinyl)-1,3,5-triazin-2-amine

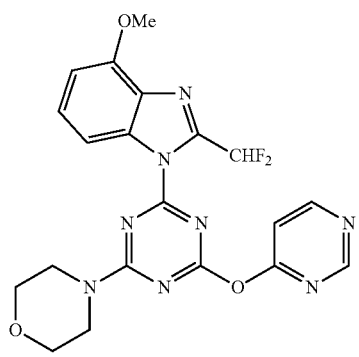 [SMILES: COc1cccc2c1nc(C(F)F)n2-c1nc(Oc2ccncn2)nc(N2CCOCC2)n1]

The compound was synthesized according to Method A.

To 0.225 g (2.37 mmol) of 4-aminopyrimidine in THF (3 mL) was added 1.30 mL of NaHMDS (2 M solution in THF) and the mixture was stirred for 10 min. A solution of 0.320 g (0.81 mmol) of 1-[4-chloro-6-(4-morpholinyl)-1,3,5-triazin-2-yl]-2-(difluoromethyl)-4-methoxy-1H-benzimidazole in THF (5 mL) was added and the resulting mixture was stirred for 1 hr. The reaction mixture was neutralized with acetic acid, diluted with water and extracted with EtOAc. The organic layer was washed with water, and aq. $NH_3$, and dried. Removal of the solvent, followed by chromatography on silica, eluting first with hexanes-EtOAc (1:1), then $CH_2Cl_2$/EtOAc (1:1) to $CH_2Cl_2$/EtOAc (1:3) gave a white powder. Recrystallization from EtOH/$CH_2Cl_2$ gave 0.058 g (16% yield) of 4-[2-(difluoromethyl)-4-methoxy-1H-benzimidazol-1-yl]-6-(4-morpholinyl)-N-(4-pyrimidinyl)-1,3,5-triazin-2-amine: mp 234-236° C.; $^1$H NMR ($CDCl_3$) δ8.91 (d, J=1.0 Hz, 1H), 8.65 (d, J=5.8 Hz, 1H), 8.23 (dd, J=5.8, 1.3 Hz, 1H), 7.99 (s, 1H), 7.93 (dd, J=8.3, 0.5 Hz, 1H), 7.47 (t, $J_{HF}$=53.4 Hz, 1H), 7.38 (t, J=8.2 Hz, 1H), 6.85 (d, J=7.8 Hz, 1H), 4.06 (s, 3H), 3.97-3.96 (m, 4H), 3.86-3.84 (m, 4H); Anal. Calcd. for $C_{20}H_{19}F_2N_9O_2 \cdot 0.31H_2O$: C, 52.1; H, 4.3; N, 27.3. Found: C, 51.7; H, 4.15; N, 27.3%.

Example 37

Synthesis of $N^5$-[4-[2-(difluoromethyl)-4-methoxy-1H-benzimidazol-1-yl]-6-(4-morpholinyl)-1,3,5-triazin-2-yl]-2,5-pyridinediamine

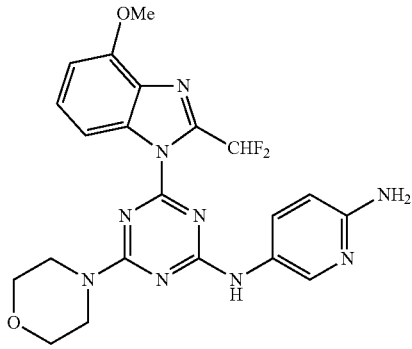 [SMILES: COc1cccc2c1nc(C(F)F)n2-c1nc(Nc2ccc(N)nc2)nc(N2CCOCC2)n1]

The compound was synthesized according to Method A.

To 0.652 g (4.69 mmol) of 2-amino-5-nitropyridine in THF (5 mL) was added 3.5 mL of NaHMDS (2M solution in THF) at 0° C. After 20 min a solution of 1.085 g (4.97 mmol) of di-tert-butyl dicarbonate in THF (6 mL) was added and the mixture was slowly warmed to room temperature overnight. Water was added, and the mixture was extracted with EtOAc (×4). The organic layer was washed with brine, dried ($Na_2SO_4$), and concentrated. Chromatography on, silica with hexanes-EtOAc (7:3), gave 0.695 g (62% yield) of tert-butyl-5-nitropyridin-2-ylcarbamate as an orange powder: $^1$H NMR ($CDCl_3$) δ 9.19 (dd, J=2.8, 0.5 Hz, 1H), 8.93 (br s, 1H), 8.46 (ddd, J=9.4, 2.8, 0.5 Hz, 1H), 8.20 (dd, J=9.5, 0.5 Hz, 1H), 1.59 (s, 9H); LCMS (APCI$^-$) m/z: 238 (MH$^+$, 100%).

To 0.314 g (1.31 mmol) of the above nitro compound in THF-MeOH (16 mL, 1:1) was added 0.460 g of 10% Pd/C and the mixture was stirred under hydrogen (40 in/Hg) for 4 hrs. The reaction mixture was filtered through celite, washed with MeOH and concentrated to give 0.277 g (99% yield) of tert-butyl 5-aminopyridin-2-yl-carbamate as a white powder: $^1$H NMR (DMSO-$d_6$) δ9.00 (br s, 1H), 7.62 (dd, J=2.7, 0.4 Hz, 1H), 7.39 (d, J=8.7 Hz, 1H), 6.94 (dd, J=8.7, 2.8 Hz, 1H), 4.92 (s, 2H), 1.44 (s, 9H).

To 0.277 g (1.33 mmol) of the above amino compound in THF (3 mL) was added 0.61 mL of n-butyllithium (2.5 M solution in hexanes) and the mixture was stirred for 10 min. A solution of 0.176 g (0.44 mmol) of 1-[4-chloro-6-(4-morpholinyl)-1,3,5-triazin-2-yl]-2-(difluoromethyl)-4-methoxy-1H-benzimidazole in THF (5 mL) was added and the resulting mixture was stirred for 1 hr at room temperature. The reaction mixture was neutralized with acetic acid, diluted with water, and extracted with EtOAc. The organic layer was washed with water and aq. $NH_3$, dried, and concentrated. Chromatography on silica, eluting with hexanes-EtOAc (7:3), then with $CH_2Cl_2$-EtOAc (3:1), gave 0.033 g (13% yield) of tert-butyl 5-{[4-[2-(difluoromethyl)-4-methoxy-1H-benzimidazol-1-yl]-6-(4-morpholinyl)-1,3,5-triazin-2-yl]amino}-2-pyridinylcarbamate: $^1$H NMR (DMSO-$d_6$) δ 10.02 (s, 1H), 9.66 (s, 1H), 8.54 (s, 1H), 8.17-7.80 (m, 4H), 7.39 (d, J=8.7 Hz, 1H), 6.97-6.93 (m, 1H), 3.98 (s, 3H), 3.82 (s, 4H), 3.74-3.72 (m, 4H), 1.48 (s, 9H).

To 0.033 g (0.06 mmol) of the above carbamate in $CH_2Cl_2$ (3 mL) was added 0.1 mL (1.30 mmol) of trifluoroacetic acid, and the mixture was stirred for 5 hrs. The reaction mixture was diluted with $CH_2Cl_2$ and aq. $NH_4OH$, and the organic layer was washed with brine, dried ($Na_2SO_4$), and concentrated. The residue was recrystallized from EtOH/$CH_2Cl_2$ to give 0.0133 g (49% yield) of $N^5$-[4-[2-(difluoromethyl)-4-methoxy-1H-benzimidazol-1-yl]-6-(4-morpholinyl)-1,3,5-triazin-2-yl]-2,5-pyridinediamine, as a brown powder: mp 267-270° C.; $^1$H NMR (DMSO-$d_6$) δ9.67-9.49 (m, 1H), 8.18-7.27 (m, 5H), 6.96 (d, J=7.6 Hz, 1H), 6.48 (d, J=8.4 Hz, 1H), 5.87-5.75 (m, 2H), 3.98 (s, 3H), 3.81 (s, 4H), 3.71 (s, 4H); HRMS (ESI) M+H$^+$ Calcd. for $C_{21}H_{22}F_2N_9O_2$: m/z 470.1859. Found: m/z 470.1867.

Example 38

Synthesis of $N^5$-[4-[2-(difluoromethyl)-4-methoxy-1H-benzimidazol-1-yl]-6-(4-morpholinyl)-1,3,5-triazin-2-yl]-$N^2$-methyl-2,5-pyridinediamine

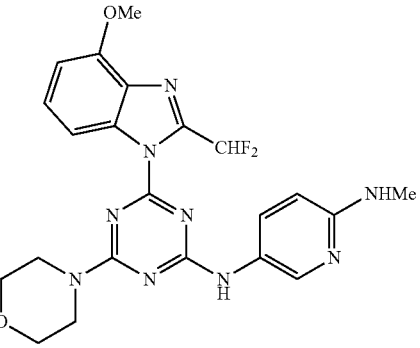

The compound was synthesized according to Method A.

To 0.652 g (4.69 mmol) of 2-amino-5-nitropyridine in THF (5 mL) was added 3.5 mL of NaHMDS (2M solution in THF) at 0° C. After 20 min, a solution of 1.085 g (4.97 mmol) of di-tert-butyl dicarbonate in THF (6 mL) was added, and the mixture was slowly warmed to room temperature overnight. Water was added, and the mixture was extracted with EtOAc (×4). The combined organic layers were washed with brine, dried ($Na_2SO_4$), and concentrated. Purification by flash column chromatography on silica, eluting with hexanes-EtOAc (7:3), gave 0.695 g (62% yield) of tert-butyl 5-nitro-2-pyridinylcarbamate as an orange powder: $^1$H NMR ($CDCl_3$) δ9.19 (dd, J=2.8, 0.5 Hz, 1H), 8.93 (br s, 1H), 8.46 (ddd, J=9.4, 2.8, 0.5 Hz, 1H), 8.20 (dd, J=9.5, 0.5 Hz, 1H), 1.59 (s, 9H); LCMS (APCI$^-$) m/z: 238 (MH$^+$, 100%).

To 0.378 g (1.58 mmol) of the above nitro compound in DMF (6 mL) at 0° C. was added 0.067 g (2.80 mmol) of sodium hydride. After 20 min, 0.12 mL (1.93 mmol) of methyl iodide was added, and the mixture was stirred for 2 hrs. Water was added, and the mixture was extracted with EtOAc (×4). The combined organic layer was washed successively with 1M HCl, sat. $NaHCO_3$ solution, and brine, dried ($Na_2SO_4$), and concentrated, to give 0.40 g (99% yield) of tert-butyl methyl(5-nitro-2-pyridinyl)carbamate: $^1$H NMR ($CDCl_3$) δ9.19 (d, J=2.7 Hz, 1H), 8.36 (dd, J=9.4, 2.7 Hz, 1H), 8.14 (dd, J=9.4, 0.3 Hz, 1H), 3.50 (s, 3H), 1.57 (s, 9H); LCMS (APCI$^-$) m/z: 253 (MH$^+$, 100%).

To 0.40 g (1.58 mmol) of the above nitro compound in MeOH (25 mL) was added 0.4 g of 10% Pd/C and the mixture was stirred under hydrogen (40 in Hg) for 4 hrs. After filtration through celite the reaction mixture was concentrated, to give 0.36 g (97% yield) of tert-butyl 5-amino-2-pyridin-2-yl (methyl)carbamate, as a yellow oil: $^1$H NMR (DMSO-$d_6$) δ7.70 (dd, J=2.9, 0.5 Hz, 1H), 7.07 (d, J=8.6 Hz, 1H), 6.93 (dd, J=8.6, 2.9 Hz, 1H), 3.12 (s, 3H), 1.39 (s, 9H).

To 0.356 g (1.53 mmol) of the above amine in THF (3 mL) was added 0.70 mL of n-butyllithium (2.5 M solution in hexanes) and the mixture was stirred for 10 min. A solution of 0.21 g (0.52 mmol) of 1-[4-chloro-6-(4-morpholinyl)-1,3,5-triazin-2-yl]-2-(difluoromethyl)-4-methoxy-1H-benzimidazole in THF (5 mL) was added, and the resulting mixture was stirred for 1 hr. The reaction mixture was neutralized with acetic acid, diluted with water, and extracted with EtOAc. The organic layer was washed with water and aq. $NH_3$, and dried. The solvent was removed under vacuum, and the product mixture was purified by flash column chromatography, eluting with $CH_2Cl_2$/EtOAc (3:1), to give 0.075 g (13% yield) of tert-butyl 5-{[4-[2-(difluoromethyl)-4-methoxy-1H-benzimidazol-1-yl]-6-(4-morpholinyl)-1,3,5-triazin-2-yl] amino}-2-pyridinyl(methyl)carbamate, as a yellow powder: $^1$H NMR (DMSO-$d_6$) δ 10.11 (s, 1H), 8.68-7.41 (m, 5H), 7.61 (d, J=9.0 Hz, 1H), 6.97 (d, J=8.1 Hz, 1H), 3.98 (s, 3H), 3.83 (s, 4H), 3.74-3.73 (m, 4H), 3.29 (s, 3H), 1.47 (s, 9H); LCMS (APCI$^+$) m/z: 585 (MH$^+$, 100%).

To 0.0750 g (0.13 mmol) of the above carbamate in $CH_2Cl_2$ (3 mL) was added 0.1 mL (1.30 mmol) of trifluoroacetic acid and the mixture was stirred for 5 hrs. After dilution with $CH_2Cl_2$, the mixture was treated with $H_2O$ and aq. $NH_3$, and the organic layer was washed with brine, dried ($Na_2SO_4$), and concentrated. The residue was recrystallized from EtOH/$CH_2Cl_2$ to give 0.0472 g (75% yield) of $N^5$-[4-[2-(difluoromethyl)-4-methoxy-1H-benzimidazol-1-yl]-6-(4-morpholinyl)-1,3,5-triazin-2-yl]-$N^2$-methyl-2,5-pyridinediamine: mp 218-221° C.; $^1$H NMR ($CDCl_3$) δ8.31-7.73 (m, 2H), 7.62 (dd, J=8.8, 2.6 Hz, 1H), 7.56-7.31 (m, 2H), 6.82-6.80 (m, 2H), 6.46 (d, J=8.8 Hz, 1H), 4.76 (br s, 1H), 4.04 (s, 3H), 3.89 (s, 4H), 3.79 (s, 4H), 2.96 (s, 3H); HRMS (ESI) M+H$^+$ Calcd. for $C_{22}H_{24}F_2N_9O_2$: m/z 484.2016. Found: m/z 484.2023.

Example 39

Synthesis of $N^5$-[4-[2-(difluoromethyl)-4-methoxy-1H-benzimidazol-1-yl]-6-(4-morpholinyl)-1,3,5-triazin-2-yl]-$N^2$,$N^2$-dimethyl-2,5-pyridinediamine

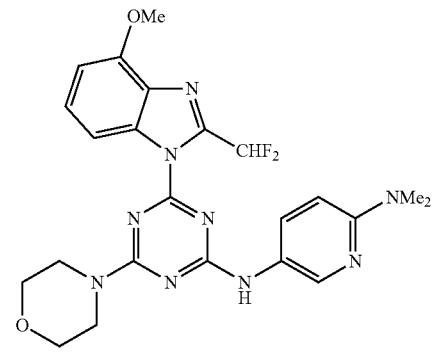 [SMILES: COc1cccc2c1nc(C(F)F)n2-c1nc(Nc2ccc(N(C)C)nc2)nc(N2CCOCC2)n1]

The compound was synthesized according to Method A.

To 0.314 g (1.99 mmol) of 2-chloro-5-nitropyridine in MeOH (1 mL) was added 5 mL of dimethylamine (2M solution in MeOH) at 0° C. and the mixture was warmed to room temperature. The reaction mixture was concentrated and extracted with EtOAc. The organic layer was washed successively with sat. $NaHCO_3$ solution and brine, dried ($Na_2SO_4$), and concentrated to give 0.313 g (94% yield) of 2-dimethylamino-5-nitropyridine as an orange powder: $^1$H NMR ($CDCl_3$) δ9.06 (d, J=2.7 Hz, 1H), 8.20 (dd, J=9.5, 2.7 Hz, 1H), 6.46 (dd, J=9.5, 0.4 Hz, 1H), 3.23 (s, 6H); LCMS (APCI$^+$) m/z: 168 (MH$^+$, 100%).

A mixture of 0.312 g (1.87 mmol) of the above nitro compound and 0.205 g of 10% Pd/C in methanol (40 mL) was stirred under hydrogen (25 in/Hg) for 5 hrs. The reaction mixture was filtered through celite, and the solvent was concentrated, to give 0.236 g (92% yield) of $N^2$,$N^2$-dimethyl-2,5-pyridinediamine: $^1$H NMR ($CDCl_3$) δ7.78 (d, J=2.9 Hz, 1H), 6.98 (dd, J=8.8, 2.9 Hz, 1H), 6.45 (dd, J=8.8, 0.5 Hz, 1H), 2.99 (s, 6H); LCMS (APCI$^+$) m/z: 138 (MH$^+$, 100%).

To 0.236 g (1.72 mmol) of the above diamine in THF (3.5 mL) was added 0.79 mL of n-butyllithium (2.5 M solution in hexanes) and the mixture was stirred for 10 min. A solution of 0.231 g (0.58 mmol) of 1-[4-chloro-6-(4-morpholinyl)-1,3,5-triazin-2-yl]-2-(difluoromethyl)-4-methoxy-1H-benzimidazole in THF (5 mL) was added and the resulting mixture was stirred for 1 hr. The reaction mixture was neutralized with acetic acid, diluted with water and extracted with EtOAc. The organic layer was washed with water and aq. $NH_3$, dried, and concentrated. Chromatography on silica eluting first with hexanes-EtOAc (1:1), then $CH_2Cl_2$-EtOAc (1:1) gave a pale brown powder. Recrystallization from ethanol/$CH_2Cl_2$ gave 0.144 g (50% yield) of $N^5$-[4-[2-(difluoromethyl)-4-methoxy-1H-benzimidazol-1-yl]-6-(4-morpholinyl)-1,3,5-triazin-2-yl]-$N^2$,$N^2$-dimethyl-2,5-pyridinediamine: mp 136-137° C.; $^1$H NMR ($CDCl_3$) δ8.35-7.83 (m, 2H), 7.63 (dd, J=9.0, 2.5 Hz, 1H), 7.57-7.29 (m, 1H), 6.81-6.80 (m, 2H), 6.57 (d, J=9.0 Hz, 1H), 4.04 (s, 3H), 3.89 (s, br, 4H), 3.79 (s, 4H), 3.13 (s, 6H); Anal. Calcd. for $C_{23}H_{25}F_2N_9O_2 \cdot 0.16$EtOH: C, 55.5; H, 5.2; N, 25.0. Found: C, 55.3; H, 5.2; N, 24.6%.

Example 40

Synthesis of 4-[2-(difluoromethyl)-4-methoxy-1H-benzimidazol-1-yl]-N-(2-methoxy-5-pyrimidinyl)-6-(4-morpholinyl)-1,3,5-triazin-2-amine

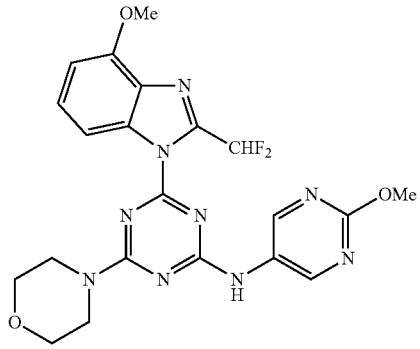 [SMILES: COc1ncc(Nc2nc(N3CCOCC3)nc(-n3c(C(F)F)nc4c(OC)cccc43)n2)cn1]

The compound was synthesized according to Method A.

To a solution of sodium methoxide (0.090 g of sodium) in MeOH (12 mL) was added 0.486 g (3.03 mmol) of 2-chloro-5-nitropyrimidine, and the mixture was heated under reflux for 1 hr. After cooling, the mixture was concentrated in vacuo, extracted with EtOAc, and washed with water. The aqueous layer was extracted with CHCl₃ and the combined organic layers were dried (Na₂SO₄), and concentrated, to give 0.347 g (75% yield) of 2-methoxy-5-nitropyrimidine as a yellow powder: $^1$H NMR (CDCl₃) δ9.31 (s, 2H), 4.17 (s, 3H); LCMS (APCI⁺) m/z: 156 (MH⁺, 100%).

To 0.342 g (2.20 mmol) of the above nitro compound in MeOH (20 mL) was added 0.30 g of 10% Pd/C and the mixture was stirred under hydrogen (25 in/Hg) for 18 hrs. The reaction mixture was filtered through celite, and concentrated, to give 0.274 g (100% yield) of 5-amino-2-methoxypyrimidine as a colorless oil: $^1$H NMR (DMSO-d₆) δ 8.05 (s, 2H), 3.94 (s, 3H); LCMS (APCI⁺) m/z: 126 (MH⁺, 100%).

To 0.274 g (2.19 mmol) of the above amino compound in THF (3 mL) was added 1.25 mL of NaHMDS (2 M solution in THF) and the mixture was stirred for 10 min. A solution of 0.31 g (0.78 mmol) of 1-[4-chloro-6-(4-morpholinyl)-1,3,5-triazin-2-yl]-2-(difluoromethyl)-4-methoxy-1H-benzimidazole in THF (5 mL) was added and the resulting mixture was stirred for 90 min. The reaction mixture was neutralized with acetic acid, diluted with water, and extracted with EtOAc. The organic layer was washed with water and aq. NH₃, dried, and concentrated. Recrystallization from EtOH/CH₂Cl₂ gave 0.098 g (26% yield) of 4-[2-(difluoromethyl)-4-methoxy-1H-benzimidazol-1-yl]-N-(2-methoxy-5-pyrimidinyl)-6-(4-morpholinyl)-1,3,5-triazin-2-amine: mp 255-258° C.; $^1$H NMR (DMSO-d₆) δ10.07 (s, 1H), 8.88-8.74 (m, 2H), 8.15-7.42 (m, 3H), 6.97 (d, J=8.0 Hz, 1H), 3.98 (s, 3H), 3.93 (s, 3H), 3.82-3.72 (m, 8H); Anal. Calcd. for $C_{21}H_{21}F_2N_6O_3$: C, 52.0; H, 4.4; N, 26.0. Found: C, 52.1; H, 4.5; N, 26.0%.

Example 41

Synthesis of N-(2-chloro-5-pyrimidinyl)-4-[2-(difluoromethyl)-4-methoxy-1H-benzimidazol-1-yl]-6-(4-morpholinyl)-1,3,5-triazin-2-amine

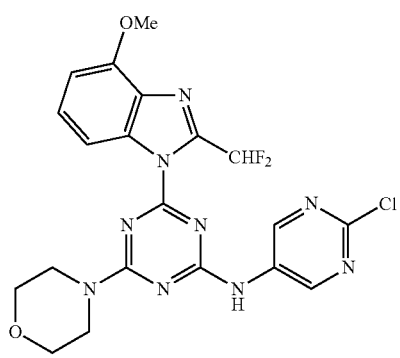 [SMILES: COc1cccc2c1nc(C(F)F)n2-c1nc(Nc2cnc(Cl)nc2)nc(N2CCOCC2)n1]

The compound was synthesized according to Method A.

A suspension of 3.5 g (63 mmol) of iron dust in 10 mL of 1.5% aq. AcOH and 35 mL of 65% EtOH was heated to 80° C., and 1.005 g (6.28 mmol) of 2-chloro-5-nitropyrimidine was added. The reaction mixture was then heated at 90° C. for 1 hr. After cooling to room temperature, the reaction mixture was neutralized with aq. NH₃, filtered through celite, and concentrated in vacuo. The residue was extracted with EtOAc (×4), and the organic layer was washed with brine, dried (Na₂SO₄), and concentrated. Chromatography on silica, eluting with hexanes/EtOAc (6:4), gave 0.49 g (60% yield) of 5-amino-2-chloropyrimidine as a yellow powder: $^1$H NMR (DMSO-d₆) δ8.03 (s, 2H); LCMS (APCI⁺) m/z: 130 (MH⁺, 100%).

A mixture of 0.28 g (0.71 mmol) of 1-[4-chloro-6-(4-morpholinyl)-1,3,5-triazin-2-yl]-2-(difluoromethyl)-4-methoxy-1H-benzimidazole, 0.076 g (0.56 mmol) of the above amine, 0.026 g (0.04 mmol) of BINAP, 0.01 g (0.04 mmol) of Pd(OAc)₂, and 0.266 g (0.82 mmol) of Cs₂CO₃ in 1,4-dioxane (4 mL) was heated at 100° C. for 3 hrs under nitrogen. The mixture was cooled to room temperature, sat. NaHCO₃ solution was added, and the resulting mixture was extracted with EtOAc (×4). The organic layer was washed with brine, dried (Na₂SO₄), and concentrated. Chromatography on silica, eluting with CH₂Cl₂/EtOAc (6:1), gave 0.10 g (36% yield) of N-(2-chloro-5-pyrimidinyl)-4-[2-(difluoromethyl)-4-methoxy-1H-benzimidazol-1-yl]-6-(4-morpholinyl)-1,3,5-triazin-2-amine, as a white powder: mp 295° C. (decomp.); $^1$H NMR (DMSO-d₆) δ 10.43 (s, 1H), 9.08 (s, 2H), 8.09-7.69 (m, 2H), 7.42 (t, J=8.0 Hz, 1H), 6.98 (d, J=7.6 Hz, 1H), 3.98 (s, 3H), 3.83 (s, 4H), 3.75-3.73 (m, 4H); Anal. Calcd. for $C_{20}H_{18}ClF_2N_9O_2$: C, 49.0; H, 3.7; N, 25.7. Found: C, 49.2; H, 3.9; N, 25.45%.

Example 42

Synthesis of N⁵-[4-[2-(difluoromethyl)-4-methoxy-1H-benzimidazol-1-yl]-6-(4-morpholinyl)-1,3,5-triazin-2-yl]-N²-[2-(dimethylamino)ethyl]-N²-methyl-2,5-pyrimidinediamine

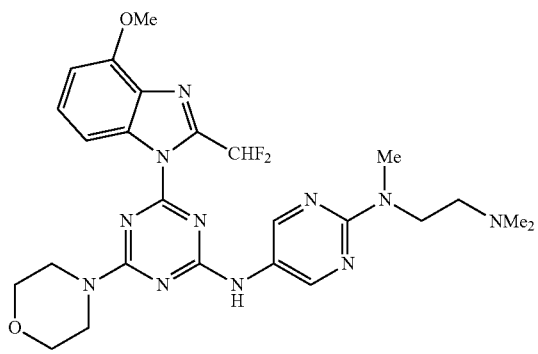 [SMILES: COc1cccc2c1nc(C(F)F)n2-c1nc(Nc2cnc(N(C)CCN(C)C)nc2)nc(N2CCOCC2)n1]

The compound was synthesized according to Method D.

To 0.101 g (0.21 mmol) of N-(2-chloro-5-pyrimidinyl)-4-[2-(difluoromethyl)-4-methoxy-1H-benzimidazol-1-yl]-6-(4-morpholinyl)-1,3,5-triazin-2-amine (Example 41) in EtOH (5 mL) was added 0.28 mL (2.14 mmol) of N,N,N'-trimethylethylenediamine, and the mixture was heated at 120° C. in a sealed tube for 1.5 hrs. Concentration of the solvent, followed by chromatography on silica, eluting first with $CH_2Cl_2$/EtOAc (1:3), and then with $CH_2Cl_2$/MeOH/$NH_3$ (95:5:0.1), gave N⁵-[4-[2-(difluoromethyl)-4-methoxy-1H-benzimidazol-1-yl]-6-(4-morpholinyl)-1,3,5-triazin-2-yl]-N²-[2-(dimethylamino)ethyl]-N²-methyl-2,5-pyrimidinediamine as a brownish oil, which solidified under vacuum: mp 96-98° C.; ¹H NMR (CDCl₃) δ8.47 (s, 1H), 8.36 (s, 1H), 8.05-7.31 (m, 3H), 7.00-6.61 (m, 2H), 4.04 (s, 3H), 3.90-3.79 (m, 10H), 3.22 (s, 3H), 2.97-2.89 (m, 2H), 2.33 (s, 6H); HRMS (ESI) M+H⁺ Calcd. for $C_{25}H_{32}F_2N_{11}O_2$: m/z 556.2703. Found: m/z 556.2694.

Example 43

Synthesis of N⁵-[4-[2-(difluoromethyl)-4-methoxy-1H-benzimidazol-1-yl]-6-(4-morpholinyl)-1,3,5-triazin-2-yl]-N²-[3-(dimethylamino)propyl]-N²-methyl-2,5-pyrimidinediamine

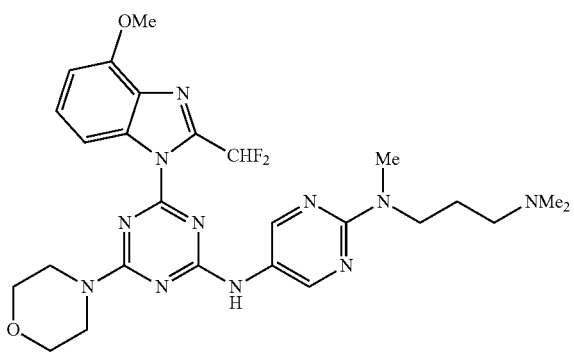 [SMILES: COc1cccc2c1nc(C(F)F)n2-c1nc(Nc2cnc(N(C)CCCN(C)C)nc2)nc(N2CCOCC2)n1]

The compound was synthesized according to Method D.
To 0.095 g (0.19 mmol) of N-(2-chloro-5-pyrimidinyl)-4-[2-(difluoromethyl)-4-methoxy-1H-benzimidazol-1-yl]-6-(4-morpholinyl)-1,3,5-triazin-2-amine (Example 41) in EtOH (5 mL) was added 0.28 mL (1.91 mmol) of N,N,N'-trimethyl-1,3-propanediamine, and the mixture was heated at 120° C. in a sealed tube for 2 hrs. Concentration of the solvent, followed by chromatography on silica, eluting first with $CH_2Cl_2$/EtOAc (1:3) and then with $CH_2Cl_2$/MeOH/$NH_3$ (95:5:0.1), gave N⁵-[4-[2-(difluoromethyl)-4-methoxy-1H-benzimidazol-1-yl]-6-(4-morpholinyl)-1,3,5-triazin-2-yl]-N²-[3-(dimethylamino)propyl]-N²-methyl-2,5-pyrimidinediamine as a yellow oil, which solidified under vacuum: mp 97-99° C.; ¹H NMR (CDCl₃) δ8.63-8.35 (m, 2H), 7.99-7.21 (m, 3H), 6.81-6.59 (m, 2H), 4.04 (s, 3H), 3.90 (s, 4H), 3.79 (s, 4H), 3.70 (t, J=7.2 Hz, 2H), 3.20 (s, 3H), 2.35 (t, J=7.2 Hz, 2H), 2.56 (s, 6H), 1.87-1.80 (m, 2H); HRMS (ESI) M+H⁺ Calcd. for $C_{26}H_{34}F_2N_{11}O_2$: m/z 570.2860. Found: m/z 570.2857.

Example 44

Synthesis of 4-[2-(difluoromethyl)-1H-benzimidazol-1-yl]-N-methyl-6-(4-morpholinyl)-N-(5-pyrimidinyl)-1,3,5-triazin-2-amine

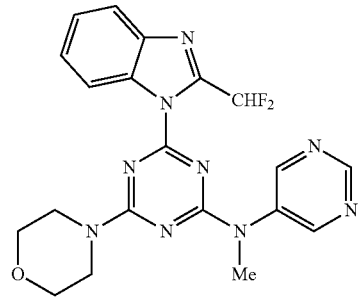 [SMILES: CN(c1cncnc1)c1nc(N2CCOCC2)nc(-n2c(C(F)F)nc3ccccc32)n1]

The compound was synthesized according to Method D.

To a solution of 99 mg (0.23 mmol) of 4-[2-(difluoromethyl)-1H-benzimidazol-1-yl]-6-(4-morpholinyl)-N-(5-pyrimidinyl)-1,3,5-triazin-2-amine (Example 22) in DMF (2 mL) was added NaH (95%, 7.9 mg, 0.31 mmol), and after 10 min iodomethane (15 μL, 0.24 mmol) was added, and the resulting mixture was stirred for 2 hrs. Water was added, and the mixture was extracted with EtOAc (×4). The organic layer was washed with brine, dried (Na₂SO₄), and concentrated. Chromatography on silica, eluting first with $CH_2Cl_2$/EtOAc (1:1) and then with $CH_2Cl_2$/EtOAc (1:2), gave a white powder (0.082 g), which was recrystallized from $CH_2Cl_2$/EtOH to give 0.073 g (72% yield) of 4-[2-(difluoromethyl)-1H-benzimidazol-1-yl]-N-methyl-6-(4-morpholinyl)-N-(5-pyrimidinyl)-1,3,5-triazin-2-amine: mp 202-205° C.; ¹H NMR (DMSO-d₆) δ9.14 (s, 1H), 8.83 (s, 2H), 8.18 (br s, 1H), 7.89-7.87 (m, 1H), 7.41-7.37 (m, 3H), 3.91 (s, br, 2H), 3.80-3.75 (m, 6H), 3.66 (s, 3H); Anal. Calcd. for $C_{20}H_{19}F_2N_9O$: C, 54.7; H, 4.4; N, 28.6. Found: C, 54.7; H, 4.4; N, 29.1%.

Example 45

Synthesis of 4-[2-(difluoromethyl)-4-methoxy-1H-benzimidazol-1-yl]-N-methyl-6-(4-morpholinyl)-N-(5-pyrimidinyl)-1,3,5-triazin-2-amine

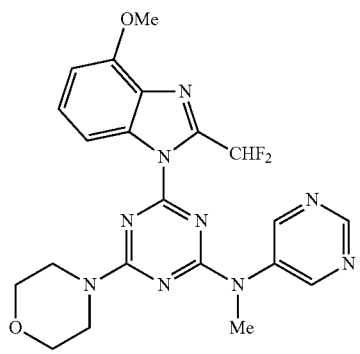 [SMILES: COc1cccc2c1nc(C(F)F)n2-c1nc(N2CCOCC2)nc(N(C)c2cncnc2)n1]

The compound was synthesized according to Method D.

To a solution of 0.1033 g (0.23 mmol) of 4-[2-(difluoromethyl)-4-methoxy-1H-benzimidazol-1-yl]-6-(4-morpholinyl)-N-(5-pyrimidinyl)-1,3,5-triazin-2-amine (Example 32) in DMF (2 mL) was added NaH (95%, 8.7 mg, 0.34 mmol), and after 10 min iodomethane (15 µL, 0.24 mmol) was added, and the resulting mixture was stirred for 2 hrs. Water was added and the mixture was extracted with EtOAc (×4). The organic layer was washed with brine, dried ($Na_2SO_4$), and concentrated. Chromatography on silica, eluting with $CH_2Cl_2$/EtOAc (1:1), gave a white powder which was recrystallized from $CH_2Cl_2$/EtOH, to give 0.061 g (56% yield) of 4-[2-(difluoromethyl)-4-methoxy-1H-benzimidazol-1-yl]-N-methyl-6-(4-morpholinyl)-N-(5-pyrimidinyl)-1,3,5-triazin-2-amine: mp 214-217° C.; $^1$H NMR (DMSO-$d_6$) δ9.13 (s, 1H), 8.98 (s, 2H), 7.66-7.28 (m, 3H), 6.93 (d, J=8.0 Hz, 1H), 3.98 (s, 3H), 3.82-3.70 (m, 8H), 3.59 (s, 3H); HRMS (ESI) M+H$^+$ Calcd for $C_{21}H_{22}F_2N_9O_2$: m/z 470.1859. Found: m/z 470.1852.

Example 46

Synthesis of 2-[2-(difluoromethyl)-1H-benzimidazol-1-yl]-6-(4-morpholinyl)-N-(3-pyridinyl)-4-pyrimidinamine

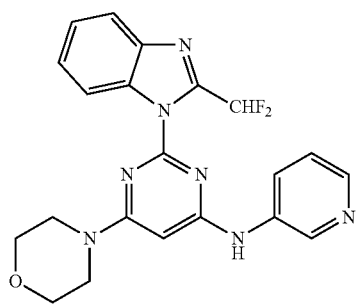 [SMILES: FC(F)c1nc2ccccc2n1-c1nc(Nc2cccnc2)cc(N2CCOCC2)n1]

The compound was synthesized according to Method A.

1-(4,6-Dichloro-2-pyrimidinyl)-2-(difluoromethyl)-1H-benzimidazole (International Publ. No. WO 2002/088112, the disclosure of which is incorporated herein by reference in its entirety) (0.315 g, 1 mmol) was added to a mixture of 3-aminopyridine (0.28 g, 3 mmol) and LDA (1.5 mL, 2 M in THF, 3 mmol) in 10 mL THF at room temperature. After 10 min, the mixture was neutralized with HOAc, diluted with water, extracted with EtOAc, and dried ($Na_2SO_4$). Chromatography on silica, eluting with $CH_2Cl_2$/EtOAc (3:2) gave a solid, which was recrystallized from i-$Pr_2$O to give 0.252 g (67% yield) of 6-chloro-2-[2-(difluoromethyl)-1H-benzimidazol-1-yl]-N-(3-pyridinyl)-4-pyrimidinamine: mp (i-$Pr_2$O) 233-236° C.; $^1$H NMR (DMSO-$d_6$) δ 10.42 (br, 1H), 8.72 (d, J=2.3 Hz, 1H), 8.43 (dd, J=4.7, 1.4 Hz, 1H), 8.26 (m, 1H), 8.01 (ddd, J=8.3, 2.5, 1.5 Hz, 1H), 7.86 (m, 1H), 7.62 (t, $J_{HF}$'=52.9 Hz, 1H), 7.48-7.42 (m, 3H), 6.86 (s, 1H); Anal. Calcd. for $C_{17}H_{11}ClF_2N_6$: C, 54.8; H, 3.0; N, 22.55. Found: C, 54.75; H, 3.0; N, 22.7%.

The above compound was refluxed with morpholine in THF to give 280 mg (98% yield) of 2-[2-(difluoromethyl)-1H-benzimidazol-1-yl]-6-(4-morpholinyl)-N-(3-Pyridinyl)-4-pyrimidinamine: mp (i-$Pr_2$O) 192-194° C.; $^1$H NMR (DMSO-$d_6$) δ9.63 (br, 1H), 8.69 (d, J=2.4 Hz, 1H), 8.27 (dd, J=4.7, 1.4 Hz, 1H), 8.23 (td, J=4.7, 2.8 Hz, 1H), 7.98 (ddd, J=8.3, 2.6, 1.5 Hz, 1H), 7.83 (td, J=6.4, 2.8 Hz, 1H), 7.70 (t, $J_{HF}$=52.7 Hz, 1H), 7.42-7.39 (m, 2H), 7.36 (dd, J=8.6, 4.8 Hz, 1H), 6.00 (s, 1H), 3.74 (m, 4H), 3.59 (m, 4H).

Example 47

Synthesis of 2-(difluoromethyl)-1-[4-(4-morpholinyl)-6-(3-pyridinyl)-1,3,5-triazin-2-yl]-1H-benzimidazole

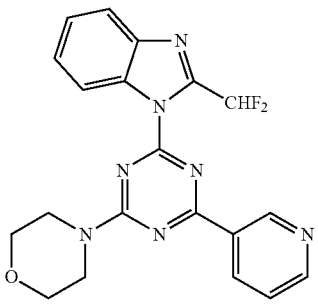 [SMILES: FC(F)c1nc2ccccc2n1-c1nc(-c2cccnc2)nc(N2CCOCC2)n1]

The compound was synthesized according to Method B.

A mixture of 1-[4-chloro-6-(4-morpholinyl)-1,3,5-triazin-2-yl]-2-(difluoromethyl)-1H-benzimidazole (0.183 g, 0.5 mmol), 3-pyridylboronic acid (92 mg, 0.75 mmol), $PdCl_2$(dppf) (28 mg), and aq. $Na_2CO_3$ (2M, 4 mL) in dioxane (20 mL) was heated under reflux under nitrogen for 1 hr. After cooling, the mixture was diluted with water, extracted with $CH_2Cl_2$, and dried. Chromatography on alumina, eluting with $CH_2Cl_2$, gave 0.13 g (64% yield) of 2-(difluoromethyl)-1-[4-(4-morpholinyl)-6-(3-pyridinyl)-1,3,5-triazin-2-yl]-1H-benzimidazole: mp (MeOH) 199-201° C.; $^1$H NMR (DMSO-$d_6$) δ 9.59 (d, J=1.6 Hz, 1H), 8.85 (dd, J=4.8, 1.7 Hz, 1H), 8.75 (td, J=8.0, 1.9 Hz, 1H), 8.50 (d, J=8.2 Hz, 1H), 7.90 (d, J=7.9 Hz, 1H), 7.86 (t, $J_{HF}$=52.6 Hz, 1H), 7.65 (ddd, J=8.0, 4.8, 0.7 Hz, 1H), 7.59 (dt, J=7.8, 1.1 Hz, 1H), 7.49 (dt, J=7.6, 1.1 Hz, 1H), 4.09 (m, 2H), 3.94 (m, 2H), 3.79 (m, 4H); Anal. Calcd. for $C_{20}H_{17}F_2N_7O$: C, 58.7; H, 4.2; N, 23.95. Found: C, 58.45; H, 4.1; N, 24.2%.

Example 48

Synthesis of 2-(difluoromethyl)-4-methoxy-1-[4-(4-morpholinyl)-6-(3-pyridinyl)-1,3,5-triazin-2-yl]-1H-benzimidazole

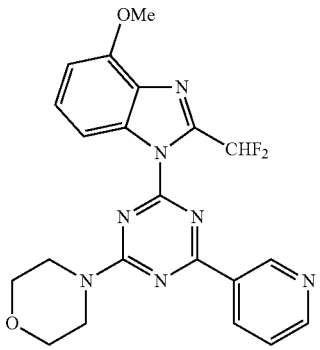 [SMILES: COc1cccc2c1nc(C(F)F)n2-c1nc(-c2cccnc2)nc(N2CCOCC2)n1]

The compound was synthesized according to Method B.

Reaction of 1-[4-chloro-6-(4-morpholinyl)-1,3,5-triazin-2-yl]-2-(difluoromethyl)-4-methoxy-1H-benzimidazole (Example 2) and 3-pyridinylboronic acid, as in Example 47, gave 2-(difluoromethyl)-4-methoxy-1-[4-(4-morpholinyl)-6-(3-pyridinyl)-1,3,5-triazin-2-yl]-1H-benzimidazole in 61% yield: mp ($CH_2Cl_2$/MeOH) 208-210° C.; $^1$H NMR (DMSO-$d_6$) δ 9.59 (dd, J=2.2, 0.7 Hz, 1H), 8.85 (dd, J=4.8, 1.7 Hz, 1H), 8.75 (dt, J=8.0, 1.9 Hz, 1H), 8.35 (dd, J=8.4, 0.4 Hz, 1H), 7.83 (t, $J_{jw}$=52.6 Hz, 1H), 7.66 (ddd, J=8.0, 4.8, 0.8 Hz, 1H), 7.50 (t, J=8.3 Hz, 1H), 7.02 (d, J=7.8 Hz, 1H), 4.09 (t, J=7.8 Hz, 2H), 4.00 (s, 3H), 3.94 (m, 2H), 3.78 (m, 4H); Anal. Calcd. for $C_{21}H_{19}F_2N_7O_4 \cdot 0.3H_2O$: C, 56.7; H, 4.4; N, 22.0. Found: C, 56.6; H, 4.0; N, 22.1%.

Example 49

Synthesis of 5-[4-[2-(difluoromethyl)-4-methoxy-1H-benzimidazol-1-yl]-6-(4-morpholinyl)-1,3,5-triazin-2-yl]-2-pyridinamine

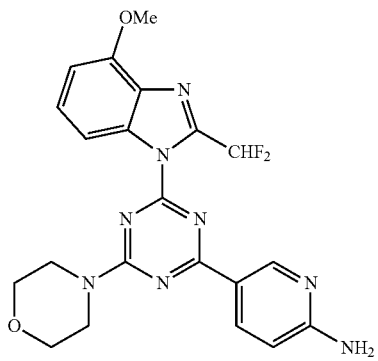 [SMILES: COc1cccc2c1nc(C(F)F)n2-c1nc(-c2ccc(N)nc2)nc(N2CCOCC2)n1]

The compound was synthesized according to Method B.

A mixture of 0.30 g (0.75 mmol) of 1-[4-chloro-6-(4-morpholinyl)-1,3,5-triazin-2-yl]-2-(difluoromethyl)-4-methoxy-1H-benzimidazole, 0.21 g (0.95 mmol) of 5-(4,4,5,5-tetramethyl-1,3,2-dioxaborolan-2-yl)-2-pyridinamine, and 0.057 g (0.08 mmol) of $PdCl_2$(dppf) in a mixture of 1,4-dioxane (30 mL) and 2M $Na_2CO_3$ solution (6 mL) was heated at 100° C. for 5 hrs under nitrogen. After cooling, the mixture was concentrated, diluted with water, and extracted with EtOAc (×4). The organic layer was washed with brine, dried ($Na_2SO_4$), and concentrated. Chromatography on silica, eluting first with $CH_2Cl_2$-EtOAc (3:1) and then with $CH_2Cl_2$-EtOAc (1:3), gave an off-white powder, which was recrystallized from $CH_2Cl_2$/EtOH to give 0.144 g (43% yield) of 5-[4-[2-(difluoromethyl)-4-methoxy-1H-benzimidazol-1-yl]-6-(4-morpholinyl)-1,3,5-triazin-2-yl]-2-pyridinamine: mp 259-261° C.; $^1$H NMR (DMSO-$d_6$) δ 9.04 (d, J=2.2 Hz, 1H), 8.32 (dd, J=8.8, 2.4 Hz, 1H), 8.04 (d, J=8.3 Hz, 1H), 7.79 (t, $J_{HF}$=52.8 Hz, 1H), 7.47 (t, J=8.2 Hz, 1H), 6.99 (d, J=7.9 Hz, 1H), 6.85 (s, 2H), 6.57 (d, J=8.8 Hz, 1H), 4.04-4.00 (m, 5H), 3.89 (br s, 2H), 3.76 (s, 4H); Anal. Calcd. for $C_{21}H_{20}F_2N_8O_2 \cdot 0.49H_2O$: C, 54.45; H, 4.6; N, 24.2. Found: C, 54.8; H, 4.2; N, 24.2%.

Example 50

Synthesis of 2-(Difluoromethyl)-4-methoxy-1-[4-(4-morpholinyl)-6-(1H-pyrazol-4-yl)-1,3,5-triazin-2-yl]-1H-benzimidazole

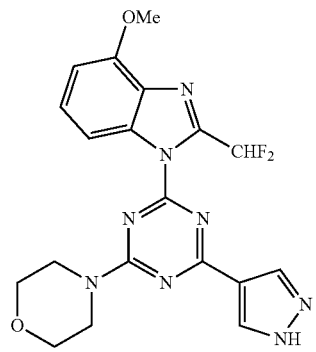 [SMILES: COc1cccc2c1nc(C(F)F)n2-c1nc(-c2cn[nH]c2)nc(N2CCOCC2)n1]

The compound was synthesized according to Method B.

Reaction of 1-[4-chloro-6-(4-morpholinyl)-1,3,5-triazin-2-yl]-2-(difluoromethyl)-4-methoxy-1H-benzimidazole with tert-butyl 4-(4,4,5,5-tetramethyl-1,3,2-dioxaborolan-2-yl)-1H-pyrazole-1-carboxylate (WO 2006/021881) by a similar procedure to Example 47 gave a mixture of 2-(difluoromethyl)-4-methoxy-1-[4-(4-morpholinyl)-6-(1H-pyrazol-4-yl)-1,3,5-triazin-2-yl]-1H-benzimidazole and tert-butyl 4-[4-[2-(difluoromethyl)-4-methoxy-1H-benzimidazol-1-yl]-6-(4-morpholinyl)-1,3,5-triazin-2-yl]-1H-pyrazole-1-carboxylate. Treatment of the mixture with TFA in $CH_2Cl_2$, as for previous examples, gave 2-(difluoromethyl)-4-methoxy-1-[4-(4-morpholinyl)-6-(1H-pyrazol-4-yl)-1,3,5-triazin-2-yl]-1H-benzimidazole in 55% yield: mp ($CH_2Cl_2$/MeOH) 289-291° C.; $^1$H NMR (DMSO-$d_6$) δ13.46 (s, 1H), 8.60 (d, J=1.4 Hz, 1H), 8.24 (d, J=1.5 Hz, 1H), 8.07 (d, J=8.0 Hz, 1H), 7.84 (t, $J_{HF}$=52.8 Hz, 1H), 7.46 (t, J=8.2 Hz, 1H), 6.99 (d, J=7.9 Hz, 1H), 4.01 (br, 2H), 3.99 (s, 3H), 3.88 (br, 2H), 3.76 (br, 4H); Anal. Calcd. for $C_{19}H_{18}F_2N_8O_2$: C, 53.3; H, 4.2; N, 26.2. Found: C, 53.1; H, 4.3; N, 26.0%.

Example 51

Synthesis of 2-(difluoromethyl)-1-[4-(4-morpholinyl)-6-(3-pyridinyl)-2-pyrimidinyl]-1H-benzimidazole

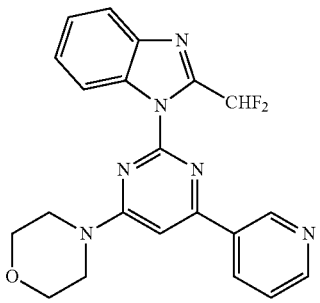 [SMILES: FC(F)c1nc2ccccc2n1-c1nc(-c2cccnc2)cc(N2CCOCC2)n1]

The compound was synthesized according to Method B.

Using a similar procedure to Example 47, reaction of 1-[4-chloro-6-(4-morpholinyl)-2-pyrimidinyl]-2-(difluoromethyl)-1H-benzimidazole (International Publ. No. WO 2008/032028, the disclosure of which is incorporated herein by reference in its entirety) and 3-pyridinylboronic acid gave 2-(difluoromethyl)-1-[4-(4-morpholinyl)-6-(3-pyridinyl)-2-pyrimidinyl]-1H-benzimidazole in 77% yield: mp ($CH_2Cl_2$/hexanes) 172-179° C.; $^1$H NMR (DMSO-$d_6$) δ 9.44 (d, J=2.2 Hz, 1H), 8.75 (dd, J=4.8, 1.5 Hz, 1H), 8.61 and 8.59 (2m, 1H), 8.39 (d, J=8.20 Hz, 1H), 7.88 (d, J=8.0 Hz, 1H), 7.82 (t, $J_{HF}$=52.8 Hz, 1H), 7.62 (dd, J=8.0, 4.8 Hz, 1H), 7.55-7.51 (m, 2H), 7.46-7.42 (m, 1H), 3.88-3.84 (m, 4H), 3.79-3.77 (m, 4H); Anal. Calcd. for $C_{21}H_{18}F_2N_6O1.9H_2O$: C, 49.1; H, 4.8; N, 15.6. Found: C, 49.0; H, 4.4; N, 15.0%

Example 52

Synthesis of 2-(difluoromethyl)-4-methoxy-1-[4-(4-morpholinyl)-6-(3-pyridinyl)-2-pyrimidinyl]-1H-benzimidazole

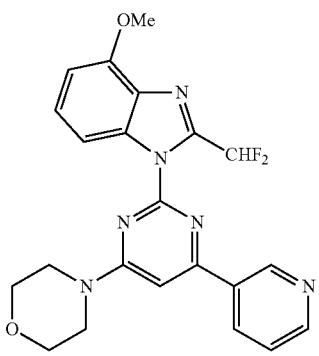 [SMILES: COc1cccc2c1nc(C(F)F)n2-c1nc(-c2cccnc2)cc(N2CCOCC2)n1]

The compound was synthesized according to Method B.

Reaction of 1-(4,6-dichloro-2-pyrimidinyl)-2-(difluoromethyl)-4-methoxy-1H-benzimidazole (International Publ. No. WO 2005/095389, the disclosure of which is incorporated herein by reference in its entirety) (50 mg, 0.145 mmol) with a ten-fold of excess morpholine in THF at room temperature gave 51 mg (89% yield) of 1-[4-chloro-6-(4-morpholinyl)-2-pyrimidinyl]-2-(difluoromethyl)-4-methoxy-1H-benzimidazole: mp ($CH_2Cl_2$/MeOH) 261-263° C.; $^1$H NMR (CDCl$_3$) δ 7.90 (dd, J=8.4, 0.7 Hz, 1H), 7.47 (t, $J_{HF}$=53.6 Hz, 1H), 7.37 (t, J=8.2 Hz, 1H), 6.82 (d, J=7.7 Hz, 1H), 6.47 (s, 1H), 4.07 (s, 3H), 3.84 (m, 4H), 3.73 (m, 4H); Anal. Calcd. for $C_{17}H_{16}ClF_2N_5O_2$: C, 51.6; H, 4.1; N, 17.7. Found: C, 51.7; H, 4.1; N, 17.9%.

Reaction of the above chloro compound with 3-pyridinylboronic acid, as in Example 47, gave 2-(difluoromethyl)-4-methoxy-1-[4-(4-morpholinyl)-6-(3-pyridinyl)-2-pyrimidinyl]-1H-benzimidazole in 85% yield: mp ($CH_2Cl_2$/hexanes) 208-210° C.; $^1$H NMR (DMSO-$d_6$) δ 9.43 (dd, J=2.3, 0.7 Hz, 1H), 8.75 (dd, J=4.8, 1.6 Hz, 1H), 8.68-8.61 and 8.59-8.58 (2m, 1H), 7.93 (dd, J=8.3, 0.5 Hz, 1H), 7.77 (t, $J_{HF}$=53.4 Hz, 1H), 7.64-7.60 (m, 1H), 7.54 (s, 1H), 7.43 (t, J=8.2 Hz, 1H), 7.00 (d, J=7.7 Hz, 1H), 4.00 (s, 3H), 3.87-3.80 (m, 4H), 3.79-3.76 (m, 4H); Anal. Calcd. for $C_{22}H_{20}F_2N_6O_2$: C, 60.3; H, 4.6; N, 19.2. Found: C, 60.1; H, 4.4; N, 19.0%.

Example 53

Synthesis of 2-(difluoromethyl)-1-[4-(6-methoxy-3-pyridinyl)-6-(4-morpholinyl)-1,3,5-triazin-2-yl]-1H-benzimidazole

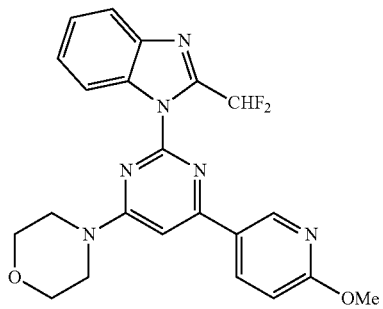 [SMILES: COc1ccc(-c2cc(N3CCOCC3)nc(-n3c(C(F)F)nc4ccccc43)n2)cn1]

The compound was synthesized according to Method B.

Reaction of 6-methoxy-3-pyridinylboronic acid and 1-[4-chloro-6-(4-morpholinyl)-2-pyrimidinyl]-2-(difluoromethyl)-1H-benzimidazole (International Publ. No. WO 2008/032028, the disclosure of which is incorporated herein by reference in its entirety), as in Example 47, gave 2-(difluoromethyl)-1-[4-(6-methoxy-3-pyridinyl)-6-(4-morpholinyl)-1,3,5-triazin-2-yl]-1H-benzimidazole in 81% yield: mp ($CH_2Cl_2$/hexanes) 224-226° C.; $^1$H NMR (DMSO-$d_6$) δ 9.09 (dd, J=2.1, 0.5 Hz, 1H), 8.54 (dd, J=8.8, 2.5 Hz, 1H), 8.37 (d, J=8.2 Hz, 1H), 7.87 (d, J=7.9 Hz, 1H), 7.80 (t, $J_{HF}$=52.8 Hz, 1H), 7.53 (td, J=7.7, 1.1 Hz, 1H), 7.45 (d, J=8.2 Hz, 1H), 7.42 (br s, 1H), 7.02 (d, J=8.7, 0.4 Hz, 1H), 3.96 (s, 3H), 3.86-3.83 (m, 4H), 3.79-3.76 (m, 4H); Anal. Calcd. for $C_{22}H_{20}F_2N_6O_2$: C, 60.3; H, 4.6; N, 19.2. Found: C, 60.4; H, 4.7; N, 19.5%.

Example 54

Synthesis of N-[3-({5-[2-[2-(difluoromethyl)-1H-benzimidazol-1-yl]-6-(4-morpholinyl)-4-pyrimidinyl]-2-pyridinyl}oxy)propyl]-N,N-dimethylamine

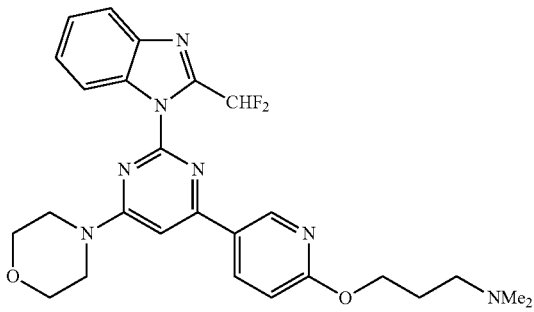 [SMILES: CN(C)CCCOc1ccc(-c2cc(N3CCOCC3)nc(-n3c(C(F)F)nc4ccccc43)n2)cn1]

The compound was synthesized according to Method B.

Similarly, reaction of 1-[4-chloro-6-(4-morpholinyl)-2-pyrimidinyl]-2-(difluoromethyl)-1H-benzimidazole and N,N-dimethyl-3-{[5-(4,4,5,5-tetramethyl-1,3,2-dioxaborolan-2-yl)-2-pyridinyl]oxy}-1-propanamine, as in Example 47, gave N-[3-({5-[2-[2-(difluoromethyl)-1H-benzimidazol-1-yl]-6-(4-morpholinyl)-4-pyrimidinyl]-2-Pyridinyl}oxy)propyl]-N,N-dimethylamine in 33% yield: mp (CH$_2$Cl$_2$/hexanes) 140-141° C.; $^1$H NMR (DMSO-d$_6$) δ 9.07 (d, J=2.2 Hz, 1H), 8.53 (dd, J=8.8, 2.5 Hz, 1H), 8.37 (d, J=8.2 Hz, 1H), 7.87 (d, J=7.9 Hz, 1H), 7.80 (t, J$_{HF}$=52.8 Hz, 1H), 7.52 (dt, J=7.8, 1.0 Hz, 1H), 7.50 (dd J=8.1, 1.0 Hz, 1H), 7.42 (s, 1H), 7.00 (d, J=8.7 Hz, 1H), 4.39 (t, J=6.6 Hz, 2H), 3.85-3.84 (m, 4H), 3.78-3.76 (m, 4H), 2.39 (t, J=7.1 Hz, 2H), 2.17 (s, 6H), 1.89 (quintet, 2H); Anal. Calcd. for C$_{26}$H$_{29}$F$_2$N$_7$O: C, 61.3; H, 5.7; N, 19.2. Found: C, 61.0; H, 5.5; N, 19.1%.

Example 55

Synthesis of 2-[2-(difluoromethyl)-1H-benzimidazol-1-yl]-6-(4-morpholinyl)-4,5'-bipyrimidine

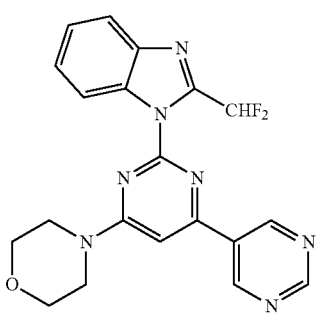 [SMILES: FC(F)c1nc2ccccc2n1-c1nc(-c2cncnc2)cc(N2CCOCC2)n1]

The compound was synthesized according to Method B.

A mixture of 1-[4-chloro-6-(4-morpholinyl)-2-pyrimidinyl]-2-(difluoromethyl)-1H-benzimidazole (200 mg, 0.547 mmol), pyrimidine-5-boronic acid (203 mg, 1.64 mmol), PdCl$_2$(dppf) (45 mg, 0.0551 mmol), and aq. K$_2$CO$_3$ (2M, 4 mL) in 1,4-dioxane (20 mL) was refluxed under nitrogen for 2.5 hrs. Additional pyrimidine-5-boronic acid (203 mg, 1.64 mmol) and PdCl$_2$(dppf) (23 mg, 0.0282 mmol) were added, and the mixture was refluxed for additional 16.5 hrs under nitrogen. The mixture was cooled to room temperature, diluted with H$_2$O, extracted with CH$_2$Cl$_2$ (4×), and the combined organic extracts were dried (Na$_2$SO$_4$), and the solvents were removed under vacuum. Chromatography on silica, eluting with CH$_2$Cl$_2$/MeOH (100:0 to 97:3), followed by recrystallization from CH$_2$Cl$_2$/MeOH/i-Pr$_2$O gave 2-[2-(difluoromethyl)-1H-benzimidazol-1-yl]-6-(4-morpholinyl)-4,5'-bipyrimidine (177 mg, 79%): mp 209-211° C.; $^1$H NMR (CDCl$_3$) δ9.37 (s, 2H), 9.37 (s, 1H), 8.37 (m, 1H), 7.93 (m, 1H), 7.59 (t, J$_{HF}$=53.7 Hz, 1H), 7.49-7.41 (m, 2H), 6.86 (s, 1H), 3.91 (m, 4H), 3.85 (m, 4H); Anal. Calcd. for C$_{20}$H$_{17}$F$_2$N$_7$O: C, 58.7; H, 4.2; N, 23.95. Found: C, 58.4; H, 3.9; N, 23.9%.

Example 56

Synthesis of 2-[2-(difluoromethyl)-4-methoxy-1H-benzimidazol-1-yl]-6-(4-morpholinyl)-4,5'-bipyrimidine

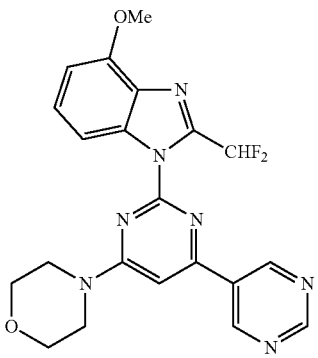 [SMILES: COc1cccc2c1nc(C(F)F)n2-c1nc(-c2cncnc2)cc(N2CCOCC2)n1]

The compound was synthesized according to Method B.

Similarly to Example 55, a mixture of 1-[4-chloro-6-(4-morpholinyl)-2-pyrimidinyl]-2-(difluoromethyl)-4-methoxy-1H-benzimidazole (106 mg, 0.268 mmol), pyrimidine-5-boronic acid (188 mg, 1.52 mmol), PdCl$_2$(dppf) (40 mg, 0.05 mmol) and aq. K$_2$CO$_3$ (2M, 4 mL) in 1,4-dioxane (20 mL) was refluxed under nitrogen for 24 hrs. After cooling to room temperature, the mixture was diluted with H$_2$O, and extracted with CH$_2$Cl$_2$ (4×). The combined organic extracts were dried (Na$_2$SO$_4$), and the solvents removed under vacuum. Chromatography on silica, eluting with CH$_2$Cl$_2$/MeOH (100:0 to 97:3), followed by recrystallization from CH$_2$Cl$_2$/MeOH/hexanes gave 2-[2-(difluoromethyl)-4-methoxy-1H-benzimidazol-1-yl]-6-(4-morpholinyl)-4,5'-bipyrimidine (89 mg, 75%): mp 222-224° C.; $^1$H NMR (CDCl$_3$) δ 9.38 (s, 2H), 9.36 (s, 1H), 7.92 (dd, J=8.4, 0.6 Hz, 1H), 7.49 (t, J=53.6 Hz, 1H), 7.38 (t, J=8.2 Hz, 1H), 6.86 (s, 1H), 6.84 (d, J=7.7 Hz, 1H), 4.07 (s, 3H), 3.89 (m, 4H), 3.85 (m, 4H); Anal. Calcd. for C$_{21}$H$_{19}$F$_2$N$_7$O$_2$0.25 MeOH: C, 57.0; H, 4.5; N, 21.9. Found: C, 56.95; H, 4.45; N, 22.0%.

Example 57

Synthesis of 2-[2-(difluoromethyl)-4-methoxy-1H-benzimidazol-1-yl]-6-(4-morpholinyl)-2'-methoxy-4,5'-bipyrimidine

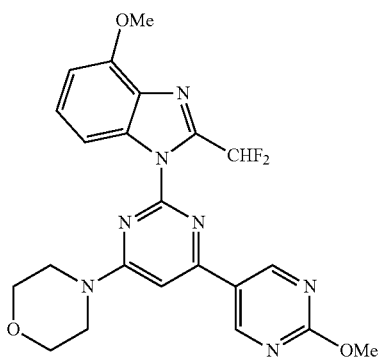 [SMILES: COc1ncc(-c2cc(N3CCOCC3)nc(-n3c(C(F)F)nc4c(OC)cccc43)n2)cn1]

The compound was synthesized according to Method B.

Similarly to Example 56, a mixture of 1-[4-chloro-6-(4-morpholinyl)-2-pyrimidinyl]-2-(difluoromethyl)-4-methoxy-1H-benzimidazole (148 mg, 0.374 mmol), 2-methoxy-5-pyrimidinylboronic acid (211 mg, 1.52 mmol), PdCl$_2$ (dppf) (40 mg, 0.05 mmol) and aq. K$_2$CO$_3$ (2M, 4 mL) in 1,4-dioxane (20 mL) was refluxed under nitrogen for 24 hrs. After cooling to room temperature, the mixture was diluted with H$_2$O, and extracted with CH$_2$Cl$_2$ (4×). The combined organic extracts were dried (Na$_2$SO$_4$), and the solvents were removed under vacuum. Chromatography on silica, eluting with CH$_2$Cl$_2$/MeOH (100:0 to 98:2), followed by recrystallization from CH$_2$Cl$_2$/MeOH/i-Pr$_2$O gave 2-[2-(difluoromethyl)-4-methoxy-1H-benzimidazol-1-yl]-6-(4-morpholinyl)-2'-methoxy-4,5'-bipyrimidine (61 mg, 35%): mp 238-241° C.; $^1$H NMR (CDCl$_3$) δ 9.18 (s, 2H), 7.91 (d, J=8.1 Hz, 1H), 7.49 (t, J$_{HF}$=53.6 Hz, 1H), 7.37 (t, J=8.2 Hz, 1H), 6.83 (d, J=7.9 Hz, 1H), 6.77 (s, 1H), 4.13 (s, 3H), 4.07 (s, 3H), 3.88 (dd, J=5.6, 3.7 Hz, 4H), 3.82 (m, 4H); Anal. Calcd. for C$_{22}$H$_{21}$F$_2$N$_7$O$_3$: C, 56.3; H, 4.5; N, 20.9. Found: C, 56.1; H, 4.3; N, 20.6%.

Example 58

Synthesis of 2-[2-(difluoromethyl)-1H-benzimidazol-1-yl]-6-(4-morpholinyl)-4,5'-bipyrimidine-2'-amine

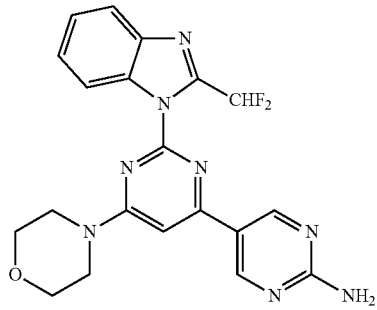 [SMILES: Nc1ncc(-c2cc(N3CCOCC3)nc(-n3c(C(F)F)nc4ccccc43)n2)cn1]

The compound was synthesized according to Method B.

Similar to Example 57, a mixture of 1-[4-chloro-6-(4-morpholinyl)-2-pyrimidinyl]-2-(difluoromethyl)-1H-benzimidazole (200 mg, 0.547 mmol), 5-(4,4,5,5-tetramethyl-1,3,2-dioxaborolan-2-yl)-2-pyrimidinylamine (302 mg, 1.38 mmol), PdCl$_2$ (dppf) (45 mg, 0.0551 mmol) and aq. K$_2$CO$_3$ (2M, 4 mL) in 1,4-dioxane (20 mL) was refluxed under nitrogen for 24 hrs. The mixture was cooled to room temperature, diluted with H$_2$O, extracted with CH$_2$Cl$_2$ (4×), and the combined organic extracts were dried (Na$_2$SO$_4$), and the solvents removed under vacuum. Chromatography on alumina, eluting with CH$_2$Cl$_2$/EtOAc (100:0 to 80:20) to CH$_2$Cl$_2$/MeOH (100:0 to 98.5:1.5), followed by recrystallization from CH$_2$Cl$_2$/MeOH/i-Pr$_2$O gave 2-[2-(difluoromethyl)-1H-benzimidazol-1-yl]-6-(4-morpholinyl)-4,5'-bipyrimidine-2'-amine (157 mg, 66% yield): mp 281-285° C.; $^1$H NMR (DMSO-d$_6$) δ 9.09 (s, 2H), 8.35 (d, J=8.2 Hz, 1H), 7.86 (d, J=8.0 Hz, 1H), 7.79 (t, J$_{jw}$=52.8 Hz, 1H), 7.52 (t, J=7.5 Hz, 1H), 7.43 (t, J=7.3 Hz, 1H), 7.32 (s, 1H), 7.24 (s, 2H), 3.82 (m, 4H), 3.77 (m, 4H).

Example 59

Synthesis of 2-[2-(difluoromethyl)-4-methoxy-1H-benzimidazol-1-yl]-6-(4-morpholinyl)-9-(3-pyridinyl)-9H-purine

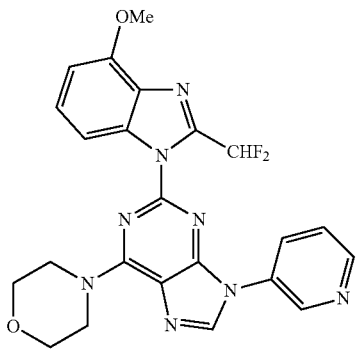 [SMILES: COc1cccc2c1nc(C(F)F)n2-c1nc(N2CCOCC2)c2ncn(-c3cccnc3)c2n1]

The compound was synthesized by a modification of Method C.

A mixture of 4-(2,6-dichloro-5-nitro-4-pyrimidinyl)morpholine (U.S. Pat. Appl. Publ. No. 2009/0181963, the disclosure of which is incorporated herein by reference in its entirety) (1.89 g, 3.6 mmol) and 3-aminopyridine (0.68 g, 7.2 mmol) in THF at −70° C. was treated with 7.2 mL of LiHMDS (1M solution in THF, 2 eq.) and the mixture was stirred at that temperature for 1.5 hrs, and then allowed to warm to room temperature. The solvent was removed and the crude product was extracted with 0.5 M HCl. After filtration, the aqueous solution was made basic with sat. Na$_2$CO$_3$, to give a precipitate, which was collected by filtration, and dried, to give 1.12 g (52% yield) of 2-chloro-6-(4-morpholinyl)-5-nitro-N-(3-pyridinyl)-4-pyrimidinamine: mp (aq. MeOH)>310° C.; $^1$H NMR (CDCl$_3$) δ 10.19 (br s, 1H), 8.74 (d, J=2.5 Hz, 1H), 8.45 (dd, J=4.8, 1.4 Hz, 1H), 8.12 (ddd, J=8.3, 2.6, 1.5 Hz, 1H), 7.35 (dd, J=8.4, 4.8 Hz, 1H), 3.81 (m, 4H), 3.61 (m, 4H).

A mixture of 0.23 g of the above nitro compound (0.68 mmol), 0.147 g (0.74 mmol) of 2-difluoromethyl-4-methoxy-1H-benzimidazole (Example 2) and 0.38 g (2.75 mmol) of powdered K$_2$CO$_3$ in 4 mL of DMSO was heated at 120° C. for 4 hrs. The reaction mixture was diluted with water, and extracted with EtOAc (×4). The combined organic layers were washed with brine, dried, and concentrated. The residue was purified by chromatography on silica, eluting first with hexanes/EtOAc (1:1), and then with CH$_2$Cl$_2$/EtOAc (2:1), to give 0.253 g (75% yield) of 2-[2-(difluoromethyl)-4-methoxy-1H-benzimidazol-1-yl]-6-(4-morpholinyl)-5-nitro-N-(3-pyridinyl)-4-pyrimidinamine, as a yellow powder: $^1$H NMR (CDCl$_3$) δ 10.26 (s, 1H), 8.72 (d, J=2.4 Hz, 1H), 8.60 (dd, J=4.8, 1.4 Hz, 1H), 7.95 (ddd, J=8.3, 2.4, 1.6 Hz, 1H), 7.45 (dd, J=8.3, 0.6 Hz, 1H), 7.40 (dd, J=8.3, 4.8 Hz, 1H), 7.18 (t, J=8.3 Hz, 1H), 7.11 (t, J$_{HF}$=53.5 Hz, 1H), 6.78 (d, J=7.8 Hz, 1H), 4.03 (s, 3H), 3.88 (t, J=4.5 Hz, 4H), 3.70 (t, J=4.5 Hz, 4H).

To 0.253 g (0.51 mmol) of the above nitro compound in MeOH (30 mL) was added 0.15 g of 5% Pt on activated carbon, and the mixture was stirred under hydrogen (30 in/Hg) for 1.5 hrs. The reaction mixture was filtered through celite, and concentrated, to give 0.203 g of crude 2-[2-(difluoromethyl)-4-methoxy-1H-benzimidazol-1-yl]-6-(4-morpholinyl)-N$^4$-(3-pyridinyl)-4,5-pyrimidinediamine: $^1$H NMR (DMSO-d$_6$) δ 8.81 (s, 1H), 8.75 (d, J=2.4 Hz, 1H), 8.27 (dd, J=4.7, 1.5 Hz, 1H), 8.02 (ddd, J=8.3, 2.4, 1.5 Hz, 1H), 7.64 (dd, J=8.3, 0.6 Hz, 1H), 7.56 (t, J$_{HF}$=53.1 Hz, 1H), 7.34 (ddd, J=8.3, 4.7, 0.5 Hz, 1H), 7.25 (t, J=8.3 Hz, 1H), 6.87 (d, J=7.7 Hz, 1H), 4.79 (s, 2H), 3.96 (s, 3H), 3.82 (t, J=4.5 Hz, 4H), 3.24 (t, J=4.5 Hz, 4H).

A mixture of 0.155 g (0.33 mmol) of the above diamine, trimethyl orthoformate (2.5 mL, 22.8 mmol), and p-toluenesulfonate monohydrate (0.05 g, 0.26 mmol) was heated at 95° C. for 4 hrs. The reaction mixture was cooled to room temperature, concentrated, and the product was recrystallized from CH$_2$Cl$_2$/EtOH, to give 0.113 g (54% over 2 steps) of 2-[2-(difluoromethyl)-4-methoxy-1H-benzimidazol-1-yl]-6-(4-morpholinyl)-9-(3-pyridinyl)-9H-purine, as an off-white powder: mp 229-231° C.; $^1$H NMR (CDCl$_3$) δ 8.97 (d, J=2.4 Hz, 1H), 8.76 (dd, J=4.8, 1.5 Hz, 1H), 8.19 (ddd, J=8.2, 2.4, 1.5 Hz, 1H), 8.09 (s, 1H), 7.77 (dd, J=8.3, 0.6 Hz, 1H), 7.57 (ddd, J=8.3, 4.8, 0.7 Hz, 1H), 7.41 (t, J$_{HF}$=53.8 Hz, 1H), 7.32 (t, J=8.2 Hz, 1H), 6.80 (d, J=7.7 Hz, 1H), 4.44 (s, br, 4H), 4.05 (s, 3H), 3.91 (t, J=4.8 Hz, 4H).

Example 60

Synthesis of 2-[2-(difluoromethyl)-4-methoxy-1H-benzimidazol-1-yl]-6-(4-morpholinyl)-9-(5-pyrimidinyl)-9H-purine

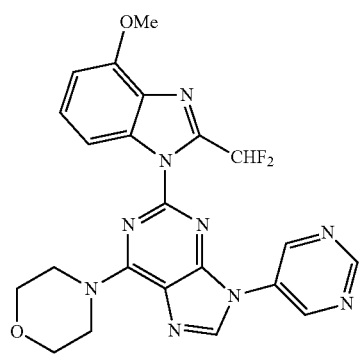 [SMILES: COc1cccc2c1nc(C(F)F)n2-c1nc(N2CCOCC2)c2ncn(-c3cncnc3)c2n1]

The compound was synthesized by a modification of Method C.

To 0.482 g (5.06 mmol) of 5-aminopyrimidine in THF (10 mL) was added 2.90 mL of NaHMDS (2 M solution in THF) at 0° C., and the mixture was stirred for 10 min. A solution of 0.5924 g (2.12 mmol) of 4-(2,6-dichloro-5-nitro-4-pyrimidinyl)morpholine (U.S. Pat. Appl. Publ. No. 2009/0181963, the disclosure of which is incorporated herein by reference in its entirety) in THF (5 mL) was added, and the resulting mixture was stirred for 15 min. The reaction mixture was neutralized with acetic acid, diluted with water, and extracted with EtOAc. The organic layer was washed with water and aq. NH$_3$, dried, and concentrated. Chromatography on silica, eluting with hexanes/EtOAc (8:2), gave 0.465 g (65% yield) of 2-chloro-6-(4-morpholinyl)-5-nitro-N-(5-pyrimidinyl)-4-pyrimidinamine as a white powder: $^1$H NMR (DMSO-d$_6$) δ 10.34 (s, 1H), 8.98 (s, 1H), 8.92 (s, 2H), 3.70 (t, J=4.8 Hz, 4H), 3.50 (t, J=4.8 Hz, 4H).

A mixture of 0.465 g (1.38 mmol) of the above nitro compound, 0.368 g (1.86 mmol) of 2-difluoromethyl-4-methoxy-1H-benzimidazole (Example 2) and 0.762 g (5.52 mmol) of powdered K$_2$CO$_3$ in 5 mL of DMSO was heated at 120° C. for 8 hrs. The reaction mixture was diluted with water, and extracted with EtOAc (×4). The organic layer was washed with brine, dried, and concentrated. Chromatography on silica, eluting first with hexanes/EtOAc (7:3) and then with CH$_2$Cl$_2$/EtOAc (1:2), gave 0.592 g (86% yield) of 2-[2-(difluoromethyl)-7-methoxy-2,3-dihydro-1H-benzimidazol-1-yl]-6-(4-morpholinyl)-5-nitro-N-(5-pyrimidinyl)-4-pyrimidinamine, as a yellow powder: $^1$H NMR (CDCl$_3$) δ 10.26 (s, 1H), 9.16 (s, 1H), 8.98 (s, 2H), 7.38 (dd, J=8.4, 0.6 Hz, 1H), 7.20 (t, J=8.4 Hz, 1H), 7.12 (t, J$_{HF}$=53.5 Hz, 1H), 6.78 (d, J=7.8 Hz, 1H), 4.01 (s, 3H), 3.87 (t, J=4.8 Hz, 4H), 3.70 (t, J=4.8 Hz, 4H).

To 0.162 g (0.33 mmol) of the above nitro compound in THF (40 mL) was added 0.2 g of 5% Pt on activated carbon, and the mixture was stirred under hydrogen (40 in/Hg) for 17 hrs. The reaction mixture was filtered through celite, and concentrated, to give 0.155 g of crude 2-[2-(difluoromethyl)-7-methoxy-2,3-dihydro-1H-benzimidazol-1-yl]-6-(4-morpholinyl)-N$^4$-(5-pyrimidinyl)-4,5-pyrimidinediamine: $^1$H NMR (CDCl$_3$) δ 8.97-8.92 (m, 3H), 7.76 (s, 1H), 7.67 (d, J=8.3 Hz, 1H), 7.43 (t, J$_{HF}$=53.8 Hz, 1H), 7.28-7.26 (m, 1H), 6.97 (s, 2H), 6.76 (d, J=7.9 Hz, 1H), 3.97 (s, 3H), 3.88 (t, J=4.6 Hz, 4H), 3.36 (t, J=4.6 Hz, 4H).

A mixture of the above crude diamine (0.155 g, 0.33 mmol), trimethyl orthoformate (2.5 mL, 22.8 mmol), and p-toluenesulfonate monohydrate (0.05 g, 0.26 mmol) was heated at 95° C. for 3 hrs. The reaction mixture was cooled and concentrated, and the residue was purified by chromatography on silica, eluting with CH$_2$Cl$_2$/EtOAc (1:3), to give 0.115 g (73% over 2 steps) of 2-[2-(difluoromethyl)-4-methoxy-1H-benzimidazol-1-yl]-6-(4-morpholinyl)-9-(5-pyrimidinyl)-9H-purine as a yellow powder: mp 248-251° C.; $^1$H NMR (CDCl$_3$) δ 9.34 (s, 1H), 9.23 (s, 2H), 8.09 (s, 1H), 7.73 (dd, J=8.4, 0.6 Hz, 1H), 7.41 (t, J$_{HF}$=53.5 Hz, 1H), 7.34 (t, J=8.2 Hz, 1H), 6.80 (d, J=7.7 Hz, 1H), 4.43 (br s, 4H), 4.05 (s, 3H), 3.91 (t, J=4.8 Hz, 4H); Anal. Calcd. for C$_{22}$H$_{19}$F$_2$N$_9$O$_2$ 0.09EtOAc: C, 55.1; H, 4.1; N, 25.9. Found: C, 55.05; H, 4.00; N, 25.5%.

Example 61

Synthesis of 6-[2-(Difluoromethyl)-4-methoxy-1H-benzimidazol-1-yl]-2-(4-morpholinyl)-9-(3-pyridinyl)-9H-purine

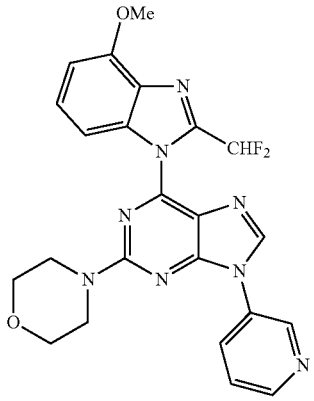 [SMILES: COc1cccc2c1nc(C(F)F)n2-c1nc(N2CCOCC2)nc2c1ncn2-c1cccnc1]

NaH (148 mg, 6.17 mmol) was added to a solution of 2-difluoromethyl-4-methoxy-1H-benzimidazole (Example 2) (638 mg, 3.22 mmol) in DMF (10 mL) at 0° C., and the mixture was warmed to room temperature and stirred for 45 min. 2,6-Dichloro-9-tetrahydro-2H-pyran-2-yl-9H-purine (800 mg, 2.93 mmol) was then added and the resulting mixture was stirred at room temperature for 5 days, quenched with $H_2O$, and extracted with EtOAc (2×). The combined organic extracts were washed with $H_2O$ (3×), dried ($Na_2SO_4$) and the solvent was removed under vacuum. Chromatography on silica, eluting with hexanes/EtOAc (100:0 to 60:40), gave 2-chloro-6-[2-(difluoromethyl)-4-methoxy-1H-benzimidazol-1-yl]-9-tetrahydro-2H-pyran-2-yl-9H-purine (645 mg, 51%): $^1$H NMR (CDCl$_3$) δ 8.38 (s, 1H), 7.52 (t, $J_{HF}$=54.2 Hz, 1H), 7.37-7.31 (m, 2H), 6.84 (m, 1H), 5.86 (dd, J=10.7, 2.5 Hz, 1H), 4.23 (ddd, J=10.0, 3.8, 1.8 Hz, 1H), 4.07 (s, 3H), 3.83 (dt, J=11.7, 2.8 Hz, 1H), 2.26 (m, 1H), 2.14 (m, 1H), 2.03 (m, 1H), 1.91-1.69 (m, 3H).

A mixture of the above chloro compound (629 mg, 1.45 mmol) and morpholine (0.65 mL, 7.43 mmol) in absolute EtOH (30 mL) was heated at 70° C. for 17 hrs. The solvent was removed under vacuum and the residue diluted with $H_2O$. The resulting precipitate was filtered, washed with $H_2O$ and aq. MeOH, and dried to give 6-[2-(difluoromethyl)-4-methoxy-1H-benzimidazol-1-yl]-2-(4-morpholinyl)-9-tetrahydro-2H-pyran-2-yl-9H-purine (633 mg, 90%) which was used in the next step without purification: $^1$H NMR (CDCl$_3$) δ 8.01 (s, 1H), 7.30 (t, $J_{HF}$=53.7 Hz, 1H), 7.32-7.23 (m, 2H), 6.80 (dd, J=7.8, 0.7 Hz, 1H), 5.67 (dd, J=10.0, 2.6 Hz, 1H), 4.19 (m, 1H), 4.06 (s, 3H), 3.88 (m, 4H), 3.83-3.75 (m, 5H), 2.17-2.05 (m, 3H), 1.88-1.67 (m, 3H).

A mixture of the above pyranyl compound (625 mg, 1.29 mmol) in HCl saturated EtOAc (50 mL) was stirred at 0° C. for 30 min, warmed to room temperature, and stirred for 24 hrs. The solid was filtered, washed with $H_2O$, and dried to give 6-[2-(difluoromethyl)-4-methoxy-1H-benzimidazol-1-yl]-2-(4-morpholinyl)-9H-purine (435 mg, 84%) which was used in the next step without purification: $^1$H NMR (DMSO-$d_6$) δ 13.21 (br s, 1H), 8.30 (s, 1H), 7.51 (t, J=52.7 Hz, 1H), 7.33 (t, J=8.1 Hz, 1H), 7.27 (d, J=8.1 Hz, 1H), 6.94 (d, J=7.4 Hz, 1H), 4.01 (s, 3H), 3.74-3.71 (m, 8H).

trans-N,N'-Dimethylcyclohexane-1,2-diamine (0.04 mL, 0.254 mmol) in DMF (6 mL) was added to a mixture of the above purine (155 mg, 0.386 mmol), 3-iodopyridine (158 mg, 0.748 mmol), CuI (37 mg, 0.194 mmol), and $Cs_2CO_3$ (264 mg, 0.811 mmol) under nitrogen. After heating the mixture at 95-100° C. for 21 hrs, additional CuI (37 mg, 0.194 mmol) and trans-N,N'-dimethylcyclohexane-1,2-diamine (0.04 mL, 0.254 mmol) were added, and the mixture was heated at 105-110° C. for 2 days under nitrogen. At this time, additional 3-iodopyridine (80 mg, 0.390 mmol), CuI (37 mg, 0.194 mmol), and trans-N,N'-dimethylcyclohexane-1,2-diamine (0.03 mL, 0.190 mmol) were added and the reaction mixture was heated for an additional 24 hrs under nitrogen. The mixture was then cooled to room temperature, diluted with $CH_2Cl_2$ and filtered through celite. The solvents were removed. Chromatography on silica, eluting with $CH_2Cl_2$/MeOH (100:0 to 98:2), followed by chromatography on silica eluting with hexanes/EtOAc (67:33 to 20:80), gave 6-[2-(difluoromethyl)-4-methoxy-1H-benzimidazol-1-yl]-2-(4-morpholinyl)-9-(3-pyridinyl)-9H-purine (62 mg, 34%): mp 206-209° C.; $^1$H NMR (CDCl$_3$) δ 9.12 (d, J=2.4 Hz, 1H), 8.74 (dd, J=4.8, 1.4 Hz, 1H), 8.14-8.11 (m, 2H), 7.57 (ddd, J=8.3, 4.8, 0.7 Hz, 1H), 7.33 (t, $J_{HF}$=53.7 Hz, 1H), 7.37-7.28 (m, 2H), 6.83 (dd, J=7.8, 0.8 Hz, 1H), 4.08 (s, 3H), 3.89 (m, 4H), 3.79 (m, 4H).

Example 62

Synthesis of 6-[2-(Difluoromethyl)-4-methoxy-1H-benzimidazol-1-yl]-2-(4-morpholinyl)-9-(5-pyrimidinyl)-9H-purine

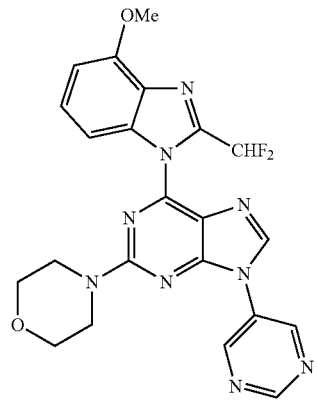 [SMILES: COc1cccc2c1nc(C(F)F)n2-c1nc(N2CCOCC2)nc2c1ncn2-c1cncnc1]

The compound was synthesized by a modification of Method C.

trans-N,N'-Dimethylcyclohexane-1,2-diamine (0.071 mL, 0.450 mmol) in DMF (5 mL) was added to a mixture of 6-[2-(difluoromethyl)-4-methoxy-1H-benzimidazol-1-yl]-2-(4-morpholinyl)-9H-purine (180 mg, 0.448 mmol), 5-bromopyrimidine (356 mg, 2.24 mmol), CuI (85 mg, 0.448 mmol), and $Cs_2CO_3$ (321 mg, 0.986 mmol) under nitrogen, and the mixture was heated at 100-105° C. for 3 days. The mixture was cooled to room temperature, diluted with $CH_2Cl_2$, and filtered through celite. The celite plug was washed with $CH_2Cl_2$ and $CH_2Cl_2$/MeOH (9:1) before the solvents were removed under vacuum. Chromatography on silica, eluting with hexanes/EtOAc (70:30 to 20:80), followed by recrystallization from EtOAc/hexanes, gave 6-[2-(difluoromethyl)-4-methoxy-1H-benzimidazol-1-yl]-2-(4-morpholinyl)-9-(5-pyrimidinyl)-9H-purine (113 mg, 53%): mp (EtOAc/hexanes) 238-240° C.; $^1$H NMR (CDCl$_3$) δ 9.47 (s, 2H), 9.30 (s, 1H), 8.89 (s, 1H), 7.53 (t, $J_{HF}$=52.6 Hz, 1H), 7.37 (t, J=8.1 Hz, 1H), 7.29 (dd, J=8.4, 0.7 Hz, 1H), 6.97 (d, J=7.5 Hz, 1H), 4.02 (s, 3H), 3.80 (m, 4H), 3.72 (m, 4H); Anal. Calcd. for $C_{22}H_{19}F_2N_9O_2$: C, 55.1; H, 4.0; N, 26.3. Found: C, 55.3; H, 4.1; N, 26.5.

Example 63

Synthesis of 2-(Difluoromethyl)-4-methoxy-1-[4-(4-morpholinyl)-6-(1H-pyrazol-1-yl)-1,3,5-triazin-2-yl]-1H-benzimidazole

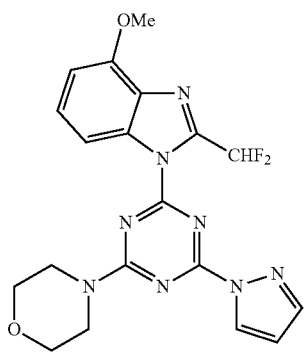 [SMILES: COc1cccc2c1nc(C(F)F)n2-c1nc(N2CCOCC2)nc(-n2cccn2)n1]

The compound was synthesized according to Method A.

A mixture of 1-[4-chloro-6-(4-morpholinyl)-1,3,5-triazin-2-yl]-2-(difluoromethyl)-4-methoxy-1H-benzimidazole (Example 2) (0.49 mg, 1.22 mmol), 1H-pyrazole (1.0 g, 14.7 mmol), and DIPEA (3 mL) was heated to 120° C. for 40 min, cooled to 20° C., and diluted with water (50 mL). The resulting precipitate was collected by filtration, washed with water, and dried. Chromatography on silica, eluting with $CH_2Cl_2$/EtOAc (4:1), gave 2-(difluoromethyl)-4-methoxy-1-[4-(4-morpholinyl)-6-(1H-pyrazol-1-yl)-1,3,5-triazin-2-yl]-1H-benzimidazole (428 mg, 82%): mp ($CH_2Cl_2$/hexanes) 274-277° C.; $^1$H NMR (DMSO-$d_6$) δ 8.79 (dd, J=2.8, 0.5 Hz, 1H), 8.14 (dd, J=8.3, 0.5 Hz, 1H), 8.01 (d, J=0.8 Hz, 1H), 7.88 (t, J=52.8 Hz, 1H), 7.49 (t, J=8.2 Hz, 1H), 7.02 (d, J=7.8 Hz, 1H), 6.70 (dd, J=2.8, 1.5 Hz, 1H), 4.01 (m, 2H), 4.00 (s, 3H), 3.93 (m, 2H), 3.80-3.75 (m, 4H); Anal. Calcd. for $C_{19}H_{18}F_2N_8O_2$: C, 53.3; H, 4.2; N, 26.2. Found: C, 53.1; H, 4.1; N, 25.9%.

Example 64

Synthesis of 2-(Difluoromethyl)-4-methoxy-1-[4-(4-morpholinyl)-6-(1H-pyrazol-1-yl)-1,3,5-triazin-2-yl]-1H-benzimidazol-6-ylamine

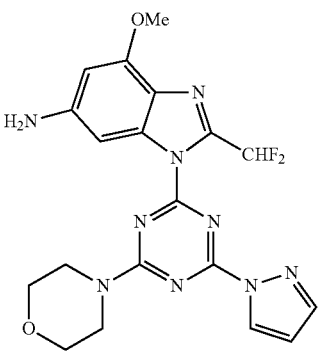 [SMILES: COc1cc(N)cc2c1nc(C(F)F)n2-c1nc(N2CCOCC2)nc(-n2cccn2)n1]

The compound was synthesized according to Method A.

A mixture of 2,3-diamino-5-nitroanisole (Horner et al., *Annalen* 1953, 579, 212) (1.10 g, 6 mmol) and difluoroacetic acid (2.31 g, 24 mmol) in polyphosphoric acid (PPA) (50 g) was heated at 130° C. in an oil bath for 1 hr. The hot solution was poured into water, and the pH was adjusted to neutral with cooling to give 2-(difluoromethyl)-4-methoxy-6-nitro-1H-benzimidazole (1.33 g, 91%): mp (EtOH/$H_2O$) 192-194° C.; $^1$H NMR (DMSO-$d_6$) δ 14.18 (br, exchangeable with $D_2O$, 1H), 8.18 (br, 1H), 7.65 (dd, J=1.4 Hz, 1H), 7.30 (t, $J_{HF}$=52.9 Hz, 1H), 4.07 (s, 3H); Anal. Calcd. for $C_9H_7F_2N_3O_3$: C, 44.45; H, 2.9; N, 17.3. Found: C, 44.75; H, 3.0; N, 17.3%.

A solution of 2-(difluoromethyl)-4-methoxy-6-nitro-1H-benzimidazole (1.22 g, 5 mmol) in MeOH (50 mL) was hydrogenated over 10% Pd on C (50 mg). After filtration to remove the catalyst Pd/C, the solution was evaporated to dryness. The residue was combined with di-tert-butyl dicarbonate (3.2 g, 15 mmol) in dioxane (20 mL), and the mixture was heated under reflux for 5 hrs. The solvent was removed under vacuum and the residue was dissolved in MeOH (30 mL) containing aqueous NaOH (2 M, 12.5 mL, 5 equiv.). The mixture was stirred at room temperature for 1 hr, neutralized with HOAc, and evaporated to dryness. The residue was extracted with EtOAc, washed with $NaHCO_3$ solution, and dried over $Na_2SO_4$. Chromatography on silica, eluting with $CH_2Cl_2$/EtOAc (9:1), gave 1.54 g (98% yield) of tert-butyl 2-(difluoromethyl)-4-methoxy-1H-benzimidazol-6-yl-carbamate: mp (i-$Pr_2O$) 189-191° C.; $^1$H NMR (DMSO-$d_6$) δ 13.0 (br, exchangeable with $D_2O$, 1H), 9.31 (br s, exchangeable with $D_2O$, 1H), 7.42 (br s, 1H), 7.15 (t, $J_{HF}$=53.4 Hz, 1H), 6.90 (br, 1H), 3.90 (s, 3H), 1.49 (s, 9H); Anal. Calcd. For $C_{14}H_{17}F_2N_3O_3$: C, 53.7; H, 5.5; N, 13.4. Found: C, 53.9; H, 5.6; N, 13.4%.

A mixture of the above benzimidazole (0.47 g, 1.5 mmol), 2,4-dichloro-6-(4-morpholinyl)-1,3,5-triazine (0.35 g, 1.5 mmol), and powdered $K_2CO_3$ (0.83 g, 6 mmol) in DMF (10 mL) was stirred at room temperature for 30 min. The reaction mixture was then diluted with water. The resulting precipitate was collected, washed with water and then MeOH, and dried to give 0.45 g (59% yield) of tert-butyl 1-[4-chloro-6-(4-morpholinyl)-1,3,5-triazin-2-yl]-2-(difluoromethyl)-4-methoxy-1H-benzimidazol-6-yl-carbamate: mp ($CH_2Cl_2$/MeOH)>300° C.; $^1$H NMR ($CDCl_3$) δ 8.45 (d, J=0.6 Hz, 1H), 7.57 (t, $J_{HF}$=53.6 Hz, 1H), 6.67 (br, exchangeable with $D_2O$, 1H), 6.63 (d, J=0.9 Hz, 1H), 4.11 (m, 2H), 4.02 (s, 3H), 3.97 (m, 2H), 3.88 (m, 2H), 3.82 (m, 2H), 1.52 (s, 9H); Anal. Calcd. for $C_{21}H_{24}ClF_2N_7O_4$: C, 49.3; H, 4.7; N, 19.15. Found: C, 49.4; H, 4.8; N, 19.2%.

Reaction of the above chloro compound with 1H-pyrazole, as in Example 63, gave tert-butyl 2-(difluoromethyl)-4-methoxy-1-[4-(4-morpholinyl)-6-(1H-pyrazol-1-yl)-1,3,5-triazin-2-yl]-1H-benzimidazol-6-ylcarbamate in 85% yield: mp ($CH_2Cl_2$/hexanes) 252-254° C.; $^1$H NMR (DMSO-$d_6$) δ 9.62 (s, 1H), 8.84 (d, J=2.3 Hz, 1H), 8.71 (br s, 1H), 7.98 (d, J=1.0 Hz, 1H), 7.93 (t, $J_{HF}$=53.2 Hz, 1H), 6.93 (d, J=1.7 Hz, 1H), 6.68 (dd, J=2.8, 1.5 Hz, 1H), 4.08 (m, 2H), 4.01 (m, 2H), 3.93 (s, 3H), 3.81-3.76 (m, 4H), 1.52 (s, 9H); Anal. Calcd. for $C_{24}H_{27}F_2N_9O_4$: C, 53.0; H, 5.0; N, 23.2. Found: C, 53.2; H, 5.2; N, 23.0%.

To a solution of the above carbamate (284 mg, 0.52 mmol) in $CH_2Cl_2$ (5 mL) was added TFA (5 mL). The reaction mixture was stirred at 20° C. for 30 hrs, basified with aq. $NH_3$, and the $CH_2Cl_2$ was removed under vacuum. The resulting precipitate was collected by filtration, washed with water, and dried. Recrystallization from $CH_2Cl_2$/MeOH gave 2-(difluoromethyl)-4-methoxy-1-[4-(4-morpholinyl)-6-(1H-pyrazol-1-yl)-1,3,5-triazin-2-yl]-1H-benzimidazol-6-ylamine in 91% yield.

Methanesulfonate salt: mp (MeOH/EtOAc)>300° C.; $^1$H NMR (DMSO-d$_6$) δ 8.79 (dd, J=2.2, 0.5 Hz, 1H), 7.99 (dd, J=1.4, 0.5 Hz, 1H), 7.87 (t, J$_{HF}$=53.0 Hz, 1H), 7.71 (s, 1H), 6.71 (dd, J=2.8, 1.6 Hz, 1H), 6.90 (br s, 1H), 4.01 (m, 2H), 3.92 (s, 3H), 3.94 (m, 2H), 3.80-3.75 (m, 4H), 2.33 (s, 6H); Anal. Calcd. for C$_{20}$H$_{23}$F$_2$N$_9$O$_5$S 0.75H$_2$O: C, 43.4; H, 4.5; N, 22.8. Found: C, 43.3; H, 4.1; N, 22.8%.

Example 65

Synthesis of 2-(Difluoromethyl)-4-methoxy-1-[4-(1-methyl-1H-pyrazol-3-yl)-6-(4-morpholinyl)-1,3,5-triazin-2-yl]-1H-benzimidazol-6-ylamine

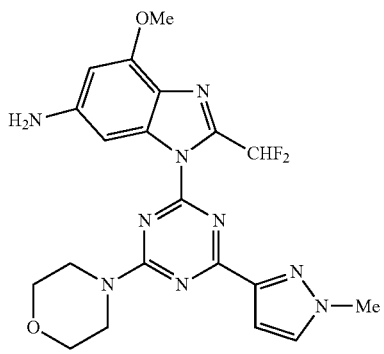 [SMILES: COc1cc(N)cc2c1nc(C(F)F)n2-c1nc(-c2ccn(C)n2)nc(N2CCOCC2)n1]

The compound was synthesized according to Method B.

A mixture of tert-butyl 1-[4-chloro-6-(4-morpholinyl)-1,3,5-triazin-2-yl]-2-(difluoromethyl)-4-methoxy-1H-benzimidazol-6-yl-carbamate (Example 64) (313 mg, 0.61 mmol), 1-methyl-1H-pyrazol-4-ylboronic acid (155 mg, 1.22 mmol), and aq. 2 M K$_2$CO$_3$ (4.1 mL) in 1,4-dioxane (20 mL) was degassed with N$_2$ for 30 min and then Pd(dppf)Cl$_2$ (30 mg) was added, and the mixture was degassed for a further 10 min. The reaction mixture was heated under reflux for 1 hr, cooled to 20° C., diluted with water, and extracted with CH$_2$Cl$_2$ (20 mL×3). The combined CH$_2$Cl$_2$ extracts were dried (Na$_2$SO$_4$) and the solvents were removed to gave a crude product which was purified by chromatography on silica, eluting with CH$_2$Cl$_2$/EtOAc (4:1) to give tert-butyl 2-(difluoromethyl)-4-methoxy-1-[4-(1-methyl-1H-pyrazol-3-yl)-6-(4-morpholinyl)-1,3,5-triazin-2-yl]-1H-benzimidazol-6-ylcarbamate (233 mg, 69% yield): mp (CH$_2$Cl$_2$/hexanes) 224-227° C.; $^1$H NMR (DMSO-d$_6$) δ 9.60 (s, 1H), 8.75 (s, 1H), 8.64 (s, 1H), 8.28 (m, 1H), 7.82 (t, J$_{HF}$=53.1 Hz, 1H), 6.92 (d, J=1.7 Hz, 1H), 3.99-3.96 (m, 4H), 3.96 (s, 3H), 3.92 (s, 3H), 3.76 (m, 4H), 1.53 (s, 9H); Anal. Calcd. for C$_{25}$H$_{29}$F$_2$N$_9$O$_4$.0.25H$_2$O: C, 53.4; H, 5.3; N, 22.4. Found: C, 53.3; H, 5.3; N, 22.3%.

Deprotection of the above carbamate with TFA/CH$_2$Cl$_2$ as in Example 64 gave 2-(difluoromethyl)-4-methoxy-1-[4-(1-methyl-1H-pyrazol-3-yl)-6-(4-morpholinyl)-1,3,5-triazin-2-yl]-1H-benzimidazol-6-ylamine in 96% yield.

Methanesulfonate salt: mp (MeOH/EtOAc) >300° C.; $^1$H NMR (DMSO-d$_6$) δ 8.59 (s, 1H), 8.27 (br s, 1H), 7.78 (t, J$_{HF}$=52.9 Hz, 1H), 7.79 (br s, 1H), 6.70 (s, 1H), 3.97 (br, 2H), 3.97 (s, 3H), 3.96 (s, 3H), 3.86 (br, 2H), 3.75 (br, 4H), 2.33 (s, 3H); Anal. Calcd. for C$_{21}$H$_{25}$F$_2$N$_9$O$_5$S: C, 45.6; H, 4.55; N, 22.8. Found: C, 45.8; H, 4.55; N, 22.9%.

Example 66

Synthesis of 2-(Difluoromethyl)-4-methoxy-1-[4-(4-morpholinyl)-6-(1H-pyrazol-4-yl)-1,3,5-triazin-2-yl]-1H-benzimidazol-6-ylamine

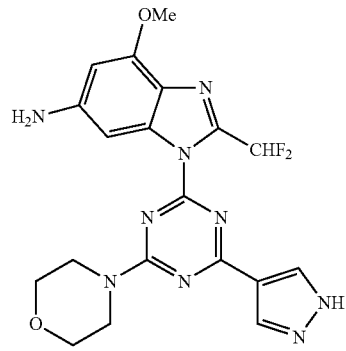 [SMILES: COc1cc(N)cc2c1nc(C(F)F)n2-c1nc(-c2cn[nH]c2)nc(N2CCOCC2)n1]

The compound was synthesized according to Method B.

Similarly to Example 50, reaction of tert-butyl 2-(difluoromethyl)-4-methoxy-1-[4-(4-morpholinyl)-6-(1H-pyrazol-1-yl)-1,3,5-triazin-2-yl]-1H-benzimidazol-6-ylcarbamate with tert-butyl 4-(4,4,5,5-tetramethyl-1,3,2-dioxaborolan-2-yl)-1H-pyrazole-1-carboxylate (WO 2006/021881) gave a mixture of tert-butyl 2-(difluoromethyl)-4-methoxy-1-[4-(4-morpholinyl)-6-(1H-pyrazol-4-yl)-1,3,5-triazin-2-yl]-1H-benzimidazol-6-ylcarbamate and tert-butyl 4-[4-[6-[(tert-butoxycarbonyl)amino]-2-(difluoromethyl)-4-methoxy-1H-benzimidazol-1-yl]-6-(4-morpholinyl)-1,3,5-triazin-2-yl]-1H-pyrazole-1-carboxylate. Deprotection of the mixture with CH$_2$Cl$_2$/TFA for 20 hrs at 20° C. gave 2-(difluoromethyl)-4-methoxy-1-[4-(4-morpholinyl)-6-(1H-pyrazol-3-yl)-1,3,5-triazin-2-yl]-1H-benzimidazol-6-ylamine, which was treated with methanesulfonic acid in MeOH, to give the methanesulfonate salt in 50% overall yield: mp (MeOH/EtOAc)>300° C.; $^1$H NMR (DMSO-d$_6$) δ 8.48 (s, 2H), 7.88 (br s, 1H), 7.79 (t, J$_f$=52.9 Hz, 1H), 6.76 (br d, J=1.3 Hz, 1H), 4.01 (m, 2H), 3.99 (s, 3H), 3.87 (m, 2H), 3.76 (m, 4H), 2.34 (s, 3H); Anal. Calcd. for C$_{20}$H$_{23}$F$_2$N$_9$O$_5$S: C, 44.5; H, 4.3; N, 23.4. Found: C, 44.5: H, 4.5; N, 23.1%.

Example 67

Synthesis of 2-(Difluoromethyl)-1-[4-(1H-imidazol-1-yl)-6-(4-morpholinyl)-1,3,5-triazin-2-yl]-4-methoxy-1H-benzimidazole

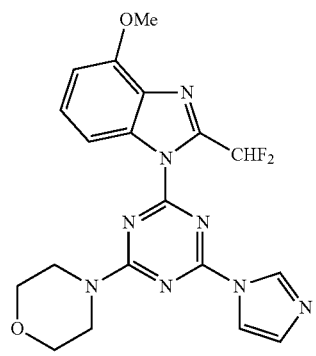 [SMILES: COc1cccc2c1nc(C(F)F)n2-c1nc(N2CCOCC2)nc(-n2ccnc2)n1]

The compound was synthesized according to Method A.

Similarly to Example 63, reaction of 1-[4-chloro-6-(4-morpholinyl)-1,3,5-triazin-2-yl]-2-(difluoromethyl)-4-methoxy-1H-benzimidazole and imidazole at 120° C. for 1 hr gave 2-(difluoromethyl)-1-[4-(1H-imidazol-1-yl)-6-(4-morpholinyl)-1,3,5-triazin-2-yl]-4-methoxy-1H-benzimidazole in 71% yield: mp (CH$_2$Cl$_2$/hexanes) 272-275° C.; $^1$H NMR (DMSO-d$_6$) δ 8.74 (s, 1H), 8.04 (t, J=1.4 Hz, 1H), 8.00 (d, J=7.8 Hz, 1H), 7.78 (t, J$_{HF}$=52.5 Hz, 1H), 7.50 (t, J=8.3 Hz, 1H), 7.22 (dd, J=1.5, 0.8 Hz, 1H), 7.02 (d, J=7.8 Hz, 1H), 4.03 (m, 2H), 4.00 (s, 3H), 3.94 (m, 2H), 3.80-3.75 (m, 4H); Anal. Calcd. for C$_{19}$H$_{18}$F$_2$N$_8$O$_2$: C, 53.3; H, 4.2: N, 26.2. Found: C, 53.6; H, 4.3; N, 26.7%.

Example 68

Synthesis of 2-(Difluoromethyl)-4-methoxy-1-[4-(4-morpholinyl)-6-(3-pyridinyl)-2-pyrimidinyl]-1H-benzimidazol-6-ylamine

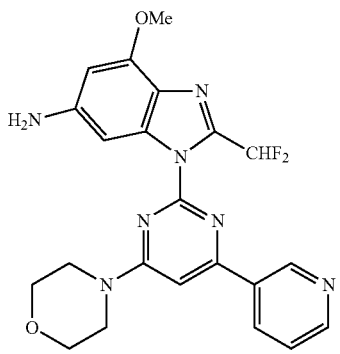 [SMILES: COc1cc(N)cc2c1nc(C(F)F)n2-c1nc(-c2cccnc2)cc(N2CCOCC2)n1]

The compound was synthesized according to Method B.

A mixture of tert-butyl 2-(difluoromethyl)-4-methoxy-1H-benzimidazol-6-yl-carbamate (Example 64) (3.13 g, 10 mmol), 4-(2,6-dichloro-4-pyrimidinyl)morpholine (2.64 g, 11 mmol), and powdered K$_2$CO$_3$ (5 g, 40 mmol) in 30 mL DMF was heated at 100° C. for 8 hrs. The mixture was cooled and diluted with water to give a precipitate which was collected and dried. Chromatography on silica eluting with CH$_2$Cl$_2$/EtOAc (19:1) gave tert-butyl 1-[4-chloro-6-(4-morpholinyl)-2-pyrimidinyl]-2-(difluoromethyl)-4-methoxy-1H-benzimidazol-6-ylcarbamate (2.49 g, 44% yield): mp (i-Pr$_2$O) 233-236° C.; $^1$H NMR (CDCl$_3$) δ 8.30 (s, 1H), 7.57 (t, J$_{HF}$=53.8 Hz, 1H), 6.64 (m, 1H), 6.63 (d, J=1.8 Hz, 1H), 6.43 (s, 1H), 4.01 (s, 3H), 3.88-3.85 (m, 4H), 3.82-3.77 (m, 4H), 1.52 (s, 9H); Anal. Calcd. for C$_{22}$H$_{25}$ClF$_2$N$_6$O$_4$: C, 51.7; H, 4.9; N, 16.45. Found: C, 52.0; H, 4.9; N, 16.6%.

Reaction of the above chloro compound (0.41 g, 0.8 mmol) with 3-pyridinylboronic acid (0.15 g, 12 mmol) as in Example 47, followed by chromatography on alumina eluting with CH$_2$Cl$_2$/EtOAc (4:1), gave tert-butyl 2-(difluoromethyl)-4-methoxy-1-[4-(4-morpholinyl)-6-(3-pyridinyl)-2-pyrimidinyl]-1H-benzimidazol-6-ylcarbamate (0.22 g, 50% yield): $^1$H NMR (DMSO-d$_6$) δ 9.53 (s, 1H), 9.45 (d, J=1.7 Hz, 1H), 8.74 (dd, J=4.7, 1.6 Hz, 1H), 8.66 (dt, J=8.3, 1.9 Hz, 1H), 8.54 (br s, 1H), 7.75 (t, J$_{HF}$=53.1 Hz, 1H), 7.58 (ddd, J=8.0, 4.8, 0.5 Hz, 1H), 7.51 (s, 1H), 6.91 (d, J=1.7 Hz, 1H), 3.93 (s, 3H), 3.92-3.88 (m, 4H), 3.81-3.78 (m, 4H), 1.51 (s, 9H).

Reaction of the above carbamate with TFA (5 mL) in CH$_2$Cl$_2$ (10 mL) for 12 hrs gave 2-(difluoromethyl)-4-methoxy-1-[4-(4-morpholinyl)-6-(3-pyridinyl)-2-pyrimidinyl]-1H-benzimidazol-6-ylamine in 94% yield: $^1$H NMR (DMSO-d$_6$) δ 9.42 (d, J=2.3 Hz, 1H), 8.74 (dd, J=4.8, 1.6 Hz, 1H), 8.58 (dt, J=8.1, 2.0 Hz, 1H), 7.64 (t, J$_{HF}$=53.6 Hz, 1H), 7.60 (ddd, J=8.0, 4.8, 0.7 Hz, 1H), 7.48 (s, 1H), 7.05 (d, J=1.7 Hz, 1H), 6.28 (d, J=1.7 Hz, 1H), 5.40 (m, 2H), 3.89 (s, 3H), 3.86-3.83 (m, 4H), 3.79-3.77 (m, 4H).

Dimethanesulfonate salt: mp (MeOH/EtOAc) 246° C. dec.; Anal. Calcd. for C$_{24}$H$_{29}$F$_2$N$_7$O$_8$S$_2$: C, 44.65; H, 4.5; N, 15.2. Found: C, 44.6; H, 4.6; N, 15.1%.

Example 69

Biological Activity

A. Inhibition of Isolated Enzyme

Compounds were evaluated for their ability to inhibit Class I PI 3-kinase enzymes p110δ/p85, p110α/p85, and p110β/p85. Reaction mixtures comprising 0.1 μg of a recombinant enzyme, 10 μg of L-α-phosphatidylinositol, and 2× Lipid Kinase Buffer (40 mM Tris-HCl, pH 7.4, 200 mM NaCl, 1 mM EDTA), which contains either DMSO only as a control or the test compound in DMSO (the final DMSO concentration is 1%), were activated by the addition of an ATP mix (5 mM MgCl$_2$, 100 μM ATP, and 0.1 μL [γ$^{33}$P]ATP). Reactions were incubated at room temperature for 1 hr, and then stopped by the addition of 1M HCl. The lipids were then extracted using a two step procedure. Firstly, 200 μL of chloroform/methanol (1:1) was added, the biphasic reactions mixed and centrifuged briefly, and the inorganic phase was removed and discarded. Following this, 80 μL of methanol:HCl (1:1) was added and the same procedure followed. The organic phase (70 μL) was then transferred to a clean 1.6 mL tube and the reactions were dried using a Speedvac, with no heating, for 30 mM. The reactions were spotted onto TLC plates (Merck Ltd) and developed for 1 hr in propanol-1:2 M acetic acid (13:7). The TLC plates were then dried at room temperature and quantified using a phosphorimager (StormImager, Amersham). Nine compound concentrations were used for each test compound to determine its IC$_{50}$ value. Each experiment was performed twice and the average IC$_{50}$ value is used herein. The results are summarized in Table 1.

B. Cellular Growth Inhibition.

The compounds were evaluated against two early passage human cell lines NZB5 and NZOV9 (Marshall et al., *Oncol. Res.* 2004, 14, 297). The cells were grown in ITS medium (α-modified minimal essential medium supplemented insulin, transferrin, selenite, and 5% fetal bovine serum) and grown on 96-well tissue culture plates under an atmosphere of 5% O$_2$, 5% CO$_2$, and 90% N$_2$. Individual wells contained 500-1,000 cells (depending on the growth rate) in a volume of 150 μL. Compounds were added at 10-fold concentration steps to a maximum of 20 μM and plates were incubated for five days, with $^3$H-thymidine being added over the last 6 hrs. Cells were harvested and incorporated radioactivity measured. Duplicate samples were analyzed for each compound dose with multiple control samples. Data were fitted by a least-squares method to an exponential of the form $y=y_0+ae^{-bx}$, where y is the radioactivity (corrected for background and normalized to 100% of the control), x is the radiation dose, and $y_0$, a, and b are variables, and the IC$_{50}$ value defined as the compound concentration reducing $^3$H-thymidine levels by 50%. The results are summarized in Table 1.

TABLE 1

Biological Activity

| Example | Enzyme IC$_{50}$* | | | Cell IC$_{50}$* | |
|---|---|---|---|---|---|
| | p110α | p110β | p110δ | NZB5 | NZOV9 |
| 1 | A | A | A | B | B |
| 2 | A | B | A | A | A |
| 3 | A | A | A | B | A |
| 4 | C | C | B | A | B |
| 5 | B | B | A | B | B |
| 6 | B | B | A | B | B |
| 7 | B | B | B | B | B |
| 8 | B | A | A | B | B |
| 9 | C | B | A | | B |
| 10 | D | D | C | D | C |
| 11 | D | D | C | D | D |
| 12 | C | C | C | D | D |
| 13 | A | A | A | B | B |
| 14 | B | B | A | C | B |
| 15 | B | | | B | B |
| 16 | A | | A | B | B |
| 17 | A | B | A | A | A |
| 18 | B | | B | B | B |
| 19 | B | | | B | B |
| 20 | A | | A | B | B |
| 21 | A | | A | B | B |
| 22 | A | | A | B | B |
| 23 | A | B | A | B | B |
| 24 | B | | | C | C |
| 25 | A | B | A | B | B |
| 26 | A | B | A | B | B |
| 27 | A | B | A | B | A |
| 28 | A | A | A | A | A |
| 29 | A | B | A | A | A |
| 30 | A | B | A | A | A |
| 31 | A | B | A | A | A |
| 32 | A | B | A | D | A |
| 33 | A | B | A | B | A |
| 34 | A | B | A | B | B |
| 35 | A | B | A | B | B |
| 36 | A | B | A | A | A |
| 37 | A | B | A | A | A |
| 38 | A | B | A | A | A |
| 39 | A | B | A | A | A |
| 40 | A | B | A | B | B |
| 41 | A | | A | | |
| 42 | A | | A | | |
| 43 | A | | A | | |
| 44 | A | | A | | |
| 45 | A | | A | | |
| 47 | A | B | A | B | B |
| 48 | A | | A | | |
| 49 | A | | A | | |
| 51 | B | | B | | |
| 52 | A | | A | | |
| 55 | B | | B | | |
| 56 | A | | B | | |
| 57 | A | | B | | |
| 60 | A | | A | | |
| 63 | A | | A | | |
| 64 | A | | A | | |
| 65 | A | | A | | |
| 66 | A | | A | | |
| 68 | A | | A | | |

*A. <0.1 μM; B. 0.1-1.0 μM; C. 1.0-10 μM; D. >10 μM

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula I, IA, or IB:

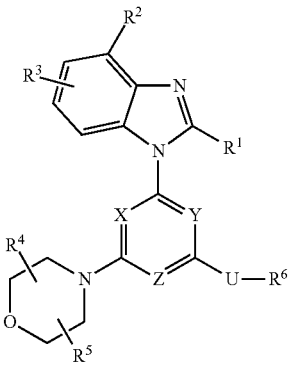

(I)

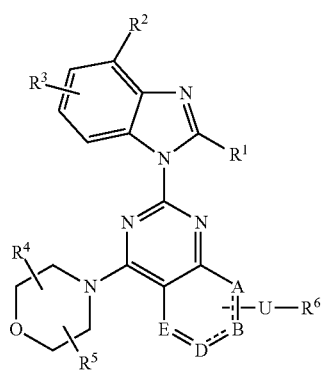

(IA)

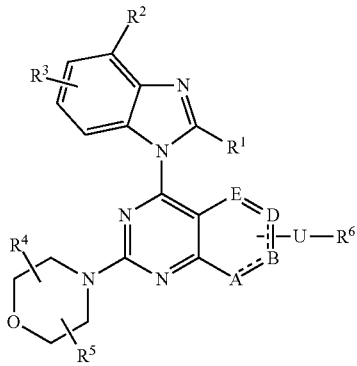

(IB)

or an enantiomer, a mixture of enantiomers, or a mixture of two or more diastereomers thereof; or a pharmaceutically acceptable salt or prodrug thereof;

wherein:

each $R^1$ is independently hydrogen, $C_{1-6}$ alkyl, —S—$C_{1-6}$ alkyl, —S(O)—$C_{1-6}$ alkyl, or —SO$_2$—$C_{1-6}$ alkyl;

each $R^2$ and $R^3$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)N$R^{1b}R^{1c}$, —C(N$R^a$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

each $R^4$ and $R^5$ is independently hydrogen or $C_{1-6}$ alkyl; or $R^4$ and $R^5$ are linked together to form a bond, $C_{1-6}$ alkylene, $C_{1-6}$ heteroalkylene, $C_{2-6}$ alkenylene, or $C_{2-6}$ heteroalkenylene;

each $R^6$ is independently $C_{6-14}$ aryl, $C_{7-15}$ aralkyl, heteroaryl, or heteroaryl-$C_{1-6}$ alkyl;

each U is independently —C(O)—, —C(O)O—, —C(O)NR$^{1a}$—, —O—, —OC(O)O—, —OC(O)NR$^{1a}$—, —NR$^{1a}$—, —NR$^{1a}$C(O)NR$^{1d}$—, —NR$^{1a}$S(O)—, —NR$^{1a}$S(O)$_2$—, —NR$^{1a}$S(O)NR$^{1d}$—, —NR$^{1a}$S(O)$_2$NR$^{1d}$—, —S—, —S(O)—, or —S(O)$_2$—;

each X, Y, and Z is N;

each A, B, D, and E is independently a bond, C, O, N, S, NR$^9$, CR$^9$, or CR$^9$R$^{10}$, where each R$^9$ and R$^{10}$ is independently hydrogen, halo, $C_{1-6}$ alkyl, $C_{2-6}$ alkenyl, or $C_{2-6}$ alkynyl; wherein the bonds between A, B, D, and E may be saturated or unsaturated; with the proviso that no more than one of A, B, D, and E are a bond; and each $R^{1a}$, $R^{1b}$, $R^{1c}$, and $R^{1d}$ is independently (i) hydrogen; or (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

wherein each alkyl, alkylene, heteroalkylene, alkenyl, alkenylene, heteroalkenylene, alkynyl, cycloalkyl, aryl, aralkyl, heteroaryl, and heterocyclyl $R^1$, $R^2$, $R^3$, $R^4$, $R^5$, $R^6$, $R^9$, $R^{10}$, $R^{1a}$, $R^{1b}$, $R^{1c}$, or $R^{1d}$ is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more substituents Q; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)NR$^b$R$^c$, —SR$^a$, —S(O)R$^a$, and —S(O)NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents Q; or (iii) R$^b$ and R$^c$ together with the N atom to which they are attached form heterocyclyl, optionally substituted with one or more substituents Q;

wherein each Q is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)NR$^f$R$^g$, —SR$^e$, —S(O)R$^e$, and —S(O)NR$^f$R$^g$, wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

2. The compound of claim 1 having the structure of Formula II, Ia, or Ib:

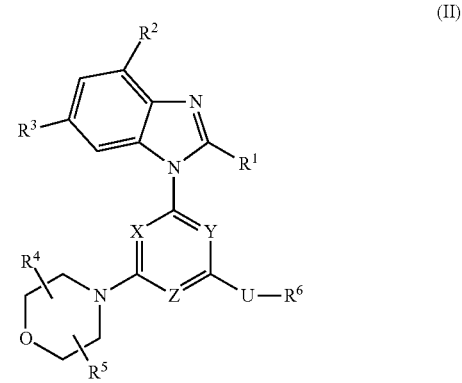

(II)

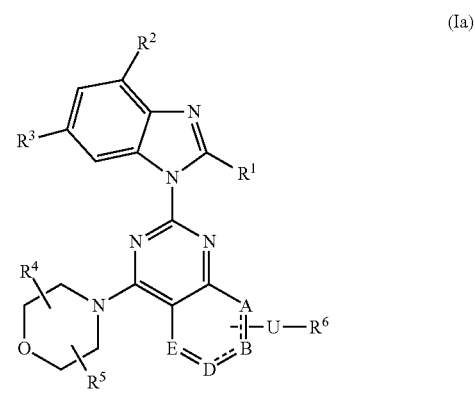

(Ia)

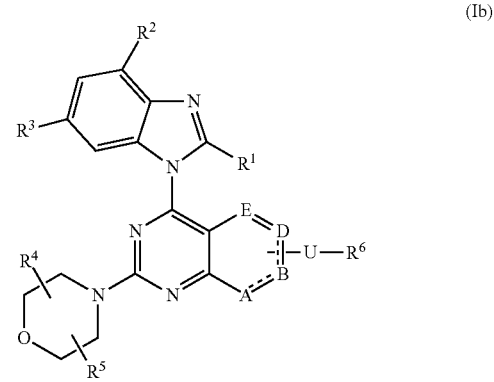

(Ib)

or an enantiomer, a mixture of enantiomers, or a mixture of two or more diastereomers thereof; or a pharmaceutically acceptable salt or prodrug thereof.

3. The compound of claim 1 having the structure of Formula VIII:

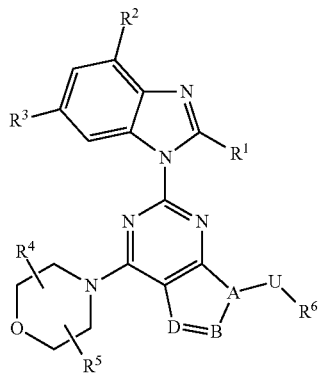

(VIII)

or an enantiomer, a mixture of enantiomers, or a mixture of two or more diastereomers thereof; or a pharmaceutically acceptable salt or prodrug thereof.

4. The compound of claim 1 having the structure of Formula IX

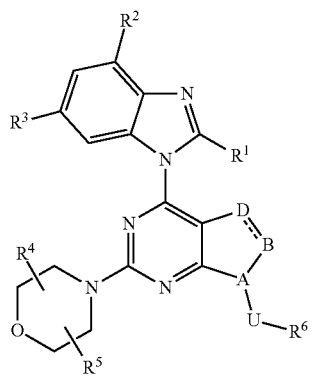

(IX)

or an enantiomer, a mixture of enantiomers, or a mixture of two or more diastereomers thereof; or a pharmaceutically acceptable salt prodrug thereof.

5. The compound of claim 1, wherein A is N.
6. The compound of claim 1, wherein B is N.
7. The compound of claim 1, wherein B is CH or $CH_2$.
8. The compound of claim 1, wherein D is N.
9. The compound of claim 1, wherein D is CH or $CH_2$.
10. The compound of claim 1, wherein $R^6$ is $C_{6-14}$ aryl, optionally substituted with one or more substituents Q.
11. The compound of claim 10, wherein $R^6$ is phenyl, optionally substituted with one or more substituents, each independently selected from the group consisting of halo, cyano, nitro, amino, hydroxyl, and methoxy.
12. The compound of claim 10, wherein $R^6$ is phenyl, aminophenyl, nitrophenyl, or methoxyphenyl.
13. The compound of claim 1, wherein $R^6$ is $C_{7-15}$ aralkyl, optionally substituted with one or more substituents Q.
14. The compound of claim 13, wherein $R^6$ is $-(CR^A R^B)_m - C_{6-14}$ aryl, and each $R^A$ and $R^B$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; and m is an integer of 1, 2, or 3; and where each alkyl, alkenyl, alkynyl, cycloalkyl, aryl, aralkyl, heteroaryl, and heterocyclyl is optionally substituted with one or more substituents Q.

15. The compound of claim 13, wherein $R^6$ is benzyl, optionally substituted with one or more substituents Q.
16. The compound of claim 13, wherein $R^6$ is benzyl or phenyl-ethyl, each optionally substituted with one or more substituents Q.
17. The compound of claim 1, wherein $R^6$ is heteroaryl, optionally substituted with one or more substituents Q.
18. The compound of claim 17, wherein $R^6$ is pyrazolyl, imidazolyl, thiazolyl, 1,2,3-triazolyl, tetrazolyl, pyridinyl, pyridazinyl, pyrimidinyl, pyrazinyl, or quinolinyl, each optionally substituted with one or more substituents Q.
19. The compound of claim 17, wherein each substituent is independently -L-$(CR^C R^D)_n$—$R^E$, where $R^C$ and $R^D$ are each independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; each optionally substituted with one or more substituents Q; $R^E$ is hydrogen, —$NR^F R^G$, or heterocyclyl; L is a bond, —O—, or —$N(R^H)$—; $R^F$, $R^G$, and $R^H$ are each independently hydrogen or $C_{1-6}$ alkyl; and n is an integer of 0, 1, 2, or 3; and where each alkyl and heterocyclyl is independently, optionally substituted with one or more substituents Q.
20. The compound of claim 19, wherein L is a bond, —O—, —NH—, or —$N(CH_3)$—.
21. The compound of claim 19, wherein $R^C$ and $R^D$ are hydrogen.
22. The compound of claim 19, wherein $R^E$ is hydrogen, methylamino, dimethylamino, pyrrolidinyl, piperidinyl, or morpholinyl, wherein the pyrrolidinyl, piperidinyl, and morpholinyl are independently, optionally substituted with methyl.
23. The compound of claim 17, wherein each substituent is independently selected from the group consisting of amino, fluoro, chloro, methyl, (dimethylamino)methyl, (dimethylamino)ethyl, (dimethylamino)propyl, morpholinylmethyl, (morpholinyl)ethyl, (morpholinyl)propyl, methoxy, (dimethylamino)ethoxy, (dimethylamino)propoxy, (morpholinyl)ethoxy, (morpholinyl)propoxy, (methyl-piperidinyl)oxy, (methyl-pyrrolidinyl)-oxy, methylamino, dimethylamino, (dimethylamino)ethylamino, (dimethylaminoethyl)-(methyl)amino, (dimethylamino)propylamino, ((dimethylamino)propyl)(methyl)amino, (morpholinyl)ethylamino, ((morpholinyl)ethyl)(methyl)amino, (morpholinyl)propylamino, ((morpholinyl)propyl)(methyl)amino, methyl-piperidinylamino, (methyl-piperidinyl)-(methyl)amino, methyl-piperazinyl, and (dimethylamino)-piperidinyl.
24. The compound of claim 18, wherein $R^6$ is pyridinyl.
25. The compound of claim 24, wherein $R^6$ is 3-pyridinyl.
26. The compound of claim 1 having the structure of Formula III:

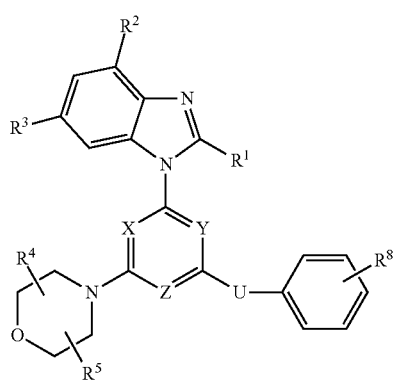

(III)

or an enantiomer, a mixture of enantiomers, or a mixture of two or more diastereomers thereof; or a pharmaceutically acceptable salt or prodrug thereof;

wherein:

U is —C(O)—, —C(O)O—, —C(O)NR$^{1a}$—, —O—, —OC(O)O—, —OC(O)NR$^{1a}$—, —NR$^{1a}$—, —NR$^{1a}$C(O)NR$^{1d}$—, —NR$^{1a}$S(O)—, —NR$^{1a}$S(O)$_2$—, —NR$^{1a}$S(O)NR$^{1d}$—, —NR$^{1a}$S(O)$_2$NR$^{1d}$—, —S—, —S(O)—, or —S(O)$_2$—; and R$^8$ is (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; each optionally substituted with one or more substituents Q; or (c) —C(O)R$^{1a}$, —C(O)OR$^{1b}$, —C(O)NR$^{1b}$R$^{1c}$, —C(NR$^a$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$—S(O)NR$^{1b}$R$^{1c}$, or —S(O)$_2$NR$^{1b}$R$^{1c}$.

27. The compound of claim 1 having the structure of Formula IV:

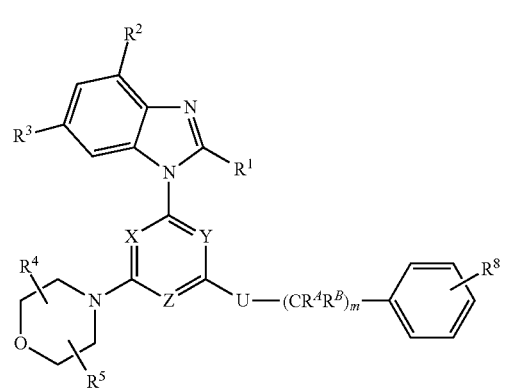

(IV)

or an enantiomer, a mixture of enantiomers, or a mixture of two or more diastereomers thereof; or a pharmaceutically acceptable salt or prodrug thereof;

wherein:

R$^8$ is (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; each optionally substituted with one or more substituents Q; or (c) —C(O)R$^{1a}$, —C(O)OR$^{1b}$, —C(O)NR$^{1b}$R$^{1c}$, —C(NR$^a$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

each R$^A$ and R$^B$ is independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; each optionally substituted with one or more substituents Q; and m is an integer of 1, 2, or 3.

28. The compound of claim 26, wherein R$^8$ is hydrogen, hydroxyl, or methoxy.

29. The compound of claim 1 having the structure of Formula V:

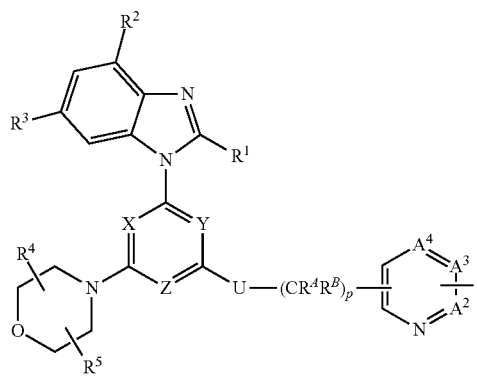

(V)

or an enantiomer, a mixture of enantiomers, or a mixture of two or more diastereomers thereof; or a pharmaceutically acceptable salt or prodrug thereof;

wherein:

A$^2$, A$^3$, and A$^4$ are each independently C, N, or CR$^8$; with the proviso that no more than one of A$^2$, A$^3$, and A$^4$ is N;

each R$^A$ and R$^B$ are each independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; each optionally substituted with one or more substituents Q;

each R$^8$ is independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; each optionally substituted with one or more substituents Q; or (c) —C(O)R$^{1a}$, —C(O)OR$^{1b}$, —C(O)NR$^{1b}$R$^{1c}$, —C(NR$^a$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and p is an integer of 0, 1, 2, or 3.

30. The compound of claim 29, wherein A$^2$, A$^3$, and A$^4$ are independently CR$^8$.

31. The compound of claim 29, wherein A$^2$ is N, and A$^3$ and A$^4$ are independently CR$^8$.

32. The compound of claim 29, wherein A$^2$ and A$^4$ are independently CR$^8$, and A$^3$ is N.

33. The compound of claim 29, wherein A$^2$ and A$^3$ are independently CR$^8$, and A$^4$ is N.

34. The compound of claim 29 having the structure of Formula VI:

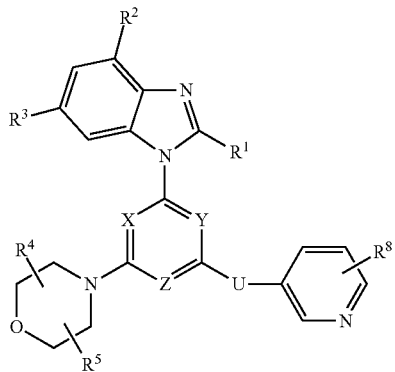

(VI)

or an enantiomer, a mixture of enantiomers, or a mixture of two or more diastereomers thereof; or a pharmaceutically acceptable salt or prodrug thereof.

35. The compound of claim 1 having the structure of Formula VII:

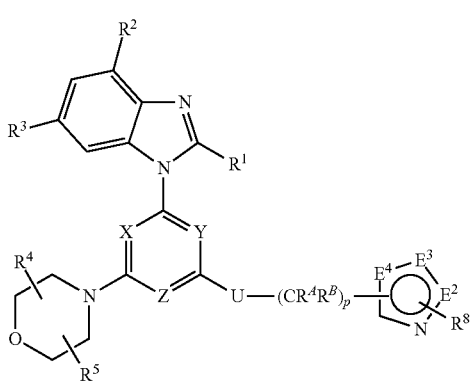

(VII)

or an enantiomer, a mixture of enantiomers, or a mixture of two or more diastereomers thereof; or a pharmaceutically acceptable salt or prodrug thereof;
wherein:
$E^2$, $E^3$, and $E^4$ are each independently C, N, O, S, $CR^8$, or $NR^8$;
each $R^A$ and $R^B$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; each optionally substituted with one or more substituents Q;
each $R^8$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; each optionally substituted with one or more substituents Q; or (c) —C(O)$R^{1a}$, —C(O)O$R^{1b}$, —C(O)N$R^{1b}R^{1c}$, —C(N$R^a$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O) N$R^{1b}R^{1c}$, —OS(O)$_2$N$R^{1b}R^{1c}$, —N$R^{1a}$C (O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; and
p is an integer of 0, 1, 2, or 3.

36. The compound of claim 35, wherein $E^2$, $E^3$, and $E^4$ are $CR^8$.

37. The compound of claim 35, wherein $E^2$ and $E^4$ are $CR^8$, and $E^3$ is $NR^8$, O, or S.

38. The compound of claim 35, wherein $E^2$ and $E^3$ are N, and $E^4$ is $CR^8$.

39. The compound of claim 35, wherein $E^2$, $E^3$, and $E^4$ are N.

40. The compound of claim 29, wherein $R^8$ is hydrogen.

41. The compound of claim 29, wherein $R^8$ is -L-(C$R^CR^D$)$_n$—$R^E$, where $R^C$ and $R^D$ are each independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; $R^E$ is hydrogen, —N$R^FR^G$, or heterocyclyl; L is a bond, —O—, or —N($R^H$)—; $R^F$, $R^G$, and $R^H$ are each independently hydrogen or $C_{1-6}$ alkyl; and n is an integer of 0, 1, 2, or 3.

42. The compound of claim 41, wherein L is a bond, —O—, —NH—, or —N(CH$_3$)—.

43. The compound of claim 41, wherein $R^C$ and $R^D$ are hydrogen.

44. The compound of claim 41, wherein $R^E$ is hydrogen, methylamino, dimethylamino, pyrrolidinyl, piperidinyl, or morpholinyl, wherein the pyrrolidinyl, piperidinyl, and morpholinyl are independently, optionally substituted with methyl.

45. The compound of claim 41, wherein $R^8$ is independently selected from the group consisting of amino, fluoro, chloro, methyl, (dimethylamino)methyl, (dimethylamino)ethyl, (dimethylamino)propyl, morpholinylmethyl, (morpholinyl)ethyl, (morpholinyl)propyl, methoxy, (dimethylamino) ethoxy, (dimethylamino)propoxy, (morpholinyl)ethoxy, (morpholinyl)propoxy, (methyl-piperidinyl)oxy, (methyl-pyrrolidinyl)oxy, methylamino, dimethylamino, (dimethylamino)ethylamino, (dimethylaminoethyl)(methyl)amino, (dimethylamino)propylamino, ((dimethylamino)propyl) (methyl)amino, (morpholinyl)ethylamino, ((morpholinyl) ethyl)(methyl)amino, (morpholinyl)propylamino, ((morpholinyl)propyl)(methyl)amino, methyl-piperidinylamino, (methyl-piperidinyl)(methyl)amino, methyl-piperazinyl, and (dimethylamino)-piperidinyl.

46. The compound of claim 27, wherein $R^A$ and $R^B$ are hydrogen.

47. The compound of claim 1, wherein $R^1$ is $C_{1-6}$ alkyl, —S—$C_{1-6}$ alkyl or —SO$_2$—$C_{1-6}$ alkyl, where each alkyl is independently, optionally substituted with one to three halo.

48. The compound of claim 47, wherein $R^1$ is methyl, fluoromethyl, difluoromethyl, trifluoromethyl, methanesulfanyl, or methanesulfonyl.

49. The compound of claim 47, wherein $R^1$ is difluoromethyl.

50. The compound of claim 47, wherein $R^1$ is methanesulfanyl.

51. The compound of claim 47, wherein $R^1$ is methanesulfonyl.

52. The compound of claim 1, wherein $R^2$ is hydrogen, $C_{1-6}$ alkyl, or —O—$C_{1-6}$ alkyl, where each alkyl is optionally substituted with one or more substituents Q.

53. The compound of claim 52, wherein $R^2$ is hydrogen.

54. The compound of claim 52, wherein $R^2$ is methoxy.

55. The compound of claim 1, wherein $R^3$ is hydrogen, amino, or $C_{1-6}$ alkyl, optionally substituted with one or more substituents Q.

56. The compound of claim 55, wherein $R^3$ is hydrogen.

57. The compound of claim 55, wherein $R^3$ is amino.

58. The compound of claim 1, wherein $R^4$ is hydrogen or $C_{1-6}$ alkyl, optionally substituted with one or more substituents Q.

59. The compound of claim 58, wherein $R^4$ is hydrogen.

60. The compound of claim 1, wherein $R^5$ is hydrogen or $C_{1-6}$ alkyl, optionally substituted with one or more substituents Q.

61. The compound of claim 60, wherein $R^5$ is hydrogen.

62. The compound of claim 1, wherein $R^4$ and $R^5$ are linked together to form a bond or $C_{1-6}$ alkylene.

63. The compound of claim 62, wherein $R^4$ and $R^5$ are linked together to form a bond, methylene, or ethylene.

64. The compound of claim 1, wherein U is —O—, —NR$^{1a}$—, —S—, —S(O)—, or —S(O)$_2$—, where $R^{1a}$ is $C_{1-6}$ alkyl, optionally substituted with one or more substituents Q.

65. The compound of claim 64, wherein U is —O—, —NH—, —NCH$_3$—, —S—, —S(O)—, or —S(O)$_2$—.

66. The compound of claim 64, wherein U is —NH—.

67. The compound of claim 1 selected from the group consisting of:

4-[2-(difluoromethyl)-1H-benzimidazol-1-yl]-6-(4-morpholinyl)-N-(3-pyridinyl)-1,3,5-triazin-2-amine;
4-[2-(difluoromethyl)-4-methoxy-1H-benzimidazol-1-yl]-6-(4-morpholinyl)-N-(3-pyridinyl)-1,3,5-triazin-2-amine;
4-[2-(difluoromethyl)-4-methoxy-1H-benzimidazol-1-yl]-N-methyl-6-(4-morpholinyl)-N-(3-pyridinyl)-1,3,5-triazin-2-amine;
4-[2-(methylsulfanyl)-1H-benzimidazol-1-yl]-6-(4-morpholinyl)-N-(3-pyridinyl)-1,3,5-triazin-2-amine;
4-[2-(methylsulfonyl)-1H-benzimidazol-1-yl]-6-(4-morpholinyl)-N-(3-pyridinyl)-1,3,5-triazin-2-amine;
4-[2-(difluoromethyl)-1H-benzimidazol-1-yl]-6-(4-morpholinyl)-N-phenyl-1,3,5-triazin-2-amine;
4-[2-(difluoromethyl)-1H-benzimidazol-1-yl]-N-methyl-6-(4-morpholinyl)-N-phenyl-1,3,5-triazin-2-amine;
N-benzyl-4-[2-(difluoromethyl)-1H-benzimidazol-1-yl]-6-(4-morpholinyl)-1,3,5-triazin-2-amine;
N-benzyl-4-[2-(difluoromethyl)-1H-benzimidazol-1-yl]-N-methyl-6-(4-morpholinyl)-1,3,5-triazin-2-amine;
2-(difluoromethyl)-1-[4-(4-morpholinyl)-6-phenoxy-1,3,5-triazin-2-yl]-1H-benzimidazole;
2-(difluoromethyl)-1-[4-(4-morpholinyl)-6-(phenylsulfanyl)-1,3,5-triazin-2-yl]-1H-benzimidazole;
2-(difluoromethyl)-1-[4-(4-morpholinyl)-6-(phenylsulfonyl)-1,3,5-triazin-2-yl]-1H-benzimidazole;
N-(2-chloro-5-pyrimidinyl)-4-[2-(difluoromethyl)-4-methoxy-1H-benzimidazol-1-yl]-6-(4-morpholinyl)-1,3,5-triazin-2-amine;
4-[2-(difluoromethyl)-1H-benzimidazol-1-yl]-N-methyl-6-(4-morpholinyl)-N-(5-pyrimidinyl)-1,3,5-triazin-2-amine;
4-[2-(difluoromethyl)-4-methoxy-1H-benzimidazol-1-yl]-N-methyl-6-(4-morpholinyl)-N-(5-pyrimidinyl)-1,3,5-triazin-2-amine;

and enantiomers, mixtures of enantiomers, or mixtures of two or more diastereomers thereof; and pharmaceutically acceptable salts and prodrugs thereof.

68. The compound of claim 1 selected from the group consisting of:

N-[4-[6-amino-2-(difluoromethyl)-4-methoxy-1H-benzimidazol-1-yl]-6-(4-morpholinyl)-1,3,5-triazin-2-yl]-N-(3-pyridinyl)amine;
$N^5$-[4-[2-(difluoromethyl)-4-methoxy-1H-benzimidazol-1-yl]-6-(4-morpholinyl)-1,3,5-triazin-2-yl]-2,5-pyridinediamine;
$N^5$-[4-[2-(difluoromethyl)-4-methoxy-1H-benzimidazol-1-yl]-6-(4-morpholinyl)-1,3,5-triazin-2-yl]-$N^2$-[3-(dimethylamino)propyl]-2,5-pyridinediamine;
$N^5$-[4-[2-(difluoromethyl)-4-methoxy-1H-benzimidazol-1-yl]-6-(4-morpholinyl)-1,3,5-triazin-2-yl]-$N^2$-[3-(dimethylamino)propyl]-$N^2$-methyl-2,5-pyridinediamine;
4-[2-(difluoromethyl)-4-methoxy-1H-benzimidazol-1-yl]-N-(6-methoxy-3-pyridinyl)-6-(4-morpholinyl)-1,3,5-triazin-2-amine;
4-[2-(difluoromethyl)-4-methoxy-1H-benzimidazol-1-yl]-N-{6-[3-(dimethylamino)propoxy]-3-pyridinyl}-6-(4-morpholinyl)-1,3,5-triazin-2-amine;
4-[2-(difluoromethyl)-1H-benzimidazol-1-yl]-6-(4-morpholinyl)-N-(5-pyrimidinyl)-1,3,5-triazin-2-amine;
4-[2-(difluoromethyl)-1H-benzimidazol-1-yl]-6-(4-morpholinyl)-N-(3-pyridazinyl)-1,3,5-triazin-2-amine;
4-[2-(difluoromethyl)-1H-benzimidazol-1-yl]-N-(1-methyl-1H-imidazol-5-yl)-6-(4-morpholinyl)-1,3,5-triazin-2-amine; and
4-[2-(difluoromethyl)-1H-benzimidazol-1-yl]-N-(1-methyl-1H-pyrazol-5-yl)-6-(4-morpholinyl)-1,3,5-triazin-2-amine; and enantiomers, mixtures of enantiomers, or mixtures of two or more diastereomers thereof; and pharmaceutically acceptable salts and prodrugs thereof.

69. The compound of claim 1 selected from the group consisting of:

4-[4-methoxy-2-(methylsulfonyl)-1H-benzimidazol-1-yl]-6-(4-morpholinyl)-N-(3-pyridinyl)-1,3,5-triazin-2-amine;
4-[2-(difluoromethyl)-1H-benzimidazol-1-yl]-6-(4-morpholinyl)-N-(2-pyridinyl)-1,3,5-triazin-2-amine;
4-[2-(difluoromethyl)-4-methoxy-1H-benzimidazol-1-yl]-6-(4-morpholinyl)-N-(2-pyridinyl)-1,3,5-triazin-2-amine;
4-[2-(difluoromethyl)-1H-benzimidazol-1-yl]-6-(4-morpholinyl)-N-(4-pyridinyl)-1,3,5-triazin-2-amine;
4-[2-(difluoromethyl)-4-methoxy-1H-benzimidazol-1-yl]-6-(4-morpholinyl)-N-(4-pyridinyl)-1,3,5-triazin-2-amine;
4-[2-(difluoromethyl)-1H-benzimidazol-1-yl]-6-(4-morpholinyl)-N-(4-pyrimidinyl)-1,3,5-triazin-2-amine;
4-[2-(difluoromethyl)-4-methoxy-1H-benzimidazol-1-yl]-6-(4-morpholinyl)-N-(4-pyrimidinyl)-1,3,5-triazin-2-amine;
4-[2-(difluoromethyl)-4-methoxy-1H-benzimidazol-1-yl]-6-(4-morpholinyl)-N-(5-pyrimidinyl)-1,3,5-triazin-2-amine;
2-(difluoromethyl)-1-[4-(4-morpholinyl)-6-(3-pyridinyloxy)-1,3,5-triazin-2-yl]-1H-benzimidazole;
2-(difluoromethyl)-4-methoxy-1-[4-(4-morpholinyl)-6-(3-pyridinyloxy)-1,3,5-triazin-2-yl]-1H-benzimidazole;
2-(difluoromethyl)-1-[4-(4-morpholinyl)-6-(5-pyrimidinyloxy)-1,3,5-triazin-2-yl]-1H-benzimidazole;
2-(difluoromethyl)-4-methoxy-1-[4-(4-morpholinyl)-6-(5-pyrimidinyloxy)-1,3,5-triazin-2-yl]-1H-benzimidazole;
4-[2-(difluoromethyl)-4-methoxy-1H-benzimidazol-1-yl]-N-(1-methyl-1H-pyrazol-4-yl)-6-(4-morpholinyl)-1,3,5-triazin-2-amine;
4-[2-(difluoromethyl)-1H-benzimidazol-1-yl]-N-(1-methyl-1H-pyrazol-4-yl)-6-(4-morpholinyl)-1,3,5-triazin-2-amine;

4-[2-(difluoromethyl)-1H-benzimidazol-1-yl]-6-(4-morpholinyl)-N-(2-pyridinylmethyl)-1,3,5-triazin-2-amine;
4-[2-(difluoromethyl)-4-methoxy-1H-benzimidazol-1-yl]-6-(4-morpholinyl)-N-(2-pyridinylmethyl)-1,3,5-triazin-2-amine;
4-[2-(difluoromethyl)-1H-benzimidazol-1-yl]-6-(4-morpholinyl)-N-(3-pyridinylmethyl)-1,3,5-triazin-2-amine;
4-[2-(difluoromethyl)-4-methoxy-1H-benzimidazol-1-yl]-6-(4-morpholinyl)-N-(3-pyridinylmethyl)-1,3,5-triazin-2-amine;
4-[2-(difluoromethyl)-1H-benzimidazol-1-yl]-6-(4-morpholinyl)-N-(4-pyridinylmethyl)-1,3,5-triazin-2-amine;
4-[2-(difluoromethyl)-4-methoxy-1H-benzimidazol-1-yl]-6-(4-morpholinyl)-N-(4-pyridinylmethyl)-1,3,5-triazin-2-amine;
4-[2-(difluoromethyl)-1H-benzimidazol-1-yl]-N-methyl-6-(4-morpholinyl)-N-(2-pyridinylmethyl)-1,3,5-triazin-2-amine;
4-[2-(difluoromethyl)-4-methoxy-1H-benzimidazol-1-yl]-N-methyl-6-(4-morpholinyl)-N-(2-pyridinylmethyl)-1,3,5-triazin-2-amine;
4-[2-(difluoromethyl)-1H-benzimidazol-1-yl]-N-methyl-6-(4-morpholinyl)-N-(3-pyridinylmethyl)-1,3,5-triazin-2-amine;
4-[2-(difluoromethyl)-4-methoxy-1H-benzimidazol-1-yl]-N-methyl-6-(4-morpholinyl)-N-(3-pyridinylmethyl)-1,3,5-triazin-2-amine;
4-[2-(difluoromethyl)-1H-benzimidazol-1-yl]-N-methyl-6-(4-morpholinyl)-N-(4-pyridinylmethyl)-1,3,5-triazin-2-amine;
4-[2-(difluoromethyl)-4-methoxy-1H-benzimidazol-1-yl]-N-methyl-6-(4-morpholinyl)-N-(4-pyridinylmethyl)-1,3,5-triazin-2-amine;
2-(difluoromethyl)-1-[4-(4-morpholinyl)-6-(2-pyridinylmethoxy)-1,3,5-triazin-2-yl]-1H-benzimidazole;
2-(difluoromethyl)-4-methoxy-1-[4-(4-morpholinyl)-6-(2-pyridinylmethoxy)-1,3,5-triazin-2-yl]-1H-benzimidazole;
2-(difluoromethyl)-1-[4-(4-morpholinyl)-6-(3-pyridinylmethoxy)-1,3,5-triazin-2-yl]-1H-benzimidazole;
2-(difluoromethyl)-4-methoxy-1-[4-(4-morpholinyl)-6-(3-pyridinylmethoxy)-1,3,5-triazin-2-yl]-1H-benzimidazole;
2-(difluoromethyl)-1-[4-(4-morpholinyl)-6-(4-pyridinylmethoxy)-1,3,5-triazin-2-yl]-1H-benzimidazole;
2-(difluoromethyl)-4-methoxy-1-[4-(4-morpholinyl)-6-(4-pyridinylmethoxy)-1,3,5-triazin-2-yl]-1H-benzimidazole;
4-[2-(difluoromethyl)-1H-benzimidazol-1-yl]-6-(4-morpholinyl)-N-[2-(2-pyridinyl)ethyl]-1,3,5-triazin-2-amine;
4-[2-(difluoromethyl)-4-methoxy-1H-benzimidazol-1-yl]-6-(4-morpholinyl)-N-[2-(2-pyridinyl)ethyl]-1,3,5-triazin-2-amine;
4-[2-(difluoromethyl)-1H-benzimidazol-1-yl]-6-(4-morpholinyl)-N-[2-(3-pyridinyl)ethyl]-1,3,5-triazin-2-amine;
4-[2-(difluoromethyl)-4-methoxy-1H-benzimidazol-1-yl]-6-(4-morpholinyl)-N-[2-(3-pyridinyl)ethyl]-1,3,5-triazin-2-amine;
4-[2-(difluoromethyl)-1H-benzimidazol-1-yl]-6-(4-morpholinyl)-N-[2-(4-pyridinyl)ethyl]-1,3,5-triazin-2-amine;
4-[2-(difluoromethyl)-4-methoxy-1H-benzimidazol-1-yl]-6-(4-morpholinyl)-N-[2-(4-pyridinyl)ethyl]-1,3,5-triazin-2-amine;
4-[2-(difluoromethyl)-1H-benzimidazol-1-yl]-N-[2-(1H-imidazol-4-yl)ethyl]-6-(4-morpholinyl)-1,3,5-triazin-2-amine;
4-[2-(difluoromethyl)-4-methoxy-1H-benzimidazol-1-yl]-N-[2-(1H-imidazol-4-yl)ethyl]-6-(4-morpholinyl)-1,3,5-triazin-2-amine;
N-[4-[6-amino-2-(difluoromethyl)-1H-benzimidazol-1-yl]-6-(4-morpholinyl)-1,3,5-triazin-2-yl]-N-(3-pyridinyl)amine;
N-[4-[2-(difluoromethyl)-6-(methylamino)-1H-benzimidazol-1-yl]-6-(4-morpholinyl)-1,3,5-triazin-2-yl]-N-(3-pyridinyl)amine;
N-[4-[2-(difluoromethyl)-4-methoxy-6-(methylamino)-1H-benzimidazol-1-yl]-6-(4-morpholinyl)-1,3,5-triazin-2-yl]-N-(3-pyridinyl)amine;
N-[4-[2-(difluoromethyl)-6-(dimethylamino)-1H-benzimidazol-1-yl]-6-(4-morpholinyl)-1,3,5-triazin-2-yl]-N-(3-pyridinyl)amine;
N-[4-[2-(difluoromethyl)-6-(dimethylamino)-4-methoxy-1H-benzimidazol-1-yl]-6-(4-morpholinyl)-1,3,5-triazin-2-yl]-N-(3-pyridinyl)amine;
4-[2-(difluoromethyl)-1H-benzimidazol-1-yl]-N-(6-methoxy-3-pyridinyl)-6-(4-morpholinyl)-1,3,5-triazin-2-amine;
4-[2-(difluoromethyl)-1H-benzimidazol-1-yl]-N-(2-methoxy-4-pyridinyl)-6-(4-morpholinyl)-1,3,5-triazin-2-amine;
4-[2-(difluoromethyl)-4-methoxy-1H-benzimidazol-1-yl]-N-(2-methoxy-4-pyridinyl)-6-(4-morpholinyl)-1,3,5-triazin-2-amine;
4-[2-(difluoromethyl)-1H-benzimidazol-1-yl]-N-(2-methoxy-5-pyrimidinyl)-6-(4-morpholinyl)-1,3,5-triazin-2-amine;
4-[2-(difluoromethyl)-4-methoxy-1H-benzimidazol-1-yl]-N-(2-methoxy-5-pyrimidinyl)-6-(4-morpholinyl)-1,3,5-triazin-2-amine;
4-[2-(difluoromethyl)-1H-benzimidazol-1-yl]-N-{6-[2-(dimethylamino)ethoxy]-3-pyridinyl}-6-(4-morpholinyl)-1,3,5-triazin-2-amine;
4-[2-(difluoromethyl)-4-methoxy-1H-benzimidazol-1-yl]-N-{6-[2-(dimethylamino)ethoxy]-3-pyridinyl}-6-(4-morpholinyl)-1,3,5-triazin-2-amine;
4-[2-(difluoromethyl)-1H-benzimidazol-1-yl]-6-(4-morpholinyl)-N-{6-[2-(4-morpholinyl)ethoxy]-3-pyridinyl}-1,3,5-triazin-2-amine;
4-[2-(difluoromethyl)-4-methoxy-1H-benzimidazol-1-yl]-6-(4-morpholinyl)-N-{6-[2-(4-morpholinyl)ethoxy]-3-pyridinyl}-1,3,5-triazin-2-amine;
4-[2-(difluoromethyl)-1H-benzimidazol-1-yl]-N-{6-[3-(dimethylamino)propoxy]-3-pyridinyl}-6-(4-morpholinyl)-1,3,5-triazin-2-amine;
4-[2-(difluoromethyl)-1H-benzimidazol-1-yl]-6-(4-morpholinyl)-N-{6-[3-(4-morpholinyl)propoxy]-3-pyridinyl}-1,3,5-triazin-2-amine;
4-[2-(difluoromethyl)-4-methoxy-1H-benzimidazol-1-yl]-6-(4-morpholinyl)-N-{6-[3-(4-morpholinyl)propoxy]-3-pyridinyl}-1,3,5-triazin-2-amine;
$N^5$-[4-[2-(difluoromethyl)-1H-benzimidazol-1-yl]-6-(4-morpholinyl)-1,3,5-triazin-2-yl]-2,5-pyridinediamine;
$N^5$-[4-[2-(difluoromethyl)-1H-benzimidazol-1-yl]-6-(4-morpholinyl)-1,3,5-triazin-2-yl]-$N^2$-methyl-2,5-pyridinediamine;

N⁵-[4-[2-(difluoromethyl)-4-methoxy-1H-benzimidazol-1-yl]-6-(4-morpholinyl)-1,3,5-triazin-2-yl]-N²-methyl-2,5-pyridinediamine;
N⁵-[4-[2-(difluoromethyl)-1H-benzimidazol-1-yl]-6-(4-morpholinyl)-1,3,5-triazin-2-yl]-N²,N²-dimethyl-2,5-pyridinediamine;
N⁵-[4-[2-(difluoromethyl)-4-methoxy-1H-benzimidazol-1-yl]-6-(4-morpholinyl)-1,3,5-triazin-2-yl]-N²,N²-dimethyl-2,5-pyridinediamine;
N⁵-[4-[2-(difluoromethyl)-1H-benzimidazol-1-yl]-6-(4-morpholinyl)-1,3,5-triazin-2-yl]-N²-[2-(dimethylamino)ethyl]-2,5-pyridinediamine;
N⁵-[4-[2-(difluoromethyl)-4-methoxy-1H-benzimidazol-1-yl]-6-(4-morpholinyl)-1,3,5-triazin-2-yl]-N²-[2-(dimethylamino)ethyl]-2,5-pyridinediamine;
N⁵-[4-[2-(difluoromethyl)-1H-benzimidazol-1-yl]-6-(4-morpholinyl)-1,3,5-triazin-2-yl]-N²-[2-(4-morpholinyl)ethyl]-2,5-pyridinediamine;
N⁵-[4-[2-(difluoromethyl)-4-methoxy-1H-benzimidazol-1-yl]-6-(4-morpholinyl)-1,3,5-triazin-2-yl]-N²-[2-(4-morpholinyl)ethyl]-2,5-pyridinediamine;
N⁵-[4-[2-(difluoromethyl)-1H-benzimidazol-1-yl]-6-(4-morpholinyl)-1,3,5-triazin-2-yl]-N²-[2-(dimethylamino)ethyl]-N²-methyl-2,5-pyridinediamine;
N⁵-[4-[2-(difluoromethyl)-4-methoxy-1H-benzimidazol-1-yl]-6-(4-morpholinyl)-1,3,5-triazin-2-yl]-N²-[2-(dimethylamino)ethyl]-N²-methyl-2,5-pyridinediamine;
N⁵-[4-[2-(difluoromethyl)-1H-benzimidazol-1-yl]-6-(4-morpholinyl)-1,3,5-triazin-2-yl]-N²-methyl-N²-[2-(4-morpholinyl)ethyl]-2,5-pyridinediamine;
N⁵-[4-[2-(difluoromethyl)-4-methoxy-1H-benzimidazol-1-yl]-6-(4-morpholinyl)-1,3,5-triazin-2-yl]-N²-methyl-N²-[2-(4-morpholinyl)ethyl]-2,5-pyridinediamine;
N⁵-[4-[2-(difluoromethyl)-1H-benzimidazol-1-yl]-6-(4-morpholinyl)-1,3,5-triazin-2-yl]-N²-[3-(dimethylamino)propyl]-2,5-pyridinediamine;
N⁵-[4-[2-(difluoromethyl)-1H-benzimidazol-1-yl]-6-(4-morpholinyl)-1,3,5-triazin-2-yl]-N²-[3-(dimethylamino)propyl]-N²-methyl-2,5-pyridinediamine;
N⁵-[4-[2-(difluoromethyl)-1H-benzimidazol-1-yl]-6-(4-morpholinyl)-1,3,5-triazin-2-yl]-N²-[3-(4-morpholinyl)propyl]-2,5-pyridinediamine;
N⁵-[4-[2-(difluoromethyl)-4-methoxy-1H-benzimidazol-1-yl]-6-(4-morpholinyl)-1,3,5-triazin-2-yl]-N²-[3-(4-morpholinyl)propyl]-2,5-pyridinediamine;
N⁵-[4-[2-(difluoromethyl)-1H-benzimidazol-1-yl]-6-(4-morpholinyl)-1,3,5-triazin-2-yl]-N²-methyl-N²-[3-(4-morpholinyl)propyl]-2,5-pyridinediamine;
N⁵-[4-[2-(difluoromethyl)-4-methoxy-1H-benzimidazol-1-yl]-6-(4-morpholinyl)-1,3,5-triazin-2-yl]-N²-methyl-N²-[3-(4-morpholinyl)propyl]-2,5-pyridinediamine;
4-[2-(difluoromethyl)-1H-benzimidazol-1-yl]-N-{6-[2-(dimethylamino)ethyl]-3-pyridinyl}-6-(4-morpholinyl)-1,3,5-triazin-2-amine;
4-[2-(difluoromethyl)-4-methoxy-1H-benzimidazol-1-yl]-N-{6-[2-(dimethylamino)ethyl]-3-pyridinyl}-6-(4-morpholinyl)-1,3,5-triazin-2-amine;
4-[2-(difluoromethyl)-1H-benzimidazol-1-yl]-6-(4-morpholinyl)-N-{6-[2-(4-morpholinyl)ethyl]-3-pyridinyl}-1,3,5-triazin-2-amine;
4-[2-(difluoromethyl)-4-methoxy-1H-benzimidazol-1-yl]-6-(4-morpholinyl)-N-{6-[2-(4-morpholinyl)ethyl]-3-pyridinyl}-1,3,5-triazin-2-amine;
4-[2-(difluoromethyl)-1H-benzimidazol-1-yl]-N-{2-[2-(dimethylamino)ethyl]-5-pyrimidinyl}-6-(4-morpholinyl)-1,3,5-triazin-2-amine;
4-[2-(difluoromethyl)-4-methoxy-1H-benzimidazol-1-yl]-N-{2-[2-(dimethylamino)ethyl]-5-pyrimidinyl}-6-(4-morpholinyl)-1,3,5-triazin-2-amine;
4-[2-(difluoromethyl)-1H-benzimidazol-1-yl]-6-(4-morpholinyl)-N-{2-[2-(4-morpholinyl)ethyl]-5-pyrimidinyl}-1,3,5-triazin-2-amine;
4-[2-(difluoromethyl)-4-methoxy-1H-benzimidazol-1-yl]-6-(4-morpholinyl)-N-{2-[2-(4-morpholinyl)ethyl]-5-pyrimidinyl}-1,3,5-triazin-2-amine;
4-[2-(difluoromethyl)-1H-benzimidazol-1-yl]-N-{5-[2-(dimethylamino)ethoxy]-3-pyridinyl}-6-(4-morpholinyl)-1,3,5-triazin-2-amine;
4-[2-(difluoromethyl)-4-methoxy-1H-benzimidazol-1-yl]-N-{5-[2-(dimethylamino)ethoxy]-3-pyridinyl}-6-(4-morpholinyl)-1,3,5-triazin-2-amine;
4-[2-(difluoromethyl)-4-methoxy-1H-benzimidazol-1-yl]-6-(4-morpholinyl)-N-{5-[2-(4-morpholinyl)ethoxy]-3-pyridinyl}-1,3,5-triazin-2-amine;
4-[2-(difluoromethyl)-1H-benzimidazol-1-yl]-6-(4-morpholinyl)-N-{5-[2-(4-morpholinyl)ethoxy]-3-pyridinyl}-1,3,5-triazin-2-amine;
4-[2-(difluoromethyl)-1H-benzimidazol-1-yl]-N-{5-[3-(dimethylamino)propoxy]-3-pyridinyl}-6-(4-morpholinyl)-1,3,5-triazin-2-amine;
4-[2-(difluoromethyl)-4-methoxy-1H-benzimidazol-1-yl]-N-{5-[3-(dimethylamino)propoxy]-3-pyridinyl}-6-(4-morpholinyl)-1,3,5-triazin-2-amine;
4-[2-(difluoromethyl)-1H-benzimidazol-1-yl]-6-(4-morpholinyl)-N-{5-[3-(4-morpholinyl)propoxy]-3-pyridinyl}-1,3,5-triazin-2-amine;
4-[2-(difluoromethyl)-4-methoxy-1H-benzimidazol-1-yl]-6-(4-morpholinyl)-N-{5-[3-(4-morpholinyl)propoxy]-3-pyridinyl}-1,3,5-triazin-2-amine;
4-[2-(difluoromethyl)-1H-benzimidazol-1-yl]-N-{2-[2-(dimethylamino)ethoxy]-4-pyridinyl}-6-(4-morpholinyl)-1,3,5-triazin-2-amine;
4-[2-(difluoromethyl)-4-methoxy-1H-benzimidazol-1-yl]-N-{2-[2-(dimethylamino)ethoxy]-4-pyridinyl}-6-(4-morpholinyl)-1,3,5-triazin-2-amine;
4-[2-(difluoromethyl)-1H-benzimidazol-1-yl]-6-(4-morpholinyl)-N-{2-[2-(4-morpholinyl)ethoxy]-4-pyridinyl}-1,3,5-triazin-2-amine;
4-[2-(difluoromethyl)-4-methoxy-1H-benzimidazol-1-yl]-6-(4-morpholinyl)-N-{2-[2-(4-morpholinyl)ethoxy]-4-pyridinyl}-1,3,5-triazin-2-amine;
4-[2-(difluoromethyl)-1H-benzimidazol-1-yl]-N-{2-[3-(dimethylamino)propoxy]-4-pyridinyl}-6-(4-morpholinyl)-1,3,5-triazin-2-amine;
4-[2-(difluoromethyl)-4-methoxy-1H-benzimidazol-1-yl]-N-{2-[3-(dimethylamino)propoxy]-4-pyridinyl}-6-(4-morpholinyl)-1,3,5-triazin-2-amine;
4-[2-(difluoromethyl)-1H-benzimidazol-1-yl]-6-(4-morpholinyl)-N-{2-[3-(4-morpholinyl)propoxy]-4-pyridinyl}-1,3,5-triazin-2-amine;
4-[2-(difluoromethyl)-4-methoxy-1H-benzimidazol-1-yl]-6-(4-morpholinyl)-N-{2-[3-(4-morpholinyl)propoxy]-4-pyridinyl}-1,3,5-triazin-2-amine;
4-[2-(difluoromethyl)-1H-benzimidazol-1-yl]-N-{2-[2-(dimethylamino)ethoxy]-5-pyrimidinyl}-6-(4-morpholinyl)-1,3,5-triazin-2-amine;
4-[2-(difluoromethyl)-4-methoxy-1H-benzimidazol-1-yl]-N-{2-[2-(dimethylamino)ethoxy]-5-pyrimidinyl}-6-(4-morpholinyl)-1,3,5-triazin-2-amine;
4-[2-(difluoromethyl)-1H-benzimidazol-1-yl]-N-{2-[3-(dimethylamino)propoxy]-5-pyrimidinyl}-6-(4-morpholinyl)-1,3,5-triazin-2-amine;

4-[2-(difluoromethyl)-4-methoxy-1H-benzimidazol-1-yl]-N-{2-[3-(dimethylamino)propoxy]-5-pyrimidinyl}-6-(4-morpholinyl)-1,3,5-triazin-2-amine;
4-[2-(difluoromethyl)-1H-benzimidazol-1-yl]-6-(4-morpholinyl)-N-{2-[2-(4-morpholinyl)ethoxy]-5-pyrimidinyl}-1,3,5-triazin-2-amine;
4-[2-(difluoromethyl)-4-methoxy-1H-benzimidazol-1-yl]-6-(4-morpholinyl)-N-{2-[2-(4-morpholinyl)ethoxy]-5-pyrimidinyl}-1,3,5-triazin-2-amine;
4-[2-(difluoromethyl)-1H-benzimidazol-1-yl]-6-(4-morpholinyl)-N-{2-[3-(4-morpholinyl)propoxy]-5-pyrimidinyl}-1,3,5-triazin-2-amine;
4-[2-(difluoromethyl)-4-methoxy-1H-benzimidazol-1-yl]-6-(4-morpholinyl)-N-{2-[3-(4-morpholinyl)propoxy]-5-pyrimidinyl}-1,3,5-triazin-2-amine;
$N^5$-[4-[2-(difluoromethyl)-4-methoxy-1H-benzimidazol-1-yl]-6-(4-morpholinyl)-1,3,5-triazin-2-yl]-$N^2$-[2-(dimethylamino)ethyl]-2,5-pyrimidinediamine;
$N^5$-[4-[2-(difluoromethyl)-1H-benzimidazol-1-yl]-6-(4-morpholinyl)-1,3,5-triazin-2-yl]-$N^2$-[2-(dimethylamino)ethyl]-2,5-pyrimidinediamine;
$N^5$-[4-[2-(difluoromethyl)-1H-benzimidazol-1-yl]-6-(4-morpholinyl)-1,3,5-triazin-2-yl]-$N^2$-[2-(dimethylamino)ethyl]-$N^2$-methyl-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-$N^2$-[2-(dimethylamino)ethyl]-$N^2$-methyl-2,5-pyrimidinediamine;
$N^5$-[4-[2-(difluoromethyl)-1H-benzimidazol-1-yl]-6-(4-morpholinyl)-1,3,5-triazin-2-yl]-$N^2$-[3-(dimethylamino)propyl]-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-$N^2$-[3-(dimethylamino)propyl]-2,5-pyrimidinediamine;
$N^5$-[4-[2-(difluoromethyl)-1H-benzimidazol-1-yl]-6-(4-morpholinyl)-1,3,5-triazin-2-yl]-$N^2$-[3-(dimethylamino)propyl]-$N^2$-methyl-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-$N^2$-[3-(dimethylamino)propyl]-$N^2$-methyl-2,5-pyrimidinediamine;
$N^5$-[4-[2-(difluoromethyl)-1H-benzimidazol-1-yl]-6-(4-morpholinyl)-1,3,5-triazin-2-yl]-$N^2$-[2-(4-morpholinyl)ethyl]-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-$N^2$-[2-(4-morpholinyl)ethyl]-2,5-pyrimidinediamine;
$N^5$-[4-[2-(difluoromethyl)-1H-benzimidazol-1-yl]-6-(4-morpholinyl)-1,3,5-triazin-2-yl]-$N^2$-methyl-$N^2$-[2-(4-morpholinyl)ethyl]-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-[2-(4-morpholinyl)ethyl]-2,5-pyrimidinediamine;
$N^5$-[4-[2-(difluoromethyl)-1H-benzimidazol-1-yl]-6-(4-morpholinyl)-1,3,5-triazin-2-yl]-$N^2$-[3-(4-morpholinyl)propyl]-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-$N^2$-[3-(4-morpholinyl)propyl]-2,5-pyrimidinediamine;
$N^5$-[4-[2-(difluoromethyl)-1H-benzimidazol-1-yl]-6-(4-morpholinyl)-1,3,5-triazin-2-yl]-$N^2$-methyl-$N^2$-[3-(4-morpholinyl)propyl]-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-[3-(4-morpholinyl)propyl]-2,5-pyrimidinediamine;
4-[2-(difluoromethyl)-1H-benzimidazol-1-yl]-N-[6-(4-methyl-1-piperazinyl)-3-pyridinyl]-6-(4-morpholinyl)-1,3,5-triazin-2-amine;
4-[2-(difluoromethyl)-4-methoxy-1H-benzimidazol-1-yl]-N-[6-(4-methyl-1-piperazinyl)-3-pyridinyl]-6-(4-morpholinyl)-1,3,5-triazin-2-amine;
4-[2-(difluoromethyl)-1H-benzimidazol-1-yl]-N-[2-(4-methyl-1-piperazinyl)-5-pyrimidinyl]-6-(4-morpholinyl)-1,3,5-triazin-2-amine;
4-[2-(difluoromethyl)-4-methoxy-1H-benzimidazol-1-yl]-N-[2-(4-methyl-1-piperazinyl)-5-pyrimidinyl]-6-(4-morpholinyl)-1,3,5-triazin-2-amine;
4-[2-(difluoromethyl)-1H-benzimidazol-1-yl]-N-{6-[4-(dimethylamino)-1-piperidinyl]-3-pyridinyl}-6-(4-morpholinyl)-1,3,5-triazin-2-amine;
4-[2-(difluoromethyl)-4-methoxy-1H-benzimidazol-1-yl]-N-{6-[4-(dimethylamino)-1-piperidinyl]-3-pyridinyl}-6-(4-morpholinyl)-1,3,5-triazin-2-amine;
4-[2-(difluoromethyl)-1H-benzimidazol-1-yl]-N-{2-[4-(dimethylamino)-1-piperidinyl]-5-pyrimidinyl}-6-(4-morpholinyl)-1,3,5-triazin-2-amine;
4-[2-(difluoromethyl)-4-methoxy-1H-benzimidazol-1-yl]-N-{2-[4-(dimethylamino)-1-piperidinyl]-5-pyrimidinyl}-6-(4-morpholinyl)-1,3,5-triazin-2-amine;
$N^5$-[4-[2-(difluoromethyl)-1H-benzimidazol-1-yl]-6-(4-morpholinyl)-1,3,5-triazin-2-yl]-$N^2$-(1-methyl-4-piperidinyl)-2,5-pyridinediamine;
$N^5$-[4-[2-(difluoromethyl)-4-methoxy-1H-benzimidazol-1-yl]-6-(4-morpholinyl)-1,3,5-triazin-2-yl]-$N^2$-(1-methyl-4-piperidinyl)-2,5-pyridinediamine;
$N^5$-[4-[2-(difluoromethyl)-1H-benzimidazol-1-yl]-6-(4-morpholinyl)-1,3,5-triazin-2-yl]-$N^2$-methyl-$N^2$-(1-methyl-4-piperidinyl)-2,5-pyridinediamine;
$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-(1-methyl-4-piperidinyl)-2,5-pyridinediamine;
$N^5$-[4-[2-(difluoromethyl)-1H-benzimidazol-1-yl]-6-(4-morpholinyl)-1,3,5-triazin-2-yl]-$N^2$-(1-methyl-4-piperidinyl)-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-$N^2$-(1-methyl-4-piperidinyl)-2,5-pyrimidinediamine;
$N^5$-[4-[2-(difluoromethyl)-1H-benzimidazol-1-yl]-6-(4-morpholinyl)-1,3,5-triazin-2-yl]-$N^2$-methyl-$N^2$-(1-methyl-4-piperidinyl)-2,5-pyrimidinediamine;
$N^5$-[4-[2-(difluoromethyl)-4-methoxy-1H-benzimidazol-1-yl]-6-(4-morpholinyl)-1,3,5-triazin-2-yl]-$N^2$-methyl-$N^2$-(1-methyl-4-piperidinyl)-2,5-pyrimidinediamine;
4-[2-(difluoromethyl)-1H-benzimidazol-1-yl]-N-{6-[(1-methyl-4-piperidinyl)oxy]-3-pyridinyl}-6-(4-morpholinyl)-1,3,5-triazin-2-amine;
4-[2-(difluoromethyl)-4-methoxy-1H-benzimidazol-1-yl]-N-{6-[(1-methyl-4-piperidinyl)oxy]-3-pyridinyl}-6-(4-morpholinyl)-1,3,5-triazin-2-amine;
4-[2-(difluoromethyl)-1H-benzimidazol-1-yl]-N-{2-[(1-methyl-4-piperidinyl)oxy]-5-pyrimidinyl}-6-(4-morpholinyl)-1,3,5-triazin-2-amine;
4-[2-(difluoromethyl)-4-methoxy-1H-benzimidazol-1-yl]-N-{2-[(1-methyl-4-piperidinyl)oxy]-5-pyrimidinyl}-6-(4-morpholinyl)-1,3,5-triazin-2-amine;
4-[2-(difluoromethyl)-1H-benzimidazol-1-yl]-N-{6-[(1-methyl-3-pyrrolidinyl)oxy]-3-pyridinyl}-6-(4-morpholinyl)-1,3,5-triazin-2-amine;
4-[2-(difluoromethyl)-4-methoxy-1H-benzimidazol-1-yl]-N-{6-[(1-methyl-3-pyrrolidinyl)oxy]-3-pyridinyl}-6-(4-morpholinyl)-1,3,5-triazin-2-amine;

4-[2-(difluoromethyl)-1H-benzimidazol-1-yl]-N-{2-[(1-methyl-3-pyrrolidinyl)oxy]-5-pyrimidinyl}-6-(4-morpholinyl)-1,3,5-triazin-2-amine;

4-[2-(difluoromethyl)-4-methoxy-1H-benzimidazol-1-yl]-N-{2-[(1-methyl-3-pyrrolidinyl)oxy]-5-pyrimidinyl}-6-(4-morpholinyl)-1,3,5-triazin-2-amine;

4-[2-(difluoromethyl)-1H-benzimidazol-1-yl]-N-{1-[2-(dimethylamino)ethyl]-1H-pyrazol-4-yl}-6-(4-morpholinyl)-1,3,5-triazin-2-amine;

4-[2-(difluoromethyl)-4-methoxy-1H-benzimidazol-1-yl]-N-{1-[2-(dimethylamino)ethyl]-1H-pyrazol-4-yl}-6-(4-morpholinyl)-1,3,5-triazin-2-amine;

4-[2-(difluoromethyl)-1H-benzimidazol-1-yl]-6-(4-morpholinyl)-N-{1-[2-(4-morpholinyl)ethyl]-1H-pyrazol-4-yl}-1,3,5-triazin-2-amine;

4-[2-(difluoromethyl)-4-methoxy-1H-benzimidazol-1-yl]-6-(4-morpholinyl)-N-{1-[2-(4-morpholinyl)ethyl]-1H-pyrazol-4-yl}-1,3,5-triazin-2-amine;

4-[2-(difluoromethyl)-1H-benzimidazol-1-yl]-N-{1-[3-(dimethylamino)propyl]-1H-pyrazol-4-yl}-6-(4-morpholinyl)-1,3,5-triazin-2-amine;

4-[2-(difluoromethyl)-4-methoxy-1H-benzimidazol-1-yl]-N-{1-[3-(dimethylamino)propyl]-1H-pyrazol-4-yl}-6-(4-morpholinyl)-1,3,5-triazin-2-amine;

4-[2-(difluoromethyl)-1H-benzimidazol-1-yl]-6-(4-morpholinyl)-N-{1-[3-(4-morpholinyl)propyl]-1H-pyrazol-4-yl}-1,3,5-triazin-2-amine;

4-[2-(difluoromethyl)-4-methoxy-1H-benzimidazol-1-yl]-6-(4-morpholinyl)-N-{1-[3-(4-morpholinyl)propyl]-1H-pyrazol-4-yl}-1,3,5-triazin-2-amine;

4-[2-(difluoromethyl)-1H-benzimidazol-1-yl]-6-(4-morpholinyl)-N-(1,3-thiazol-5-yl)-1,3,5-triazin-2-amine;

4-[2-(difluoromethyl)-4-methoxy-1H-benzimidazol-1-yl]-6-(4-morpholinyl)-N-(1,3-thiazol-5-yl)-1,3,5-triazin-2-amine;

4-[2-(difluoromethyl)-1H-benzimidazol-1-yl]-N-{2-[(dimethylamino)methyl]-1,3-thiazol-5-yl}-6-(4-morpholinyl)-1,3,5-triazin-2-amine;

4-[2-(difluoromethyl)-4-methoxy-1H-benzimidazol-1-yl]-N-{2[(dimethylamino)methyl]-1,3-thiazol-5-yl}-6-(4-morpholinyl)-1,3,5-triazin-2-amine;

4-[2-(difluoromethyl)-1H-benzimidazol-1-yl]-6-(4-morpholinyl)-N-[2-(4-morpholinylmethyl)-1,3-thiazol-5-yl]-1,3,5-triazin-2-amine;

4-[2-(difluoromethyl)-4-methoxy-1H-benzimidazol-1-yl]-6-(4-morpholinyl)-N-[2-(4-morpholinylmethyl)-1,3-thiazol-5-yl]-1,3,5-triazin-2-amine;

4-[2-(difluoromethyl)-4-methoxy-1H-benzimidazol-1-yl]-N-(1-methyl-1H-imidazol-5-yl)-6-(4-morpholinyl)-1,3,5-triazin-2-amine;

4-[2-(difluoromethyl)-1H-benzimidazol-1-yl]-N-(1-methyl-1H-1,2,3-triazol-5-yl)-6-(4-morpholinyl)-1,3,5-triazin-2-amine;

4-[2-(difluoromethyl)-4-methoxy-1H-benzimidazol-1-yl]-N-(1-methyl-1H-1,2,3-triazol-5-yl)-6-(4-morpholinyl)-1,3,5-triazin-2-amine;

4-[2-(difluoromethyl)-1H-benzimidazol-1-yl]-N-(2-methyl-2H-1,2,3-triazol-4-yl)-6-(4-morpholinyl)-1,3,5-triazin-2-amine;

4-[2-(difluoromethyl)-4-methoxy-1H-benzimidazol-1-yl]-N-(2-methyl-2H-1,2,3-triazol-4-yl)-6-(4-morpholinyl)-1,3,5-triazin-2-amine;

4-[2-(difluoromethyl)-1H-benzimidazol-1-yl]-N-(1-methyl-1H-1,2,3-triazol-4-yl)-6-(4-morpholinyl)-1,3,5-triazin-2-amine;

4-[2-(difluoromethyl)-4-methoxy-1H-benzimidazol-1-yl]-N-(1-methyl-1H-1,2,3-triazol-4-yl)-6-(4-morpholinyl)-1,3,5-triazin-2-amine;

4-[2-(difluoromethyl)-1H-benzimidazol-1-yl]-N-(2-methyl-2H-tetrazol-5-yl)-6-(4-morpholinyl)-1,3,5-triazin-2-amine;

4-[2-(difluoromethyl)-4-methoxy-1H-benzimidazol-1-yl]-N-(2-methyl-2H-tetrazol-5-yl)-6-(4-morpholinyl)-1,3,5-triazin-2-amine;

4-[2-(difluoromethyl)-1H-benzimidazol-1-yl]-N-(1-methyl-1H-tetrazol-5-yl)-6-(4-morpholinyl)-1,3,5-triazin-2-amine;

4-[2-(difluoromethyl)-4-methoxy-1H-benzimidazol-1-yl]-N-(1-methyl-1H-tetrazol-5-yl)-6-(4-morpholinyl)-1,3,5-triazin-2-amine;

$N^5$-[4-[2-(difluoromethyl)-1H-benzimidazol-1-yl]-6-(4-morpholinyl)-1,3,5-triazin-2-yl]-2,5-pyrimidinediamine;

$N^5$-[4-[2-(difluoromethyl)-4-methoxy-1H-benzimidazol-1-yl]-6-(4-morpholinyl)-1,3,5-triazin-2-yl]-2,5-pyrimidinediamine;

4-[2-(difluoromethyl)-1H-benzimidazol-1-yl]-6-(4-morpholinyl)-N-(2-pyrazinyl)-1,3,5-triazin-2-amine;

4-[2-(difluoromethyl)-4-methoxy-1H-benzimidazol-1-yl]-6-(4-morpholinyl) -N-(2-pyrazinyl)-1,3,5-triazin-2-amine;

$N^2$-[4-[2-(difluoromethyl)-1H-benzimidazol-1-yl]-6-(4-morpholinyl)-1,3,5-triazin-2-yl]-2-pyrazinediamine;

$N^2$-[4-[2-(difluoromethyl)-4-methoxy-1H-benzimidazol-1-yl]-6-(4-morpholinyl)-1,3,5-triazin-2-yl]-2-pyrazinediamine;

$N^2$-[4-[2-(difluoromethyl)-1H-benzimidazol-1-yl]-6-(4-morpholinyl)-1,3,5-triazin-2-yl]-2,6-pyrazinediamine;

$N^2$-[4-[2-(difluoromethyl)-4-methoxy-1H-benzimidazol-1-yl]-6-(4-morpholinyl) -1,3,5-triazin-2-yl]-2,6-pyrazinediamine;

4-[2-(difluoromethyl)-1H-benzimidazol-1-yl]-N-(6-methoxy-2-pyrazinyl)-6-(4-morpholinyl)-1,3,5-triazin-2-amine;

4-[2-(difluoromethyl)-4-methoxy-1H-benzimidazol-1-yl]-N-(6-methoxy-2-pyrazinyl)-6-(4-morpholinyl)-1,3,5-triazin-2-amine; and N-[4-[6-amino-2-(difluoromethyl)-4-methoxy-1H-benzimidazol-1-yl]-6-(4-morpholinyl)-1,3,5-triazin-2-yl]-N-(3-pyridinyl)amine;

and enantiomers, mixtures of enantiomers, or mixtures of two or more diastereomers thereof; and pharmaceutically acceptable salts and prodrugs thereof.

70. The compound of claim 1 selected from the group consisting of:

N-[4-[2-(difluoromethyl)-1H-benzimidazol-1-yl]-6-(4-morpholinyl)-1,3,5-triazin-2-yl]-3-quinolinamine;

4-[2-(difluoromethyl)-1H-benzimidazol-1-yl]-6-(4-morpholinyl)-N-(2-pyrimidinyl)-1,3,5-triazin-2-amine;

4-[2-(difluoromethyl)-1H-benzimidazol-1-yl]-6-(4-morpholinyl)-N-(4-pyrimidinyl)-1,3,5-triazin-2-amine;

4-[2-(difluoromethyl)-1H-benzimidazol-1-yl]-6-(4-morpholinyl)-N-(5-pyrimidinyl)-1,3,5-triazin-2-amine;

4-[2-(difluoromethyl)-1H-benzimidazol-1-yl]-N-(4-methoxy-3-pyridinyl)-6-(4-morpholinyl)-1,3,5-triazin-2-amine;

4-[2-(difluoromethyl)-4-methoxy-1H-benzimidazol-1-yl]-N-(6-fluoro-3-pyridinyl)-6-(4-morpholinyl)-1,3,5-triazin-2-amine;

N-(6-chloro-3-pyridinyl)-4-[2-(difluoromethyl)-4-methoxy-1H-benzimidazol-1-yl]-6-(4-morpholinyl)-1,3,5-triazin-2-amine;

4-(2-(difluoromethyl)-4-methoxy-1H-benzimidazol-1-yl)-N-(6-methoxypyrimidin-4-yl)-6-morpholino-1,3,5-triazin-2-amine;

4-[2-(difluoromethyl)-4-methoxy-1H-benzimidazol-1-yl]-6-(4-morpholinyl)-N-(3-pyridazinyl)-1,3,5-triazin-2-amine; and 4-[2-(difluoromethyl)-4-methoxy-1H-benzimidazol-1-yl]-N-(6-methoxy-3-pyridazinyl)-6-(4-morpholinyl)-1,3,5-triazin-2-amine;

and enantiomers, mixtures of enantiomers, or mixtures of two or more diastereomers thereof; and pharmaceutically acceptable salts and prodrugs thereof.

71. A pharmaceutical composition comprising the compound of claim 1, or an enantiomer, a mixture of enantiomers, or a mixture of two or more diastereomers thereof; or a pharmaceutically acceptable salt or prodrug thereof; and one or more pharmaceutically acceptable carriers.

72. The pharmaceutical composition of claim 71, further comprising a second therapeutic agent.

73. The pharmaceutical composition of claim 71, wherein the composition is formulated for single dose administration.

74. The pharmaceutical composition of claim 71, wherein the composition is formulated as oral, parenteral, or intravenous dosage form.

75. The pharmaceutical composition of claim 74, wherein the oral dosage form is a tablet or capsule.

76. The compound of claim 14, wherein m is 2.

77. The compound of claim 76, wherein each $R^A$ is independently hydrogen or $C_{1-6}$ alkyl optionally substituted with one or more substituents Q.

78. The compound of claim 76, wherein each $R^A$ is independently hydrogen or methyl.

79. The compound of claim 76, wherein each $R^B$ is independently hydrogen or $C_{1-6}$ alkyl optionally substituted with one or more substituents Q.

80. The compound of claim 76, wherein each $R^B$ is independently hydrogen or methyl.

81. The compound of claim 76, wherein each $R^A$ and $R^B$ is independently hydrogen or methyl.

82. The compound of claim 27, wherein m is 2.

83. The compound of claim 82, wherein each $R^A$ is independently hydrogen or $C_{1-6}$ alkyl optionally substituted with one or more substituents Q.

84. The compound of claim 82, wherein each $R^A$ is independently hydrogen or methyl.

85. The compound of claim 82, wherein each $R^B$ is independently hydrogen or $C_{1-6}$ alkyl optionally substituted with one or more substituents Q.

86. The compound of claim 82, wherein each $R^B$ is independently hydrogen or methyl.

87. The compound of claim 82, wherein each $R^A$ and $R^B$ is independently hydrogen or methyl.

* * * * *